United States Patent
Giblin et al.

(10) Patent No.: US 7,232,821 B2
(45) Date of Patent: Jun. 19, 2007

(54) (2-((2-ALKOXY)-PHENYL)-CYCLOPENT-1ENYL) AROMATIC CARBO AND HETEROCYCLIC ACID AND DERIVATIVES

(75) Inventors: Gerard Martin Paul Giblin, Welwyn (GB); Adrian Hall, Welwyn (GB); David Nigel Hurst, Welwyn (GB); Ian Reginald Kilford, Welwyn (GB); Xiao Qing Lewell, Stevenage (GB); Alan Naylor, Stevenage (GB); Riccardo Novelli, Welwyn (GB)

(73) Assignee: Glaxo Group Limited (GB)

( * ) Notice: Subject to any disclaimer, the term of this patent is extended or adjusted under 35 U.S.C. 154(b) by 275 days.

(21) Appl. No.: 10/508,761

(22) PCT Filed: Apr. 7, 2003

(86) PCT No.: PCT/EP03/03661

§ 371 (c)(1),
(2), (4) Date: Sep. 22, 2004

(87) PCT Pub. No.: WO03/084917

PCT Pub. Date: Oct. 16, 2003

(65) Prior Publication Data

US 2005/0239802 A1    Oct. 27, 2005

(30) Foreign Application Priority Data

Apr. 8, 2002 (GB) .................... 0208045.5
Feb. 7, 2003 (GB) .................... 0302881.8

(51) Int. Cl.
- A61K 31/535 (2006.01)
- A61K 31/50 (2006.01)
- A61K 31/445 (2006.01)
- A61K 31/40 (2006.01)
- A61K 31/195 (2006.01)

(52) U.S. Cl. .................... 514/239.5; 514/247; 514/255; 514/256; 514/327; 514/424; 514/563; 514/568; 548/543; 560/59; 562/469; 562/432; 562/452; 546/322; 546/326; 546/301; 544/172; 544/224; 544/406; 544/407

(58) Field of Classification Search .................... 562/463, 562/469, 432, 452; 514/689, 256, 255.01, 514/277, 239.2, 239.5, 247, 327, 424, 563, 514/568, 255; 546/318, 356, 322, 301; 544/403, 544/335, 389, 172; 548/543; 560/59
See application file for complete search history.

(56) References Cited

U.S. PATENT DOCUMENTS

| | | | |
|---|---|---|---|
| 5,344,991 A | 9/1994 | Reitz et al. | |
| 5,420,287 A | 5/1995 | Reitz et al. | |
| 5,424,450 A | 6/1995 | Boswell et al. | |
| 5,474,995 A | 12/1995 | Ducharme et al. | |
| 5,512,681 A | 4/1996 | Boswell et al. | |
| 5,663,180 A | 9/1997 | Reitz et al. | |
| 5,811,459 A | 9/1998 | Oldfield et al. | |
| 5,840,746 A | 11/1998 | Ducharme et al. | |
| 5,972,986 A | 10/1999 | Seibert et al. | |
| 6,136,839 A | 10/2000 | Isakson et al. | |
| 6,440,963 B1 | 8/2002 | Leonardi et al. | |
| 6,495,149 B1 | 12/2002 | Scavone et al. | |
| 2002/0045605 A1 | 4/2002 | Kargman et al. | |

FOREIGN PATENT DOCUMENTS

| | | |
|---|---|---|
| DE | 4032522 | 4/1992 |
| DE | 4034728 | 5/1992 |
| DE | 20211496 | 11/2002 |
| EP | 131302 | 1/1985 |
| EP | 540009 | 5/1993 |
| EP | 03/03661 | 9/1993 |
| EP | 1251126 | 10/2002 |
| EP | 1264847 | 12/2002 |
| GB | 2272899 | 6/1994 |
| JP | 04076087 | 3/1992 |

(Continued)

OTHER PUBLICATIONS

Stock et. al., "The Prostaglandin E2 EP1 receptor mediates pain perception and regulates blood pressure", J. Clin. Invest. 17: 325-331.*

Whitesell, J.K., et al. "Synthesis and Resolution of a New Chiral C2-Symmetric Bisphenol: Trans-1,2-Bis(2-Hydroxyphenyl)cyclopentane." Tetrahedron Letters, 1997, 38(15), pp. 2589-2592.

Rathore, R., et al. "Efficient Hydrogenation of Sterically Hindered Olefins with Borane-Methyl Sulfide Complex." Journal of Organic Chemistry, 1996, 61(16), pp. 5246-5256.

(Continued)

*Primary Examiner*—Bernard Dentz
*Assistant Examiner*—Binta Robinson
(74) *Attorney, Agent, or Firm*—J. Scott Young

(57) ABSTRACT

Compounds of formula (I) or a pharmaceutically acceptable derivative thereof:

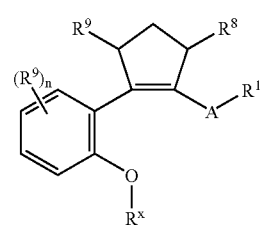

(I)

wherein A, $R^1$, $R^2$, $R^x$, $R^8$, $R^9$ and n are as defined in the specification, a process for the preparation of such compounds, pharmaceutical compositions comprising such compounds and the use of such compounds in medicine.

12 Claims, No Drawings

FOREIGN PATENT DOCUMENTS

| | | |
|---|---|---|
| JP | 04235933 | 8/1992 |
| JP | 05224442 | 9/1993 |
| JP | 06065213 | 3/1994 |
| JP | 2002363748 | 12/2002 |
| WO | WO 93/04045 | 3/1993 |
| WO | WO 93/04046 | 3/1993 |
| WO | WO 94/05658 | 3/1994 |
| WO | WO 95/00501 | 1/1995 |
| WO | WO 95/05372 | 2/1995 |
| WO | WO 95/11883 | 5/1995 |
| WO | WO 95/17393 | 6/1995 |
| WO | WO 96/11676 | 4/1996 |
| WO | WO 96/36623 | 11/1996 |
| WO | WO 96/37496 | 11/1996 |
| WO | WO 96/41645 | 12/1996 |
| WO | WO 97/03667 | 2/1997 |
| WO | WO 97/11701 | 4/1997 |
| WO | WO 97/16435 | 5/1997 |
| WO | WO 97/38986 | 10/1997 |
| WO | WO 98/16227 | 4/1998 |
| WO | WO 98/25896 | 6/1998 |
| WO | WO 98/55468 | 12/1998 |
| WO | WO 99/17776 | 4/1999 |
| WO | WO 99/58487 | 11/1999 |
| WO | WO 00/47553 | 8/2000 |
| WO | WO 00/53149 | 9/2000 |
| WO | WO 00/59506 | 10/2000 |
| WO | WO 01/19814 | 3/2001 |
| WO | WO 01/081332 | 11/2001 |
| WO | WO 02/099435 | 12/2002 |

OTHER PUBLICATIONS

Malik, O.P., et al. "Studies on Cannabinoids: Part III. Synthesis of 9,10,11,11a-Tetrahydro-6H,8H-Pyrido(1,2-c [1,3]benzoxazine." Indian Journal of Chemistry, Section B: Organic Chemistry Including Medicinal Chemistry, 1976, 14B(12), pp. 975-978.

Ahmad, et al.; Prostaglandin EP1 Receptor Contributes to Excitotoxicity and Focal Ischemic Brain Damage; Toxicological Sciences; Oct. 19, 2005; 69(1): 265-270; Oxford University Press.

Kawahara, et al.; A Prostaglandin E2 Receptor Subtype EP1 Receptor Antagonist (ONO-8711) Reduces Hyperalgesia, Allodynia, and C-fos Gene Expression in Rats with Chronic Nerve Constriction; Aneslh Analg; 2001: 93: 1012-7; International Anesthesia Research Society.

Kawano, et al.; Prostaglandin E2 EP1 Receptors: Downstream Effectors of Cox-2 Neurotoxicity; Nature Medicine; Feb. 2006; 12(2); 225-229; Nature Publishing Group.

Omote, et al.; The Effects of Intrathecal Administration of an Antagonist for Prostaglandin E Receptor Subtype EP1 on Mechanical and Thermal Hyperalgesia in a Rat Model of Postoperative Pain; Anesth Analg; 2002; 95; 1708-12; International Anesthesia Research Society.

Omote, et al.; The Effects of Peripheral Administration of a Novel Selective Antagonist for Prostaglandin E Receptor Subtype EP1, ONO-8711, in a Rat Model of Postoperative Pain; Anesth Analg; 2001; 92; 233-6; International Anesthesia Research Society.

Stock, et al.; The Prostaglandin E2 EP1 Receptor Mediates Pain Perception and Regulates Blood Pressure; The Journal of Clinical Investigation: Feb. 2001; 107(3); 325-331.

* cited by examiner

(2-((2-ALKOXY)-PHENYL)-CYCLOPENT-1ENYL) AROMATIC CARBO AND HETEROCYCLIC ACID AND DERIVATIVES

This application is filed pursuant to 35 U.S.C. §371 as a United States National Phase Application on International Application No. PCT/EP03/03661, filed 7 Apr. 2003, which claims priority to Great Britain Priority Patent Application Ser. Nos. 0208045.5 and 0302881.8, filed 8 Apr. 2002 and 7 Feb. 2003, respectively.

This invention relates to cyclopentene compounds, to processes for their preparation, to pharmaceutical compositions containing them and to their use in medicine, in particular their use in the treatment of prostaglandin mediated diseases.

The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion. We have now found a novel group of compounds which bind with high affinity to the $EP_1$ receptor.

A number of review articles describe the characterization and therapeutic relevance of the prostanoid receptors as well as the most commonly used selective agonists and antagonists: *Eicosanoids; From Biotechnology to Therapeutic Applications*, Folco, Samuelsson, Maclouf, and Velo eds, Plenum Press, New York, 1996, chap. 14, 137–154 and Journal of Lipid Mediators and Cell Signalling, 1996, 14, 83–87 and *Prostanoid Receptors, Structure, Properties and Function*, S Narumiya et al, Physiological Reviews 1999, 79 (4), 1193–126. An article from *The British Journal of Pharmacology*, 1994, 112, 735–740 suggests that Prostaglandin $E_2$ ($PGE_2$) exerts allodynia through the $EP_1$ receptor subtype and hyperalgesia through $EP_2$ and $EP_3$ receptors in the mouse spinal corn. Furthermore an article from *The Journal of Clinical Investigation*, 2001, 107 (3), 325 shows what in the $EP_1$ knock-out mouse pain-sensitivity responses are reduced by approximately 50%. Two papers from *Anesthesia and Analgesia* have shown that (2001, 93, 1012–7) an $EP_1$ receptor antagonist (ONO-8711) reduces hyperalgesia and allodynia in a rat model of chronic constriction injury, and that (2001, 92, 233–238) the same antagonist inhibits mechanical hyperalgesia in a rodent model of post-operative pain. S. Sarkar et al in *Gastroenterology*, 2003, 124 (1), 18–25 demonstrate the efficacy of $EP_1$ receptor antagonists in the treatment of visceral pain in a human model of hypersensitivity. Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects. Moreover, by sparing potentially beneficial prostaglandin pathways, these agents may have enhanced efficacy over NSAIDS and/or COX-2 inhibitors.

In The American Physiological Society (1994, 267, R289–R-294), studies suggest that $PGE_2$-induced hyperthermia in the rat is mediated predominantly through the $EP_1$ receptor. WO 96/06822 (Mar. 7, 1996), WO 96/11902 (Apr. 25, 1996), EP 752421-A1 (Jan. 8, 1997) and WO 01/19814 (22 Mar. 2001) disclose compounds as being useful in the treatment of prostaglandin mediated diseases.

Accordingly the present invention provides compounds of formula (I):

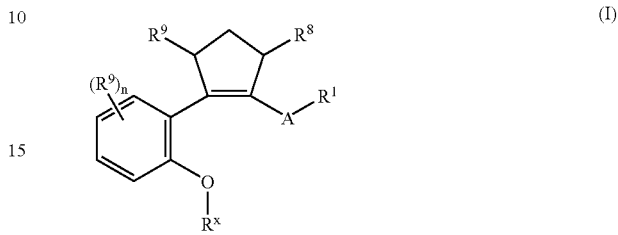

wherein:
A represents an optionally substituted phenyl, or an optionally substituted 5- or 6-membered heterocyclyl ring, or an optionally substituted bicyclic heterocyclyl group;
$R^1$ represents $CO_2R^4$, $CONR^5R^6$, $CH_2CO_2R^4$, optionally substituted alkyl, optionally substituted alkenyl, optionally substituted $SO_2$alkyl, $SO_2NR^5R^6$, $NR^5CONR^5R^6$, $CONR^5R^6$, 2H-tetrazol-5-yl-methyl or optionally substituted heterocyclyl;
$R^2$ independently represents halo, optionally substituted alkyl, CN, $SO_2R^5$, $SR^5$, $NO_2$, optionally substituted aryl, $CONR^5R^6$ or optionally substituted heteroaryl;
$R^x$ represents optionally substituted alkyl wherein 1 or 2 of the non-terminal carbon atoms may optionally be replaced by a group independently selected from $NR^4$, O or $SO_n$, wherein n is 0, 1 or 2: or $R^x$ may be optionally substituted $CQ_2$-heterocyclyl or optionally substituted $CQ_2$-phenyl wherein Q is independently selected from hydrogen and $CH_3$;
$R^4$ represents hydrogen or an optionally substituted alkyl;
$R^5$ represents hydrogen or an optionally substituted alkyl;
$R^6$ represents hydrogen or an optionally substituted alkyl, optionally substituted $SO_2$aryl, optionally substituted $SO_2$heterocyclyl group, CN, optionally substituted $CH_2$aryl or $COR^7$;
$R^7$ represents hydrogen, optionally substituted heteroaryl or optionally substituted aryl;
$R^8$ and $R^9$ independently represent hydrogen or alkyl; and
n is an integer from 0 to 2;

wherein when A is a 6-membered ring the $R^1$ and cyclopentene group are attached to carbon atoms 1,2-, 1,3- or 1,4- relative to each other, and when A is a five-membered ring or bicyclic heterocyclyl group the $R^1$ and cyclopentene group are attached to substitutable carbon atoms 1,2- or 1,3- relative to each other;

or pharmaceutically acceptable derivatives thereof.

When A is a six membered ring, preferably $R^1$ is attached to the group A in the 3 position relative to the bond attaching A to the cyclopentene ring.

Preferably $R^1$ represents $CO_2R^4$, where $R^4$ is hydrogen or $C_{1-4}$alkyl.

Preferably A is selected from phenyl, pyridyl, pyridazinyl, pyrazinyl or pyrimidinyl, all of which may be optionally substituted. In an other aspect, A is selected from an optionally substituted phenyl, pyridyl, pyridazinyl, pyrazinyl or pyrimidinyl; more preferably A is pyridyl or an optionally substituted phenyl; most preferably A is optionally substituted phenyl. In an alternative aspect A is pyridyl.

In an alternative aspect:

A represents an optionally substituted phenyl, or an optionally substituted 5 or 6-membered heterocyclyl group;

$R^1$ represents $CO_2R^4$, $CONR^5R^6$, $CH_2CO_2R^4$, optionally substituted $C_{1-6}$alkyl, optionally substituted $C_{1-6}$alkenyl, $SO_2C_{1-4}$alkyl, $SO_2NR^5R^6$, $NR^5CONR^5R^6$, tetrazolyl or $CONR^5R^6$;

$R^2$ independently represents halo, optionally substituted $C_{1-6}$alkyl, CN, $SO_2R^5$, $SR^5$, $NO_2$, optionally substituted aryl, $CONR^5R^6$ or optionally substituted heteroaryl;

$R^x$ represents optionally substituted $C_{1-8}$alkyl or optionally substituted —$CH_2$-phenyl;

$R^4$ represents hydrogen or an optionally substituted $C_{1-6}$alkyl;

$R_5$ represents hydrogen or an optionally substituted $C_{1-6}$alkyl;

$R^6$ represents hydrogen or an optionally substituted $C_{1-6}$alkyl, optionally substituted $SO_2$aryl, optionally substituted $SO_2$heterocyclyl group, CN, optionally substituted $CH_2$aryl or $COR^7$;

$R^7$ represents hydrogen or an optionally substituted aryl;

$R^8$ and $R^9$ independently represent hydrogen or $C_{1-6}$alkyl;

n is an integer from 0 to 2;

wherein $R^1$ is attached to the group A in the 3 or 4 position relative to the bond attaching A to the cyclopentene ring;

or pharmaceutically acceptable derivatives thereof.

In a further aspect, A is optionally substituted phenyl or a 5 or 6-membered heterocyclyl group.

Optional substituents for A when a phenyl group include up to four substituents, preferably 0 or 1 substituent, independently selected from halogen, $NR^5R^6$, $NR^5COC_{1-6}$alkyl, $NR^5SO_2C_{1-6}$alkyl, $OR^5$, $C_{1-6}$alkyl and $NR^{10}R^{11}$ wherein $R^{10}$ and $R^{11}$ together with the nitrogen atom to which they are attached form a morpholine ring, a 5- or 6-membered lactam ring or a 5- or 6-membered cyclic sulphonamide, wherein $R^5$ and $R^6$ are as defined above. Preferably optional substituents for A are selected from halogen, $NR^5R^6$, $NHCOC_{1-6}$alkyl, $NHSO_2C_{1-6}$alkyl, $C_{1-6}$alkyl and $NR^{10}R^{11}$.

In an alternative aspect optional substituents for A when a phenyl group include up to four substituents independently selected from $C_{1-6}$alkyl, $C_{1-6}$alkoxy and halogen. Preferably A when a phenyl group is optionally substituted by up to 2 substituents.

Optional substituents for A when a 5- or 6-membered heterocyclyl group include $NH_2$. When A is pyridyl it may be substituted on the ring nitrogen by an oxygen to give a pyridine N-oxide.

In an alternative aspect $R^1$ represents $CO_2R^4$, $CONR^5R^6$, $CH_2CO_2R^4$, optionally substituted $C_{1-6}$alkyl, optionally substituted $C_{1-6}$alkenyl, $SO_2C_{1-6}$alkyl, $SO_2NR^5R^6$, $NR^5CONR^5R^6$, tetrazolyl or $COSO_2NR^5R^6$.

In another aspect $R^2$ independently represents halo, optionally substituted $C_{1-6}$-alkyl, CN, $SO_2R^5$, $NO_2$, optionally substituted aryl, $CONR^5R^6$ or optionally substituted heteroaryl.

In an alternative aspect $R^6$ represents hydrogen or an optionally substituted $C_{1-6}$alkyl, optionally substituted $SO_2$aryl, optionally substituted $SO_2$heterocyclyl group, CN, or $COR^7$.

Preferably $R^1$ represents $CO_2R^4$. More preferably $R^1$ represents $CO_2H$.

Preferably $R^2$ represents halo, optionally substituted $C_{1-6}$-alkyl e.g. $C_{1-4}$alkyl and $CF_3$, CN, $SC_{1-6}$alkyl, e.g $SCH_3$ or $SO_2C_{1-6}$alkyl, e.g. $SO_2CH_3$. Alternatively $R^2$ represents halogen, optionally substituted $C_{1-6}$alkyl, for example $CF_3$, CN or $SO_2C_{1-6}$alkyl.

Preferably $R^4$ represents hydrogen or $C_{1-3}$alkyl.

Preferably $R^5$ represents hydrogen or $C_{1-3}$alkyl.

Preferably $R^6$ represents hydrogen or $C_{1-3}$alkyl.

Preferably $R^8$ represents methyl or hydrogen, more preferably $R^8$ represents hydrogen.

Preferably $R^9$ represents hydrogen.

Preferably n is 0 or 1.

When $R^x$ represents an optionally substituted alkyl this group is preferably $C_{1-8}$alkyl, more preferably the alkyl group is $CH_2C_{5-6}$cycloalkyl.

$R^x$ preferably represents $CH_2$phenyl optionally substituted by one, two or three, preferably one or two substituents selected from Cl, Br, F, $CF_3$, $C_{1-4}$alkyl and $OC_{1-4}$alkyl or $R^x$ is $CH_2C_{5-6}$cycloalkyl.

Preferred compounds of formula (I) are compounds of formula (II):

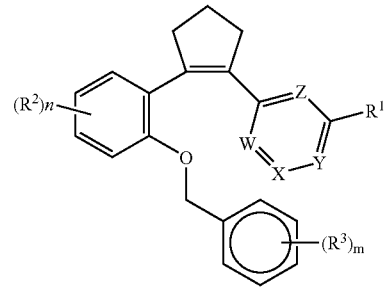

(II)

wherein:

$R^1$ is $CO_2R^4$;

$R^2$ is halo, optionally substituted $C_{1-6}$alkyl e.g. $C_{1-4}$alkyl and $CF_3$, CN, $SC_{1-6}$alkyl, or $SO_2C_{1-6}$alkyl;

$R^3$ independently represents halo, optionally substituted $OC_{1-6}$alkyl, or optionally substituted $C_{1-6}$alkyl;

m is an integer from 0 to 3;

n is an integer from 0 to 2;

W, X, Y and Z each represents $CR^{12}$ or N wherein at least two of W, X, Y or Z is $CR^{12}$; and when each of W, X, Y, and Z is $CR^{12}$ then each $R^{12}$ is independently selected from hydrogen, halogen, $NR^5R^6$, $NHCOC_{1-6}$alkyl, $NHSO_2C_{1-6}$alkyl, $C_{1-6}$alkyl and $NR^{10}R^{11}$, and when at least one of W, X, Y and Z represents N then each $R^{12}$ is selected from hydrogen or $NH_2$;

or pharmaceutically acceptable derivatives thereof.

In an alternative aspect of compounds of formula II:

$R^1$ is $CO_2R^4$;

$R^2$ is halogen, optionally substituted $C_{1-6}$alkyl e.g. $CF_3$, CN, $SC_{1-6}$alkyl or $SO_2C_{1-6}$alkyl;

$R^3$ independently represents halo or an optionally substituted $OC_{1-6}$alkyl, or $C_{1-6}$alkyl;

m is an integer from 0 to 2;

n is an integer from 0 to 2;

W, X, Y and Z represents CH or N wherein at least two of W, X, Y or Z is CH;

or pharmaceutically acceptable derivatives thereof.

In another aspect $R^2$ is halogen, optionally substituted $C_{1-6}$alkyl e.g. $CF_3$, CN, or $SO_2C_{1-6}$alkyl.

In a further aspect $R^3$ represents halo, optionally substituted $C_{1-4}$alkyl e.g. $CF_3$, or optionally substituted $OC_{1-4}$ alkyl, more preferably $R^3$ is halo or OMe.

Compounds of formula (I) include:

{2-[5-chloro-2-(benzyloxy)-phenyl]-cyclopent-1-enyl}-benzoic acid;
3-{2-[2-(benzyloxy)-phenyl]cyclopent-1-enyl]-benzoic acid;
3-{2-[5-bromo-2-(benzyloxy)phenyl-cyclopent-1-enyl}-benzoic acid;
3-{2-[5-bromo-2-(4-Chlorobenzyloxy)-phenyl]-cyclopent-1-enyl}-benzoic acid;
3-{2-[5-bromo-2-(4-fluorobenzyloxy)-phenyl]-cyclopent-1-enyl}-benzoic acid;
3-{2-[5-bromo-2-(3,4-dichlorobenzyloxy)-penyl]-cyclopent-1-enyl}-benzoic acid;
3-{2-[5-bromo-2-(2,4-difluorobenzyloxy)-phenyl]-cyclopent-1-enyl}-benzoic acid;
3-{2-[5-bromo-2-(4-chloro-2-fluorobenzyloxy)-phenyl]-cyclopent-1-enyl}-benzoic acid;
3-{2-[5-bromo-2-(4-methoxybenzyloxy)-phenyl]-cyclopent-1-enyl}-benzoic acid;
5-{2-[5-chloro-2-(chlorobenzyloxy)-phenyl]-cyclopent-1-enyl}-nicotinic acid;
5-{2-[5-chloro-2-(benzyloxy)-phenyl]-cyclopent-1-enyl}-nicotinic acid;
5-{2-[5-chloro-2-(4-fluorobenzyloxy)-phenyl]-cyclopent-1-enyl}-nicotinic acid;
5-{2-[5-chloro-2-(3,4-dichlorobenzyloxy)-phenyl]-cyclopent-1-enyl}-nicotinic acid;
5-{2-[5-chloro-2-(2,4-difluorobenzyloxy)-phenyl]-1-enyl}-nicotinic acid;
5-{2-[5-chloro-2-(4-chloro-2-fluorobenzyloxy)-phenyl]-cyclopent-1-enyl}-nicotinic acid;
5-{2-[5-chloro-2-(4-methoxybenzyloxy)-phenyl]-cyclopent-1-enyl}-nicotinic acid;
5-{2-[5-bromo-2-(benzyloxy)-phenyl]-cyclopent-1-enyl}-nicotinic acid;
5-{2-[5-bromo-2-(4-chlorobenzyloxy)-phenyl]-cyclopent-1-enyl}-nicotinic acid;
5-{2-[5-bromo-2-(4-fluorobenzyloxy)-phenyl]-cyclopent-1-enyl}-nicotinic acid;
5-{2-[5-bromo-2-(2,4-difluorobenzyloxy)-phenyl]-cyclopent-1-enyl}-nicotinic acid;
5-{2-[5-bromo-2-(4-chloro-2-fluorobenzyloxy)-phenyl]-cyclopent-1-enyl}-nicotinic acid;
5-{2-[5-bromo-2-(4-methoxybenzyloxy)-phenyl]-cyclopent-1-enyl}-nicotinic acid;
5-{2-[5-bromo-2-(cyclohexylmethoxy)-phenyl]-cyclopent-1-enyl}-nicotinic acid;
5-{2-[5-trifluoromethyl-2-(4-chlorobenzyloxy)-phenyl]-cyclopent-1-enyl}-nicotinic acid;
5-{2-[5-trifluoromethyl-2-(4-fluorobenzyloxy)-phenyl]-cyclopent-1-enyl}-nicotinic acid;
5-{2-[5-trifluoromethyl-2-(2,4-difluorobenzyloxy)-phenyl]-cyclopent-1-enyl}-nicotinic acid;
5-{2-[5-trifluoromethyl-2-(4-chloro-2-fluorobenzyloxy)-phenyl]-cyclopent-1-enyl}-nicotinic acid;
5-{2-[5-trifluoromethyl-2-(cyclohexylmethoxy)-phenyl]-cyclopent-1-enyl}-nicotinic acid;
6-{2-[5-chloro-2-(2,4-difluorobenzyloxy)-phenyl]-cyclopent-1-enyl}-pyridine-2-carboxylic acid;
6-{2-[5-chloro-2-(4-chloro-2-fluorobenzyloxy)-phenyl]-cyclopent-1-enyl}-pyridine-2-carboxylic acid;
6-{2-[5-chloro-2-(4-chlorobenzyloxy)-phenyl]-cyclopent-1-enyl}-pyridine 2-carboxylic acid;
6-{2-[5-chloro-2-(4-fluorobenzyloxy)-phenyl]-cyclopent-1-enyl}-pyridine 2-carboxylic acid;
3-{2-[5-methylsulfonyl-2-(benzyloxy)-phenyl]-cyclopent-1-enyl}-benzoic acid;
3-{2-[5-methylsulfonyl-2-(benzyloxy)-phenyl]-cyclopent-1-enyl}-benzoic acid;
3-{2-[5-methylsulfonyl-2-(4-fluoro-benzyloxy)-phenyl]-cyclopent-1-enyl}-benzoic acid;
3-{2-[5-methanesulfonyl-2-(4-fluoro-benzyloxy)-phenyl]-cyclopent-1-enyl}-benzoic acid;
3-{2-[5-methylsulfonyl-2-(2,4-difluoro-benzyloxy)-phenyl]-cyclopent-1-enyl}-benzoic acid;
3-{2-[5-methanesulfonyl-2-(2,4-difluoro-benzyloxy)-phenyl]cyclopent-1-enyl}-benzoic acid;
3-{2-[2-(2,4-difluoro-benzyloxy)-phenyl]-cyclopent-1-enyl}-benzoic acid;
3-{2-[2-(4-chloro-2-fluoro-benzyloxy)-phenyl]-cyclopent-1-enyl}-benzoic acid;
3-{2-[2-(4-methoxy-benzyloxy)-phenyl]-cyclopent-1-enyl}-benzoic acid;
3-{2-[5-cyano-2-(benzyloxy)-phenyl]-cyclopent-1-enyl}-benzoic acid;
3-{2-[5-cyano-2-(2,4-difluoro-benzyloxy)-phenyl]-cyclopent-1-enyl}-benzoic acid;
2-{2-[5-chloro-2-(benzyloxy)phenyl]cyclopent-1-enyl}-pyrimidine-4-carboxylic acid;
6-{2-[5-methyl-2-(benzyloxy)phenyl]cyclopent-1-enyl}-pyridine-2-carboxylic acid;
6-{2-[5-methyl-2-(4-fluorobenzyloxy)phenyl]cyclopent-1-enyl}pyridine-2-carboxylic acid;
6-{2-[5-methyl-2-(2,4-difluorobenzyloxy)phenyl]cyclopent-1-enyl}pyridine-2-carboxylic acid;
2-{2-[5-trifluoromethyl-2-(4-fluorobenzyloxy)phenyl]cyclopent-1-enyl}pyridine-4-carboxylic acid;
2-{2-[5-trifluoromethyl-2-(benzyloxy)phenyl]cyclopent-1-enyl}pyridine-4-carboxylic acid;
4-{2-[5-trifluoromethyl-2-(4-fluorobenzyloxy)phenyl]cyclopent-1-enyl}pyridine-2-carboxylic acid;
4-{2-[5-trifluoromethyl-2-(benzyloxy)phenyl]cyclopent-1-enyl}pyridine-2-carboxylic acid;
6-{2-[5-trifluoromethyl-2-(benzyloxy)phenyl]cyclopent-1-enyl}-3-aminopyrazine-2-carboxylic acid;
2-{2-[5-trifluoromethyl-2-(4-fluorobenzyloxy)phenyl]cyclopent-1-enyl}pyrimidine-4 carboxylic acid;
2-{2-[5-chloro-2-(4-fluorobenzyloxy)phenyl]cyclopent-1-enyl}pyrimidine-4-carboxylic acid;
6-{2-[5-methyl-2-(benzyloxy)phenyl]cyclopent-1-enyl}-pyrazine-2-carboxylic acid;
3-{2-[5-methyl-2-(benzyloxy)phenyl]cyclopent-1-enyl}-6-aminobenzoic acid;
6-{2-[5-trifluoromethyl-2-(benzyloxy)phenyl]cyclopent-1-enyl}pyridine-2-carboxylic acid;
6-{2-[5-trifluoromethyl-2-(4-fluorobenzyloxy)phenyl]cyclopent-1-enyl}pyridine-2-carboxylic acid;
6-{2-[5-trifluoromethyl-2-(2,4-difluorobenzyloxy)phenyl]cyclopent-1-enyl}pyridine-2-carboxylic acid;
3-{2-[5-trifluoromethyl-2-(benzyloxy)phenyl]cyclopent-1-enyl}-6-aminobenzoic acid;
3-{2-[5-trifluoromethyl-2-(4-fluorobenzyloxy)phenyl]cyclopent-1-enyl}-6-aminobenzoic acid;
3-{2-[5-trifluoromethyl-2-(2-difluorobenzyloxy)phenyl]cyclopent-1-enyl}-6-aminobenzoic acid;
3-{2-[5-trifluoromethyl-2-(benzyloxy)phenyl]cyclopent-1-enyl}-6-acetamidobenzoic acid;
3-{2-[5-trifluoromethyl-2-(4-fluorobenzyloxy)phenyl]cyclopent-1-enyl}-6-acetamidobenzoic acid;

3-{2-[5-trifluoromethyl-2-(2,4-difluorobenzyloxy)phenyl]cyclopent-1-enyl}-6-acetamidobenzoic acid;
3-{2-[5-trifluoromethyl-2-(benzyloxy)phenyl]cyclopent-1-enyl}-5-propionamidobenzoic acid;
3-{2-[5-trifluoromethyl-2-(4-fluorobenzyloxy)phenyl]cyclopent-1-enyl}-5-propionamidobenzoic acid;
3-{2-[5-trifluoromethyl-2-(2,4-difluorobenzyloxy)phenyl]cyclopent-1-enyl}-5-propionamidobenzoic acid;
3-{2-[5-bromo-2-(benzyloxy)phenyl]cyclopent-1-enyl}-5-propionamidobenzoic acid;
3-{2-[5-bromo-2-(4-fluorobenzyloxy)phenyl]cyclopent-1-enyl}-5-propionamidobenzoic acid;
3-{2-[5-bromo-2-(2,4-difluorobenzyloxy)phenyl]cyclopent-1-enyl}-5-propionamidobenzoic acid;
5-{2-[trifluoromethyl-2-(benzyloxy)phenyl]cyclopent-1-enyl}nicotinic acid N-oxide;
5-{2-[5-fluoro-2-(4-fluorobenzyloxy)phenyl]cyclopent-1-enyl}-3-(propionamido)benzoic acid;
5-{2-[5-methyl-2-(4-fluorobenzyloxy)phenyl]cyclopent-1-enyl}-3-(propionamido)benzoic acid;
5-{2-[5-methyl-2-(2,4-difluorobenzyloxy)phenyl]cyclopent-1-enyl}-3-(propionamido)benzoic acid;
5-[2-(2-benzyloxy-5-chlorophenyl)cyclopent-1-enyl]-2-methylbenzoic acid;
5-[2-(2-benzyloxy-5-chlorophenyl)-cyclopent-1-enyl]-2-propionylaminobenzoic acid;
2-{2-[5-chloro-2-(2,4-difluorobenzyloxy)phenyl]cyclopent-1-enyl}isonicotinic acid;
2-{2-[5-chloro-2-(4-fluorobenzyloxy)phenyl]cyclopent-1-enyl}isonicotinic acid;
2-{2-[5-chloro-2-benzyloxyphenyl]cyclopent-1-enyl}isonicotinic acid;
2-{2-[5-bromo-2-(4-fluorobenzyloxy)phenyl]cyclopent-1-enyl}isonicotinic acid;
5-[2-(2-benzyloxy-5-chlorophenyl)cyclopent-1-enyl]-3-propionylaminobenzoic acid;
5-[2-(2-benzyloxy-5-chlorophenyl)cyclopent-1-enyl]-3-isobutyrylaminobenzoic acid;
5-{2-[5-trifluoromethyl-2-(benzyloxy)phenyl]cyclopent-1-enyl-}-3-(2-oxo-pyrrolidin-1-yl)benzoic acid;
5-{2-[5-trifluoromethyl-2-(4-fluorobenzyloxy)phenyl]cyclopent-1-enyl}-3-(2-oxo-pyrrolidin-1-yl)benzoic acid;
5-{2-[5-chloro-2-(4-fluorobenzyloxy)phenyl]cyclopent-1-enyl}-3-(2-oxo-pyrrolidin-1-yl)benzoic acid;
5-{2-[5-trifluoromethyl-2-(4-fluorobenzyloxy)phenyl]cyclopent-1-enyl}-(2-oxo-piperidin-1-yl)benzoic acid;
5-{2-[5-trifluoromethyl-2-(benzyloxy)phenyl]cyclopent-1-enyl}-3-(2-oxo-piperidin-1-yl)benzoic acid;
5-{2-[5-chloro-2-(4-fluorobenzyloxy)phenyl]cyclopent-1-enyl}-3-(2-oxo-piperidin-1-yl)benzoic acid;
6-{2-[5-trifluoromethyl-2-(benzyloxy)phenyl]cyclopent-1-enyl}pyrazine-2-carboxylic acid;
6-{2-[5-chloro-2-(benzyloxy)phenyl]cyclopent-1-enyl}pyrazine-2-carboxylic acid;
6-{2-[5-chloro-2-(4-fluorobenzyloxy)phenyl]cyclopent-1-enyl}pyrazine-2-carboxylic acid;
5-{2-[5-trifluoromethyl-2-(benzyloxy)phenyl]cyclopent-1-enyl}-3-aminobenzoic acid;
5-{2-[5-trifluoromethyl-2-(4-fluorobenzyloxy)phenyl]cyclopent-1-enyl}-3-aminobenzoic acid;
5-{2-[5-chloro-2-(benzyloxy)phenyl]cyclopent-1-enyl}-3-aminobenzoic acid;
5-{2-[5-chloro-2-(4-fluorobenzyloxy)phenyl]cyclopent-1-enyl}-3-aminobenzoic acid;
5-{2-[5-chloro-2-(2-(4-fluorobenzyloxy)phenyl]cyclopent-1-enyl}-3-aminobenzoic acid;
5-{2-[5-chloro-2-(4-fluorobenzyloxy)phenyl]cyclopent-1-enyl}-3-methanesulphonylaminobenzoic acid;
5-{2-[5-trifluoromethyl-2-(benzyloxy)phenyl]cyclopent-1-enyl}-3-methanesulphonylaminobenzoic acid;
5-{2-[5-trifluoromethyl-2-(4-fluorobenzyloxy)phenyl]cyclopent-1-enyl}-methanesulphonylaminobenzoic acid;
5-{2-[5-trifluoromethyl-2-(2,4-difluorobenzyloxy)phenyl]cyclopent-1-enyl}-3-methanesulphonylaminobenzoic acid;
5-{2-[5-trifluoromethyl-2-(4-fluorobenzyloxy)phenyl]cyclopent-1-enyl}-3-acetamidobenzoic acid;
5-{2-[5-trifluoromethyl-2-(2,4-difluorobenzyloxy)phenyl]cyclopent-1-enyl}-3-acetamidobenzoic acid;
5-{2-[5-trifluoromethyl-2-(benzyloxy)phenyl]cyclopent-1-enyl}-3-acetamidobenzoic acid;
5-{2-[5-chloro-2-(2,4-difluorobenzyloxy)phenyl]cyclopent-1-enyl}-3-acetamidobenzoic acid;
5-{2-[5-chloro-2-(4-fluorobenzyloxy)phenyl]cyclopent-1-enyl}-3-acetamidobenzoic acid;
5-{2-[5-chloro-2-(benzyloxy)phenyl]cyclopent-1-enyl}-3-acetamidobenzoic acid;
5-{2-[5-trifluoromethyl-2-(benzyloxy)phenyl]cyclopent-1-enyl}-3-(morpholin-4-yl)benzoic acid;
5-{2-[5-trifluoromethyl-2-(4-fluorobenzyloxy)phenyl]cyclopent-1-enyl}-3-(morpholin-4-yl)benzoic acid;
5-{2-[5-chloro-2-(4-fluorobenzyloxy)phenyl]cyclopent-1-enyl}-3-(morpholin-4-yl)benzoic acid;
5-{2-[5-chloro-2-(4-fluorobenzyloxy)phenyl]cyclopent-1-enyl}-3-methylaminobenzoic acid;
5-{2-[5-trifluoromethyl-2-(4-fluorobenzyloxy)phenyl]cyclopent-1-enyl}-3-methylaminobenzoic acid;
5-{2-[5-trifluoromethyl-2-(benzyloxy)phenyl]cyclopent-1-enyl}-3-methylaminobenzoic acid;
2-{2-[5-trifluoromethyl-2-(2,4-difluorobenzyloxy)phenyl]cyclopent-1-enyl}pyridine-4-carboxylic acid;
2-{2-[5-bromo-2-(2,4-difluorobenzyloxy)phenyl]cyclopent-1-enyl}pyridine-4-carboxylic acid;
2-{2-[5-bromo-2-(benzyloxy)phenyl]cyclopent-1-enyl}-pyridine-4-carboxylic acid;
2-{2-[5-trifluoromethyl-2-(2,4-difluorobenzyloxy)phenyl]cyclopent-1-enyl}pyrazine-5-amino-6-carboxylic acid;
2-{2-[5-chloro-2-(benzyloxy)phenyl]cyclopent-1-enyl}-5-aminopyrazine-6-carboxylic acid;
3-{2-[5-trifluoromethyl-2-(benzyloxy)phenyl]cyclopent-1-enyl}-5-methylbenzoic acid;
3-{2-[5-chloro-2-(benzyloxy)phenyl]cyclopent-1-enyl}-5-methylbenzoic acid;
6-{2-[5-chloro-2-(2,4-difluorobenzyloxy)phenyl]cyclopent-1-enyl}pyrazine-2-carboxylic acid;
5-{2-[5-trifluoromethyl-2-(2,4-difluorobenzyloxy)phenyl]cyclopent-1enyl}-3-(morpholin-4-yl)benzoic acid;
5-{2-[5-chloro-2-(benzyloxy)phenyl]cyclopenten-1-enyl)-3-morpholin-4-ylbenzoic acid;
5-{2-[5-chloro-2-(2,4-difluorobenzyloxy)phenyl]cyclopenten-1-enyl}-3-(morpholin-4-yl)benzoic acid;
5-{2-[5-chloro-2,4-difluorobenzyloxy)phenyl]cyclopenten-1-enyl}-3-methanesulphonylaminobenzoic acid;
5-{2-[5-chloro-2-(benzyloxy)phenyl]cyclopent-1-enyl}-methanesulphonylamino benzoic acid;
5-{2-[5-trifluoromethyl-2-(benzyloxy)phenyl]cyclopent-1-enyl}-3-diethylaminobenzoic acid;
6-{2-[5-methyl-2-(4-fluorobenzyloxy)phenyl]cyclopent-1-enyl}pyrazine-2-carboxylic acid;
6-{2-[5-methyl-2-(2,4-difluorobenzyloxy)phenyl]cyclopent-1-enyl}pyrazine-2-carboxylic acid;
6-{2-[5-fluoro-2-(benzyloxy)phenyl]cyclopent-1-enyl}-pyridine-2-carboxylic acid;

6-{2-[5-fluoro-2-(4-fluorobenzyloxy)phenyl]cyclopent-1-enyl}-pyridine-2-carboxylic acid;
6-{2-[5-fluoro-2-(2,4-difluorobenzyloxy)phenyl]cyclopent-1-enyl}pyridine-2-carboxylic acid;
6-{2-[5-chloro-2-(benzyloxy)phenyl]cyclopent-1-enyl}pyridazine carboxylic acid;
6-{2-[5-chloro-2-(4-fluorobenzyloxy)phenyl]cyclopent-1-enyl}-pyridazine-carboxylic acid;
6-{2-[5-chloro-2-(2,4-difluorobenzyloxy)phenyl]cyclopent-1-enyl}pyridazine-4-carboxylic acid;
5-{2-[5-chloro-2-(2,4-difluorobenzyloxy)phenyl]cyclopent-1-enyl}2-methylbenzoic acid;
5-[2-(2-(4-fluorobenzyloxy)-5-chlorophenyl)cyclopent-1-enyl]-2-methylbenzoic acid;
5-[2-(2-(4-fluorobenzyloxy)-5-chlorophenyl)cyclopent-1-enyl]-2-fluorobenzoic acid;
5-[2-(2-benzyloxy)-5-chlorophenyl)cyclopent-1-enyl]-2-fluorobenzoic acid;
5-{2-[5-trifluoromethyl-2-(benzyloxy)phenyl]cyclopent-1-enyl}nicotinic acid;
4-{2-[2-(benzyloxy)phenyl]cyclopent-1-enyl}-benzoic acid;
4-{2-[5-chloro-2-(benzyloxy)phenyl]cyclopent-1-enyl}benzoic acid;
3-{2-[5-chloro-2-(4-fluorobenzyloxy)phenyl]cyclopent-1-enyl}-5-methylbenzoic acid;
3-{2-[5-chloro-2-(2,4-difluorobenzyloxy)phenyl]cyclopent-1-enyl}5-methylbenzoic acid;
3-{2-[5-trifluoromethyl-2-(4-fluorobenzyloxy)phenyl]cyclopent-1-enyl}-5-methylbenzoic acid;
3-{2-[5-trifluoromethyl-2-(2,4-difluorobenzyloxy)phenyl]cyclopent-1-enyl}5-methylbenzoic acid;
3-{2-[5–2-chloro-2-(benzyloxy)phenyl]cyclopent-1-enyl}-5-fluorobenzoic acid;
3-{2-[5-chloro-2-(4-fluorobenzyloxy)phenyl]cyclopent-1-enyl}-5-fluorobenzoic acid;
3-{2-[5-chloro-2-(2,4-difluorobenzyloxy)phenyl]cyclopent-1-enyl}-5-fluorobenzoic acid;
3-{2-[5-trifluoromethyl-2-(4-fluorobenzyloxy)phenyl]cyclopent-1-enyl}5-fluorobenzoic acid;
3-{2-[5-trifluoromethyl-2-(2,4-difluorobenzyloxy)phenyl]cyclopent-1-enyl-5-fluorobenzoic acid;
2-{2-[2-(4-fluorobenzyloxy)phenyl]-cyclopent-1-enyl}isonicotinic acid;
6-{2-[5-chloro-2-(benzyloxy)phenyl]cyclopent-1-enyl}pyridine-2-carboxylic acid;
6-{2-[5-chloro-2-(4-bromobenzyloxy)phenyl]cyclopent-1-enyl}pyridine-2-carboxylic acid;
6-{2-[5-chloro-2-(2-chloro-4-fluorobenzyloxy)phenyl]cyclopent-1-enyl}pyridine-2-carboxylic acid;
6-(2)-[5-chloro-2-(2,4,6-trifluorobenzyloxy)phenyl]cyclopent-1-enyl}pyridine-2-carboxylic acid;
6-{2-[5-chloro-2-(2,6-difluorobenzyloxy)phenyl]cyclopent-1-enyl}-pyridine-2-carboxylic acid;
6-{2-[5-chloro-2-(2-fluoro-4-trifluoromethylbenzyloxy)phenyl]cyclopent-1-enyl}-pyridine-2-carboxylic acid;
6-{2-[5-chloro-2-(3,4-difluorobenzyloxy)phenyl]cyclopent-1-enyl}pyridine-2-carboxylic acid;
6-{2-[5-chloro-2-(2,3-difluorobenzyloxy)phenyl]cyclopent-1-enyl}-pyridine-2-carboxylic acid;
6-{2-[5-chloro-2-(4-methylbenzyloxy)phenyl]cyclopent-1-enyl}pyridine-2-carboxylic acid;
6-{2-[5-chloro-2-(4-trifluoromethylbenzyloxy)phenyl]cyclopent-1-enyl}pyridine-2-carboxylic acid;
3-{2-[5-trifluoromethyl-2-(2,4-difluorobenzyloxy)phenyl]cyclopent-1-enyl}-5-aminobenzoic acid;
2-{2-([5-trifluoromethyl-2-(benzyloxy)phenyl]cyclopent-1-enyl}pyrimidine-4-carboxylic acid;
5-{2-[5-methyl-2-(benzyloxy)phenyl]cyclopent-1-enyl}-2-acetamidobenzoic acid;
3-{2-[5-trifluoromethyl-2-(benzyloxy)phenyl]cyclopent-1-enyl}-6-fluorobenzoic acid;
5-{2-[5-trifluoromethyl-2-(benzyloxy)phenyl]cyclopent-1-enyl}-2-methylbenzoic acid;
5-{2-[5-chloro-2-(2,4-fluorobenzyloxy)phenyl]cyclopent-1-enyl}-3-(2-oxopyrrolidin-1-yl)benzoic acid;
5-{2-[5-chloro-2-(benzyloxy)phenyl]cyclopent-1-enyl}-3-(2-oxopyrrolidin-1-yl)benzoic acid;
5-{2-[5-trifluoromethyl-2-(2,4-difluorobenzyloxy)phenyl]cyclopent-1-enyl}-3-(2-oxopyrrolidin-1-yl)benzoic acid;
5-{2-[5-chloro-2-(2,4-fluorobenzyloxy)phenyl]cyclopent-1-enyl}-3-(2-oxopiperidin-1-yl)benzoic acid;
5-{2-[5-chloro-2-(benzyloxy)phenyl]cyclopent-1-enyl}-3-(2-oxopiperidin-1-yl)benzoic acid; and
5-{2-[5-trifluoromethyl-2-(2,4-difluorobenzyloxy)phenyl]cyclopent-1-enyl}-3-(2-oxopiperidin-1-yl)benzoic acid and pharmaceutically acceptable derivatives thereof.

Preferred compounds include the compounds of Examples 19, 29, 32, 52, 90, 140 and 153.

Preferably compounds are selective for $EP_1$ over $EP_3$. More preferably the compounds are 100 fold selective, more preferably 1000 fold selective for $EP_1$ over $EP_3$.

The invention is described using the following definitions unless otherwise indicated.

The term "pharmaceutically acceptable derivative" means any pharmaceutically acceptable salt, ester, salt of such ester or solvate of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds, and that the compounds of formula (I) may be derivatised at more than one position.

It will be appreciated that, for pharmaceutical use, the salts referred to above will be physiologically acceptable salts, but other salts may find use, for example in the preparation of compounds of formula (I) and the physiological acceptable salts thereof. Pharmaceutically acceptable salts include those described by Berge, Bighley and Monkhouse, J. Pharm. Sci., 1977, 66, 1–19. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropyl amine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acid.

Preferred examples of pharmaceutically acceptable salts include those formed from maleic, fumaric, benzoic, ascorbic, pamoic, succinic, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

The compounds of formula (I) may be prepared in crystalline or non-crystalline form, and crystalline, may be optionally hydrated or solvated. This invention includes in its scope stoichiometric hydrates as well as compounds containing variable amounts of water.

Suitable solvates include pharmaceutically acceptable solvates, such as hydrates.

Solvates include stoichiometric solvates and non-stoichiometric solvates.

The terms "halogen" or "halo" are used to represent fluorine, chlorine, bromine or iodine.

The term "alkyl" as a group or part of a group means a straight, branched or cyclic chain alkyl group or combinations thereof, for example a methyl, ethyl, n-propyl, i-propyl, n-butyl, s-butyl, t-butyl, pentyl, hexyl, 1,1-dimethylethyl, cyclopentyl or cyclohexyl or combinations thereof such as cyclohexylmethyl and cyclopentylmethyl. Unless otherwise defined, preferably "alkyl" is $C_{1-8}$alkyl, more preferably "alkyl" is $C_{1-6}$alkyl.

The term "alkoxy" as a group or as part of a group means a straight, branched or cyclic chain alkyl group having an oxygen atom attached to the chain, for example a methoxy, ethoxy, n-propoxy, i-propoxy, n-butoxy, s-butoxy, t-butoxy group, pentoxy, hexyloxy group, cyclopentoxy or cyclohexyloxy group. Preferably "alkoxy" is $C_{1-6}$ alkoxy.

The term "haloalkyl" means an alkyl group, including straight, branched or cyclic structures, of the indicated number of carbon atoms in which one or more hydrogen atoms have been replaced by halogen atoms, with up to complete substitution of all hydrogen atoms with halo groups. Preferably "haloalkyl" is $C_{1-6}$haloalkyl, $C_{1-6}$haloalkyl, for example, includes $C_{1-6}$fluoroalkyl, e.g. $CF_3$, $CF_2CF_3$ and the like.

The term "haloalkoxy" means an alkoxy group, including straight, branched or cyclic structures, of the indicated number of carbon atoms in which one or more hydrogen atoms have been replaced by halogen atoms, with up to complete substitution of all hydrogen atoms with halo groups. Preferably "haloalkoxy" is $C_{1-6}$haloalkoxy. $C_{1-6}$haloalkoxy, for example, includes $C_{1-6}$fluoroalkoxy e.g. $OCF_3$, $OCF_2CF_3$ and the like.

The term "alkenyl" means linear or branched structures and combinations thereof, of the indicated number of carbon atoms, having at least one carbon-to-carbon double bond, wherein hydrogen may be replaced by an additional carbon to carbon double bond. Preferably "alkenyl" is $C_{2-6}$alkenyl. $C_{2-6}$alkenyl, for example, includes ethenyl, propenyl, 1-methylethenyl, butenyl and the like.

The term "heterocyclyl" as a group or as part of a group means an aromatic or non-aromatic five or six membered ring which contains from 1 to 4 heteroatoms selected from nitrogen, oxygen or sulfur and unsubstituted or substituted by, for example, up to three substituents. Examples of 5-membered heterocyclyl groups include furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl or tetrazolyl. Examples of 6-membered heterocyclyl groups are pyridyl, pyridazinyl, pyrimidinyl, pyrazinyl, triazinyl or tetrazinyl.

The term "aryl" as a group or part of a group means a 5- or 6-membered aromatic ring, for example phenyl, or a 7 to 12 membered bicyclic ring system where at least one of the rings is aromatic, for example naphthyl. An aryl group may be optionally substituted by one or more substituents, for example up to 4, 3 or 2 substituents. Preferably the aromatic group is phenyl.

The term "heteroaryl" as a group or as part of a group means a monocyclic five or six membered aromatic ring, or a fused bicyclic aromatic ring system comprising two of such monocyclic five or six membered aromatic rings. These heteroaryl rings contain one or more heteroatoms selected from nitrogen, oxygen or sulfur, where N-oxides, sulfur oxides and sulfur dioxides are permissible heteroatom substitutions. A heteroaryl group may be optionally substituted by one or more substituents, for example up to 3 or up to 2 substituents. Examples of "heteroaryl" used herein include furyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyrimidinyl, quinolinyl, isoquinolinyl, benzofuryl, benzothienyl, indolyl, and indazolyl.

The term "bicyclic heterocyclyl" when used herein means a fused bicyclic aromatic or non-aromatic bicyclic heterocyclyl ring system comprising up to four, preferably one or two, heteroatoms each selected from oxygen, nitrogen and sulphur. Each ring may have from 4 to 7, preferably 5 or 6, ring atoms. A bicyclic heteroaromatic ring system may include a carbocyclic ring. Examples of bicyclic heterocyclyl groups include quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl or naphthyridinyl.

When the heteroatom nitrogen replaces a carbon atom in an alkyl group, or when nitrogen is present in a heteroaryl, heterocyclyl or bicyclic heterocyclyl group, the nitrogen atom will, where appropriate be substituted by one or two substituents selected from hydrogen and $C_{1-8}$alkyl, preferably hydrogen and $C_{1-6}$-alkyl, more preferably hydrogen.

Optional substituents for alkyl or alkenyl groups are OH, $CO_2R^4$, $NR^4R^5$, (O), $OC_{1-6}$alkyl or halo, wherein $R^4$ and $R^5$ are as herein before defined. An alkyl or alkenyl group may be substituted by one or more optional substituents, for example up to 5, 4, 3, or 2 optional substituents.

Unless otherwise defined, optional substituents for aryl, heteroaryl or heterocyclyl moieties as a group or part of a group are selected from optionally substituted $C_{1-6}$alkyl, optionally substituted $C_{1-6}$alkoxy and halogen. Alternative optional substituents include $C_{1-6}$alkyl, $C_{1-6}$alkoxy and halogen.

Compounds of formula (I) can be prepared as set forth in the following schemes and in the examples. The following processes form another aspect of the present invention.

For example, compounds of formula (I) may be prepared by the general route below:

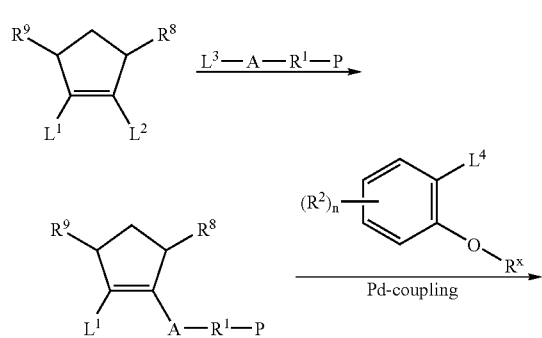

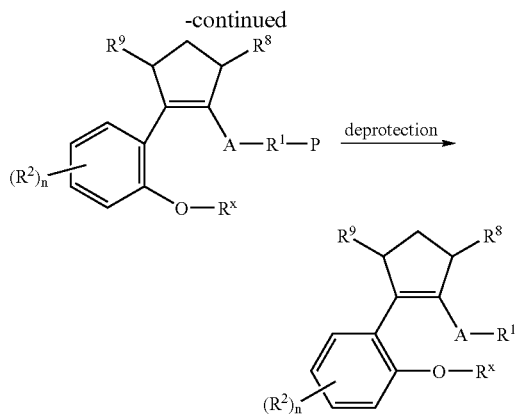

wherein $L^1$, $L^2$, are leaving groups for example halo, or triflate; $L^3$ and $L^4$ is an activating group, for example selected from stannanes including trialkylstannane, and boranes including boronic acid and boronate; P is a protecting group, for example methyl, ethyl or substituted benzyl esters; and A, $R^8$, $R^9$ and $R^x$ are as defined for compounds of formula (I). $L^1$ can be converted to $L^{1'}$, wherein $L^{1'}$ is an activating group for example a stannane or a boronic acid or boronic ester, and in this situation $L^4$ can be halo or triflate.

Alternatively compounds of formula (I) may be prepared according to the route described below:

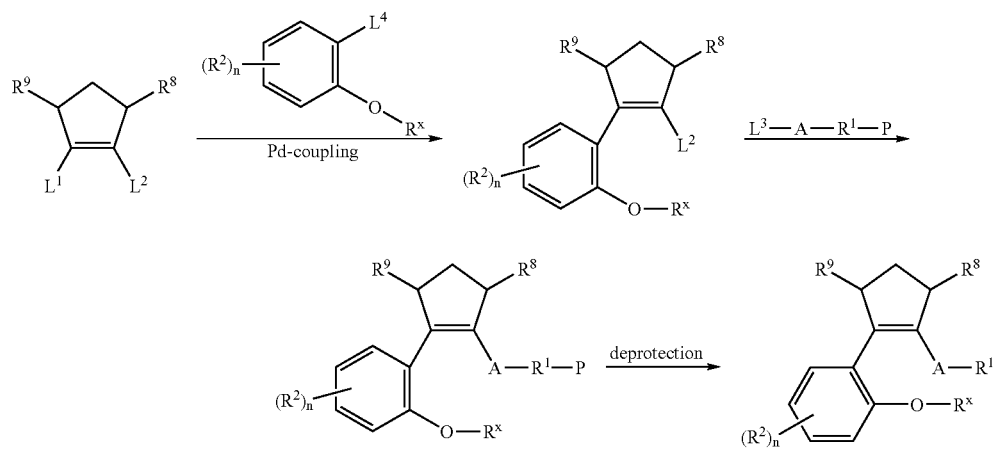

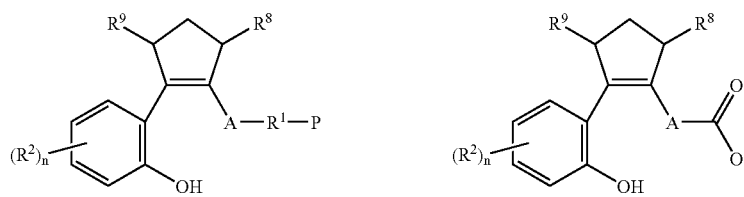

wherein $L^1$, $L^2$, $L^3$, $L^4$ and P are as defined above and A, $R^8$, $R^9$ and $R^x$ are as defined for compounds of formula (I). $L^1$ can be converted to $L^{1'}$, wherein $L^{1'}$ is an activating group, for example, a stannane or a boronic ester, and in this situation $L^4$ can be halo or triflate.

The preparation and reactions of boronic acids and esters is reviewed in Suzuki et al, *Synth. Commun.*, 1981, 11, 513; Martin et al, *Acta. Chim. Scand.*, 1993, 47, 221; and Miyaura et al, *Chem. Rev.*, 1995, 95, 2457.

Certain substituents in reaction intermediates and compounds of formula (I) may be converted to other substituents by conventional methods known to those skilled in the art.

For example, when $R^x$ is methyl, cleavage of the ether to give the phenol is carried out using, for example, sodium methanethiolate. Conversion to another $R^x$ group, for example a substituted benzyl group, may be effected by reaction of the phenol with a suitable substituted benzyl bromide. The skilled person will appreciate that conversion of the protecting group P to another protecting group P may also occur under the reaction conditions used. When $R^x$ is benzyl, cleavage of the ether to give the phenol may be carried out using, for example, HBr in acetic acid. The resulting phenol can then be converted to another group $R^x$ as described above.

It will be appreciated by those skilled in the art that it may be necessary to protect certain reactive substituents during some of the above procedures. Standard protection and deprotection techniques, such as those described in Greene T. W. 'Protective groups in organic synthesis', New York, Wiley (1981), can be used. For example, carboxylic acid groups can be protected as esters. Deprotection of such groups is achieved using conventional procedures-known in the art. It will be appreciated that protecting groups may be interconverted by conventional means.

Cyclopentene intermediates of the formula:

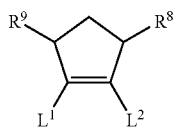

wherein $L^1$, $L^2$ are as defined above and $R^8$ and $R^9$ are as hereinbefore defined for compounds of formula (I) are commercially available or may be readily prepared according to known methods.

Compounds of the formula:

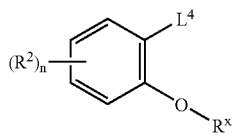

wherein $L^4$ is as hereinbefore defined, and $R^x$ and $R^2$ are as defined for compounds of formula (I) are commercially available, or may readily be prepared by methods known to those skilled in the art, for example from suitable commercially available anisoles or phenols using methods as described in the examples.

Compounds of the formula:

wherein $L^3$ and P are as defined above and $R^1$ and A are as hereinbefore defined for compounds of formula (I) are commercially available or may readily be prepared, for example, from suitable halobenzoic acid esters according to known methods, for example using methods as described in the examples.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The compounds of the invention bind to the $EP_1$ receptor and are therefore useful in treating $EP_1$ receptor mediated diseases.

In view of their ability to bind to the $EP_1$ receptor, the compounds of the invention may be useful in the treatment of the disorders that follow. Thus, the compounds of formula (I) may be useful as analgesics. For example they may be useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea. The compounds of the invention may also be useful in the treatment of visceral pain.

The compounds of the invention may be particularly useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) may also be useful in the treatment of fever.

The compounds of formula (I) may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendinitis, bursitis, and Sjogren's syndrome.

The compounds of formula (I) are also useful in the treatment of immunological diseases such as autoimmune diseases, immunological deficiency diseases or organ transplantation. The compounds of formula (I) are also effective in increasing the latency of HIV infection.

The compounds of formula (I) are also useful in the treatment of diseases of abnormal platelet function (e.g. occlusive vascular diseases).

The compounds of formula (I) are also useful for the preparation of a drug with diuretic action.

The compounds of formula (I) are also useful in the treatment of impotence or erectile dysfunction.

The compounds of formula (I) are also useful in the treatment of bone disease characterised by abnormal bone metabolism or resorbtion such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis.

The compounds of formula (I) are also useful for attenuating the hemodynamic side effects of non-steroidal anti-inflammatory drugs (NSAID's) and cyclooxygenase-2 (COX-2) inhibitors.

The compounds of formula (I) are also useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

The compounds of formula (I) are also useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment. The compounds of formula (I) are also useful in the treatment of neuroprotection and in the treatment of neurodegeneration following stroke, cardiac arrest, pulmonary bypass, traumatic brain injury, spinal cord injury or the like.

The compounds of formula (I) are also useful in the treatment of tinnitus.

The compounds of formula (I) are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compounds of formula (I) are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of formula (I) are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

It is to be understood that reference to treatment includes both treatment of established symptoms and prophylactic treatment, unless explicitly stated otherwise.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by the action of $PGE_2$ at $EP_1$ receptors.

According to a further aspect of the invention, we provide a method of treating a human or animal subject suffering from a condition which is mediated by the action of $PGE_2$ at $EP_1$ receptors which comprises administering to said subject an effective amount of a compound of formula (I) or a pharmaceutically acceptable derivative thereof.

According to a further aspect of the invention we provide a method of treating a human or animal subject suffering from a pain, inflammatory, immunological, bone, neurodegenerative or renal disorder, which method comprises administering to said subject an effective amount of a compound of formula (I) or a pharmaceutically acceptable derivative thereof.

According to a yet further aspect of the invention we provide a method of treating a human or animal subject suffering from inflammatory pain, neuropathic pain or visceral pain which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a medicament for the treatment of a condition which is mediated by the action of $PGE_2$ at $EP_1$ receptors.

According to another aspect of the invention we provide the use of a compound of formula (I) or a pharmaceutically acceptable derivative thereof for the manufacture of a medicament for the treatment or prevention of a condition such as a pain, inflammatory, immunological, bone, neurodegenerative or renal disorder.

According to another aspect of the invention we provide the use of a compound of formula (I) or a pharmaceutically acceptable derivative thereof for the manufacture of a medicament for the treatment or prevention of a condition such as inflammatory pain, neuropathic pain or visceral pain.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, we provide a pharmaceutical composition comprising a compound of formula (I) or a pharmaceutically acceptable derivative thereof adapted for use in human or veterinary medicine.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The $EP_1$ receptor compounds for use in the instant invention may be used in combination with other therapeutic agents, for example COX-2 inhibitors, such as celecoxib, deracoxib, rofecoxib, valdecoxib, parecoxib or COX-189; 5-lipoxygenase inhibitors; NSAID's, such as diclofenac, indomethacin, nabumetone or ibuprofen; leukotriene receptor antagonists; DMARD's such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B ssubtype; $EP_4$ receptor ligands; $EP_2$ receptor ligands; $EP_3$ receptor ligands; $EP_4$ antagonists; $EP_2$ antagonists and $EP_3$ antagonists; cannabanoid receptor ligands; bradykinin receptor ligands and vanilloid receptor ligand. When the compounds are used in combination with other therapeutic agents, the compounds may be administered either sequentially or simultaneously by any convenient route.

Additional COX-2 inhibitors are disclosed in U.S. Pat. No. 5,474,995 U.S. Pat. No. 5,633,272; U.S. Pat. No. 5,466,823, U.S. Pat. No. 6,310,099 and U.S. Pat. No. 6,291,523; and in WO 96/25405, WO 97/38986, WO 98/03484, WO 97/14691, WO99/12930, WO00/26216, WO00/52008, WO00/38311, WO01/58881 and WO02/1874.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of compounds of formula (I) or their pharmaceutically acceptable derivatives for the treatment of man is from 0.01 to 30 mg/kg body weight per day and more particularly 0.1 to 10 mg/kg body weight per day, calculated as the free base, which may be administered as a single or divided dose, for example one to four times per day The dose range for adult human beings is generally from 8 to 2000 mg/day, such as from 20 to 1000 mg/day, preferably 35 to 200 mg/day, calculated as the free base.

The precise amount of the compounds of formula (I) administered to a host, particularly a human patient, will be the responsibility of the attendant physician. However, the dose employed will depend on a number of factors including the age and sex of the patient, the precise condition being treated and its severity, and the route of administration.

No unacceptable toxicological effects are expected with compounds of the invention when administered in accordance with the invention.

All publications, including but not limited to patents and patent applications, cited in this specification are herein incorporated by reference as if each individual publication were specifically and individually indicated to be incorporated by reference herein as though fully set forth.

The following non-limiting Examples illustrate the preparation of pharmacologically active compounds of the invention.

EXAMPLES

Mass Directed Auto-Purification Systems

Hardware

Waters 600 gradient pump
Waters 2700 sample manager
Waters Reagent Manager

Micromass ZMD mass spectrometer
Gilson 202—fraction collector
Gilson Aspec—waste collector Software
  Micromass Masslynx version 3.5

Column

The column used is typically a Supelco ABZ+ column whose dimensions are 10 mm internal diameter by 100 mm in length. The stationary phase particle size is 5 µm.

Solvents
A. Aqueous solvent=Water+0.1% Formic Acid
B. Organic solvent=MeCN: Water 95:5+0.05% Formic Acid
Make up solvent=MeOH: Water 80:20+50 mMol Ammonium Acetate
Needle rinse solvent=MeOH:Water:DMSO (N,N-dimethyl sulfoxide) 80:10:10

Methods

There are five methods used depending on the analytical retention time of the compound of interest.

They all have a 15-minute runtime, which comprises of a 10-minute gradient followed by a 5-minute column flush and re-equilibration step.
MDP 1.5–2.2=0–30% B
MDP 2.0–2.8=5–30% B
MDP 2.5–3.0=15–55% B
MDP 2.8–4.0=30–80% B
MDP 3.8–5.5=50–90% B Flow Rate
  All of the above methods have a flow rate of 20 ml/min.

Compound I: 4-Chloro-2-iodophenol (Tetrahedron, 1995, 51, 8555)

2-Amino-4-chlorophenol (ex Aldrich) (50 g 0.35 mol) was dissolved in 2.5 M hydrochloric acid (500 ml), cooled to 0° C. and a solution of sodium nitrite (25.3 g, 0.37 mol) in water (50 ml) was slowly added over 20 minutes at 0–5° C., stirred for 30 minutes, then a solution of potassium iodide (70 g, 0.42 mol.) in water (100 ml) was added slowly at 0° C. The reaction mixture was then allowed to warm to 10° C. over 3 hours. The product was then extracted with ethyl acetate (200 ml), washed with 10% sodium bisulphite, water, and was dried over magnesium sulphate and evaporated down to dryness. The product was purified by column chromatography with 5% ethylacetate in hexane to give an orange solid. wt. 62 g. 70% yield.

Compound II: 2-Benzyloxy-5-chloro-iodobenzene

4-Chloro-2-iodophenol (57 g. 0.22M was dissolved in acetonitrile (500 mls), caesium carbonate (72.6 g, 0.22M.) was added slowly giving rise to an exotherm (19–24° C.) over 30 minutes. The reaction mixture was then kept at 24° C. for a further 5 hours. The reaction mixture was then stirred at 40° C. for 4 hours, then stirred at room temperature over night. The reaction mixture was filtered and evaporated down to a pink/brown solid. After trituration with water (200 ml) the suspension was filtered and recrystallised from hexane (200 ml) giving the title compound 50.2 g, 65% yield. A second crop gave a further 22.7 g.
  Total yield after drying 88%.
  Rt=13.20 min.

Compound III: (2-Benzyloxy-5-chlorophenyl)-boronic acid (WO 01/19814 A2)

2-Benzyloxy-5-chlorophenyl iodide (5 g 0.0145 mol) in diethyl ether/tetrahydrofuran (100:30) was cooled to −100° C. n-Butyl lithium, 1.6M solution in hexanes (10 mL, 0.016 mol) was added dropwise over 15 min under nitrogen. The reaction mixture was then allowed to rise to −70° C. for 1 h. Triethylborate (9 mL, 0.03 mol) was added dropwise under nitrogen. The cooling bath was then removed and the reaction mixture was stirred at room temperature overnight. The reaction mixture was then quenched with 2N hydrochloric acid (40 mL) and stirred vigorously at room temperature for 1 h. The product was then extracted with ethyl acetate, dried over magnesium sulphate and evaporated down to an oil. Purification was carried out on a Biotage (90 g cartridge) with ether/iso-hexane (50:50) to give the required product (wt; 2.8 g i.e. 74% yield).

Compound IV: (2-Bromo-cyclopenten-1-enyl)-trimethylstannane n-Butyllithium, 1.6M in hexanes, (58 mL, 92.0 mmol) in THF (50 mL) was cooled under nitrogen to −75° C. 1,2-Dibromocyclopentene (10.00 g, 44.3 mmol) in dry THF (10 mL) was added dropwise over ~10 minutes. The mixture was stirred at −75° C. for a further 20 minutes and then allowed to reach 0° C. The reaction mixture was then re-cooled to −75° C. and trimethyltin chloride (8.85 g, 44.3 mmol) in THF (30 mL) was added, under nitrogen, over ~10 minutes. After stirring at −75° C. for 30 minutes the reaction was allowed to reach room temperature and then stirred for 2 hours. The reaction mixture was then evaporated down to an oil and partitioned between brine and dichloromethane (100/200 mL). After shaking thoroughly, the organic layer was dried (magnesium sulphate), filtered and evaporated to give an oil. (13.15 g, ~80% pure).

$^1$H NMR (400 MHz CDCl$_3$) 0.25 (9H, s), 1.91–2.2 (2H, m), 2.38–2.47 (2H, m), 2.64–2.73 (2H, m).

Compound V: 6-Bromopyridine-2-carboxylic acid methyl ester

6-Bromopyridine-2-carboxylic acid (6.000 g) was heated in refluxing methanol (180 mL) containing conc. sulphuric acid (2 mL) for 4 hrs. The reaction mixture was then cooled to ~0° C. and conc. ammonia (4.8 mL) was added. The resulting solution was evaporated to give a white residue. This white solid was partitioned between brine and dichloromethane (100/100 mL). After thorough shaking the organic layer was dried (magnesium sulphate) and evaporated to give a white solid.
  (6.300 g, 98%).

$^1$H NMR (400 MHz, CDCl$_3$) 4.00 (3H, s), 7.66–7.74 (2H, m), 8.07–8.13 (1H, m).

Example 1

{2-[5-chloro-2-(benzyloxy)-phenyl]-cyclopent-1-enyl}-benzoic acid a) 3(2-Bromocyclopent-1-enyl)-benzoic acid ethyl ester 1,2-Dibromocyclopentene (Ex Aldrich, 27,732-0) (5 g, 0.0221 mol), (3-ethoxycarbonylphenyl) boronic acid (Ex Combiblocks inc. BB-2117-005) (4.26 g, 0.0221 mol), Pd(0) [PPh$_3$]$_4$ (0.5 g) and potassium carbonate (5 g) were stirred at 80° C. under nitrogen for 18 h in dimethoxyethane (30 mL). The reaction mixture was then filtered through Kieselguhr and evaporated down to an oil. Purification was carried out on a Biotage (90 g column) using isohexane containing a gradient of dichloromethane (0–30%) to give the required product (wt: 1.15 g i.e. 30% yield)

$^1$H NMR (400 MHz, CDCl$_3$) 1.40 (3H, t, J=7 Hz), 2.00–2.12 (2H, m), 2.75–2.94 (4H, m's), 4.39 (2H, q, J=7 Hz), 7.43 (1H, t, J=8 Hz), 7.85 (1H, d, J=8 Hz), 7.96 (1H, d, J=8 Hz), 8.22 (1H. s).

LC/MS rt 3.82, [MH+9 295, 297.

b) 3-{2-[5-chloro-2-(benzyloxy)-phenyl]-cyclopent-1-enyl}-benzoic acid ethyl ester 3-(2-Bromocyclopent-1-enyl)-benzoic acid ethyl ester (0.148 g, 0.0005 mol), Pd(0)[PPh$_3$]$_4$ (30 mg), potassium carbonate (0.2 g) and (2-benzyloxy-5-chlorophenyl) boronic acid (150 mg, 0.0005 mol) in dimethoxyethane (5 mL) were refluxed for 17 h under nitrogen. The reaction mixture was then filtered through Kieselghur and evaporated down to an oil. Purification was carried out on a Water's separation pack (10 g) with dichloromethane/isohexane giving the product (85 mg).

$^1$H NMR (400 MHz, CDCl$_3$) 1.31 (3H, t, J=7 Hz), 2.01–2.12 (2H, m), 2.81–2.88 (4H, m's), 4.28 (2H, q, J=8 Hz), 4.93 (2H, s), 6.81 (1H, d, J=8 Hz), 7.02, (1H, d, J=2 Hz), 7.10–7.33 (8H, m's excess), 7.76–7.86 (2H, m).

LC/MS rt 4.21, [MH+] 433.

c) 3-{2-[5-chloro-2-(benzyloxy)-phenyl]-cyclopent-1-enyl-benzoic acid

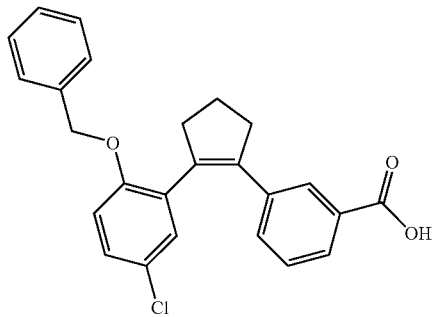

3-{2-[5-chloro-2-(benzyloxy)-phenyl]-cyclopent-1-enyl}-benzoic acid ethyl ester (80 mg) was refluxed for 1 h in methanol/2N sodium hydroxide (10:10 mL). The reaction mixture was then evaporated down to 3 mL. 2N Hydrochloric acid (10 mL) was added and the product extracted with dichloromethane (2×10 mL), dried over magnesium sulphate and evaporated down to an oil which solidified on standing (wt: 70 mg).

$^1$H NMR (400 MHz, CDCl$_3$) 2.00–2.18 (2H, m), 2.80–3.50 (4H, m's), 4.94 (2H, s), 6.82 (1H, d J=9 Hz), 7.02 (1H, d, J=2 Hz), 7.10–7.40 (8H, m's excess), 7.86 (1H, d, J=7 Hz), 7.90 (1H, s).

LC/MS RT=3.63 min [MH–] 403, 404.

Example 2

3-{2-[2-benzyloxy)-phenyl]-cyclopent-1-enyl]-benzoic acid a) 3-{2-[2-(benzyloxy)-phenyl]-cyclopent-1-enyl]-benzoic acid 3-(2-Bromo-cyclopent-1-enyl] benzoic acid ethyl ester (0.148 g, 0.0005 mol), tetrakis-triphenylphosphine palladium (o) (30 mg), potassium carbonate (0.200 g) and (2-benzyloxyphenyl) boronic acid (0.110 g, 0.5 mmol) in dimethoxyethane (5 mL) were refluxed for 17 h under nitrogen. The reaction mixture was then filtered through Keiselghur and evaporated down to an oil. Purification was carried out on a Waters separation pack (10 g) cartridge with dichloromethane/iso hexane giving the product (120 mg).

$^1$H NMR (400 MHz, CDCl$_3$) 1.30 (3H, t, J=7 Hz), 2.01–2.13 (2H, m), 2.84–2.99 (4H, m's), 4.27 (2H, q, J=7 Hz), 5.00 (2H, s), 6.85 (1H, td, J=1 Hz, J=7 Hz), 6.92 (1H, d, J=8 Hz), 7.02 (1H, d, J=7 Hz), 7.11–7.34 (8H, m's excess), 7.76 (1H, d, J=8 Hz), 7.85 (1H, s).

LC/MS RT=4.09 min.

b) 3-{2-[2-(benzyloxy)-phenyl]cyclopent-1-enyl]-benzoic acid

3-[2-(2-Benzyloxyphenyl)-cyclopent-1-enyl] benzoic acid ethyl ester (120 mg) was refluxed for 1 h in methanol/2N sodium hydroxide (10/10 mL). The reaction mixture was then evaporated down to 3 mL on a rotary evaporator. 2N Hydrochloric acid was added. The product was extracted with dichloromethane (2×10 mL), dried over magnesium sulphate and evaporated down to an oil which solidified on standing (wt: 100 mg).

$^1$H NMR (400 MHz, CDCl$_3$) 2.01–2.13 (2H, m), 2.85–3.00 (4H, m's), 5.00 (2H, s), 6.86 (1H, t, J=7 Hz), 6.92 (1H, d, J=8 Hz), 7.02 (1H, dd, J=2 Hz, J=7 Hz), 7.12–7.35 (8H, m's excess), 7.82 (1H, d, J=8 Hz), 7.91 (1H, s).

LC/MS RT=3.81 min [MH+] 371, [MH–] 369.

General Procedure 1

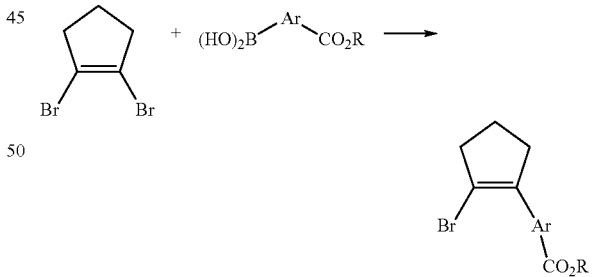

3-{2-Bromocyclopent-1-enyl)-benzoic acid ethyl ester 1,2-Dibromocyclopentene (Aldrich) (5.000 g, 22.1 mmol), (3-ethoxycarbonylphenyl) boronic acid (Combiblocks) (4.260 g, 22.1 mmol), tetrakistriphenylphosphine-palladium(0) (0.500 g) and potassium carbonate (5.000 g) were stirred at 80° C. under nitrogen for 18 h in dimethoxyethane (30 mL). The reaction mixture was then filtered through Kieselguhr and evaporated down to give an oil.

Purification by chromatography using iso-hexane containing a gradient of dichloromethane (0–30%) gave the required product (1.150 g, 30% yield).

General Procedure 2

3-(2-Bromo-cyclopent-1-enyl)benzoic acid ethyl ester (2-Bromo-cyclopent-1-enyl)trimethyl stannane (~80% pure) (13.150 g, 43.7 mmol), ethyl-3-iodobenzoate (24.000 g, 87.4 mmol), triphenylarsine (4.000 g) and tris(dibenzylideneacetone)palladium (0) (1.500 g), were heated in dimethylformamide (20 mL) at 100° C., under nitrogen for 92 hours. The reaction mixture was then filtered through highflo, thoroughly washed with dichloromethane, reduced to an oil, and purified by chromatography with iso-hexane containing ether (2%–50%) to give the title compound (4.000 g, 28%).

$^1$H NMR (400 MHz, CDCl$_3$), 1.40 (3H, t, J=7 Hz), 2.00–2.21 (2H, m), 2.76–2.83 (2H, m), 2.80–2.91 (2H, m), 4.33–4.45 (2H, m), 7.43 (1H, t, J=8 Hz), 7.83 (1H, d, J=8 Hz), 7.92–7.98 (1H, d, J=8 Hz), 8.20 (1H, s).

LC/MS [MH+] 297 Rt=3.87 min.

5-(2-Bromocyclopent-1-enyl)nicotinic acid ethyl ester

Prepared According to General Procedure 2
(2-Bromocyclopent-1-enyl)trimethyl stannane (13.7 g, 44.30 mmol)
ethyl-5-bromonicotinate (14.0 g, 60.0 mmol)
tris(dibenzylideneacetone)palladium (0) (1.500 g)
triphenylarsine (4.0 g)
dimethylformamide (20 mL)
Heated at 100° C. for 92 hours
Product (7.0 g, 56%).
LC/MS (CF104055-1) [MH+] 298

$^1$H NMR (400 MHz, CDCl$_3$), 1.42 (3H, t, J=7 Hz), 2.06–2.16 (2H, m), 2.77–2.85 (2H, m), 2.86–2.93 (2H, m), 8.50 (1H, s), 9.00 (1H, d, J=2.2 Hz), 9.15 (1H, d, J=2 Hz).

6-(2-Bromocyclopent-1-enyl)pyridine-2-carboxilic acid methyl ester

Prepared Using General Procedure 2:
(2-Bromocyclopent-1-enyl)trimethylstannane (6.0 g, 19.4 mmol)
6-bromopyridine-2-carboxylic acid methyl ester (6.0 g, 26.0 mmol
tris(dibenzylideneacetone)palladium (0) (1.0 g)
triphenylarsine (2.0 g) were heated at 115° C. for 40 hrs in dimethylformamide (20 mL).
Product (2.7 g). This oil was carried through the next stage without further purification.
LC/MS (CF105919–1) [MH+] 284 Rt=3.21 min.

General Procedure 3

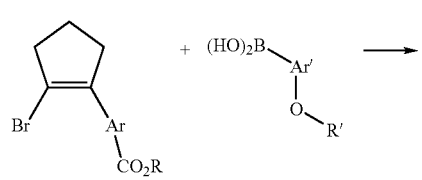

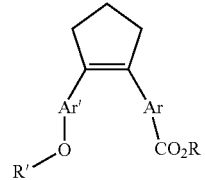

3-{2-[5-chloro-2-(benzyloxy)-phenyl]-cyclopent-1-enyl}-benzoic acid ethyl ester 3-(2-Bromocyclopent-1-enyl)-benzoic acid ethyl ester (148 mg, 0.5 mmol), tetrakis(triphenylphosphine)palladium (0) (30 mg), potassium carbonate (0.20 g) and (2-benzyloxy-5-chlorophenyl) boronic acid (150 mg, 0.5 mmol) in dimethoxyethane (5 mL) were refluxed for 17 h under nitrogen. The reaction mixture was then filtered through Kieselguhr and evaporated down to an oil. Purification was carried out on a Water's separation pack (10 g) with dichloromethane/iso-hexane to give the product (85 mg).

LC/MS [MH+] 433 Rt=4.21 min.

$^1$NMR (400 MHz, CDCl$_3$) 1.31 (3H, t, J=7 Hz), 2.01–2.12 (2H, m), 2.81–2.88 (4H, m), 4.28 (2H, q, J=7 Hz), 4.93 (2H, s), 6.81 (1H, d, J=9 Hz), 7.02 (1H, J=2 Hz), 7.10–7.33 (8H, m), 7.76–7.86 (2H, m).

3-{2-[2-(benzyloxy)-phenyl]-cyclopent-1-enyl]-benzoic acid ethyl ester

Prepared Using General Procedure 3
3-(2-Bromo-cyclopent-1-enyl] Benzoic acid ethyl ester (148 mg, 0.5 mmol)
tetrakis(triphenylphosphine)palladium (0) (30 mg)
potassium carbonate (200 mg)
(2-benzyloxyphenyl) boronic acid (110 mg, 0.5 mmol)
dimethoxyethane (5 mL) were refluxed for 17 h under nitrogen.
Product (120 mg).
LC/MS: Rt=4.09 min.

$^1$NMR (400 MHz, CDCl$_3$) 1.30 (3H, t, J=7 Hz), 2.01–2.13 (2H, m), 2.84–2.99 (4H, m), 4.28 (2H, q, J-7 Hz), 5.00 (2H, s), 6.85 (1H, td, J=7 Hz, J=7 Hz), 6.92 (1H, d, J=8 Hz), 7.02 (1H, dd, J=2 Hz, J-7 Hz), 7.11–7.34 (8H, m), 7.76 (1H, d, J=8 Hz), 7.85 (1H, s).

3-{2-[5-Bromo-2-(methoxy)phenyl]-cyclopent-1-enyl}-benzoic acid ethyl ester

Prepared Using General Procedure 3
3-(2-Bromocyclopent-1-enyl)benzoic acid ethyl ester (1.00 g, 3.40 mmol)
3-bromo-6-methoxyphenylboronic acid (1.656 g, 7.20 mmol)
tetrakis(triphenylphosphine)palladium (0) (2.7 g) (200 mg)
potassium carbonate (2.0 g)
dimethoxyethane (10 mL)
reflux 24 hours.
product (416 mg, 35%).

$^1$H MNR (400 MHz, CDCl$_3$) 1.34 (3H, t, J=7 Hz), 2.03–2.13 (2H, m), 2.79–2.85 (2H, m), 2.92–2.98 (2H, m), 3.61 (3H, s), 4.31 (2H, q, J=6.5 Hz), 6.73 (1H, d, J=9 Hz), 7.13 (1H, d, J=2.5 Hz), 7.16–7.25 (2H, m), 7.31 (1H, dd, J=2.5 Hz, J=11 Hz), 7.77–7.82 (1H, m) 7.85 (1H, s).

5-{2-[5-Chloro-2-(methoxy)phenyl]-cyclopent-1-enyl}-nicotinic acid ethyl ester Prepared by General Procedure 3
5-(2-Bromocyclopent-1-enyl)nicotinic acid ethyl ester (1.480 g, 5.0 mmol)
3-chloro-6-methoxyphenylboronic acid (1.490 g, 8.0 mmol)
tetrakis(triphenylphosphine)palladium (0) (0.300 g)
potassium carbonate (2.000 g)
dimethoxyethane (20 mL)
reflux 92 hrs
product (1.500 g, 85%).
LC/MS [MH+] 358 Rt=3.73 min.
$^1$H NMR (400 MHz, CDCl$_3$) 1.36 (3H, t, J=7 Hz), 2.07–2.26 (2H, m), 2.82–2.88 (2H, m), 2.93–2.99 (2H, m), 3.63 (3H, s), 4.35 (2H, q, J=7 Hz), 6.79 (1H, d, J=9 Hz), 6.98 (1H, d, J=3 Hz), 7.19 (1H, dd, J=3 Hz, J=11 Hz), 8.30 (1H, t, J=4 Hz), 8.45 (1H, d, J=2 Hz), 8.94 (1H, d, J=2 Hz).

5-{2-[5-Bromo-2-(methoxy)-phenyl]-cyclopent-1-enyl}-nicotinic acid ethyl ester Prepared by General Procedure 3
5-(2-Bromocyclopent-1-enyl)-nicotinic acid ethyl ester (2.000 g, 6.7 mmol)
3-bromo-6-methoxyphenylboronic acid (2.300 g, 10.0 mmol)
tetrakis(triphenylphosphine)palladium (0) (0.300 g)
anhydrous potassium carbonate (2.500 g)
dimethoxyethane (20 mL)
reflux 24 hrs
product (1.100 g, 41%).
$^1$H MNR (400 MHz, CDCl$_3$) 1.36 (3H, t, J=7 Hz), 2.06–2.16 (2H, m), 2.80–2.90 (2H, m) 2.91–2.99 (2H, m), 3.63 (3H, s), 4.35 (2H, q, J=7 Hz), 6.74 (1H, d, J=4 Hz), 7.13 (1H, d, J=3 Hz), 7.33 (1H, dd, J=2 Hz, J=9.5 Hz), 8.03 (1H, t, J=2 Hz), 8.45 (1H, d, J=2 Hz), 8.94 (1H, d, J=2 Hz).
LC/MS (CF105233-1) [MH+] 404 Rt=3.77 min.

5-{2-[5-Trifluoromethyl-2-(methoxy)-phenyl]-cyclopent-1-enyl}-nicotinic acid ethyl ester Prepared by General Procedure 3
5-(2-Bromocyclopent-1-enyl}-nicotinic acid ethyl ester (1.480 g, 5.0 mmol)
2-methoxy-5-trifluoromethylphenylboronic acid (1.750 g, 8.0 mmol)
tetrakis(triphenylphosphine)palladium (0) (0.3000 g)
potassium carbonate (2.0 g)
dimethoxyethane (20 mL)
reflux 24 hr
product (2.00 g, 100%).
$^1$H NMR (400 MHz, CDCl$_3$) 1.34 (3H, t, J=7 Hz), 1.90–2.18 (2H, m), 2.85–2.93 (2H, m), 2.94–2.32 (2H, m), 3.69 (3H, s), 4.33 (2H, q, J=7 Hz), 6.93 (1H, d, J=8 Hz), 7.27 (1H, d, J=4 Hz), 7.50 (1H, dd, J=2 Hz, J=9 Hz), 8.00 (1H, t, J=8 Hz), 8.43 (1H, d, J=3 Hz), 8.94 (1H, d, J=3 Hz).
LC/MS (CF104952-1) [MH+] 392 Rt=3.76 min.

6-{2-[5-Chloro-2-(methoxy)-phenyl]-cyclopent-1-enyl}-pyridine-2-carboxylic acid methyl ester Prepared by General Procedure 3
6-(2-Bromocyclopent-1-enyl}-pyridine-2-carboxylic acid methyl ester (2.700 g, ~60%, 9.5 mmol)
3-chloro-6-methoxyphenylboronic acid (1.800 g, 10.0 mmol)
tetrakis(triphenylphosphine)palladium (0) (0.500 g)
potassium carbonate (2.500 g)
dimethoxyethane (20 mL)
reflux 24 hrs
product (0.700 g, ~74% pure).
LC/MS [MH+] 344 Rt=3.62.

General Procedure 4

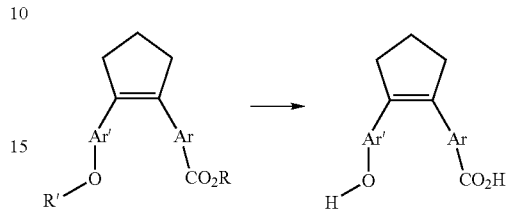

3-{2-[5-Bromo-2-(hydroxy)-phenyl]-cyclopent-1-enyl}-benzoic acid

3-{2-[5-Bromo-2-(methoxy)-phenyl]-cyclopent-1-enyl}-benzoic acid ethyl ester (416 mg, 10.0 mmol) in dichloromethane (5 mL) was cooled under nitrogen to ~40° C. and was treated with a molar solution of borontribromide in dichloromethane (20 mL, 20.0 mmol). The reaction mixture was then allowed to reach room temperature and kept stirring over night. The reaction mixture was then quenched with ice/water (50/50 mL) and more dichloromethane (30 mL) was added. After stirring vigorously for 1.5 hr. the organic layer was separated, dried (magnesium sulphate), evaporated down and chromatographed with 1% methanol in dichloromethane to give (300 mg, 80%).
$^1$H NMR (400 MHz, CDCl$_3$) 2.08–2.19 (2H, m), 2.82–2.90 (2H, m), 3.00–3.08 (2H, m), 6.72 (1H, d, J=4 Hz), 7.24–7.40 (4H, m), 7.94 (1H, d, J=4 Hz), 7.99 (1H, s).
LC/MS [MH–] 359 Rt=3.74 min.

General Procedure 5

6-{2-[5-Chloro-2-(4-chloro-benzyloxy)-phenyl]-cyclopent-1-enyl}-pyridine-2-carboxylic acid 4-chloro-benzyl ester 6-{2-[5-Chloro-2-(hydroxy)-phenyl]-cyclopent-1-enyl}-pyridine-2-carboxylic acid (97 mg, 0.30 mmol) was refluxed in 2-butanone (4 mL) with 4-chlorobenzyl bromide (140 mg, 0.70 mmol) and potassium carbonate (1.0 g) under nitrogen for five hours. The reaction mixture was then filtered through highflo, evaporated down to an oil and chromatographed on a Water's sep-pak (10 g) with ether/iso-hexane (15/85) to give (160 mg, 92%).
LC/MS [MH+] 556 Rt=5.5 min.
$^1$H NMR (400 MHz, CDCl$_3$) 2.03–2.12 (2H, m), 2.84–2.92 (2H, m), 3.06–3.14 (2H, m), 4.85 (2H, s), 5.33

(2H, s), 6.76 (1H, d, J=8 Hz), 7.02–7.13 (5H, m), 7.24–7.29 (2H, m), 7.32–7.40 (4H, m), 7.47 (1H, t, J=8 Hz), 7.81 (1H, d, J=2 Hz).

6-{2-[5-Chloro-2-(4-fluorobenzyloxy)-phenyl]-cyclopent-1-enyl}-pyridine-2-carboxylic 4-fluorobenzyl ester Prepared According to General Procedure 5.
Product (150 mg, 92%).
LC/MS (CF106348-1) [MH+] 532 Rt=4.27 min.
$^1$H NMR (400 MHz, CDCl$_3$) 2.02–2.11 (2H, m), 2.84–2.91 (2H, m), 3.06–3.13 (2H, m), 4.86 (2H, s), 5.34 (2H, s), 6.78 (1H, d, J=8 Hz), 6.92–6.99 (2H, m), 7.01–7.16 (2H, m), 7.40–7.50 (3H, m), 7.81 (1H, d, J=8 Hz).

General Procedure 6

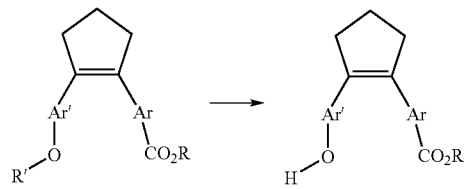

5-{2-[5-Chloro-2-(hydroxy)-phenyl]cyclopent-1-enyl}-nicotinic acid ethyl ester 5-{2-[5-Chloro-2-(methoxy)-phenyl]-cyclopent-1-enyl}-nicotinic acid ethyl ester (1.500 g, 4.20 mmol) in dry dichloromethane (20 mL) was cooled to −75° C. Boron tribromide, 1M solution in DCM, (40 mL, 40.0 mmol) was added and the reaction mixture stirred at −75° C. for a further hour. The temperature of the reaction was then allowed to rise to −15° C. and kept at −15° C. for a further 2 hours, and was then quenched in ice/water (50 g/50 mL). More dichloromethane (60 mL) was added and the resulting mixture was stirred vigorously for ~2 hrs. The layers were separated and the organic layer was washed with saturated sodium bicarbonate, dried (magnesium sulphate), filtered and reduced to an oil. The oil was then purified by chromatography to give the title compound (0.800 g, 60%).
LC/MS [MH+] 344 Rt=3.56.
$^1$NMR (400 MHz, CDCl$_3$) 1.38 (3H, t, J=7 Hz), 2.10–2.20 (2H, m), 2.86–2.95 (2H, m), 2.96–3.05 (2H, m), 4.38 (2H, q, J=7 Hz), 6.74 (1H, d, J=8 Hz), 7.03–7.12 (2H, m), 8.27 (1H, s), 8.53 (1H, s), 8.94 (1H, s).

5-{2-[5-Bromo-2-(hydroxy)-phenyl]-cyclopent-1-enyl}-nicotinic acid ethyl ester Prepared by general procedure 6
5-{2-[5-Bromo-2-(methoxy)-phenyl]-cyclopent-1-enyl}-nicotinic acid ethyl ester (1.100 g, 2.70 mol)
dichloromethane (10 mL)
boron tribromide (1 Molar solution in dichloromethane) (30 mL)
product (0.53 g, 53%).
$^1$H NMR (400 MHz, CDCl$_3$) 1.39 (3H, q, J=7 Hz), 2.14–2.25 (2H, m), 2.90–3.10 (4H, m), 4.43 (2H, q, J=7 Hz), 6.80 (1H, d, J=8 Hz), 6.93 (1H, d, J=8 Hz), 7.23–7.30 (1H, m), 8.60 (1H, s), 8.65 (1H, s), 8.93 (1H, s).
LC/MS [MH+] 390 Rt=3.58 min.

5-{2-[5-Trifluoromethyl-2-(hydroxy)-phenyl]cyclopent-1-enyl}-nicotinic acid ethyl ester Prepared by general procedure 6
5-{2-[5-Trifluoromethyl-2-(methoxy)-phenyl]-cyclopent-1-enyl}-nicotinic acid ethyl ester
(0.500 g, 1.20 mmol)
dichloromethane (10 mL)
boron tribromide (1M solution in dichloromethane) (20 mL)
product (0.480 g)
$^1$H NMR (400 MHz, CDCl$_3$) 1.36 (3H, t, J=7 Hz), 2.13–2.20 (2H, m), 2.87–2.95 (2H, m), 2.97–3.07 (2H, m), 4.37 (2H, q, J=7 Hz), 6.70 (1H, d, J=8 Hz), 7.23–7.34 (2H, m), 8.17 (1H, s), 8.44 (1H, d, J=1.6 Hz), 8.95 (1H, d, J=1.6 Hz).
LC/MS [MH+] 378 Rt=3.60 min.

6-{2-[5-Chloro-2-(hydroxy)-phenyl]-cyclopent-1-enyl}-pyridine-2-carboxylic acid methyl ester Prepared by general procedure 6
6-{2-[5-Chloro-2-(methoxy)-phenyl]-cyclopent-1-enyl}-pyridine-2-carboxylic acid methyl ester (0.700 g, ~75% pure)
dichloromethane (5 mL)
borontribromide (1M in dichloromethane) (10 mL).

Two products isolated:
6-{2-[5-Chloro-2-(hydroxy)-phenyl}cyclopent-1-enyl}-pyridine-2-carboxylic acid methyl ester (0.200 g)
LC/MS [MH+] 330 Rt-3.45 min.
$^1$H NMR (400 MHz, CDCl$_3$) 2.07–2.17 (2H, m), 2.85–2.93 (2H, m), 3.02–3.09 (2H, m), 3.97 (3H, s), 7.02 (1H, d, J=4.5 Hz), 7.06 (1H, d, J=1.5 Hz), 7.14 (1H, dd, J=1.5 Hz, J=5.5 Hz), 7.49 (1H, d, J=4 Hz), 7.83 (1H, t, J=7.5 Hz), 7.94 (1H, d, J=4 Hz), 9.37 (1H, s).
6-{2-[5-Chloro-2-(hydroxy)-phenyl]-cyclopent-1-enyl}-pyridine-2-carboxylic acid (0.195 g)
LC/MS [MH+] 315 Rt=3.08 min
$^1$H NMR (400 MHz, CDCl$_3$) 2.12–2.22 (2H, m), 2.87–2.96 (2H, m), 3.05–3.13 (2H, m), 6.95 (1H, d, J=9 Hz), 7.06 (1H, d, J=2.5 Hz), 7.18 (1H, dd, J=3 Hz, J=1 Hz), 7.47 (1H, d, J=8 Hz), 7.87 (1H, t, J=8.5 Hz), 8.03 (1H, d, J=7 Hz).

General Procedure 7

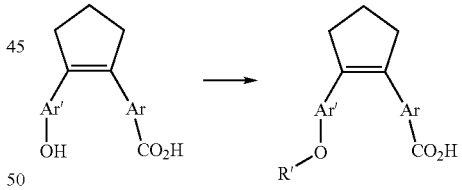

Example 3

3-{2-[5-bromo-2-(benzyloxy)-phenyl]-cyclopent-1-enyl}-benzoic acid

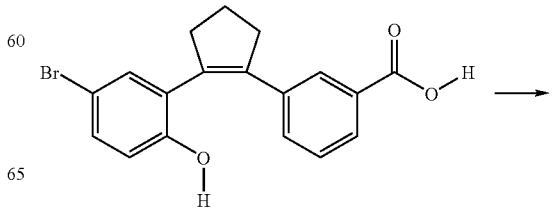

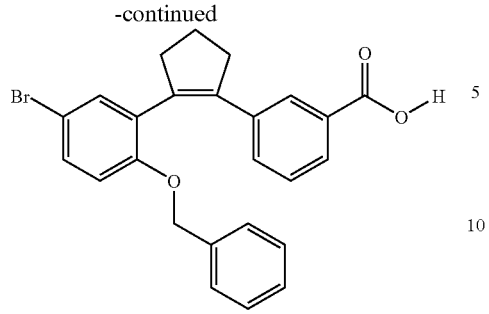

3-{2-[5-Bromo-2-(hydroxy)-phenyl]-cyclopent-1-enyl}-benzoic acid (0.04 g, 0.12 mmol), benzyl bromide (0.038 g, 0.22 moles), potassium hydroxide (~0.15 g), in dimethyl sulphoxide (1.5 mL) were stirred at room temperature over 8 hrs under nitrogen. The reaction mixture was then quenched with ice/water (10/10 mL), stirred at room temperature for ~1.5 hrs, acidified with 2N hydrochloric acid to pH~3 and extracted with dichloromethane. The organic extract was then dried (magnesium sulphate) and concentrated down to an oil and was then chromatographed on Waters sep-pak cartridge (10 g) giving (0.028 g, 54%).

LC/MS [MH−] 449 Rt=4.19 min.

$^1$H NMR (400 MHz, CDCl$_3$) 2.03–2.12 (2H, m), 2.83–2.90 (2H, m), 2.91–2.97 (2H, m), 4.94 (2H, s), 6.77 (1H, d, J=9 Hz), 7.14–7.23 (4H, m), 7.23–7.34 (5H, m), 7.85 (1H, d, J=7.5 Hz), 7.89 (1H, s).

Example 4

3-{2-[5-Bromo-2-(4-Chlorobenzyloxy)-phenyl]-cyclopent-1-enyl}-benzoic acid

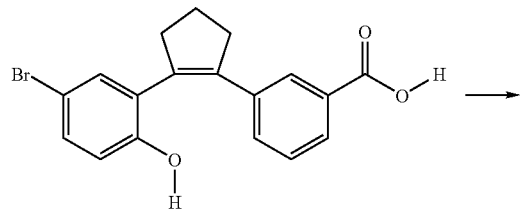

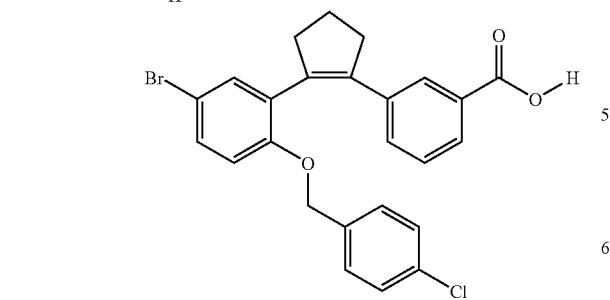

Prepared according to general procedure 7
Product (22 mg, 31%)
LC/MS (CF104431-1) [MH−] 483 Rt=4.36 min.

Example 5

3-{2-[5-Bromo-2-(4-fluorobenzyloxy)-phenyl]-cyclopent-1-enyl}-benzoic acid

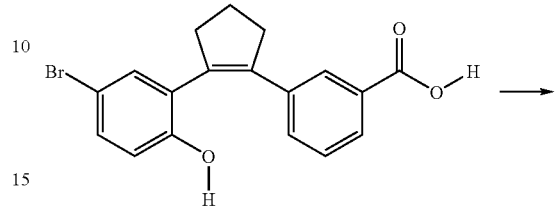

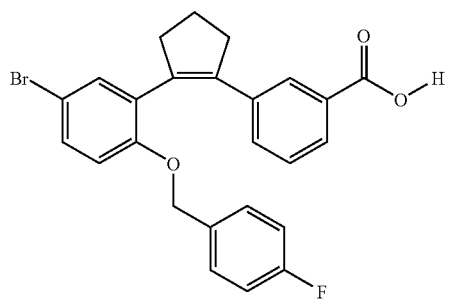

Prepared according to general procedure 7
Product (22 mg, 32%)
LC/MS [MH−] 467 Rt=4.19 min.

Example 6

3-{2-[5-Bromo-2-(3,4-dichlorobenzyloxy)-penyl]-cyclopent-1-enyl}-benzoic acid

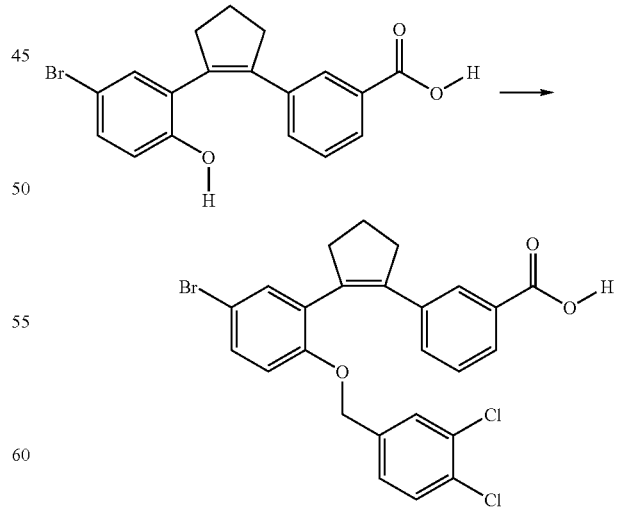

Prepared according to general procedure 7
Product (18 mg, 24%)
LC/MS [MH−] 517 Rt=4.53 min ~60% pure

Example 7

3-{2-[5-Bromo-2-(2,4-difluorobenzyloxy)-phenyl]-cyclopent-1-enyl}-benzoic acid

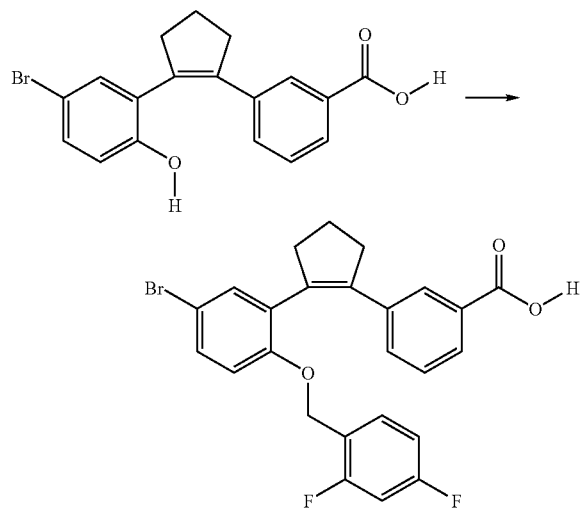

Prepared according to general procedure 7
Product (27 mg, 38%)
$^1$H NMR (400 MHz, CDCl$_3$) 2.03–2.12 (2H, m), 2.79–2.86 (2H, m), 2.90–2.97 (2H, m), 4.92 (2H, s), 6.74–6.83 (3H, m), 7.08–7.28 (4H, m), 7.32 (1H, dd, J=3 Hz, J=11 Hz), 7.84–7.88 (2H, m).

Example 8

3-{2-[5-Bromo-2-(4-chloro-2-fluorobenzyloxy)-phenyl]-cyclopent-1-enyl}-benzoic acid

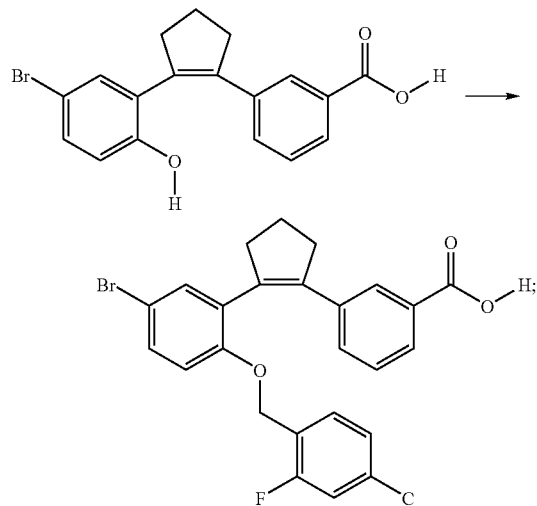

Prepared according to general procedure 7
Product (19 mg, 26%)
LC/MS [MH−] 501 Rt=4.39 min.

$^1$H NMR (400 MHz, CDCl$_3$) 2.03–2.13 (2H, m), 2.79–2.87 (2H, m), 2.90–2.98 (2H, m), 4.93 (2H, s), 6.77 (1H, d, J=8 Hz), 7.03–7.28 (6H, m), 7.31 (1H, dd, J=3 Hz, J=10 Hz) 7.83–7.87 (2H, m).

Example 9

3-{2-[5-Bromo-2-(4-methoxybenzyloxy)-phenyl]-cyclopent-1-enyl}-benzoic acid

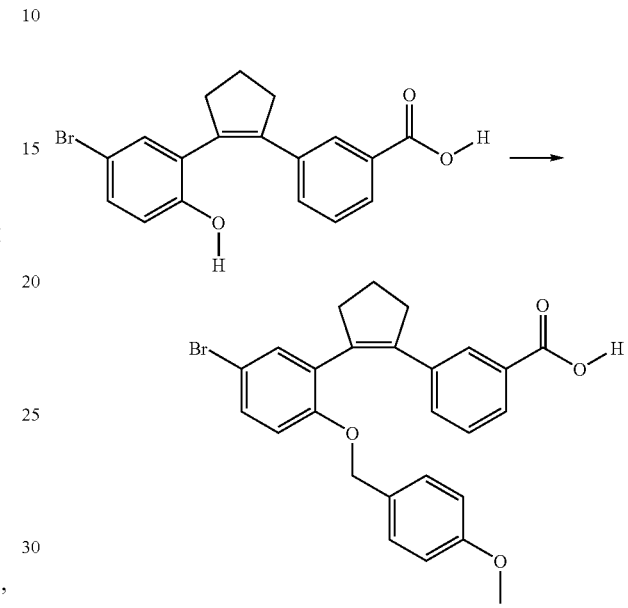

Prepared according to general procedure 7
Product (14 mg, 20%).
LC/MS [MH−] 479 Rt=4.15 min.

General Procedure 8

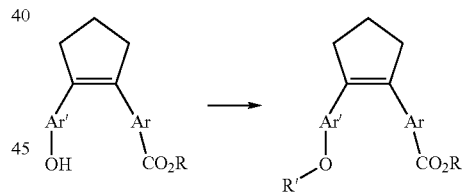

5-{2-[5-Chloro-2-(4-chlorobenzyloxy)-phenyl]-cyclopent-1-enyl}-nicotinic acid ethyl ester 5-{2-[5-Chloro-2-(hydroxy)-phenyl]-cyclopent-1-enyl}-nicotinic acid ethyl ester (138 mg, 0.43 mmol) was treated with 4 chlorobenzyl bromide (0.130 g, 60 mmol) and potassium carbonate (1.000 g) and 2-butanone (5 mL) at reflux for 18 hrs. Upon cooling, the mixture was filtered through highflo and reduced down to an oil. The product was purified using a Water's sep-pak cartridge (10 g) to give (90 mg, 44%).
LC/MS [MH+] 468 Rt=4.19 min.

5-{2-[5-Chloro-2-(4-fluorobenzyloxy)-phenyl]-cyclopent-1-enyl}-nicotinic acid ethyl ester Prepared according to general procedure 8
Product (80 mg, 41%)
LC/MS [MH+] 452 Rt=4.05 min.

¹H NMR (400 MHz, CDCl₃) 1.35 (3H, t, J=7 Hz), 2.05–2.14 (2H, m), 2.82 (2H, m), 2.89–2.96 (2H, m), 4.34 (2H, q, J=7 Hz), 4.86 (2H, s), 6.83 (1H, d, J=9 Hz), 6.94–7.20 (6H, m), 7.94 (1H, t, J=8 Hz), 8.43 (1H, d, J=4 Hz), 8.92 (1H, d, J=4 Hz).

5-{2-[5-Chloro-2-(3,4-dichlorobenzyloxy)-phenyl]-cyclopent-1-enyl}-nicotinic acid ethyl ester Prepared according to general procedure 8
Product (10 mg, 45%)
LC/MS [MH+] 504 Rt=4.32 min.

5-{2-[5-Chloro-2-(2,4-difluorobenzyloxy)-phenyl]-cyclopent-1-enyl}-nicotinic acid ethyl ester Prepared according to general procedure 8
Product (105 mg, 51%)
LC/MS [MH+] 470 Rt=4.07 min.
¹H NMR (400 MHz, CDCl₃) 1.36 (3H, t, J=7 Hz), 2.04–2.13 (2H, m), 2.80–2.88 (2H, m), 2.88–2.96 (2H, m), 4.35 (2H, q, J=7 Hz), 4.92 (2H, s), 6.74–6.84 (2H, m), 6.87 (1H, d, J=9 Hz), 7.04 (1H, d, J=3 Hz), 7.08–7.17 (1H, q, J=8 Hz), 7.19 (1H, dd, J=3.5 Hz, J=10 Hz), 7.94 (1H, t, J=4 Hz), 8.40 (1H, d, J=2 Hz), 8.92 (1H, d, J=2 Hz).

5{2-[5-chloro-2-(4-chloro-2-fluorobenzyloxy)-phenyl}-cyclopent-1-enyl]-nicotinic acid ethyl ester Prepared according to general procedure 8
Product (90 mg, 42%)
LC/MS [MH+] 486 Rt=4.20 min.
¹H NMR (400 MHz, CDCl₃) 1.35 (3H, t, J=7 Hz), 2.05–2.14 (2H, m), 2.81–2.89 (2H, m), 2.89–2.97 (2H, m), 4.34 (2H, q, J=7 Hz), 4.93 (2H, s), 6.86 (1H, d, J=9 Hz), 7.02–7.12 (4H, m), 7.19 (1H, dd, J=3 Hz, J=11 Hz), 7.95 (1H, t, J=4 Hz), 8.43 (1H, d, J=2 Hz), 8.92 (1H, d, J=1 Hz).

5-{2-[5-Chloro-2-(4-methoxybenzyloxy)-phenyl)]-cyclopent-1-enyl}-nicotinic acid ethyl ester Prepared according to general procedure 8
Product (95 mg, 47%)
LC/MS [MH+] 464 Rt=4.02 min.

5-{2-[5-Bromo-2-(4-chlorobenzyloxy)-phenyl]-cyclopent-1-enyl}-nicotinic acid ethyl ester Prepared according to general procedure 8
Product (16 mg, 16%)
LC/MS [MH+]514 Rt=4.22 min
¹H NMR (CDCl₃) 1.36 (3H, t, J=7.5 Hz), 2.05–2.15 (2H, m), 2.82–2.89 (2H, m), 2.89–2.96 (2H, m), 4.30–4.39 (2H, q, J=7.5 Hz), 4.86 (2H, s), 6.76 (1H, d, J=8 Hz), 7.08 (1H, d, J=7.5 Hz), 7.19 (1H, d, J=2 Hz), 7.23–7.34 (4H, m), 7.95 (1H, s), 8.43 (1H, s), 8.92 (1H, s).

5-{2-[5-Bromo-2-(benzyloxy)-phenyl]-cyclopent-1-enyl}-nicotinic acid ethyl ester Prepared according to general procedure 8
Product (16 mg, 17%)
LC/MS [MH+] 480 Rt=4.09 min.
¹H NMR (400 MHz, CDCl₃) 1.34 (3H, t, J=8 Hz), 2.05–2.14 (2H, m), 2.83–2.90 (2H, m), 2.90–2.97 (2H, m), 4.35 (2H, q, J=8 Hz), 4.92 (2H, s), 6.79 (1H, d, J=8 Hz), 7.14–7.20 (3H, m), 7.23–7.33 (4H, m), 7.90 (1H, s), 8.45 (1H, s), 8.92 (1H, s).

5-{2-[5-Bromo-2-(4-fluorobenzyloxy)-phenyl]-cyclopent-1-enyl}-nicotinic acid ethyl ester Prepared according to general procedure 8
Product (14 mg, 15%).
LC/MS [MH+] 498 Rt=4.09 min.
¹H NMR (400 MHz, CDCl₃) 1.36 (3H, t, J=7 Hz), 2.04–2.13 (2H, m), 2.82–2.89 (2H, m), 2.89–2.96 (2H, m), 4.35 (2H, q, J=7 Hz), 4.86 (2H, s), 6.78 (1H, d, J=7.5 Hz), 6.98 (2H, t, J=7.5 Hz), 7.08–7.16 (2H, m), 7.19 (1H, s), 7.31 (1H, d, J=9 Hz), 7.94 (1H, s), 8.44 (1H, s), 8.92 (1H, s).

5-{2-[5-Bromo-2-(2,4-difluorobenzyloxy)-phenyl]-cyclopent-1-enyl}-nicotinic acid ethyl ester Prepared According to General Procedure 8
Product (44 mg, 44%)
LC/MS [MH+] 516 Rt=4.10 min.
¹H NMR (400 MHz, CDCl₃) 1.36 (3H, t, J=7 Hz), 2.03–2.13 (2H, m), 2.80–2.88 (2H, m), 2.87–2.96 (2H, m), 4.34 (2H, q, J=7 Hz), 4.91 (2H, s), 7.74–6.85 (3H, m), 7.08–7.16 (1H, bq, J=7.5 Hz), 7.18 (1H, d, J=2 Hz), 7.30–7.35 (1H, m), 7.95 (1H, s), 8.42 (1H, s) 8.92 (1H, s).

5-{2-[5-Bromo-2-(4-chloro-2-fluorobenzyloxy)-phenyl]-cyclopent-1-enyl}-nicotinic acid ethyl ester Prepared According to General Procedure 8
Product (41 mg, 41%).
LC/MS [MH+] 532 t=4.24 min.
¹H NMR (400 MHz, CDCl₃) 1.36 (3H, t, J=6.5 Hz), 2.05–2.14 (2H, m), 2.80–2.89 (2H, m), 2.89–2.97 (2H, m), 4.36 (2H, m), 4.93 (2H, s), 6.80 (1H, d, J=7 Hz), 7.03–7.21 (4H, m), 7.33 (1H, d, J=6.5 Hz), 7.95 (1H, s), 8.43 (1H, s), 8.92 (1H, s).

5-{2-[5-Bromo-2-(cyclohexylmethoxy)-phenyl]-cyclopent-1-enyl}-nicotinic acid ethyl ester Prepared According to General Procedure 8
Product (53 mg, 56%)
LC/MS [MH+] 486 Rt=4.47 min.
¹H NMR (400 MHz, CDCl₃) 0.89 (3H, m) 1.03–1.28 (4H, m), 1.36 (3H, t, J=7 Hz), 1.50–1.72 (4H, m), 2.05–2.15 (2H, m), 2.79–2.88 (2H, m), 2.88–2.98 (2H, m), 3.62 (2H, d, J=6 Hz), 4.35 (2H, q, J=7 Hz), 6.72 (1H, d, J=8 Hz), 7.10 (1H, s), 7.28–7.33 (1H, m), 8.2 (1H, s), 8.45 (1H, s), 8.93 (1H, s).

5-{2-[5-Trifluoromethyl-2-(4-Chlorobenzyloxy)-phenyl]-cyclopent-1-enyl}-nicotinic acid ethyl ester Prepared According to General Procedure 8
Product (19 mg, 14%).
¹H NMR (400 MHz, CDCl₃) 1.33 (3H, t, J=7 Hz), 2.08–2.17 (2H, m), 2.86–2.98 (4H, m), 4.33 (2H, q, J=7 Hz), 4.93 (2H, s), 6.94 (1H, d, J=4.3 Hz), 7.09 (2H, d, J=8 Hz), 7.24–7.36 (3H, m), 7.48 (1H, dd, J=2 Hz, J=10 Hz), 7.93 (1H, d, J=4 Hz), 8.41 (1H, d, J=2 Hz), 9.92 (1H, d, J=2 Hz).

5-{2-[5-Trifluoromethyl-2-(4-fluorobenzyloxy)-phenyl]-cyclopent-1-enyl}-nicotinic acid ethyl ester Prepared According to General Procedure 8
Product (29 mg, 22%)
LC/MS [MH+] 486 Rt=4.05 min.
$^1$H NMR (400 MHz, CDCl$_3$) 1.33 (3H, t, J=7 Hz), 2.06–2.16 (2H, m), 2.80–2.98 (4H, m), 4.33 (2H, q, J=7.5 Hz), 4.92 (2H, s), 6.93–7.03 (3H, m), 7.10–7.16 (2H, m), 7.34 (1H, d, J=2 Hz), 7.49 (1H, dd, J=3 Hz), 7.92 (1H, t, J=2 Hz), 8.40 (1H, d, J=2 Hz), 8.92 (1H, d, J=4Hz).

5-{2-[5-Trifluoromethyl-2-(2,4-difluorobenzyloxy)-phenyl]-cyclopent-1-enyl}-nicotinic acid ethyl ester Prepared According to General Procedure 8
Product (42 mg, 31%).
LC/MS [MH+] 504 Rt=4.07 min.
$^1$H NMR (400 MHz, CDCl$_3$) 1.33 (3H, t, J=7.2 Hz), 2.06–2.16 (2H, m), 2.83–2.91 (2H, m), 2.91–2.98 (2H, m), 4.33 (2H, q, J=7 Hz), 4.99 (2H, s), 6.76–6.84 (2H, m), 7.01 (1H, d, J=9 Hz), 7.12 (1H, q, J=8 Hz), 7.33 (1H, d, J=2 Hz), 7.51 (1H, dd, J=2 Hz, J=10 Hz), 7.92 (1H, t, J=4 Hz), 8.40 (1H, d, J=2 Hz), 8.92 (1H, d, J=2 Hz).

5-{2-[5-Trifluoromethyl-2-(4-chloro-2-fluorobenzyloxy)-phenyl]-cyclopent-1enyl}-nicotinic acid ethyl ester Prepared According to General Procedure 8
Product (47 mg, 35%).
$^1$H NMR (400 MHz, CDCl$_3$) 1.33 (3H, t, J=7 Hz), 2.06–2.17 (2H, m), 2.84–2.92 (2H, m), 2.92–2.99 (2H, m), 4.33 (2H, q, J=7 Hz), 5.00 (2H, s), 6.99 (1H, d, J=8 Hz), 7.04–7.12 (3H, m), 7.33 (1H, d, J=2 Hz), 7.51 (1H, dd, J=3 Hz), 7.92 (1H, t, J=4 Hz), 8.41 (1H, d, J=2 Hz). 8.92 (1H, d, J=2 Hz).

5-{2-[5-Trifluoromethyl-2-(cyclohexylmethoxy)-phenyl]cyclopent-1-enyl}-nicotinic acid ethyl ester Prepared According to General Procedure 8
Product (46 mg, 36%)
LC/MS [MH+] 474 Rt=4.41 min.

6-{2-[5-Chloro-2-(2,4-difluorobenzyloxy)-phenyl]-cyclopent-1-enyl}-pyridine-2-carboxylic acid methyl ester Prepared According to General Procedure 8
Product (124 mg, 90%).
LC/MS [MH+] 456 Rt=4.01 min
$^1$H NMR (400 MHz, CDCl$_3$) 2.03–2.12 (2H, m), 2.83–2.90 (2H, m), 3.06–3.14 (2H, m), 3.93 (3H, s), 4.93 (2H, s), 6.74–6.83 (2H, m), 6.85 (1H, d, J=9 Hz), 7.01–7.08 (2H, m,), 7.13–7.20 (2H, m), 7.48 (1H, t, J=8 Hz), 7.83 (1H, d, J=8 Hz).

6-{2-[5-Chloro-2-(4-chloro-2-fluorobenzyloxy)-phenyl]-cyclopent-1-enyl-}pyridine-2-carboxylic acid methyl ester Prepared According to General Procedure 8
Product (135 mg, 94%)
LC/MS (CF106321-1) [MH+] 472 Rt=4.15 min.

$^1$H NMR (400 MHz CDCl$_3$) 2.03–2.12 (2H, m), 2.84–2.9 (2H, m), 3.07–3.14 (2H, m), 3.93 (3H, s), 4.93 (2H, s), 6.83 (1H, d, J=8 Hz), 7.01–7.15 (5H, m), 7.15–7.20 (1H, dd, J=3 Hz, J=11 Hz), 7.48 (1H, t, J=7.5 Hz), 7.83 (1H, d, J=8 Hz).

General Procedure 9: Ester Hydrolysis

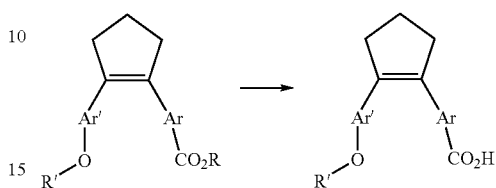

Example 1

3-{2-[5-chloro-2-(benzyloxy)-phenyl]-cyclopent-1-enyl}-benzoic acid

3-{2-[5-chloro-2-(benzyloxy)-phenyl)cyclopent-1-enyl]-benzoic acid ethyl ester (80 mg) was refluxed for 1 h in methanol/2N sodium hydroxide (10:10 mL). The reaction mixture was then evaporated down to 3 mL. 2N Hydrochloric acid (10 mL) was added and the product extracted with dichloromethane (2×10 mL), dried (magnesium sulphate) and evaporated to give an oil which solidified on standing (70 mg).
LC/MS [MH−] 403 Rt=3.63 min

Example 2

3-[2-(2-Benzyloxy-phenyl)-cyclopent-1-enyl]-benzoic acid

Prepared According to General Procedure 9
Product (100 mg).
LC/MS [MH−] 369 Rt=3.81 min.

General Procedure 10

Example 10

5-{2-[5-Chloro-2-(4-chlorobenzyloxy)-phenyl]-cyclopent-1-enyl}-nicotinic acid

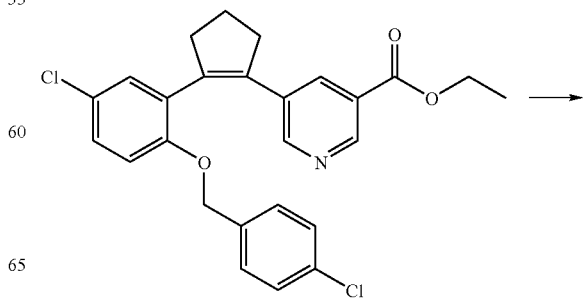

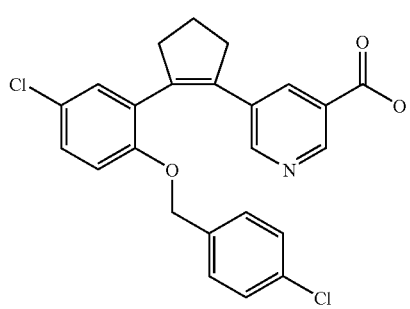

5-{2-[5-Chloro-2-(4-chlorobenzyloxy)-phenyl]-cyclopent-1-enyl}-nicotinic acid ethyl ester (90 mg) was hydrolysed in methanol (3 mL) and 2N sodium hydroxide (2 mL) at 60° C. with stirring for 2 hrs. The reaction mixture was then reduced down to ~1 mL, diluted with water (10 mL) and treated with a few drops of glacial acetic acid to make the solution ~pH5. The product was then extracted twice with dichloromethane (10 mL) dried (magnesium sulphate), and evaporated to give the title compound (75 mg).

LC/MS [MH+] 440 Rt=4.22 min.

Example 11

5-{2-[5-Chloro-2-(benzyloxy)-phenyl]-cyclopent-1-enyl}-nicotinic acid

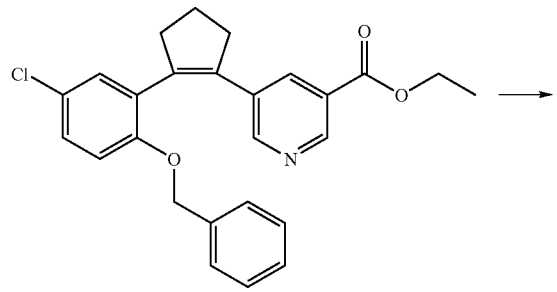

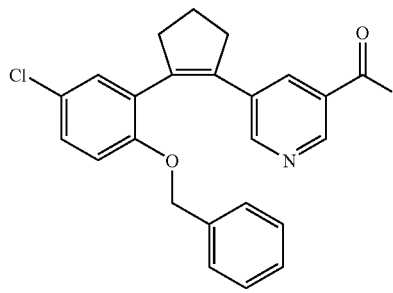

Prepared According to General Procedure 10

Product (95 mg, yield).

$^1$H NMR (400 MHz, CDCl$_3$) 2.06–2.16 (2H, m), 2.85–2.99 (4H, m), 4.93 (2H, s), 6.85 (1H, d, J=8 Hz), 7.4 (1H, d, J=3 Hz), 7.13–7.22 (3H, m), 7.22–7.34 (3H, m), 8.65 (1H, t, J=4 Hz), 8.49 (1H, d, J=2 Hz), 9.01 (1H, d, J=2 Hz).

Example 12

5-{2-[5-Chloro-2-(4-fluorobenzyloxy)-phenyl]-cyclopent-1-enyl}-nicotinic acid

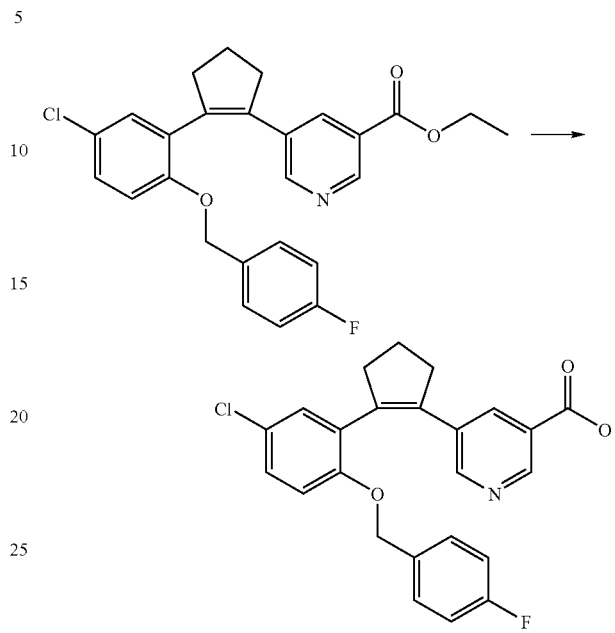

Prepared According to General Procedure 10

(60 mg, 81%)

LC/MS [MH+] 424 Rt=3.99 min.

$^1$H NMR (400 MHz, CDCl$_3$) 2.06–2.16 (2H, m), 2.84–2.98 (4H, m), 4.86 (2H, s), 6.83 (1H, d, J=7.5 Hz), 6.99 (2H, t, J=7.5 Hz), 7.65 (1H, d, J=2 Hz), 7.1–7.2 (3H, m), 8.05 (1H, s), 8.49 (1H, b.s), 9.02 (1H, b.s).

Example 13

5-{2-[5-Chloro-2-(3,4-dichlorobenzyloxy)-phenyl]-cyclopent-1-enyl}-nicotinic acid

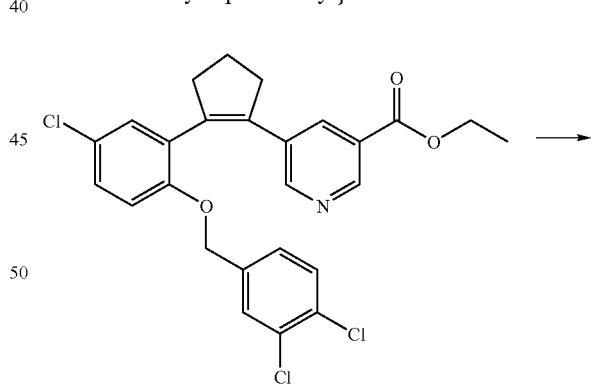

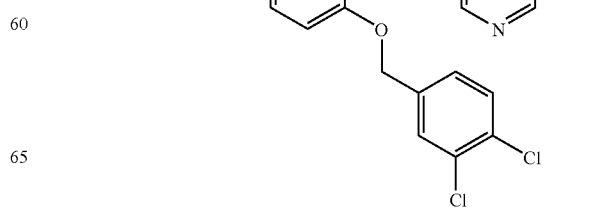

Prepared According to General Procedure 10
Product (87 mg, 92%)
LC/MS [MH+] 476 Rt=4.43 min.

Example 14

5-{2-[5-Chloro-2-(2,4-difluorobenzyloxy)-phenyl]-cyclopent-1-enyl}-nicotinic acid

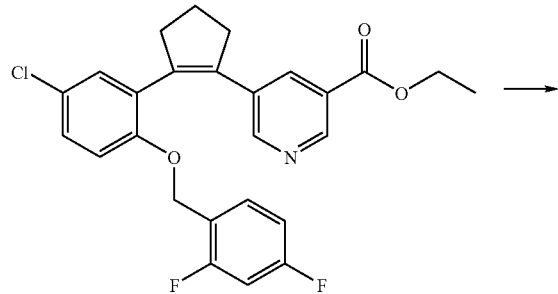

↓

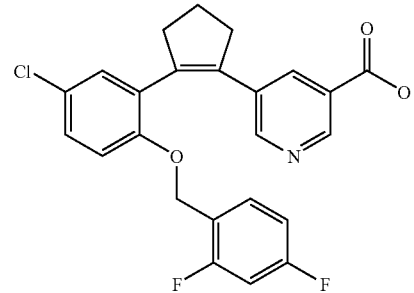

Prepared According to General Procedure 10
Product (95 mg, 96%)
LC/MS [MH+] 442 Rt=4.00 min.
¹H NMR (400 MHz, CDCl₃) 2.50–2.15 (2H, m), 2.81–2.89 (2H, m), 2.89–2.98 (2H, m), 4.92 (2H, s), 6.74–6.9 (3H, m), 7.05 (1H, d, J=2 Hz), 7.11–7.22 (2H, m), 8.05 (1H, s) 8.47 (1H, s), 9.05 (1H, m).

Example 15

5-{2-[5-Chloro-2-(4-chloro-2-fluorobenzyloxy)-phenyl]-cyclopent-1-enyl}-nicotinic acid

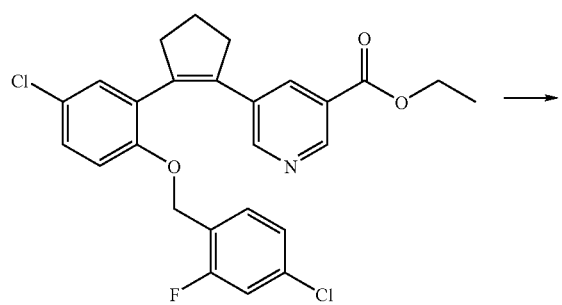

↓

-continued

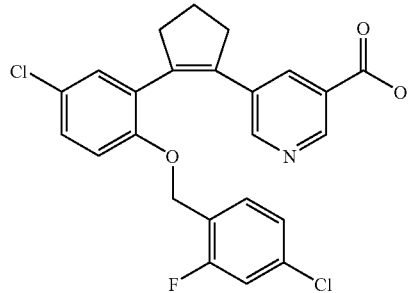

Prepared According to General Procedure 10
Product (75 mg, 89%).
LC/MS [MH+] 458 Rt=4.22 min.
¹H NMR (400 MHz, CDCl₃) 2.06–2.16 (2H, m), 2.83–2.91 (2H, m), 2.91–2.99 (2H, m), 4.93 (2H, s), 6.86 (1H, d, J=8 Hz), 7.03–7.15 (4H, m), 7.18 (1H, dd, J=3 Hz, J=9.5 Hz), 8.05 (1H, s), 8.48 (1H, d, J=2 Hz), 9.1 (1H, s).

Example 16

5-{2-[5-Chloro-2-4-methoxybenzyloxy)-phenyl]-cyclopent-1-enyl}-nicotinic acid

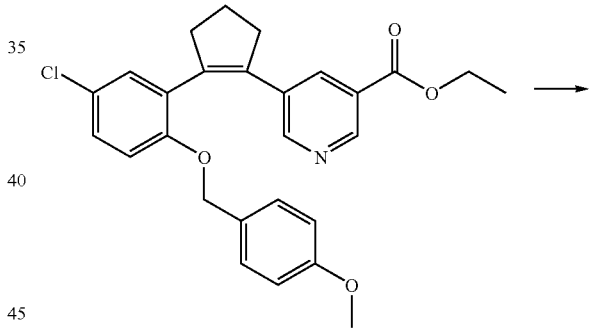

↓

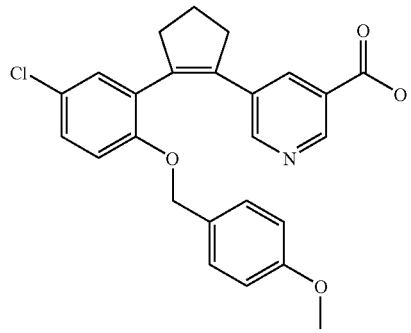

Prepared According to General Procedure 10
Product (78 mg, 87%).
LC/MS [MH+] 436 Rt=3.92 min.

Example 17

5-{2-[5-Bromo-2-(benzyloxy)-phenyl]-cyclopent-1-enyl}-nicotinic acid

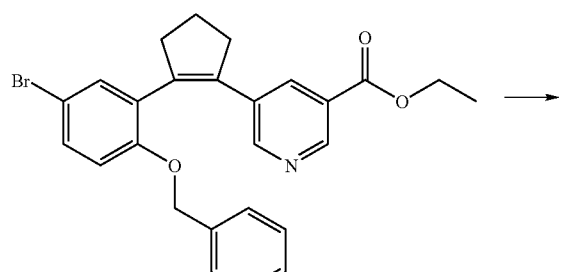

Prepared According to General Procedure 10
Product (11 mg, 73%).
LC/MS [MH+] 450 Rt=4.06 min
$^1$H NMR (400 MHz, CDCl$_3$) 2.06–2.15 (2H, m), 2.84–2.98 (4H, m), 4.93 (2H, s), 6.80 (1H, d, J=8 Hz), 7.15–7.21 (3H, m), 7.23–7.34 (4H, m), 8.05 (1H, s), 8.49 (1H, s), 8.99 (1H, s).

Example 18

5-{2-[5-Bromo-2-(4-chlorobenzyloxy)-phenyl]-cyclopent-1-enyl}-nicotinic acid

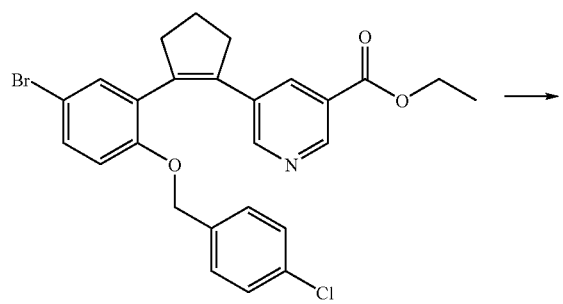

Prepared According to General Procedure 10
Product (40 mg, 70%)
LC/MS [MH+] 486 Rt=4.27 min.
$^1$NMR (400 MHz, CDCl$_3$) 2.06–2.16 (2H, m), 2.84–2.92 (2H, m), 2.92–2.98 (2H, m), 4.86 (2H, s), 6.76 (1H, d, J=8 Hz), 7.10 (2H, d, J=8 Hz), 7.21 (1H, s), 7.24–7.36 (3H, m), 8.03 (1H, s), 8.48 (1H, s), 8.99 (1H, s).

Example 19

5-{2-[5-bromo-2-(4-fluorobenzyloxy)-phenyl]-cyclopent-1-enyl}-nicotinic acid

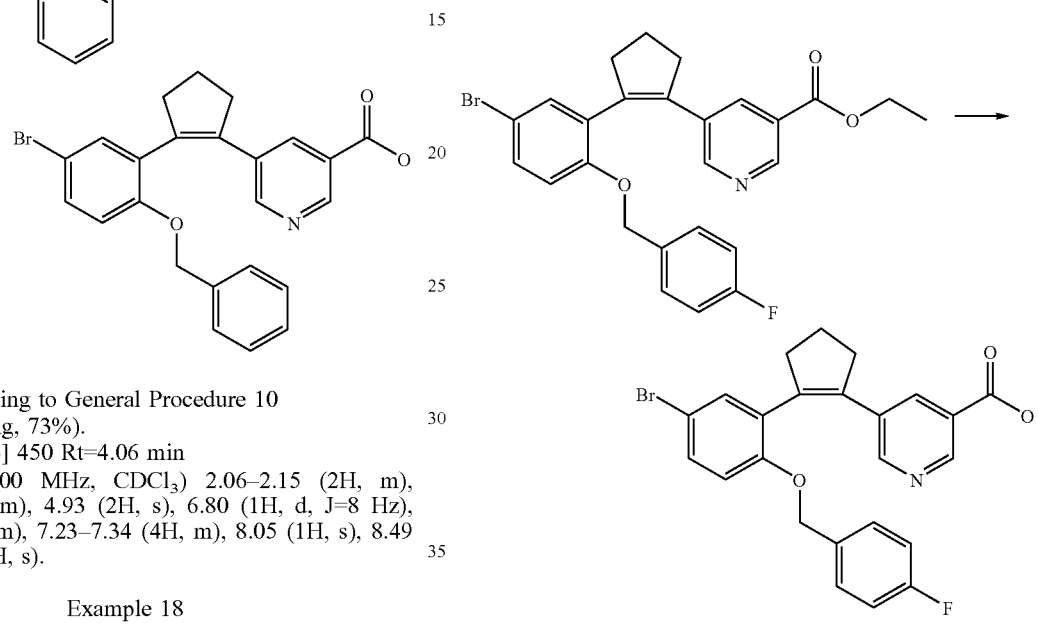

Prepared According to General Procedure 10
Product (19 mg, 76%)
LC/MS (CF105499-1) [MH+] 470 Rt=4.05 min
$^1$H NMR (400 MHz, CDCl$_3$) 2.06–2.15 (2H, m), 2.83–2.97 (4H, m), 4.86 (2H, s), 6.78 (1H, d, J=8 Hz), 6.98 (2H, t, J=7 Hz), 7.10–7.17 (2H, m), 7.20 (1H, s), 7.31 (1H, dd, J=2 Hz, J=10 Hz), 8.02 (1H, s), 8.48 (1H, s), 8.99 (1H, s).

Example 20

5-{2-[6-Bromo-2-(2,4-difluorobenzyloxy)-phenyl]-cyclopent-1-enyl}-nicotinic acid

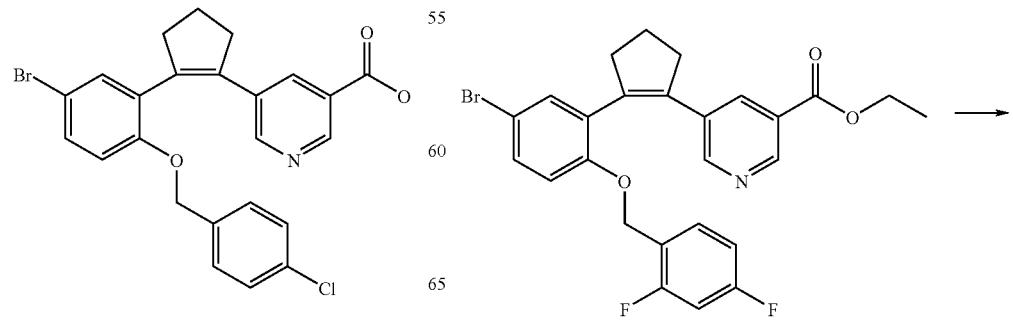

-continued

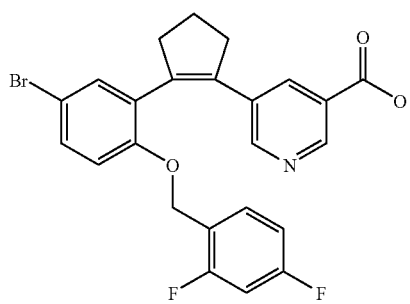

Prepared According to General Procedure 10
Product (3 mg, 73%)
LC/MS [MH+] 4.88 Rt-4.06 min.
$^1$H NMR (400 MHz, CDCl$_3$) 2.05–2.15 (2H, m), 2.81–2.90 (2H, m), 2.90–2.98 (2H, m), 4.93 (2H, s), 6.76–6.87 (3H, m), 7.10–7.23 (2H, m), 7.3–7.36 (1H, d, J=9 Hz), 8.04 (1H, s), 8.48 (1H, s), 9.00 (1H, s).

Example 21

5-{2-[5-Bromo-2-(4-chloro-2-fluorobenzyloxy)-phenyl]-cyclopent-1-enyl}-nicotinic acid

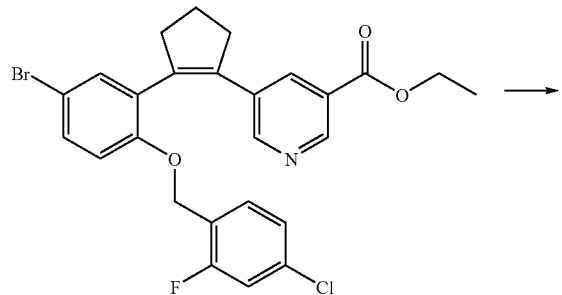

Prepared According to General Procedure 10
Product (3 mg, 80%)
LC/MS [MH+] 505 Rt=4.29 min.
$^1$H NMR (400 MHz, CDCl$_3$) 2.06–2.15 (2H, m), 2.82–2.90 (2H, m), 2.90–2.98 (2H, m), 4.93 (2H, s), 6.81 (1H, d, J=8 Hz), 7.03–7.18 (3H, m), 7.19 (1H, s), 7.33 (1H, d, J=8 Hz), 8.03 (1H, s), 8.47 (1H, s), 8.99 (1H, s).

Example 22

5-{2-[5-Bromo-2-(4-methoxybenzyloxy)-phenyl]-cyclopent-1-enyl}-nicotinic acid

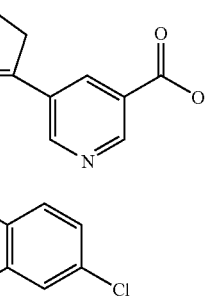

Prepared According to General Procedure 10
Product (12 mg, 92%)
LC/MS [MH+] 481 Rt=4.01 min.
$^1$H NMR (400 MHz, CDCl$_3$) 2.04–2.14 (2H, m), 2.83–2.96 (4H, m), 3.76 (3H, s), 4.83 (2H, s), 6.77–6.86 (3H, m), 7.08 (2H, d, J=8 Hz), 7.18 (1H, d, J=2.6 Hz), 7.30 (1H, dd, J=2 Hz, J=4 Hz), 8.02 (1H, s), 8.46 (1H, s), 8.99 (1H, s).

Example 23

5-{2-[5-Bromo-2-(cyclohexylmethoxy)-phenyl]-cyclopent-1-enyl}-nicotinic acid

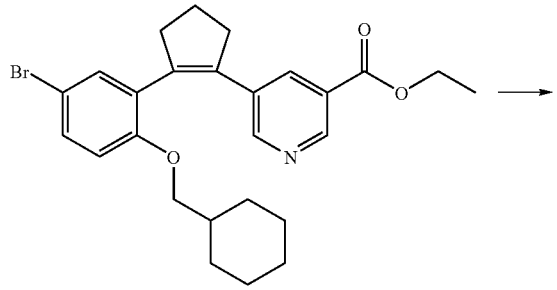

-continued

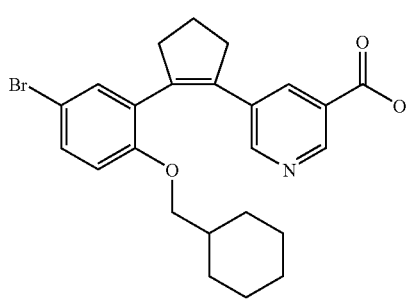

Prepared According to General Procedure 10

Product (48 mg, 96%)

LC/MS [MH+] 458 Rt=4.60 min.

Example 24

5-{2-[5-Trifluoromethyl-2-(4-chlorobenzyloxy)-phenyl]-cyclopent-1-enyl}-nicotinic acid

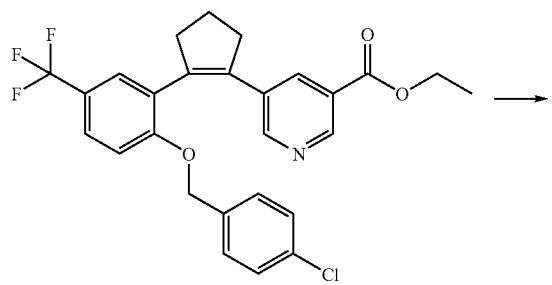

Prepared According to General Procedure 10

Product (16 mg, 89%)

LC/MS [MH+] 474 Rt=4.11 min.

$^1$H NMR (400 MHz, CDCl$_3$) 2.08–2.18 (2H, m), 2.86–2.99 (4H, m), 4.93 (2H, s) 6.95 (1H, d, J=8 Hz), 7.11 (2H, d, J=8 Hz), 7.23–7.37 (3H, m), 7.48 (1H, dd, J=2 Hz, J=9 Hz), 8.1 (1H, s), 8.44 (1H, s), 8.97 (1H, s).

Example 25

5-{2-[5-Trifluoromethyl-2-(4-fluorobenzyloxy)-phenyl]-cyclopent-1-enyl}-nicotinic acid

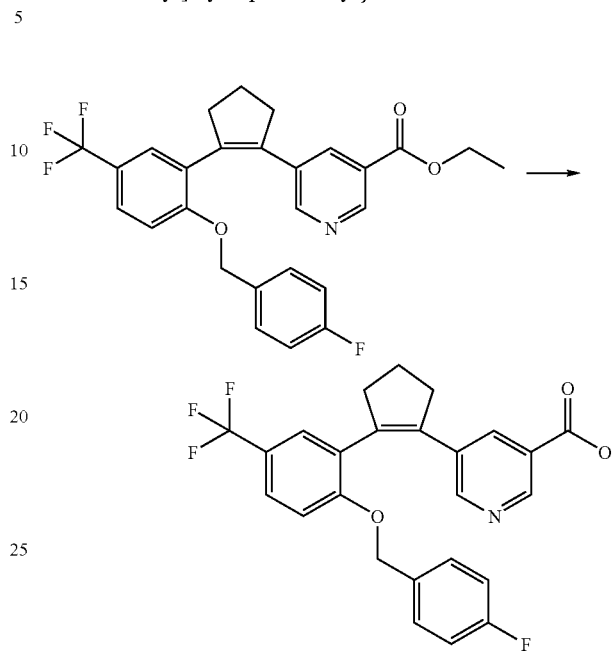

Prepared According to General Procedure 10
Product (22 mg, 81%)
LC/MS [MH+] 458 Rt=3.93 min.
$^1$H NMR (400 MHz, CDCl$_3$) 2.07–2.17 (2H, m), 2.87–2.90 (4H, m), 4.93 (2H, s), 6.93–7.04 (3H, m), 7.11–7.18 (2H, m), 7.35 (1H, s), 7.48 (1H, d, J=8 Hz), 8.03 (1H, s), 8.4 (1H, (1H, s).

Example 26

5-{2-[5-Trifluoromethyl-2-(2,4-difluorobenzyloxy)-phenyl]-cyclopent-1-enyl}-nicotinic acid

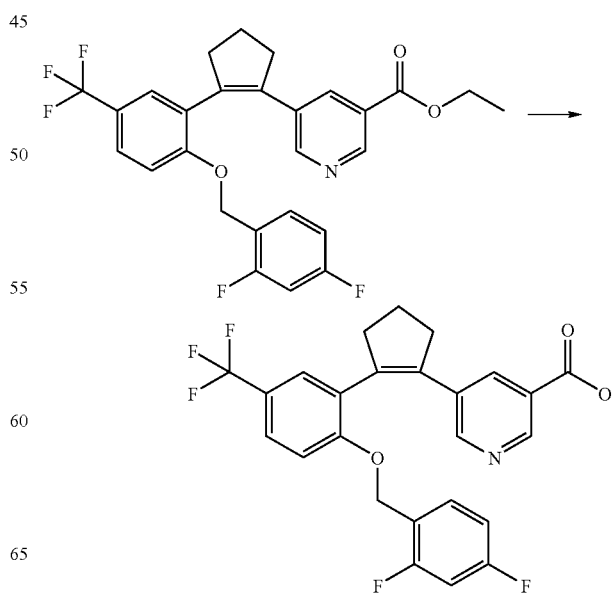

Prepared According to General Procedure 910
Product (35 mg, 88%)
LC/MS [MH+] 476 Rt=3.95 min.
$^1$H NMR (400 MHz, CDCl$_3$) 1.70–1.83 (2H, m), 2.5–2.78 (4H, m), 4.88 (2H, s), 6.65–6.75 (2H, m), 6.81–6.88 (1H, m), 7.03–7.12 (2H, m), 7.38–7.35 (1H, d, J=9 Hz), 7.86 (2H, s) 8.68 (1H, s).

Example 27

5-{2-[5-Trifluoromethyl-2-(4-chloro-2-fluorobenzyloxy)-phenyl]-cyclopent-1-enyl}-nicotinic acid

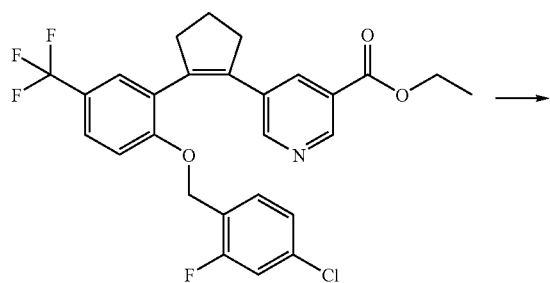

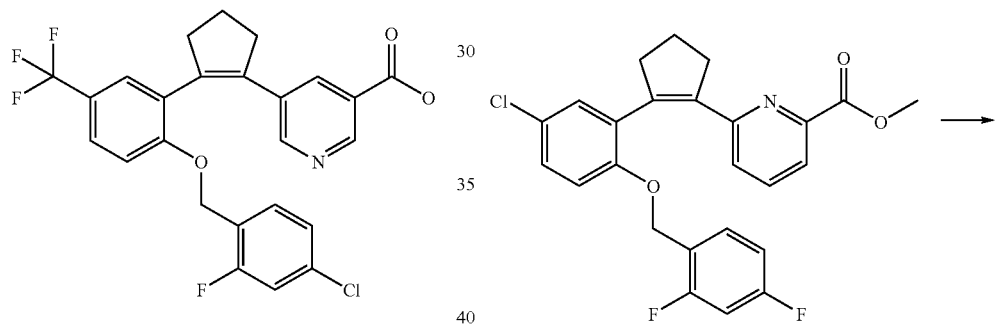

Prepared According to General Procedure 10
Product (38 mg, 86%)
LC/MS [MH−] 490 Rt=4.11 min.
$^1$H NMR (400 MHz, CDCl$_3$) 2.07–2.17 (2H, m), 2.85–2.99 (4H, m), 5.10 (2H, s), 6.99 (1H, d, J=8 Hz), 7.05–7.16 (3H, m), 7.34 (1H, d, J=2 Hz), 7.46–7.54 (1H, m), 8.04 (1H, s), 8.43 (1H, s), 8.96 (1H, s).

Example 28

5-{2-[5-Trifluoromethyl-2-(cyclohexylmethoxy)-phenyl]-cyclopent-1-enyl]-nicotinic acid

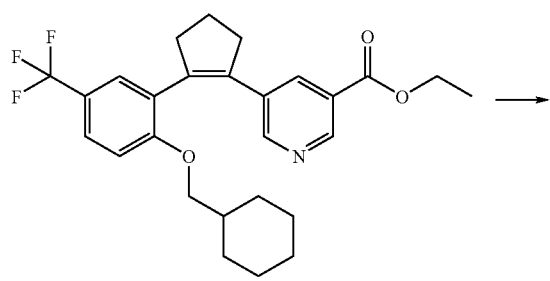

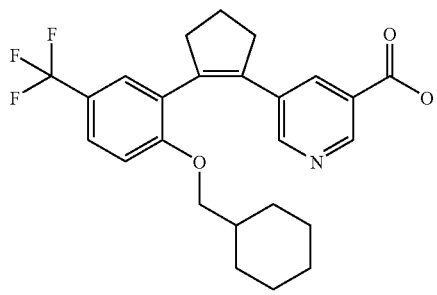

Prepared According to General Procedure 10
Product (37 mg, 86%)
LC/MS (CF105897-1) [MH+] 446.1 Rt=4.36 min.

Example 29

6-{2-[5-Chloro-2-(2,4-difluorobenzyloxy)-phenyl]cyclopent-1-enyl}-pyridine-2-carboxylic acid

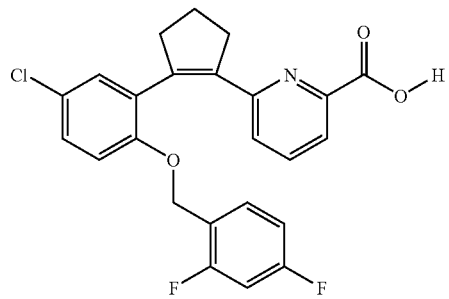

Prepared According to General Procedure 10
Product (92 mg, 76%)
LC/MS [MH+] 442 Rt=3.84 min
$^1$H NMR (400 MHz, CDCl$_3$) 2.06–2.16 (2H, m), 2.84–2.92 (2H, m), 2.97–3.5 (2H, m), 4.93 (2H, s), 6.71–6.78 (2H, m), 6.95 (1H, d, J=8 Hz) 7.05–7.13 (2H, m), 7.23–7.30 (2H, m), 7.71 (1H, t, J=7.5 Hz), 7.91 (1H, d, J=8 Hz).

Example 30

6-{2-[5-Chloro-2-(4-chloro-2-fluorobenzyloxy)-phenyl]-cyclopent-1-enyl}-pyridine-2-carboxylic acid

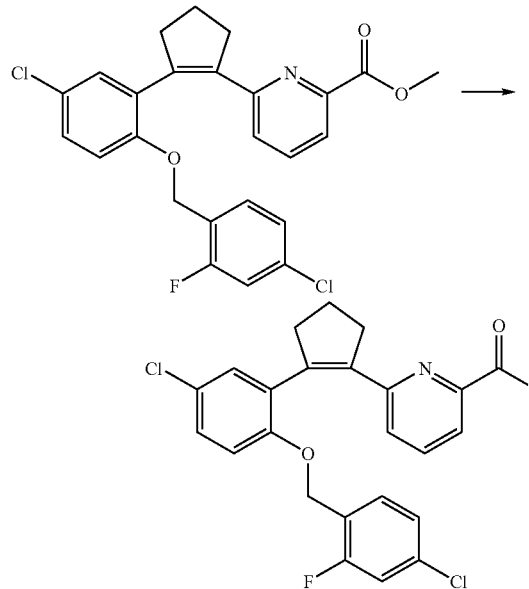

Prepared According to General Procedure 10
Product (112 mg, 85%)
LC/MS [MH+] 458 Rt=4.02 min
$^1$H NMR (400 MHz, CDCl$_3$) 2.07–2.17 (2H, m), 2.85–2.92 (2H, m), 2.98–3.05 (2H, m), 4.93 (2H, s), 6.93 (1H, d, J=8 Hz) 6.98-7.08 (3H, m), 7.11 (1H, d, J=3 Hz), 7.24–7.30 (2H, m), 7.72 (1H, t, J=8 Hz), 7.90 (1H, d, J=7 Hz).

Example 31

6-{2-[5-Chloro-2-4-chlorobenzyloxy)-phenyl]-cyclopent-1-enyl}pyridine 2-carboxylic acid

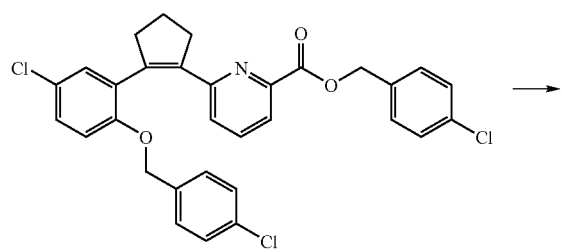

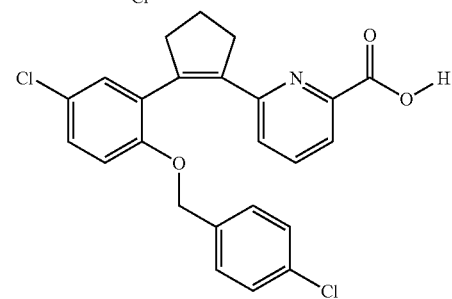

Prepared According to General Procedure 10
Product (70.0 mg, 56%)
LC/MS [MH+] 440 Rt=3.99 min.
$^1$H NMR (400 MHz CDCl$_3$) 2.07–2.17 (2H, m), 2.87–2.93 (2H, m), 2.98–3.05 (2H, m), 4.87 (2H, s), 6.89 (1H, d, J=8 Hz), 7.05 (1H, d, J=7.5 Hz), 7.1 (1H, d, J=3 Hz), 7.20–7.35 (5H, m), 7.15 (1H, t, J=7.5 Hz), 7.91 (1H, d, J=7 Hz).

Example 32

6-{2-[5-chloro-2-(4-fluorobenzyloxy)-phenyl]-cyclopent-1-enyl}-pyridine 2-carboxylic acid

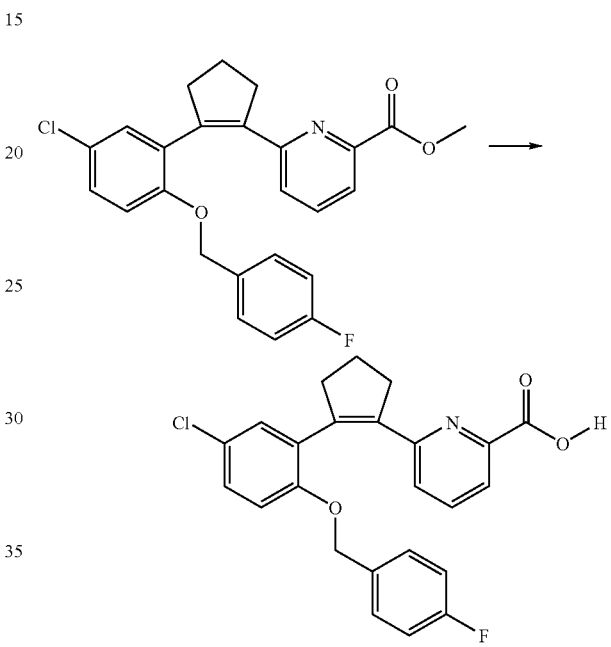

Prepared According to General Procedure 10
Product (60 mg, 50%)
LC/MS [MH+] 424 Rt=3.80 min.
$^1$H NMR (400 MHz CDCl$_3$) 2.07–2.16 (2H, m), 2.86–2.93 (2H, m), 2.98–3.05 (2H, m), 4.97 (2H, s), 6.87–6.97 (2H, m), 7.01–7.12 (4H, m), 7.21–7.37 (2H, m), 7.71 (1H, t, J=7 Hz), 7.91 (1H, d, J=7.5 Hz).

Example 33

3-{2-[5-methylsulfonyl-2-(benzyloxy)-phenyl]-cyclopent-1-enyl}-benzoic acid a) 2-Methoxy-5-methylthiophenylboronic acid 1.6M butyllithium in hexanes (3.5 ml, 5.6 mmol) was added dropwise to a stirred solution of 2-bromo-4-methylthioanisole (1.165 g, 5 mmol) in anhydrous tetrahydrofuran (30 ml) at −100° C. under nitrogen and stirred for 5 minutes then warmed to −78° C. for 1 hour. Triisopropyl borate (2.82 g, 15 mmol) was added dropwise and the mixture allowed to warm to room temperature. Hydrochloric acid (30 ml, 30 mmol) were added and the mixture stirred vigorously for 1 hour. The organic phase was separated, washed with brine, dried (MgSO$_4$), evaporated to dryness and the residue purified on Biotage using ethyl acetate/iso-hexane (3:7) to yield the title compound as a white solid. (616 mg, 62%).

¹H NMR (CDCl₃) δ: 2.47 (3H, s), 3.91 (3H, s), 5.82 (2H, s), 6.87 (1H, d, J=8 Hz), 7.41 (1H, dd, J=8 Hz, 2 Hz), 7.81 (1H, d, J=2 Hz).

b) 3-{2-[5-methylsulfonyl-2-(methoxy)-phenyl]-cyclopent-1-enyl}-benzoic acid ethyl ester A mixture of 2-methoxy-5-methylthiophenylboronic acid (594 mg, 3 mmol), 3-(2-bromo-cyclopent-1-enyl)-benzoic acid ethyl ester (885 mg, 3 mmol), potassium carbonate (2.76 g, 20 mmol) and tetrakis(triphenylphosphine)palladium(0) (347 mg, 0.3 mmol) was stirred and heated in 1:1 toluene/ethanol (30 ml) at 90° C. under nitrogen for 4 hours. After cooling the mixture was diluted with diethyl ether/water and the organic phase dried (MgSO₄), evaporated to dryness and the reside purified on Biotage using ethyl acetate/iso-hexane (1:19) to yield the title compound as a white solid. (790 mg, 71%).
¹H NMR (CDCl₃) δ: 1.33 (3H, t, J=7 Hz), 2.09 (2H, m), 2.27 (3H, s), 2.87 (2H, m), 2.96 (2H, m), 3.66 (3H, s), 4.32, (2H, q, J=7 Hz), 6.80–7.28 (5H, m), 7.77–7.85 (2H, m).
LC/MS t=4.03, [MH+] 369.1.

c) 3-{2-[5-methylsulfonyl-2-(hydroxy)-phenyl]-cyclopent-1-enyl}-benzoic acid

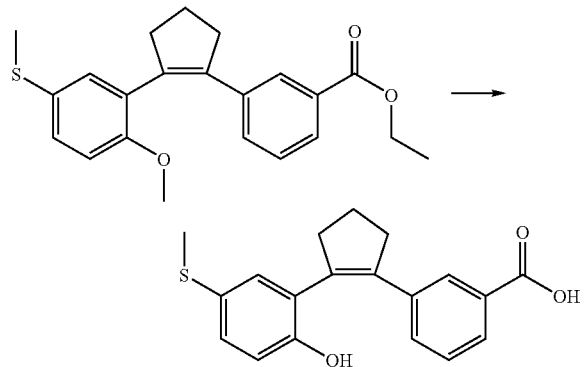

A mixture of sodium methanethiolate (700 mg, 10 mmol) and (3-{2-[5-methylsulfanyl-2-(methoxy-)-phenyl]-cyclopent-1-enyl}-benzoic acid ethyl ester (720 mg, 1.96 mmol) in dimethylformamide (15 ml) was stirred and heated at 120° C. under nitrogen for 5 hours. After cooling the mixture was diluted with diethyl ether/water and the aqueous phase separated and acidified with hydrochloric acid then extracted with diethyl ether. The organic phase was dried (MgSO₄), evaporated to dryness and the residue triturated with diethyl ether/iso-hexane to yield the title compound as a white solid, (437 mg, 68%).
¹H NMR (CDCl₃) δ: 2.14 (2H, m), 2.88 (2H, t, J=8 Hz), 3.05, (2H, J=8 hz), 4.90 (1H, br s), 6.78, (1H, d, J=7 Hz), 7.16–7.39 (4H, m), 7.92 (1H, d, J=8 Hz), 7.99 (1H, s).
LC/MS t=3.54, [MH−] 325.

Standard Alkylation Procedure d) 3-{2-[5-methylsulfonyl-2-(benzyloxy)-phenyl]-cyclopent-1-enyl}-benzoic acid benzyl ester A stirred mixture of 3-{2-[5-methylsulfonyl-2-(hydroxy)-phenyl]-cyclopent-1-enyl}-benzoic acid (65 mg, 0.2 mmol), potassium carbonate (138 mg, 1 mmol) and benzyl bromide (75 mg, 0.44 mmol) in acetone (4 ml) was refluxed for 16 hours then cooled and diluted with diethyl ether/water. The organic phase was dried (MgSO₄), evaporated to dryness and purified using Biotage with ethyl acetate/iso-hexane (1:19) to yield the title compound as a colourless gum. (85 mg, 84%).
¹H NMR (CDCl₃) δ: 2.06 (2H, m), 2.24 (3H, s), 2.90 (4H, m), 4.92 (2H, s), 5.28 (2H, s), 6.78 (1H, d, J=9 Hz), 6.97, d, J=2 Hz), 7.09–7.38 (13H, m), 7.81 (1H, d, J=8 Hz), 7.86 (1H, s).
LC/MS t=4.43, [MH+] 507.1.

Standard Hydrolysis Procedure e) 3-{2-[5-methylsulfonyl-2-(benzyloxy)-phenyl]-cyclopent-1-enyl}-benzoic acid

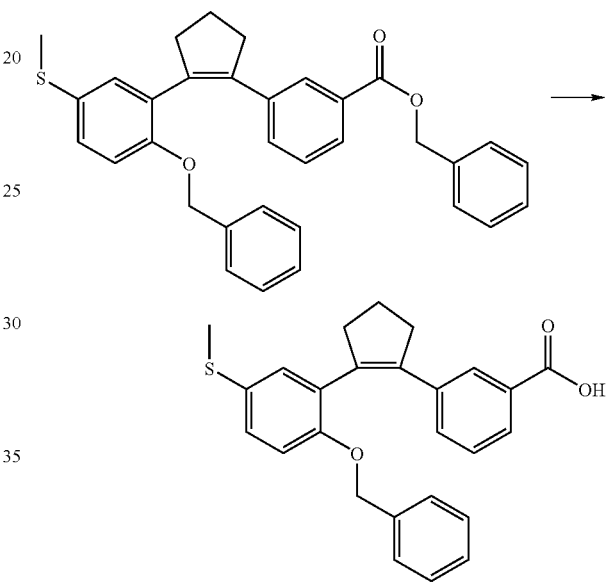

A solution of 3-{2-[5-methylsulfonyl-(benzyloxy)-phenyl]-cyclopent-1-enyl}-benzoic acid benzyl ester (30 mg, 0.059 mmol) in ethanol (5 ml) and 2M sodium hydroxide (1 ml) was left at room temperature for 20 hours then diluted with water, washed with ether and the aqueous phase separated, acidified with 2M hydrochloric acid and extracted with ether. The organic extract was dried (MgSO₄), evaporated to dryness and the residue triturated with iso-hexane to yield the title compound as a white solid. (14 mg, 57%).
¹H NMR (CDCl₃) δ: 2.08 (2H, m), 2.28, (3H, s), 2.92 (4H, m), 4.97 (2H, s), 6.85 (1H, d, J=9 Hz), 7.00 (1H, d, J=2 Hz), 7.14–7.33 (8H, m), 7.83 (1H, d, J=8 Hz), 7.91 (1H, s).
LC/MS t=4.07, [MH−] 415.1.

Example 34

3-{2-[5-methylsulfonyl-2-(benzyloxy)-phenyl]-cyclopent-1-enyl}-benzoic acid

Standard Oxidation Procedure a) 3-{2-[5-methanesulfonyl-2-(benzyloxy)-phenyl]-cyclopent-1-enyl}-benzoic acid benzyl ester 3-Chloroperbenzoic acid (53 mg, 0.236 mmol) was added to a solution of 3-{2-[5-methylsulfonyl 2-(benzyloxy)-phenyl]-cyclopent-1-enyl}-benzoic acid benzyl ester (51 mg, 0.1 mmol) in dichloromethane (4 ml) and left at room temperature for 2.5 hours. The resulting solution was diluted with ether and washed with sodium thisulphate solution and sodium bicarbonate solution then dried ($MgSO_4$), evaporated to dryness and the residue purified using Biotage with ethyl acetate/iso-hexane (1:4) to yield the title compound as a colourless gum. (31 mg, 58%).

$^1$H NMR ($CDCl_3$) δ: 2.08 (2H, m), 2.72 (3H, s), 2.91 (4H, m), 5.04 (2H, s), 5.25 (2H, s), 6.93 (1H, d, J=9 Hz), 7.21–7.39 (12H, m), 7.52 (1-H, d, J=2 Hz), 7.68 (1H, dd, J=9 Hz, 2 Hz), 7.74 (1H, s), 7.81 (1H, d, J=8 Hz).

b) 3-{2-[5-methanesulfonyl-2-(benzyloxy)-phenyl]-cyclopent-1-enyl}-benzoic acid

Prepared from 3-{2-[5-methanesulfonyl-2-(benzyloxy)-phenyl]-cyclopent-1-enyl}-benzoic acid benzyl ester using the standard hydrolysis procedure.

$^1$H NMR ($CDCl_3$) δ: 2.11 (2H, m), 2.84, (3H, s), 2.92 (4H, m), 5.09 (2H, s), 7.03 (1H, d, J=8 Hz), 7.21–7.35 (7H, m), 7.60 (1H, d, J=2 Hz), 7.76–7.84 (3H, m).
LC/MS t=3.56 [MH−] 447.1.

Using the standard alkylation, hydrolysis and oxidation procedures the following compounds were prepared:

Example 35

3-{2-[5-methylsulfanyl-2-4-fluoro-benzyloxy)-phenyl]-cyclopent-1-enyl}-benzoic acid a) 3-{2-[5-methylsulfonyl-2-(4-fluoro-benzyloxy)-phenyl]-cyclopent-1-enyl}-benzoic acid 4-fluoro-benzyl ester $^1$H NMR ($CDCl_3$) δ: 2.05 (2H, m), 2.26 (3H, s), 2.85 (2H, t, J=8 Hz), 2.93 (2H, t, J=8 Hz), 4.85 (2H, s), 5.24 (2H, s), 6.77 (1H, d, J=8 Hz), 6.95–7.35 (12H, m), 7.77–7.82 (2H, m).
LC/MS t=4.42, [MH+] 543.1.

b) 3-{2-[5-methylsulfonyl-2-(4-fluoro-benzyloxy)-phenyl]-cyclopent-1-enyl}-benzoic acid $^1$H NMR ($CDCl_3$) δ: 2.07 (2H, m), 2.30 (3H, s), 2.87 (2H, t, J=8 Hz), 2.94 (2H, t, J=8 Hz), 4.90 (2H, s), 6.83 (1H, d, J=9 Hz). 6.97–7.02 (3H, m), 7.14–7.28 (5H, m), 7.83 (1H, d, J=8 Hz), 7.89 (1H, s).
LC/MS t=4.06, [MH−] 433.

Example 36

3-{2-[5-methanesulfonyl-2-(4-fluoro-benzyloxy)-phenyl]-cyclopent-1-enyl}-benzoic acid a) 3-{2-[5-methanesulfonyl-2-(4-fluoro-benzyloxy)-phenyl}-cyclopent-1-enyl]-benzoic acid 4-fluoro-benzyl ester $^1$H NMR ($CDCl_3$) δ: 2.06 (2H, m), 2.80 (3H, s), 2.85–2.94 (4H, m) 4.97 (2H, s), 5.23 (2H, s), 6.94–7.35 (8H, m), 7.57 (2H, m), 7.72–7.80 (3H, m), 7.97 (1H, d), 8.08 (1H, s).

b) 3-{2-[5-methanesulfonyl-2-(4-fluoro-benzyloxy)-phenyl]-cyclopent-1-enyl}-benzoic acid $^1$H NMR ($CDCl_3$) δ: 2.10 (2H, m), 2.87 (3H, s), 2.87–2.98 (4H, m), 5.02 (2H, s), 6.99–7.02 (3H, m), 7.16–7.28 (4H, m), 7.62 (1H, d, J=2 Hz), 7.78–7.84 (3H, m).
LC/MS t=3.57, [MH−] 465.1.

Example 37

3-{2-[5-methylsulfonyl-2-(2,4-difluoro-benzyloxy)-phenyl]-cyclopent-1-enyl}-benzoic acid a) 3-{2-[5-methylsulfonyl-2-(2,4-difluoro-benzyloxy)-phenyl]-cyclopent-1-enyl}-benzoic acid benzyl ester $^1$H NMR ($CDCl_3$) δ: 2.06 (2H, m), 2.27 (3H, s), 2.84 (2H, t, J=8 Hz), 2.91 (2H, t, J=8 Hz), 4.91 (2H, s), 5.30 (2H, s), 6.74–6.89 (5H, m), 6.98 (1H, d, J=2 Hz), 7.11–7.26 (4H, m), 7.37 (1H, q, J=7 Hz), 7.76–7.79 (2H, m).
LC/MS t=4.46, [MH+] 579.1.

b) 3-{2-[5-methylsulfonyl-2-(2,4-difluoro-benzyloxy)-phenyl]-cyclopent-1-enyl}-benzoic acid $^1$H NMR ($CDCl_3$) δ: 2.07 (2H, m), 2.30 (3H, s), 2.86 (2H, t, J=8 Hz), 2.94 (2H, t, J=8 Hz), 4.95 (2H, s), 6.76–6.88 (2H, m), 7.02 (1H, d, J=2 Hz), 7.14–7.26 (4H, m), 7.82 (1H, d, J=8 Hz), 7.87 (1H, s).
LC/MS t=4.09, [MH−] 451.1.

Example 38

3-{2-[5-methanesulfonyl-2-(2,4-difluoro-benzyloxy)-phenyl]-cyclopent-1-enyl}-benzoic acid a) 3-{2-[5-methanesulfonyl-2-(2,4-difluoro-benzyloxy)-phenyl]-cyclopent-1-enyl}-benzoic acid benzyl ester $^1$H NMR ($CDCl_3$) δ: 2.07 (2H, m), 2.81 (3H, s), 2.85 (2H, t, J=8 Hz), 2.91 (2H, t, J=8 Hz), 5.03 (2H, s), 5.28 (2H, s), 6.80–6.90 (4H, m), 6.99 (1H, d, J=7 Hz), 7.08–7.21 (3H, m), 7.34–7.44 (1H, m), 7.55–7.61 (1H, m), 7.75–8.10 (3H, m).

b) 3-{2-[5-methanesulfonyl-2-(2,4-difluoro-benzyloxy)-phenyl]-cyclopent-1-enyl}-benzoic acid $^1$H NMR ($CDCl_3$) δ: 2.09 (2H, m), 2.88 (3H, s), 2.85–2.96 (4H, m), 5.07 (2H, s), 6.80–6.84 (2H, m), 7.06 (1H, d, J=8 Hz), 7.12–7.26 (3H, m), 7.62 (1H, d, J=2 Hz), 7.76 (1H, s), 7.80–7.84 (2H, m).
LC/MS t=3.59, [MH−] 483.

Example 2

3-{2-[(2-Benzyloxy)-phenyl]-cyclopent-1-enyl}-benzoic acid a) 3-[2-(2-Methoxy-phenyl)-cyclopent-1-enyl]-benzoic acid ethyl ester A mixture of 2-methoxyphenylboronic acid (510 mg, 3.36 mmol), 3-(2-bromo-cyclopent-1-enyl)-benzoic acid ethyl ester (840 mg, 2.85 mmol), potassium carbonate (3.18 g, 23.04 mmol) and tetrakis(triphenylphosphine)palladium(0) (370 mg, 0.32 mmol) was stirred and heated in 1:1 toluene/ethanol (30 ml) at 90° C. under nitrogen for 4 hours. After cooling the mixture was diluted with diethyl ether/water and the organic phase dried ($MgSO_4$), evaporated to dryness and the residue purified on Biotage using ethyl acetate/iso-hexane (1:19) to yield the title compound as a colourless gum. (615 mg, 67%).

¹H NMR (CDCl₃) δ: 1.32 (3H, t, J=7 Hz), 2.09 (2H, m), 2.86 (2H, t, J=8 Hz), 2.95 (2H, t, J=8 Hz), 3.68 (3H, s), 4.29 (2H, q, J=7 Hz), 6.82–7.26 (6H, m), 7.76 (1H, d, J=8 Hz), 7.84 (1H,s).

b) 3-{2-[2-(Hydroxy)-phenyl]-cyclopent-1-enyl}-benzoic acid

3-[2-(2-Methoxy-phenyl)-cyclopent-1-enyl]-benzoic acid ethyl ester (610 mg, 1.89 mmol) was dissolved in 1M boron tribromide in dichloromethane solution (18.9 ml, 18.9 mmol) and left at room temperature for 18 hours. The resulting solution was poured onto ice and extracted with dichloromethane. The organic extract was dried (MgSO₄), evaporated to dryness and purified by chromatography using biotage with iso-hexane containing a gradient of ethyl acetate (20–40%) to yield the title compound as a light brown solid. (186 mg, 35%).

¹H NMR (CDCl₃) δ: 2.14 (2H, m), 2.89 (2H, t, J=8 Hz), 3.05 (2H, t, J=8 Hz), 4.9 (1H, br s), 6.84 (1H, d, J=8 Hz), 6.93 (1H, t, J=7 Hz), 7.18–7.38 (4H, m), 7.91 (1H, d, J=8 Hz), 7.99 (1H, s).

LC/MS t=3.44, [MH−] 279.

Using the standard alkylation and hydrolysis procedures the following compounds were prepared.

c) 3-{2-[2-(Benzyloxy)-phenyl]-cyclopent-1-enyl}-benzoic acid benzyl ester

¹H NMR (CDCl₃) δ: 2.06 (2H, m), 2.90 (4H, m), 4.94 (2H, s), 5.27 (2H, s), 6.80–6.87 (2H, m), 7.00 (1H, d, J=2 Hz), 7.13–7.36 (12H, m), 7.79 (1H, d, J=8 Hz), 7.85 (1H, s), LC/MS t=4.37, [MH+] 443.1.

d) 3-{2-[2-(Benzyloxy)-phenyl]-cyclopent-1-enyl}-benzoic acid

¹H NMR (CDCl₃) δ: 2.08 (2H, m), 2.92 (4H, m), 5.00 (2H, s), 6.88 (1H, t, J=8 Hz), 6.92 (1H, d, 8 Hz), 7.02 (1H, dd, J=8 Hz, 2 Hz), 7.16–7.31 (8H, m), 7.81 (1H, d, J=8 Hz), 7.91 (1H, s).

LC/MS t=3.98, [MH−]369.1.

Examples 39 to 41 were prepared using the standard alkylation and hydrolysis procedures.

Example 39

3-{2-[2-(2,4-Difluoro-benzyloxy)-phenyl]-cyclopent-1-enyl}-benzoic acid a) 3-{2-[2-(2,4-Difluoro-benzyloxy)-phenyl]-cyclopent-1-enyl}-benzoic acid 2,4-difluoro-benzyl ester ¹H NMR (CDCl₃) δ: 2.05 (2H, m), 2.85 (2H, t, J=8 Hz), 2.91 (2H, t, J=8 Hz), 4.94 (2H, s), 5.28 (2H, s), 6.74–7.37 (15H, m), 7.76 (1H, d, J=8 Hz), 7.79 (1H, s).

b) 3-{2-[2-(2,4-Difluoro-benzyloxy)-phenyl]-cyclopent-1-enyl}-benzoic acid

¹H NMR (CDCl₃) δ: 2.07 (2H, m), 2.87 (2H, t, J=8 Hz), 2.94 (2H, t, J=8 Hz), 4.99 (2H, s), 6.76–6.82 (2H, m), 6.87–6.95 (2H, m), 7.04 (1H, dd, J=8 Hz, 2 Hz) 7.14–7.26 (4H, m), 7.81 (1H, d, J=8 Hz), 7.87 (1H,s).

LC/MS t=4.02, [MH−] 405.1.

Example 40

3-{2-[2-(4-chloro-2-fluoro-benzyloxy)-phenyl]-cyclopent-1-enyl}-benzoic acid a) 3-{2-[2-(4-Chloro-2-fluoro-benzyloxy)-phenyl]-cyclopent-1-enyl}-benzoic acid 4-chloro-2-fluoro-benzyl ester ¹H NMR (CDCl₃) δ: 2.06 (2H, m), 2.85 (2H, t, J=8 Hz), 2.92 (2H, t, J=8 5.29 (2H, s), 6.86 (2H, m), 7.01–7.30 (10H, m), 7.75–7.79 (2H, m).

b) 3-{2-[2-(4-Chloro-2-fluoro-benzyloxy)-phenyl]-cyclopent-1-enyl}-benzoic acid

¹H NMR (CDCl₃) δ: 2.08 (2H, m), 2.87 (2H, t, J=8 Hz), 2.95 (2H, t, J=8 Hz), 4.99 (2H, s), 6.88–6.92 (2H, m), 7.04–7.07 (3H, m), 7.14–7.26 (4H, m) 7.81 (1H, d, J=8 Hz), 7.86 (1H, s).

LC/MS t=4.21, [MH−] 421.0, 422.9.

Example 41

3-{2-[2-4-Methoxy-benzyloxy)-phenyl]-cyclopent-1-enyl}-benzoic acid a) 3-{2-[2-(4-Methoxy-benzyloxy)-phenyl]-cyclopent-1-enyl}-benzoic acid 4-methoxy-benzyl ester ¹H NMR (CDCl₃) δ: 2.04 (2H, m), 2.88 (4H, m) 3.78 (3H, s), 3.82 (3H, s), 4.87 (2H, s), 5.20 (2H, s), 6.79–6.98 (7H, m), 7.11–7.32 (7H, m), 7.77 (1H, d, J=8 Hz), 7.83 (1H, s).

b) 3-{2-[2-(4-Methoxy-benzyloxy)-phenyl]-cyclopent-1-enyl}-benzoic acid

¹H NMR (CDCl₃) δ: 2.06 (2H, m), 2.91 (4H, m), 3.79 (3H, s), 4.92 (2H, s), 6.82–6.87 (2H, m), 6.93 (1H, d, J=8 Hz), 7.01 (1H, dd, J=8 Hz, 2 Hz)) 7.13–7.26 (6H, m), 7.81 (1H, d, J=8 Hz), 7.89 (1H,s).

LC/MS t=3.94, [MH−] 399.1.

Example 42

3-{2-[5-cyano-2-(benzyloxy)-phenyl]-cyclopent-1-enyl}-benzoic acid a) 5-Cyano-2-methoxyphenylboronic acid This compound was prepared in a similar manner to that described for 2-methoxy-5-methylthio phenylboronic acid.

¹H NMR (DMSO-d₆) δ: 3.85 (3H,s), 7.13 (1H, d, J=9 Hz), 7.78 (1H, d, J=2 Hz), 7.84 (1H, dd, J=8 Hz, 2 Hz) 8.03 (2H, br s).

LC/MS t=2.13, [MH+] 178.

b) 3-{2-[5-Cyano-2-(methoxy)-phenyl]-cyclopent-1-enyl}-benzoic acid ethyl ester

This compound was prepared in a similar manner to that described for 3-{2-[5-methylsulfonyl-2-(methoxy)-phenyl]-cyclopent-1-enyl}-benzoic acid ethyl ester.

¹H NMR (CDCl₃) δ: 1.34 (3H, t, J=7 Hz), 2.10 (2H, m), 2.82 (2H, t, J=7 Hz), 2.96 (2H, t, J=7 Hz), 3.72 (3H, s), 4.31, (2H, q, J=7 Hz), 6.90 (1H d, J=9 Hz), 7.17–7.28 (3H, m) 7.53 c) 3-{2-[5-Cyano-2-(hydroxy)-phenyl]-cyclopent-1-enyl}-benzoic acid

This compound was prepared in a similar manner to that described for 3-[2-(2-hydroxy-phenyl)-cyclopent-1-enyl]-benzoic acid.

$^1$H NMR (CDCl$_3$) δ: 2.17 (2H, m), 2.88 (2H, t, J=8 Hz), 3.06 (2H, t, J=8 Hz), 5.6 (1H, br s), 6.89 (1H, d, J=8 Hz), 7.28–7.36 (2H, m), 7.48 (1H, dd, J=8 Hz, 2 Hz), 7.53 (1H, d, J=2 Hz), 7.94 (2H, m).

LC/MS t=3.36, [MH−] 304.1 d) 3-{2-[5-cyano-2-(benzyloxy)-phenyl]-cyclopent-1-enyl}-benzoic acid

Prepared using the standard alkylation and hydrolysis procedures.

$^1$H NMR (CDCl$_3$) δ: 2.08 (2H, m), 2.86 (2H, t, J=8 Hz), 2.93 (2H, t, J=8 Hz), 5.03 (2H,s), 5.6 (1H, brs) 6.9 (1H, d, J=8 Hz), 7.15–7.5 (9H, m), 7.8–8.0 (2H, m).

LC/MS t=3.81, [MH−] 394.1

Example 43

3-{2-[5-cyano-2-(2,4-difluoro-benzyloxy)-phenyl]-cyclopent-1-enyl}-benzoic acid Prepared using the standard alkylation and hydrolysis procedure.

$^1$H NMR (CDCl$_3$) δ:2.08 (2H, m), 2.83 (2H, t, 8 Hz), 2.94 (2H, t, J=8 Hz), 5.02 (2H,s), 5.8 (1H, br s) 6.82–6.84 (2H, m), 6.97 (1H, d, J=8 Hz), 7.1–7.5 (4H, m), 7.79 (1H,s), 7.86(1H, m).

LC/MS t=3.84,[MH−] 430.1.

General Procedure A

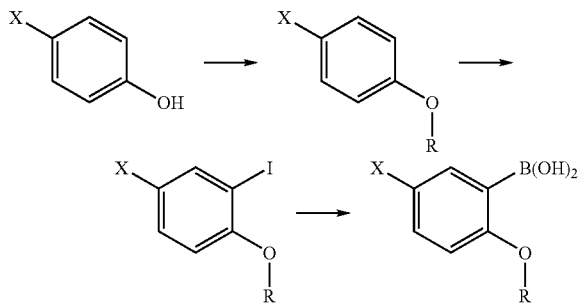

A(i) 4-(Benzyloxy)Benzotrifluoride

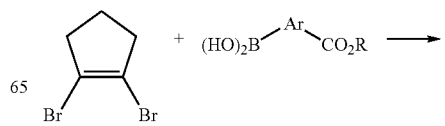

A solution of 4-hydroxybenzotrifluoride (8.55 g, 52.78 mmol) in acetone (200 ml) was treated with benzyl bromide (9.87 g, 6.86 ml , 58.05 mmol) and potassium carbonate (10.94 g, 79.16 mmol). The mixture was stirred and heated to reflux under nitrogen for 3 h. After cooling, diethyl ether (400 ml) and water (400 ml) were added and the aqueous phase re-extracted with diethyl ether (100 ml). The combined organic layers were washed with water, dried (MgSO$_4$) and the solvent removed in vacuo to leave the title compound as a white solid. (12.71 g, 95%)

$^1$H NMR (CDCl$_3$) δ: 5.11 (2H,s), 7.03 (2H, d, J=9 Hz), 7.34–7.44 (5H, m), 7.55 (2H, d, J=9 Hz).

A(ii) 2-Benzyloxy-5-(trifluoromethyl)iodobenzene

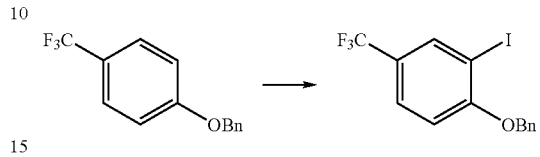

A solution of 4-(benzyloxy)benzotrifluoride (12.71 g, 50.4 mmol) in acetonitrile (300 ml) was stirred under nitrogen and 1-(chloromethyl)-4-fluoro-1,4-diazoniabicyclo[2.2.2]octane bis(tetrafluoroborate) (17.75 g, 50.4 mmol) and iodine (6.4 g, 25.2 mmol) added. The mixture was stirred at room temperature for 88 h. The solvent was evaporated and the residue partitioned between ethyl acetate (400 ml) and water (400 ml). The organic layer was washed with water, dried (MgSO$_4$) and evaporated to an orange oil which was purified by flash chromatography (silica gel, 5% ethyl acetate: isohexane) to give the title compound as an orange oil (15.07 g, 79%)

$^1$H NMR (CDCl$_3$) δ:5.21 (2H, s), 6.89 (1H, d J=9 Hz), 7.32–7.55 (6H, m), 8.04 (1H, d, J=2 Hz).

A(iii) 2-Benzyloxy-5-trifluoromethyl)benzeneboronic Acid

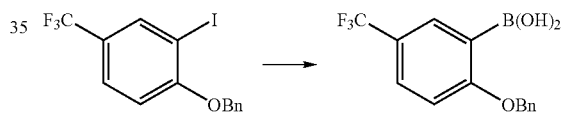

A solution of 4-benzyloxy-3-iodobenzotrifluoride (15.07 g, 39.85 mmol) in tetrahydrofuran (200 ml) was cooled to −40° C. with stirring under nitrogen. 2M isopropylmagnesium chloride in diethyl ether (39.85 ml, 79.7 mmol) was added dropwise and the mixture stirred at −40° C. for 40 minutes, then cooled to −75° C. Trimethyl borate (8.3 g, 9.2 ml, 79.7 mmol) was added at −75° C. over 10 minutes and the reaction stirred and allowed to reach 0° C. over 1 h. 1M hydrochloric acid (200 ml) was added and the mixture stirred vigorously for 1 h. The layers were separated and the aqueous layer extracted with diethyl ether (100 ml). The combined organic layers were washed with water, dried (MgSO$_4$) and evaporated. The residue was flash chromatographed (silica gel, 5–20% ethyl acetate: isohexane) to give the title compound as a white solid. (7.71 g, 65%).

$^1$H NMR (CDCl$_3$) δ:5.20 (2H, s), 5.79 (2H, s), 7.05 (1H, d, J=9 Hz), 7.39–7.44 (5H, m), 7.68 (1H, dd J=2 Hz, J=9 Hz), 8.15 (1H, d, J=2 Hz).

General Procedure 1

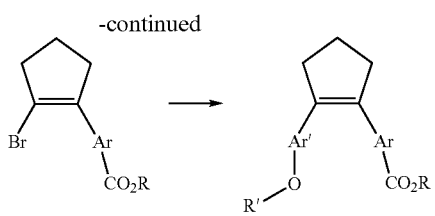

1(a(i)) 3-(2-Bromocyclopent-1-enyl)benzoic acid ethyl ester 1,2-Dibromocyclopentene (5.0 g, 22.1 mmol), (3-ethoxycarbonylphenyl) boronic acid (Combiblocks) (4.260 g, 22.1 mmol), tetrakistriphenylphosphinepalladium(0) (0.500 g) and potassium carbonate (5.0 g) were stirred at 80° C. under nitrogen for 18 h in dimethoxyethane (30 mL). The reaction mixture was then filtered through Kieselguhr and evaporated down to give an oil.

Purification by chromatography using iso-hexane containing a gradient of dichloromethane (0–30%) gave the required product (1.150 g, 30% yield).

1(a(ii)) 3-amino-5-(2-bromo-cyclopent-1-enyl)-benzoic acid methyl ester

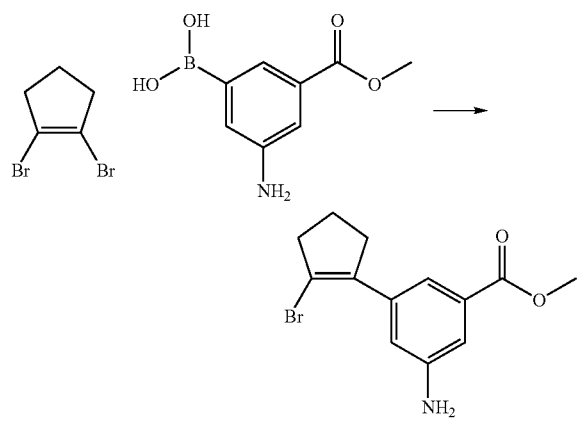

(3-amino-5-methoxycarbonylphenyl)boronic acid (2.66 g, 13.6 mmol), Pd(0) [PPh$_3$]$_4$ (1.57 g, 1.36 mmol), potassium carbonate (15 g, 108 mmol) and 1,2-dibromocyclopentene (12 g, 53 mmol) in toluene-ethanol (1:1 60 mL) were stirred at 90° C., under nitrogen, for 2 hrs. Upon cooling, the reaction mixture was poured into water and extracted with ethyl acetate (40×3 mL). The combined organic layers were dried over MgSO$_4$ and concentrated. Purification was carried out on a Biotage® using isohexane containing a gradient of ethyl acetate (0–20%) to give the required product as yellow solid (3.5 g, 87%). $^1$H NMR (CDCl$_3$):1.96–2.0 (2H,m), 2.50 (2H,t,J=7.4), 2.67 (2H,t,J=7.4), 3.80 (2H,bs), 3.88 (3H,s), 7.14 (1H,s), 7.28 (1H,s), 7.59 (1H,s). LC/MS [MH+]=296, 298 Rt=3.38.

I(b) 3-[2-(2-Benzyloxy-5-chlorophenyl)cyclopent-1-enyl]benzoic acid ethyl ester 3-(2-Bromocyclopent-1-enyl)-benzoic acid ethyl ester (148 mg, 0.5 mmol), tetrakis(triphenylphosphine)palladium (0) (30 mg), potassium carbonate (0.20 g) and (2-benzyloxy-5-chlorophenyl) boronic acid (150 mg, 0.5 mmol) in dimethoxyethane (5 mL) were refluxed for 17 h under nitrogen. The reaction mixture was then filtered through Kieselghur and evaporated down to an oil. Purification was carried out on a Water's separation pack (10 g) with dichloromethane/iso-hexane to give the product (85 mg). LC/MS [MH+] 433 Rt=4.21 min. $^1$H NMR (400 MHz, CDCl$_3$) 1.31 (3H, t, J=7 Hz), 2.01–2.12 (2H, m), 2.81–2.88 (4H, m), 4.28 (2H, q, J=7 Hz), 4.93 (2H, s), 6.81 (1H, d, J=9 Hz), 7.02 (1H, J=2 Hz), 7.10–7.33 (8H, m), 7.76–7.86 (2H, m).

General Procedure B

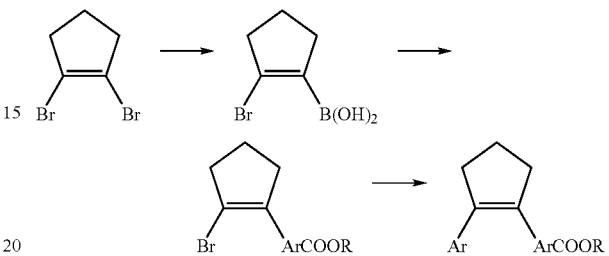

General Procedure B(i)

2-Bromocyclopent-1-Enylboronic Acid

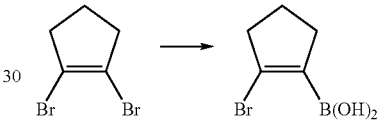

1,2-dibromocyclopentene (10.1 g, 0.044 mol) was dissolved in 100 mL of tetrahydrofuran, cooled to −78° C. and n-butyllithium, 1.6 M solution in hexane (28 mL, 0.044 mol), was added dropwise over 20 minutes under nitrogen. The mixture was stirred at −78° C. for further 20 minutes, then triisopropylborate (20.8 mL, 0.089 mol) was added dropwise. The cooling bath was then removed and the reaction mixture was allowed to reach room temperature. The reaction mixture was then quenched with 1M HCl (40 mL) and stirred vigorously at room temperature for 15 minutes. The organic layer was then separated, dried over magnesium sulphate and evaporated down. The residue was triturated with dichloromethane to yield the title compound as a white solid (2.2 g, 26%). $^1$H NMR (CD$_3$OD):1.92–1.98 (2H, m), 2.50–2.55 (2H, m), 2.73–2.78 (2H, m), 5.02 (2H,s),

General Procedure B(ii)

3-(2-Bromo-Cyclopent-1-Enyl)-6-Methylbenzoic Acid Ethyl Ester

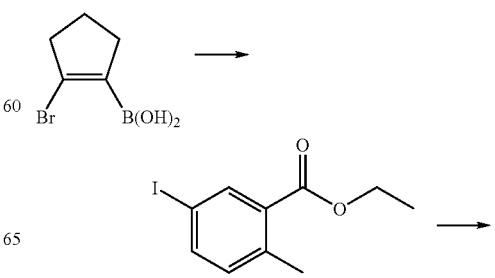

-continued

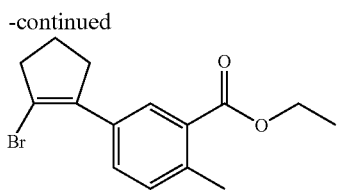

a) A solution of 5-amino-2-methylbenzoic acid ethyl ester (500 mg, 2.8 mmol) and iodine (425 mg, 1.68 mmol) in toluene (20 ml) was cooled to 0° C. and treated with t-butyl nitrite (303 mg, 2.94 mmol). The reaction mixture was stirred at 0° C. for 1 hour then at room temperature over the weekend. The reaction mixture was washed with 10% aq sodium thiosulphate (20 ml), and brine (20 ml), dried and evaporated. Flash chromatography [silica, iso-hexane/ EtOAc, 9:1] gave 5-iodo-2-methylbenzoic acid ethyl ester as a brown oil 510 mg 63%. $^1$H NMR (CDCl$_3$):1.39 (3H, t, J=12 Hz), 2.53 (3H, s), 4.36 (2H, q, J=12 Hz), 6.97 (1H,d, J=12 Hz), 7.37 (1H, d, J=12 Hz), 8.20 (1H, s).

b) 5-iodo-2-methyl-benzoic acid ethyl ester (500 mg, 1.72 mmol), 2-bromo-cyclopent-1-enylboronic acid (330 mg, 1.72 mmol), potassium carbonate (1.9 g, 13.8 mmol), Pd(0) [PPh$_3$]$_4$ (100 mg, 0.086 mmol) in toluene-ethanol (1:1 60 mL) were stirred at 90° C., under nitrogen, for 4 hrs. Upon cooling, the reaction mixture was poured into water and extracted with ether (50 mL). The organic layers was dried (MgSO$_4$), filtered and concentrated. Purification was carried out on a Biotage® using 20% of ethyl acetate in iso-hexane to give the required product as yellow oil (390 mg, 73%). $^1$HNMR (CDCl$_3$):1.39 (3H, t, J=12 Hz), 2.01–2.08 (2H, m), 2.59 (3H, s), 2.77(2H,m), 2.85(2H,m), 4.36 (2H, q,J=12 Hz), 7.24 (1H, t, J=12 Hz), 7.65 (1H, d, J=12 Hz), 8.12(1H,s).

General Procedure B(iii)

5-{2-[5-Chloro-2-Benzyloxyphenyl]Cyclopenten-1-Enyl}- 2-Methylbenzoic Acid Ethyl Ester

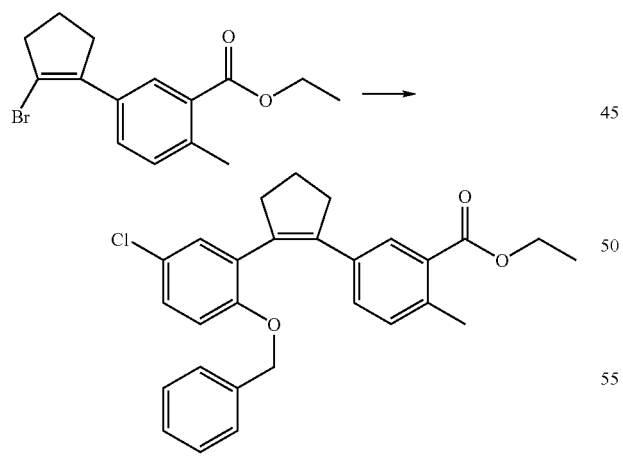

(5-chloro-2-benzyloxyphenyl)boronic acid (150 mg, 0.5 mmol), Pd(0)[PPh$_3$]$_4$ (25 mg, 0.021 mmol), potassium carbonate (483 mg, 3.36 mmol) and (3-(2-bromo-cyclopent-1-enyl)-6-methylbenzoic acid ethyl ester (130 mg, 0.42 mmol) in toluene-ethanol (1:1 10 mL) were stirred at 90° C., under nitrogen, for 2 hrs. Upon cooling, the reaction mixture was poured into water and extracted with ethyl acetate (3×20 mL). The combined organic layers were dried (MgSO$_4$), filters and concentrated. The residue was purified on a Biotage® using 5% of ethyl acetate in iso-hexane to give the required product as white solid (114 mg, 61%). $^1$HNMR (CDCl$_3$):1.27(3H,t, J=12 Hz), 2.01–2.08(2H, m), 2.51(3H, s), 2.83(2H, t, J=6 Hz), 2.90(2H, t, J=6 Hz), 4.94(2H, s), 6.80(1H, d, J=Hz), 6.97–7.70 (9H, m), 7.70(1H, s). LC/MS; Rt=4.22 [M+H] 447 (1 Cl)

General Procedure C

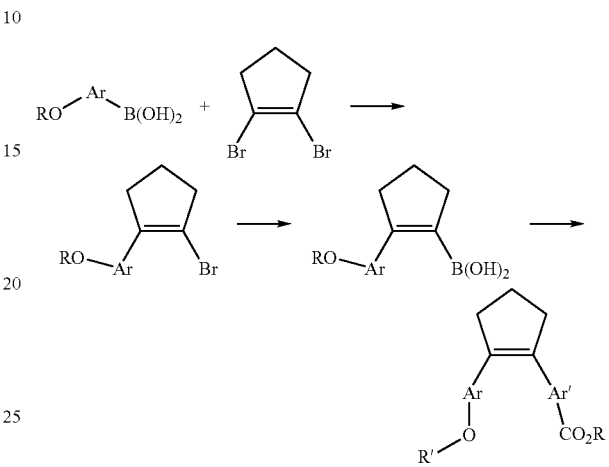

General Procedure C(i)

1-Bromo-2-(2-Benzyloxy-5-Chlorophenyl)Cyclopentene

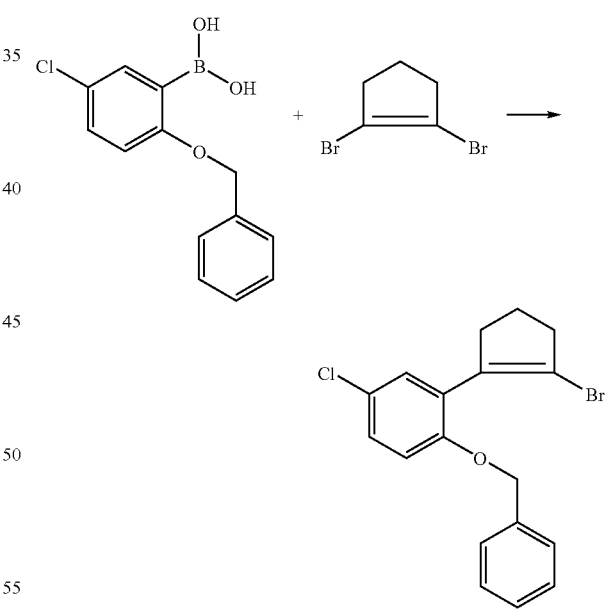

A mixture of 1,2-dibromocyclopentene (1.72 g, 7.6 mmol), 2-benzyloxy-5-chlorophenylboronic acid (500 mg, 1.9 mmol), potassium carbonate (2.1 g, 15.2 mmol) and tetrakis (triphenyl phosphine)palladium(0) (220 mg, 0.19 mmol) was stirred and heated in 1:1 toluene/ethanol (15 ml) at 90° C. under nitrogen for 2 hours. After cooling the mixture was diluted with diethyl ether/water and the organic phase dried (magnesium sulphate), evaporated to dryness and the residue purified by chromatography on silica (2% ethyl acetate in iso-hexane then 10% dichloromethane in iso-hexane) to yield the title compound as a white solid (427 mg, 62%). $^1$H NMR (CDCl$_3$) δ:1.99–2.07 (2H, m), 2.67–2.72 (2H, m), 2.76–2.81 (2H, m), 5.06 (2H, s), 6.85 (1H, d, J=9 Hz), 7.17–7.38 (7H, m).

General Procedure C(ii)

2-(2-Benzyloxy-5-Chlorophenyl)Cyclopentene-1-Boronic Acid

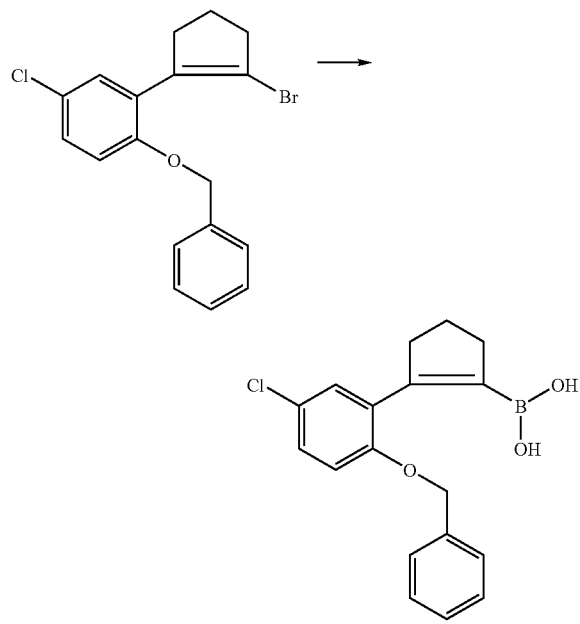

A solution of n-butyllithium (0.73 ml, 1.6M in hexanes, 1.17 mmol) was added to a solution of 1-bromo-2-(2-benzyloxy-5-chlorophenyl)cyclopentene (424 mg, 1.17 mmol) in anhydrous tetrahydrofuran (12 ml) at −78° C. under nitrogen. The resulting solution was stirred for 15 minutes and triisopropyl borate (440 mg, 2.34 mmol) was added. The mixture was allowed to warm to room temperature, 1M hydrochloric acid (20 ml) was added and stirred vigorously for 15 minutes. After diluting with ether the organic phase was dried (magnesium sulphate), evaporated and purified by chromatography on silica (1:4 ethyl acetate/iso-hexane) to give the title compound as a white solid (214 mg, 58%). LC/MS: Rt 3.4, [2 MH−] 637.3.

General Procedure C(iii)

2-{2-[5-Chloro-2-(Benzyloxy)Phenyl]Cyclopent-1-Enyl}Pyrimidine-4-Carboxylic Acid Ethyl Ester

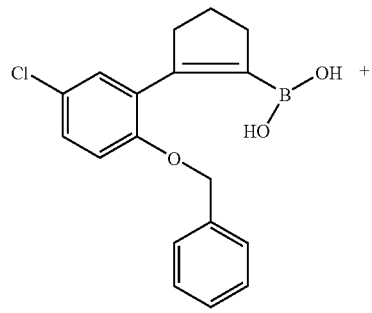

-continued

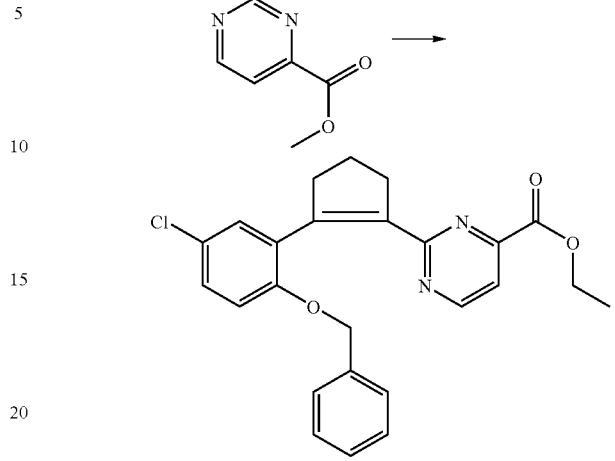

A mixture of 2-chloropyrimidine-4-carboxylic acid methyl ester (114 mg, 0.66 mmol), 2-(2-benzyloxy-5-chlorophenyl)cyclopentene-1-boronic acid (209 mg, 0.66 mmol), potassium carbonate (729 mg, 5.28 mmol) and tetrakis(triphenylphosphine)palladium(0) (76 mg, 0.066 mmol) was stirred and heated in 1:1 toluene/ethanol (6 ml) at 90° C. under nitrogen for 2 hours. After cooling the mixture was diluted with diethyl ether/water and the organic phase dried (magnesium sulphate), evaporated to dryness and the residue purified by chromatography on silica (12% ethyl acetate in iso-hexane) to yield the title compound as a colourless gum (109 mg, 38%). LC/MS: Rt 3.8 [MH+] 435.3, 437.3.

General Procedure D

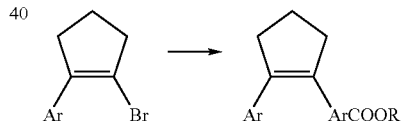

5-[2-(2-Benzyloxy-5-Chlorophenyl)Cyclopent-1-Enyl]-3-Aminobenzoic Acid Methyl Ester

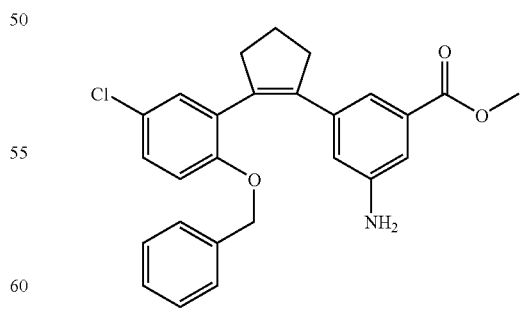

A mixture of 3-amino-5-methoxycarbonylphenylboronic acid (161 mg, 0.82 mmol), Pd(0) [PPh$_3$]$_4$ (50 mg, 5 mol %), potassium carbonate (905 mg, 6.6 mmol) and 2-(2-benzyloxy-5-chloro)phenyl-1-bromocyclopent-1-ene (298 mg, 0.82 mmol) in toluene-ethanol (1:1 10 mL) were stirred at 90° C., under nitrogen, for 2 hrs. After cooling the reaction mixture was poured onto water (10 ml) and extracted with diethyl ether (2×10 ml). The combined extracts were dried and evaporated. Flash chromatography [EtOAc/Iso-hexane 5:95-1:4] gave the product as a yellow oil 200 mg 56% LC/MS: Rt=4.00 [M+H] 434 (1 Cl)

General Procedure 4

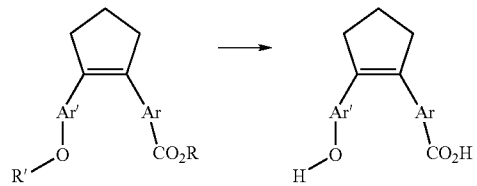

3-[2-5-Bromo-2-Hydroxyphenyl)Cyclopent-1-Enyl]-Benzoic Acid

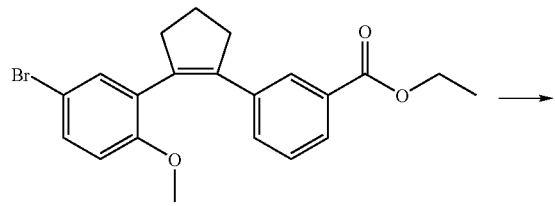

3-[2-(5-Bromo-2-methoxyphenyl)cyclopent-1-enyl]benzoic acid ethyl ester (416 mg, 10.0 mmol) in dichloromethane (5 mL) was cooled under nitrogen to ~40° C. and was treated with a molar solution of borontribromide in dichloromethane (20 mL, 20.0 mmol). The reaction mixture was then allowed to reach room temperature and kept stirring over night. The reaction mixture was then quenched with ice/water (50/50 mL) and more dichloromethane (30 mL) was added. After stirring vigorously for 1.5 hr, the organic layer was separated, dried (magnesium sulphate), evaporated down and chromatographed with 1% methanol in dichloromethane to give the title compound. (300 mg, 80%). $^1$H NMR (400 MHz, CDCl$_3$) 2.08–2.19 (2H, m), 2.82–2.90 (2H, m), 3.00–3.08 (2H, m), 6.72 (1H, d, J=4 Hz), 7.24–7.40 (4H, m), 7.94 (1H, d, J=4 Hz), 7.99 (1H, s). LC/MS [MH−] 359 Rt=3.74 min.

General Procedure 5

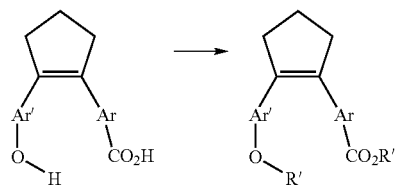

6-{2-[5-Chloro-2-(4-Chlorobenzyloxy)Phenyl]Cyclopent-1-Enyl}Pyridine-2-Carboxylic Acid 4-Chlorobenzyl Ester

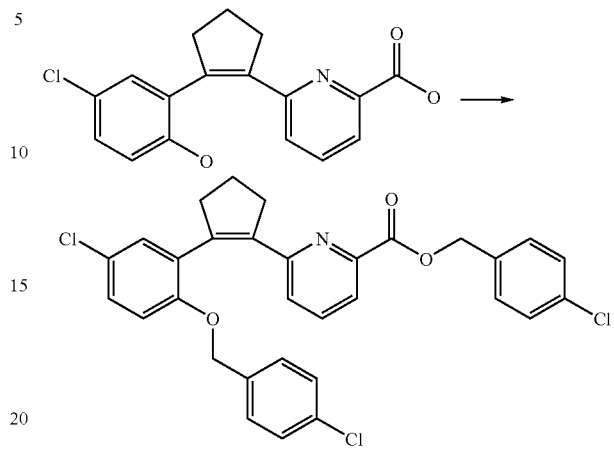

6-[2-(5-Chloro-2-hydroxyphenyl)cyclopent-1-enyl]pyridine-2-carboxylic acid (97 mg, 0.30 mmol) was refluxed in 2-butanone (4 mL) with 4-chlorobenzyl bromide (140 mg, 0.70 mmol) and potassium carbonate (1.0 g) under nitrogen for five hours. The reaction mixture was then filtered through highflo, evaporated down to an oil and chromatographed on a Water's sep-pak (10 g) with ether/isohexane (15/85) to give the title compound. (160 mg, 92%). LC/MS [MH+] 556 Rt=5.5 min.

General Procedure E

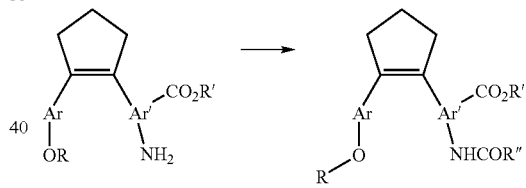

5-[2-(2-Benzyloxy-5-Chlorophenyl)-Cyclopent-1-enyl]-2-Propionylaminobenzoic Acid Methyl Ester

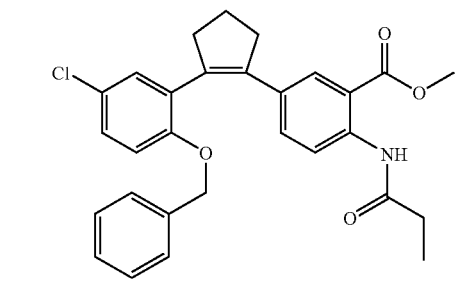

A mixture of 5-[2-(2-benzyloxy-5-chlorophenyl)-cyclopent-1-enyl]-2-aminobenzoic acid methyl ester (55 mg, 0.12 mmol), propionyl chloride (13 mg, 0.14 mmol), and triethylamine (15 mg, 0.14 mmol) in dichloromethane (2 ml) was stirred at room temperature for 30 minutes. The reaction mixture was diluted with EtOAc (10 ml) and washed with 5% NaHCO$_3$ (10 ml), 2M HCl (10 ml), water (10 ml) and brine (10 ml). The organic phase was dried and evaporated to give the product as a colourless glass 50 mg 85%. LC/MS: Rt=4.09[M+H] 490 (1 Cl).

General Procedure F

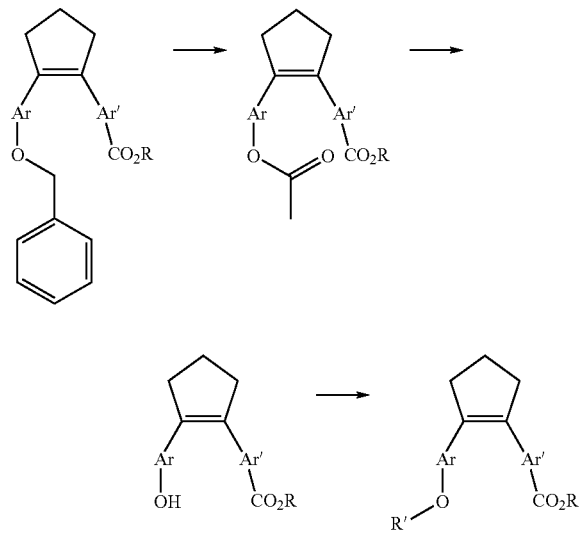

F(i) 6-[2-(5-Methyl-2-Acetoxyphenyl)Cyclopent-1-Enyl] Pyridine-2-Carboxylic Acid Ethyl Ester F(ii) 6-[2-(5-Methyl-2-Hydroxyphenyl)Cyclopent-1-Enyl] Pyridine-2-Carboxylic Acid Ethyl Ester

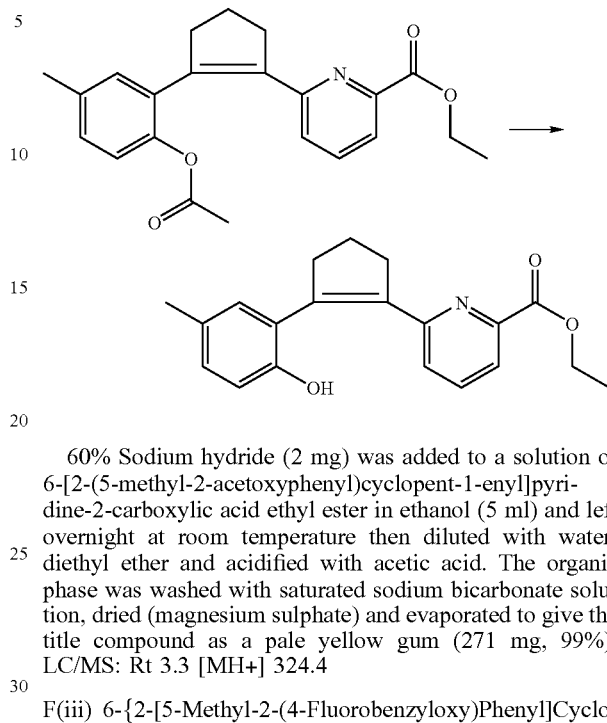

60% Sodium hydride (2 mg) was added to a solution of 6-[2-(5-methyl-2-acetoxyphenyl)cyclopent-1-enyl]pyridine-2-carboxylic acid ethyl ester in ethanol (5 ml) and left overnight at room temperature then diluted with water/diethyl ether and acidified with acetic acid. The organic phase was washed with saturated sodium bicarbonate solution, dried (magnesium sulphate) and evaporated to give the title compound as a pale yellow gum (271 mg, 99%). LC/MS: Rt 3.3 [MH+] 324.4

F(iii) 6-{2-[5-Methyl-2-(4-Fluorobenzyloxy)Phenyl]Cyclopent-1-Enyl}Pyridine-2-carboxylic Acid Ethyl Ester

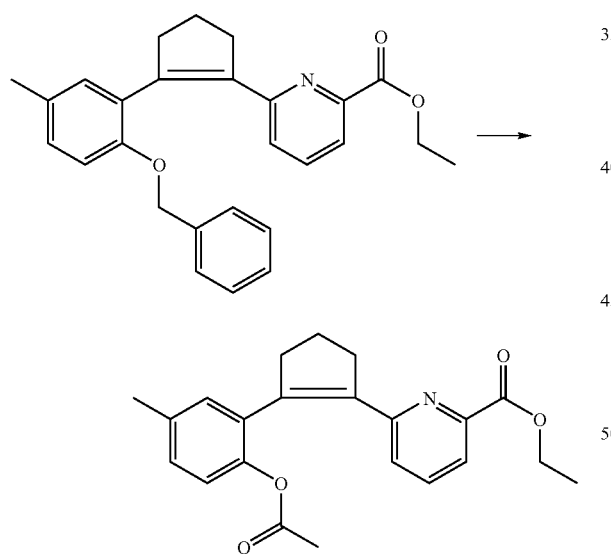

6-{2-[5-Methyl-2-(benzyloxy)phenyl]cyclopent-1-enyl}-pyridine-2-carboxylic acid ethyl ester (351 mg, 0.85 mmol) was dissolved in 48% hydrogen bromide in acetic acid (5 ml) and left at room temperature for 2 hours. The resulting mixture was poured into water/diethyl ether and basified with potassium carbonate. The organic phase was separated, dried (magnesium sulphate) and chromatographed on silica to give the title compound as a colourless gum (310 mg, 100%). LC/MS: Rt 3.4 [MH+] 366.4

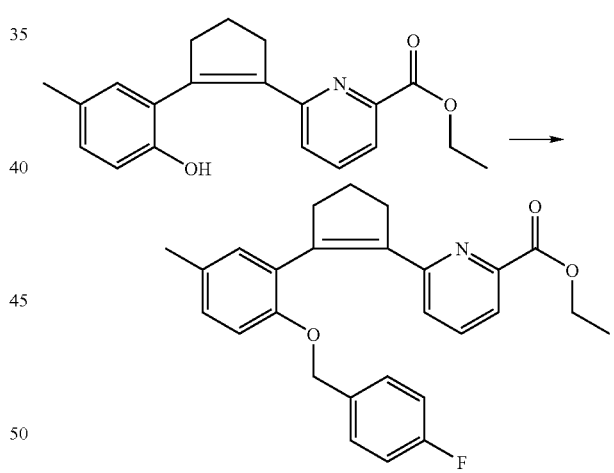

A mixture of 6-[2-(5-methyl-2-hydroxyphenyl)cyclopent-1-enyl]pyridine-2-carboxylic acid ethyl ester (129 mg, 0.4 mmol), 4-fluorobenzyl bromide (83 mg, 0.44 mmol) and potassium carbonate (138 mg, 1 mmol) in acetone (4 ml) was stirred and refluxed for 20 hours. After cooling the mixture was diluted with water/diethyl ether and the organic phase dried (magnesium sulphate) evaporated and purified by chromatography on silica (8% ethyl acetate in isohexane) to give the title compound as a colourless gum (148 mg, 86%). $^1$H NMR (CDCl$_3$)δ:1.41 (3H, t, J=7 Hz), 2.04–2.09 (2H, m), 2.18 (3H, s), 2.88–2.91 (2H, m), 3.11–3.15 (2H,m), 4.41 (2H, q, J=7 Hz), 4.91 (2H, s), 6.80 (1H, d, J=8 Hz), 6.87 (1H, d, J=2 Hz), 6.95–7.04 (4H, m), 7.17–7.21 (2H, m), 7.40 (1H, t, J=8 Hz), 7.79 (1H, d, J=8 Hz).

General Procedure G

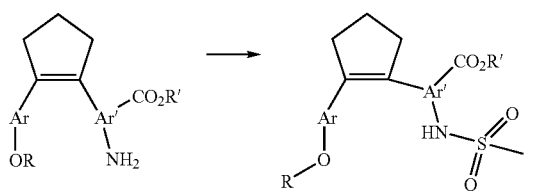

5-{2-[5-Trifluoromethyl-2-(Benzyloxy)Phenyl]Cyclopent-1-Enyl}-3-Methanesulphonylamino Benzoic Acid Ethyl Ester

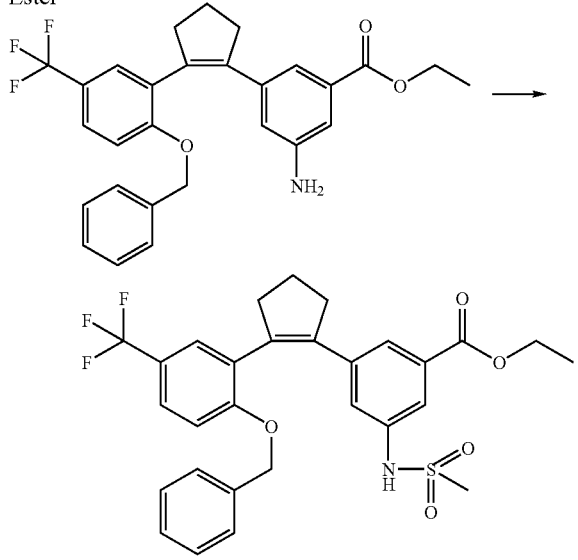

5-{2-[5-trifluoromethyl-2-(benzyloxy)phenyl]cyclopent-1-enyl)-3-aminobenzoic acid ethyl ester (60 mg, 0.12 mmol), pyridine (11 µL, 0.137 mmol), methane sulphonyl chloride (11 µL, 0.137 mmol), and a catalytic amount of DMAP in 2 mL of dichloromethane were stirred at room temperature for 2 hrs. The reaction mixture was poured into water and extracted with ethyl acetate (3×10 mL). The combined organic layers were dried (MgSO₄), filtered and concentrated. Purification was carried out on a SPE using iso-hexane containing a gradient of ethyl acetate (5–30%) to give the required product as yellow oil (55 mg, 78%). ¹H NMR (CDCl3):1.32 (3H,t,J=7.1), 2.06–2.13 (2H,m), 2.60 (3H,s), 2.88 (2H,t,J=7.4), 2.92–296(2H,m), 4.31 (2H,q, J=7.1), 5.11 (2H,s), 6.42 (1H,s), 7.04 (1H,d,J=8.6), 7.11 (1H,s), 7.23–7.30 (5H,m), 7.33(1H,d), 7.54 (1H,s), 7.66 (1H,s). LC/MS[MH−]=558 Rt=4.11.

General Procedure H

5-{2-[5-Chloro-2-(Benzyloxy)phenyl]Cyclopent-1-Enyl}-3-Morpholin-4-yl-Benzoic Acid Ethyl Ester

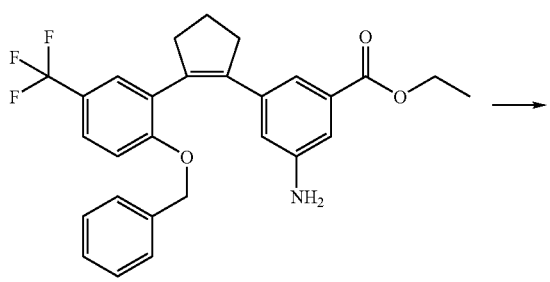

-continued

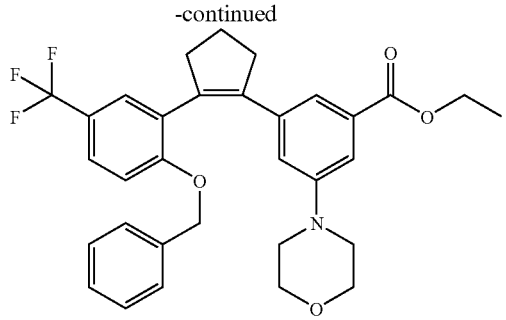

5-{2-[5-trifluoromethyl-2-benzyloxyphenyl]cyclopent-1-enyl}-3-aminobenzoic acid ethyl ester (198 mg, 0.41 mmol), bis(2-bromoethyl)ether (0.15 mL, 1.2 mmol), potassium carbonate (568 mg, 4.1 mmol) in 2.5 mL of 2-butanone were refluxed for 24 hrs. Upon cooling, the reaction mixture was poured into water and extracted with ethyl acetate (3×10 mL). The combined organic layers were dried (MgSO₄), filtered and concentrated. Purification was carried out on a SPE using iso-hexane containing a gradient of ethyl acetate (5–20%) to give the required product as yellow oil. ¹H NMR (CDCl₃):1.31(3H,t,J=7.1), 2.07–2.11(2H,m), 2.79(4H,t, J=4.8), 2.87(2H,t,J=7.3), 2.95(2H,t,J=7.5), 3.69(4H,t,J=4.8), 4.28 (2H,q,J=7.1), 5.29(2H,s), 6.72(1H,s), 6.93(1H,d, J=8.6), 7.16–7.42 (9H,m). LC/MS[MH+]=552, 553 Rt=4.37.

General Procedure J

5-{2-[5-Trifluoromethyl-2-(Benzyloxy)Phenyl]Cyclopent-1-Enyl}-3-(4-Chloro-Butanoylamino)-Benzoic Acid Ethyl Ester

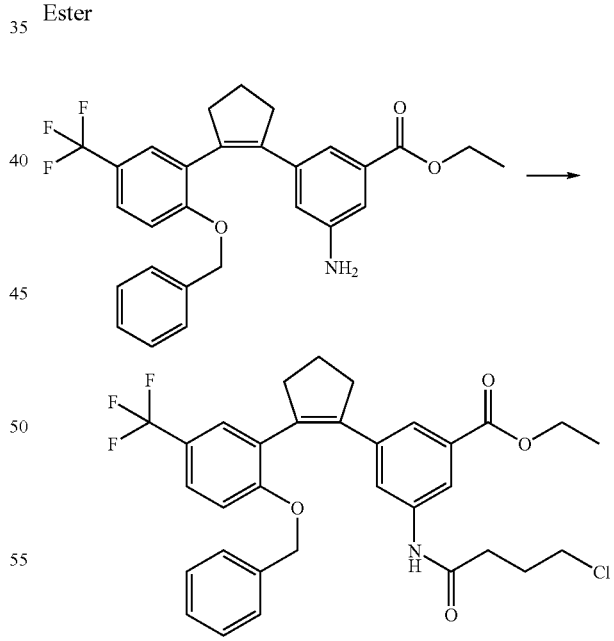

4-chlorobutyryl chloride (0.026 mL, 0.22 mmol), was added dropwise to a solution of 5-{2-[5-tryfluoromethyl-2-(benzyloxy)phenyl]cyclopent-1-enyl}-3-aminobenzoic acid ethyl ester (100 mg, 0.21 mmol) and triethylamine (0.032 mL, 0.22 mmol) in DCM (4 mL). The resulting mixture was stirred for 2 hrs at room temperature, then was poured into a saturated solution of (NaHCO₃ 10 mL) and extracted with ethyl acetate (20 mL). The organic phase was then washed sequentially with 2M HCl, H₂O and brine. The organic layer was then dried over MgSO₄ and evaporated to give a yellow oil that was used with no further purification. ¹H NMR (CDCl₃):1.24(3H,t,J=7.1), 2.01–2.18 (4H,m), 2.50(2H,t, J=6.7), 2.87(4H,m), 3.62(2H,t,J=6.0), 4.23(2H,q,J=7.1), 5.04(2H,s), 6.95(1H,d,J=8.6), 7.05–7.54 (9H, m), 7.84(1H, s).

General Procedure K

5-{2-[5-Trifluoromethyl-2-(Benzyloxy)Phenyl]Cyclopent-1-Enyl}-3-(2-Oxo-Pyrrolidin-1 -yl)-Benzoic Acid Ethyl Ester

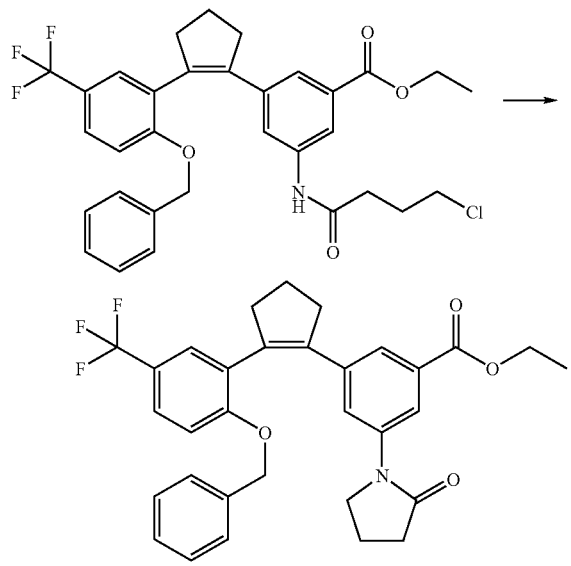

5-{2-[5-trifluoromethyl-2-(benzyloxy)phenyl]cyclopent-1-enyl}-3-(4-chloro-butanoylamino) -benzoic acid ethyl ester (140 mg, 0.24 mmol) and NaH (10.5 mg, 0.26 mmol, 60% dispersion in oil) in THF (3 mL), were stirred at room temperature for 4 hrs. The reaction mixture was poured into water and extracted with ethyl acetate (10×3 mL), the combined organic layers were dried over MgSO₄ and concentrated. Purification was carried out on a Biotage® using 40% of ethyl acetate in iso-hexane to give the required product as an orange oil (60 mg, 46%). ¹H NMR (CDCl₃): 1.26(3H,t,J=7.1), 2.01–2.18(4H,m), 2.52(2H,t,J=6.7), 2.88 (2H,t,J=7.6), 2.97(2H,t,J=7.4), 3.44(2H,t,J=7.0), 4.26(2H,q, J=7.2), 5.06(2H,s), 6.96(1H,d,J=8.6), 7.18–7.58 (9H, m), 8.09(1H, s).

Standard Hydrolysis Procedure

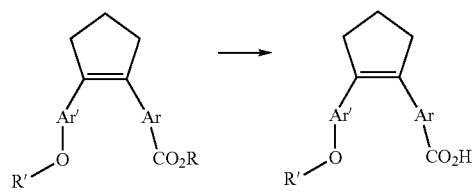

The ester (0.5 mmol) was dissolved in methanol or ethanol (2 ml) and 2M sodium hydroxide (1 ml) added. The mixture was stirred at from room temperature to reflux for from 30 minutes to 20 hours until the reaction was complete by tlc. The solution was diluted with water then extracted with isohexane or diethyl ether and acidified to pH4 with either hydrochloric acid or acetic acid. The mixture was extracted with diethyl ether or dichloromethane. The organic solution was dried over magnesium sulphate and evaporated to give the title compound.

4-[(4-Fluorobenzyl)oxy]benzotrifluoride

Prepared by general procedure A(i) but using 4-fluorobenzyl bromide instead of benzyl bromide.

¹H NMR (CDCl₃): δ:5.07 (2H, s), 7.02 (2H, d, J=9 Hz), 7.07–7.11 (2H, m), 7.39–7.42 (2H, m), 7.52 (2H, d, J=9 Hz)

2-[(4Fluorobenzyl)oxy]-5-trifluoromethyliodobenzene

Prepared by general procedure A(ii) but using 4-[(4-fluorobenzyl)oxy] benzotrifluoride instead of 4-(benzyloxy) benzotrifluoride.

¹H NMR (CDCl₃): δ:5.16 (2H, s), 6.88 (1H, d, J=9 Hz), 7.08–7.13 (2H, m), 7.44–7.48 (2H, m), 7.54–7.57 (1H, dd, J=2 Hz, J=9 Hz), 8.04 (1H, d, J=2 Hz).

2-[(4-Fluorobenzyl)oxy]-5-trifluoromethylbenzeneboronic Acid

Prepared by general procedure A(iii) but using 4-[(4-fluorobenzyl)oxy]-3-iodobenzotrifluoride instead of 4-benzyloxy-3-iodobenzotrifluoride.

¹H NMR (d₆DMSO) δ:5.22 (2H, s), 7.20–7.26 (3H, m), 7.54–7.58 (2H, m), 7.71 (1H, d, J=9 Hz), 7.75 (1H, s), 8.03 (2H, s).

4-[(2,4-Difluorobenzyl)oxy]benzotrifluoride

Prepared by general procedure A(i) but using 2,4-difluorobenzyl bromide instead of benzyl bromide.

¹H NMR (CDCl₃): δ:5.12 (2H, s), 6.89 (2H, dt, J=2 Hz, J=9 Hz), 7.02–7.05 (2H, d, J=9 Hz), 7.33–7.49 (1H, q, J=8 Hz, J=15 Hz), 7.56 (2H, d, J=9 Hz)

2-[(2,4-Difluorobenzyl)oxy]-5-trifluoromethyliodobenzene

Prepared by general procedure A(ii) but using 4[(2,4-difluorobenzyl)oxy] benzotrifluoride instead of 4-(benzyloxy)benzotrifluoride.

¹H NMR (CDCl₃): δ: 5.21 (2H, s), 6.84–6.95 (3H, m), 7.55–7.65 (2H, m), 8.04 (1H, s)

2-[(2,4-Difluorobenzyl)oxy]-5-trifluoromethylbenzeneboronic Acid

Prepared by general procedure A(iii) but using 4-[(2,4-difluorobenzyl)oxy]-3-iodobenzotrifluoride instead of 4-benzyloxy-3-iodobenzotrifluoride.

¹H NMR (d₆DMSO) δ:5.26 (2H, s), 7.16 (1H, dt, J=2 Hz, J=9 Hz) 7.27 (1H, d, J=9 Hz), 7.33 (1H, dt, J=2 Hz, J=9 Hz), 7.68–7.75 (3H, m), 8.01 (2H, s).

2-Benzyloxy-5-bromoiodobenzene.

Prepared as general procedure A(i) from 2-iodo-4-bromophenol $^1$H NMR (CDCl$_3$):5.10 (2H, s), 6.69(1H, d, J=9 Hz), 7.23–7.46 (6H, m), 7.88(1H,s).

2-Benzyloxy-5-bromobenzeneboronic acid

Prepared as general procedure A(iii) from 2-benzyloxy-5-bromoiodobenzene.

$^1$H NMR (CDCl$_3$):5.12 (2H,s), 5.78(2H,s), 6.58(1H,d,J=9 Hz), 7.34–7.39(5H,m), 7.40 (1H,d,J=9 Hz), 7.95 (1H,s).
LC/MS: Rt=3.44 [M–H] 305, 307 (1Br)

2-(4-Fluorobenzyl)oxy-5-bromoiodobenzene

Prepared as general procedure A(i) from 2-iodo-4-bromophenol.

$^1$H NMR (CDCl$_3$):5.06 (2H, s), 6.69 (1H, d, J=9 Hz), 7.07–7.10 (2H, m), 7.35–7.45(3H,m), 7.89 (1H, s).

2-(4-Fluorobenzyl)oxy-5-bromobenzeneboronic Acid

Prepared as general procedure A(iii) from 2-(4-fluorobenzyl)oxy-5-bromoiodobenzene.

$^1$H NMR (CDCl$_3$):5.07(2H, s), 5.83(2H, s), 6.84(1H, d, J=9 Hz), 7.10(2H, m), 7.37(2H, m), 7.50(1H, d, J=9 Hz), 7.95 (1H, s).

2-(2,4-Difluorobenzyl)oxy-5-bromoiodobenzene

Prepared as general procedure A(i) from 2-iodo-4-bromophenol.

$^1$H NMR (CDCl$_3$):5.12(2H, s), 6.74–6.95(3H, m), 7.40(1H, d, J=9 Hz), 7.57–7.63(1H, m), 7.90 (1H, s).

2-(2,4-Difluorobenzyl)oxy-bromobenzeneboronic Acid

Prepared as general procedure A(iii) from 2-(2,4-difluorobenzyl)oxy-5-bromoiodobenzene.

$^1$H NMR (CDCl$_3$):5.14(2H, s), 5.77(2H, br s), 6.86–6.95 (3H, m), 7.36–7.42(1H, m), 7.52(1H, d, J=9 Hz), 7.95(1H, s).

2-[(4-Fluorobenzyl)oxy]-5-chloroiodobenzene

Prepared as general procedure A(i) from 2-iodo-5-chlorophenol.

$^1$HNMR (CDCl$_3$):5.08 (2H, s), 6.75(1H, d, J=8 Hz), 7.06 (1H, d, J=8 Hz), 7.07(1H, d, J=8 Hz), 7.23(1H, s), 7.43–7.46 (2H, m), 7.76(1H, s).

2-[(4-Fluorobenzyl)oxy]-5-chlorobenzeneboronic Acid

Prepared as general procedure A(iii) from 2-[(4-fluorobenzyl)oxy]5-chloroiodobenzene $^1$H NMR (CDCl$_3$):5.07(2H, s), 6.89(1H, d, J=8 Hz), 7.09 (2H, m), 7.35–7.40(3H, m), 7.81 (1H, s).

1-Bromo-2-[2-(4-fluorobenzyloxy)-5-trifluoromethylphenyl)cyclopentene

Prepared by general procedure C(i) but using 2-(4-fluorobenzyloxy)-5-trifluoromethylphenylboronic acid instead of 2-benzyloxy-5-chlorophenylboronic acid.
LC/MS: Rt 4.26 [MH–] 414.9

2-(2-Benzyloxy-5-trifluoromethylphenyl)cyclopentene-1-boronic Acid

Prepared as a colourless gum by general procedure C(ii) but using 1-bromo-2-(2-benzyloxy-5-trifluoromethylphenyl)cyclopentene instead of 1-bromo-2-(2-benzyloxy-5-chlorophenyl)cyclopentene.
LC/MS: Rt 3.66 [2M-H$_2$O—] 705.1

1-Bromo-2-[2-4-fluorobenzyloxy)-5-chlorophenyl] cyclopentene

Prepared by general procedure C(i) but using 2-(4-fluorobenzyloxy)-5-chlorophenylboronic acid instead of 2-benzyloxy-5-chlorophenylboronic acid.

$^1$H NMR (CDCl$_3$) δ:1.99–2.06 (2H, m), 2.64–2.69 (2H, m), 2.76–2.81 (2H, m), 5.01 (2H, s), 6.83 (1H, d, J=9 Hz), 7.04–7.09 (2H, m), 7.17–7.36 (4H, m).

2-[2-(4-Fluorobenzyloxy)-5-chlorophenyl]cyclopentene-1-boronic acid

Was prepared as a colourless gum by general procedure C(ii) but using 1-bromo-2-[2-(4-fluorobenzyloxy)-5-chlorophenyl]cyclopentene instead of 1-bromo-2-(2-benzyloxy-5-chlorophenyl)cyclopentene.
LC/MS: Rt 3.42 [2M-H$_2$O—] 675.3

3-(2-Bromocyclopent-1-enyl)-6-aminobenzoic acid ethyl ester

Prepared by general procedure B(ii) but using 2-amino-5-iodobenzoic acid ethyl ester instead of 5-iodo-2-methylbenzoic acid ethyl ester.

$^1$H NMR (CDCl$_3$)δ:1.39 (3H, t, J=7 Hz), 1.98–2.06 (2H, m), 2.71–2.76 (2H, m), 2.81–2.86 (2H, m) 4.33 (2H, q, J=7 Hz), 5.80 (2H, br s), 6.65 (1H, d, J=9 Hz), 7.65 (1H, dd, J=9 Hz, 2 Hz), 8.14 (1H, d, J=2 Hz).

1-Bromo-2-(2-benzyloxy-5-methylphenyl)cyclopentene

Was prepared as a white solid by general procedure C(i) but using 2-benzyloxy-5-methylphenylboronic acid instead of 2-benzyloxy-5-chlorophenylboronic acid.

$^1$H NMR (CDCl$_3$)δ:2.01–2.07 (2H, m), 2.30 (3H, s), 2.69–2.74 (2H, m), 2.76–2.80 (2H, m), 5.05 (2H, s), 6.83 (1H, d, J=9 Hz), 7.02–7.08 (2H, m), 7.30–7.40 (5H, m).

2-(2-Benzyloxy-5-methylphenyl)cyclopentene-1-boronic acid

Was prepared in 46% yield as a white solid by general procedure C(ii) but using 1-bromo-2-(2-benzyloxy-5-methylphenyl)cyclopentene instead of 1-bromo-2-(2-benzyloxy-5-chlorophenyl)cyclopentene.

$^1$H NMR (CDCl$_3$)δ:1.90–1.97 (2H, m), 2.27 (3H, s), 2.63–2.68 (2H, m), 2.72–2.76 (2H, m), 4.49 (2H, s), 5.05

(2H, s), 6.88 (1H, d, J=8 Hz), 6.98 (1H, d, J=2 Hz), 7.04 (1H, dd, J=8 Hz, 2 Hz), 7.26–7.36 (5H, m).

6-{2-[5-Methyl-2-(benzyloxy)phenyl]cyclopent-1-enyl}-pyridine-2-carboxylic acid ethyl ester Prepared in 80% yield as a colourless gum by general procedure C(iii) but using 2-(2-benzyloxy-5-methylphenyl)cyclopentene-1-boronic acid instead of 2-(2-benzyloxy-5-chlorophenyl)cyclopentene-1-boronic acid and 6-bromopicolinic acid methyl ester instead of 2-chloropyrimidine-4-carboxylic acid methyl ester.

LC/MS: Rt 3.9 [MH+] 414.4.

5-{2-[5-trifluoromethyl-2-benzyloxyphenyl]cyclopenten-1-enyl}-3-aminobenzoic acid ethyl ester Prepared by general procedure B(iii) using (5-trifluoromethylphenyl-2-(benzyloxy)boronic acid and 3-amino-5-(2-bromocyclopent-1-enyl}-benzoic acid methyl ester.

$^1$HNMR (CDCl3): 1.25 (3H,t), 2.04–2.08 (2H,m), 2.84-292 (4H,m), 3.53 (2H,br s), 4.21 (2H, q), 5.02 (2H, s), 6.54 (1H, s),6.93 (1H,d, J=8.6), 7.12–7.29 (8H,m), 7.32 (1H, d, J=8.5).
LC/MS[MH+]=482 Rt=4.12

6-{2-[5-Methyl-2-(2,4-difluorobenzyloxy)phenyl]cyclopent-1-enyl}pyridine-2-carboxylic acid ethyl ester Prepared by general method F(iii) but using 2,4-difluorobenzyl bromide instead of 4-fluorobenzyl bromide.

LC/MS: Rt 3.9 [MH+] 450.4.

2-[2-(4-Fluorobenzyloxy)-5-trifluoromethylphenyl]cyclopentene-1-boronic acid Prepared in 40% yield as a colourless gum by general method C(ii) but using 1-bromo-2-[2-(4-fluorobenzyloxy)-5-trifluoromethylphenyl]cyclopentene instead of 1-bromo-2-(2-benzyloxy-5-chlorophenyl)cyclopentene.

LC/MS: Rt 3.66, [2MH-H$_2$O—] 741.0

2-{5-Trifluoromethyl-2-(4-fluorobenzyloxy)phenyl]cyclopent-1-enyl}-pyridine-4-carboxylic acid ethyl ester Prepared by general procedure C(iii) but using 2-[2-(4-fluorobenzyloxy)-5-trifluoromethylphenyl]cyclopentene-1-boronic acid instead of 2-(2-benzyloxy-5-chlorophenyl)cyclopentene-1-boronic acid and 2-bromoisonicotinic acid ethyl ester instead of 2-chloropyrimidine-4-carboxylic acid methyl ester.

LC/MS: Rt 4.19, [MH+] 486.1.

4-{2-[5-Trifluoromethyl-2-(4-fluorobenzyloxy)phenyl]cyclopent-1-enyl}pyridine-2-carboxylic acid ethyl ester Prepared by general procedure C(iii) but using 2-[2-(4-fluorobenzyloxy)-5-trifluoromethylphenyl]cyclopentene-1-boronic acid instead of 2-(2-benzyloxy-5-chlorophenyl)cyclopentene-1-boronic acid and 4-iodoipicolinic acid methyl ester instead of 2-chloropyrimidine-4-carboxylic acid methyl ester.

LC/MS: Rt 4.02, [MH+] 486.1

2-{2-[5-Trifluoromethyl-2-(benzyloxy)phenyl]cyclopent-1-enyl}-pyridine-4-carboxylic acid ethyl ester Prepared by general procedure C(iii) but using 2-[2-benzyloxy)-5-trifluoromethylphenyl]cyclopentene-1-boronic acid instead of 2-(2-benzyloxy-5-chlorophenyl)cyclopentene-1-boronic acid and 2-bromoisonicotinic acid ethyl ester instead of 2-chloropyrimidine-4-carboxylic acid methyl ester.

LC/MS: Rt 4.19, [MH+] 468.1

4-{2-[5-Trifluoromethyl-2-(benzyloxy)phenyl]cyclopent-1-enyl}-pyridine-2-carboxylic acid ethyl ester Prepared by general procedure C(iii) but using 2-[2-(benzyloxy)-5-trifluoromethylphenyl]cyclopentene-1-boronic acid instead of 2-(2-benzyloxy-5-chlorophenyl)cyclopentene-1-boronic acid and 4-iodoipicolinic acid methyl ester instead of 2-chloropyrimidine-4-carboxylic acid methyl ester.

$^1$H NMR (CDCl$_3$)δ:1.35 (3H, t, J=7 Hz), 2.10–2.15 (2H, m), 2.89–2.97 (4H, m), 4.38 (2H, q, J=7 Hz) 4.99 (2H, s), 6.98–7.03 (2H, m), 7.15–7.17 (2H, m), 7.26–7.33 (5H, m), 7.51 (1H, dd, J=7 Hz, 2 Hz), 7.78 (1H, d, J=1 Hz), 8.45 (1H, d, J=5 Hz).

6-{2-[5-Trifluoromethyl-2-(benzyloxy)phenyl]cyclopent-1-enyl}-3-aminopyrazine-2-carboxylic acid ethyl ester Prepared by general procedure C(iii) but using 2-[2-(benzyloxy)-5-trifluoromethylphenyl]cyclopentene-1-boronic acid instead of 2-(2-benzyloxy-5-chlorophenyl)cyclopentene-1-boronic acid and 3-amino-6-bromopyrazine-2-carboxylic acid methyl ester instead of 2-chloropyrimidine 4-carboxylic acid methyl ester.

LC/MS: Rt 4.08, [MH+] 484.1

2-{2-[5-Trifluoromethyl-2-(4-fluorobenzyloxy)phenyl]cyclopent-1-enyl}pyrimidine-4-carboxylic acid ethyl ester Prepared by general procedure C(iii) but using 2-[2-(4-fluorobenzyloxy)-5-trifluoromethylphenyl]cyclopentene-1-boronic acid instead of 2-(2-benzyloxy-5-chlorophenyl)cyclopentene-1-boronic acid.

LC/MS: Rt 3.8, [MH+] 487.3

2-{2-[5-Trifluoromethyl-2-(4-fluorobenzyloxy)phenyl]cyclopent-1-enyl}pyrimidine-4-carboxylic Acid Ethyl Ester Was prepared by general procedure C(iii) but using 2-[2-(4-fluorobenzyloxy)-5-chlorophenyl]cyclopentene-1-boronic acid instead of 2-(2-benzyloxy-5-chlorophenyl)cyclopentene-1-boronic acid.

LC/MS: Rt 3.8, [MH+] 453.3, 455.3

6-{2-[5-Methyl-2-(benzyloxy)phenyl]cyclopent-1-enyl}pyrazine-2-carboxylic acid ethyl ester Prepared by general procedure C(iii) but using 2-[2-(benzyloxy)-5-methylphenyl]cyclopentene-1-boronic acid instead of 2-(2-benzyloxy-5-chlorophenyl)cyclopentene-1-boronic acid and 6-chloropyrazine-2-carboxylic acid ethyl ester instead of 2-chloropyrimidine-4-carboxylic acid methyl ester.

LC/MS: Rt 3.8, [MH+] 415.5

3-{2-[5-Methyl-2-(benzyloxy)phenyl]cyclopent-1-enyl}-6-aminobenzoic acid ethyl ester Prepared by general procedure C(iii) but using 2-(2-benzyloxy-5-methylphenyl)cyclopentene-1-boronic acid instead of 2-(2-benzyloxy-5-chlorophenyl)cyclopentene-1-boronic acid and 2-amino-5-iodobenzoic acid ethyl ester instead of 2-chloropyrimidine-4-carboxylic acid methyl ester.

LC/MS: Rt 4.0 [MH+] 428.5

6-{2-[5-Trifluoromethyl-2-(benzyloxy)phenyl]cyclopent-1-enyl}-pyridine-2-carboxylic acid methyl ester Prepared by general procedure 3 but using 6-(2-bromocyclopent-1enyl)pyridine-2-carboxylic acid methyl ester instead of 3-(2-bromocyclopent-1-enyl)benzoic acid ethyl ester and 2-benzyloxy-5-trifluoromethylphenylboronic acid instead of 5-chloro-2-methoxyphenylboronic acid.

LC/MS: Rt 4.04 [MH+] 454.1

6-{2-[5-Trifluoromethyl-2-(4-fluorobenzyloxy)phenyl]cyclopent-1-enyl}pyridine-2-carboxylic acid methyl ester Prepared by general procedure 3 but using 6-(2-bromocyclopent-1-enyl)-pyridine-2-carboxylic acid methyl ester instead of 3-(2-bromocyclopent-1-enyl)-benzoic acid ethyl ester and 2-(4-fluorobenzyloxy)-5-trifluoromethylphenylboronic acid instead of 5-chloro-2-methoxyphenylboronic acid.

LC/MS: Rt 4.04 [MH+] 472.1

6-{2-[5-Trifluoromethyl-2-(2,4-difluorobenzyloxy)phenyl]cyclopent-1-enyl}-pyridine-2-carboxylic acid methyl ester Prepared by general procedure 3 but using 6-(2-bromocyclopent-1-enyl)-pyridine-2-carboxylic acid methyl ester instead of 3-(2-bromocyclopent-1-enyl)benzoic acid ethyl ester and 2-(2,4-difluorobenzyloxy)-5-trifluoromethylphenylboronic acid instead of 5-chloro-2-methoxyphenylboronic acid.

LC/MS: Rt 4.08 [MH+] 490.1

3-{2-[5-Trifluoromethyl-2-(benzyloxy)phenyl]cyclopent-1-enyl}-6-aminobenzoic acid ethyl ester Prepared by general procedure C(iii) but using 2-benzyloxy-5-trifluoromethylphenylboronic acid instead of 2-benzyloxy-5-chlorophenylboronic acid and 3-(2-bromocyclopent-1-enyl)-6-aminobenzoic acid ethyl ester instead of 3-(2-bromo-cyclopent-1-enyl)-6-methylbenzoic acid ethyl ester.

LC/MS: Rt 4.32 [MH+] 482.0.

3-{2-[5-Trifluoromethyl-2-(4-fluorobenzyloxy)phenyl]cyclopent-1-enyl}-6-aminobenzoic acid ethyl ester Prepared by general procedure C(iii) but using 2-(4-fluorobenzyloxy)-5-trifluoromethylphenylboronic acid instead of 2-(benzyloxy)-5-chlorophenylboronic acid and 3-(2-bromocyclopent-1-enyl)-6-aminobenzoic acid ethyl ester instead of 3-(2-bromo-cyclopent-1-enyl)-6-methylbenzoic acid ethyl ester.

LC/MS: Rt 4.32 [MH+] 500.0.

3-{2-[5-Trifluoromethyl-2-(2,4-difluorobenzyloxy)phenyl]cyclopent-1-enyl}-6-aminobenzoic acid ethyl ester Prepared by general procedure C(iii) but using 2-(2,4-difluorobenzyloxy)-5-trifluoromethylphenylboronic acid instead of 2-(benzyloxy)-5-chlorophenylboronic acid and 3-(2-bromocyclopent-1-enyl)-6-aminobenzoic acid ethyl ester instead of 3-(2-bromo-cyclopent-1-enyl)-methylbenzoic acid ethyl ester.

LC/MS: Rt 4.35 [MH+] 518.0.

3-{2-[5-Trifluoromethyl-2-(benzyloxy)phenyl]cyclopent-1-enyl}-6-acetamidobenzoic acid ethyl ester Prepared by general procedure E but using acetyl chloride instead of propionyl chloride and 3-{2[5-trifluoromethyl-2-(benzyloxy)phenyl]cyclopent-1-enyl}-6-aminobenzoic acid ethyl ester instead of 5-[2-(2-benzyloxy-5-chlorophenyl)cyclopent-1-enyl]-2-aminobenzoic acid methyl ester.

LC/MS: Rt 4.0 [MH+] 524.4

3-{2-[5-Trifluoromethyl-2-(4-fluorobenzyloxy)phenyl]cyclopent-1-enyl}-6-acetamidobenzoic acid ethyl ester Prepared by general procedure E but using acetyl chloride instead of propionyl chloride and 3-{2[5-trifluoromethyl-2-(4-fluorobenzyloxy)phenyl]cyclopent-1-enyl}-6-aminobenzoic acid ethyl ester instead of 5-[2-(2-benzyloxy-5-chlorophenyl)-cyclopent-1-enyl]-2-aminobenzoic acid methyl ester.

LC/MS: Rt 4.0 [MH+] 542.4.

3-{2-[5-Trifluoromethyl-2-(2,4-difluorobenzyloxy)phenyl]cyclopent-1-enyl}-6-acetamidobenzoic acid ethyl ester Prepared by general procedure E but using acetyl chloride instead of propionyl chloride and (3-{2-[5-trifluoromethyl-2-(2,4-difluorobenzyloxy)phenyl]cyclopent-1-enyl}-6-aminobenzoic acid ethyl ester instead of 5-[2-(2-benzyloxy-5-chlorophenyl)-cyclopent-1-enyl]-2-aminobenzoic acid methyl ester.

LC/MS: Rt 4.0 [MH+] 560.4

3-{2-[5-Trifluoromethyl-2-(benzyloxy)phenyl]cyclopent-1-enyl}-5-propionamidobenzoic acid ethyl ester Prepared by general procedure E but using 3-{2-[5-trifluoromethyl-2-(benzyloxy)phenyl]cyclopent-1-enyl}-5-aminobenzoic acid ethyl ester instead of 5-[2-(2-benzyloxy-5-chlorophenyl)cyclopent-1-enyl]-2-aminobenzoic acid methyl ester.

LC/MS: Rt 4.15 [MH−] 536.1

3-{2-[5-Trifluoromethyl-2-(4-fluorobenzyloxy)phenyl]cyclopent-1-enyl}-5-propionamidobenzoic acid ethyl ester Prepared by general procedure E but using 3-{2-[5-trifluoromethyl-2-(4-fluorobenzyloxy)phenyl]cyclopent-1- enyl}-5-aminobenzoic acid ethyl ester instead of 5-[2-(2-benzyloxy-5-chlorophenyl)cyclopent-1-enyl]-2-aminobenzoic acid methyl ester.

LC/MS: Rt 4.16 [MH−] 554.2

3-{2-[5-Trifluoromethyl-2-(2,4-difluorobenzyloxy)phenyl]cyclopent-1-enyl}-5-propionamidobenzoic acid methyl ester Prepared by general procedure E but using 3-{2-[5-trifluoromethyl-2-(2,4-difluorobenzyloxy)phenyl]cyclopent-1-enyl}-5-aminobenzoic acid methyl ester instead of 5-[2-(2-benzyloxy-5-chlorophenyl)cyclopent-1-enyl]-2-aminobenzoic acid methyl ester.

LC/MS: Rt 4.07 [MH−] 558.2

5-[2-(2-Benzyloxy-5-chlorophenyl)cyclopent-1-enyl]-2-aminobenzoic acid methyl ester Prepared by general procedure C(iii) but using 2-amino-5-bromobenzoic acid methyl ester instead of 2-chloropyrimidine-4-carboxylic acid methyl ester.

LC/MS: Rt 3.8 [MH+] 434.3, 436.3.

3-{2-[5-Bromo-2-(benzyloxy)phenyl]cyclopent-1-enyl}-5-aminobenzoic acid methyl ester Prepared by general procedure 3 but using 3-amino-5-(2-bromocyclopent-1-enyl)benzoic acid methyl ester instead of 3-(2-bromocyclopent-1-enyl)benzoic acid ethyl ester and 2-(benzyloxy)-5-bromophenylboronic acid instead of 5-chloro-2-methoxyphenylboronic acid.

LC/MS: Rt 4.03 [MH+] 478.0, 480.0.

3-{2-[5-Bromo-2-(4-fluorobenzyloxy)phenyl]cyclopent-1-enyl}-5-aminobenzoic acid methyl ester Prepared by general procedure 3 but using 3-amino-5-(2-bromocyclopent-1-enyl)benzoic acid methyl ester instead of 3-(2-bromocyclopent-1-enyl)benzoic acid ethyl ester and 2-(4-fluorobenzyloxy)-5-bromophenylboronic acid instead of 5-chloro-2-methoxyphenylboronic acid.

LC/MS: Rt 4.04 [MH+] 496.0, 498.0

3-{2-[5-Bromo-2-(2,4-difluorobenzyloxy)phenyl]cyclopent-1-enyl}-5-aminobenzoic acid methyl ester Prepared by general procedure 3 but using 3-amino-5-(2-bromocyclopent-1-enyl)benzoic acid methyl ester instead of 3-(2-bromocyclopent-1-enyl)benzoic acid ethyl ester and 2-(2,4-difluorobenzyloxy)-5-bromophenylboronic acid instead of 5-chloro-2-methoxyphenylboronic acid.

LC/MS: Rt 4.07 [MH+] 514.0, 516.0.

3-{2-[5-Bromo-2-(benzyloxy)phenyl]cyclopent-1-enyl}-5-propionamidobenzoic acid methyl ester Prepared by general procedure E but using 3-{2-[5-bromo-2-(benzyloxy)phenyl]cyclopent-1-enyl}-5-aminobenzoic acid methyl ester instead of 5-[-(2-benzyloxy-5-chlorophenyl)-cyclopent-1-enyl]-2-aminobenzoic acid methyl ester.

LC/MS: Rt 4.08 [MH+] 534.1, 536.1

3-{2-[5-Bromo-2-(4-fluorobenzyloxy)phenyl]cyclopent-1-enyl}-5-propionamidobenzoic acid methyl ester Prepared by general procedure E but using 3-{2-[5-bromo-2-(4-fluorobenzyloxy)phenyl]cyclopent-1-enyl}-5-aminobenzoic acid methyl ester instead of 5-[2-(2-benzyloxy-5-chlorophenyl)-cyclopent-1-enyl]-2-aminobenzoic acid methyl ester.

LC/MS: Rt 4.09 [MH+] 552.0, 554.0

3-{2-[5-Bromo-2-(2,4-difluorobenzyloxy)phenyl]cyclopent-1-enyl}-5-propionamidobenzoic acid methyl ester Prepared by general procedure E but using 3-{2-[5-bromo-2-(2,4-difluorobenzyloxy)phenyl]cyclopent-1-enyl}-5-aminobenzoic acid methyl ester instead of 5-[2-(2-benzyloxy-5-chlorophenyl)cyclopent-1-enyl]-2-aminobenzoic acid methyl ester.

LC/MS: Rt 4.12 [MH+] 570.1, 572.1.

3-{2-[5-Methyl-2-(benzyloxy)phenyl]cyclopent-1-enyl}-6-acetamidobenzoic acid ethyl ester Prepared by general procedure E but using acetyl chloride instead of propionyl chloride and 3-{2-[5-methyl-2-(benzyloxy)phenyl]cyclopent-1-enyl}-6-aminobenzoic acid ethyl ester instead of 5-[2-(2-benzyloxy-5-chlorophenyl)-cyclopent-1-enyl]-2-aminobenzoic acid methyl ester.

LC/MS: Rt 4.0 [MH+] 470.4.

4-Fluoro-2-(2-bromocyclopent-1-enyl)anisole

Prepared using general procedure C(i) but using 2-methoxy-5-fluorophenylboronic acid instead of 2-benzyloxy-5-chlorophenylboronic acid.

$^1$H NMR (CDCl$_3$): δ: 2.02–2.10 (2H, m), 2.67–2.72 (2H, m), 2.78–2.82 (2H, m), 3.79 (3H, s), 6.80–6.83 (1H, dd, J=5 Hz, J=9 Hz), 6.93–7.00 (2H, m).

5-[2-(5-fluoro-2-methoxyphenyl)cyclopent-1-enyl]-3-aminobenzoic acid methyl ester 4-Fluoro-2-(2-bromocyclopent-1-enyl)anisole (271 mg, 1 mmol), (3-amino-5-methoxycarbonyl)phenylboronic acid (195 mg, 1 mmol) and potassium carbonate (1.1 g, 8 mmol) were stirred under nitrogen in 1:1 toluene: ethanol (4 ml) and tetrakis(triphenylphosphine)palladium(0) (116 mg, 0.1 mmol) added. The resulting mixture was heated at 80° C. in a Smithcreator® microwave for 20 minutes. After cooling, diethyl ether (10 ml) and water (10 ml) were added. The organic layer was washed with water, dried (MgSO$_4$) and evaporated. The product was purified by flash chromatography (silica gel, 10–30% ethyl acetate: isohexane) to give the title compound as a pale orange solid (143 mg, 42%).

LC/MS [MH+]=342, RT=3.57 min.

5-[2-(5-fluoro-2-methoxyphenyl)cyclopent-1-enyl]-3-propionamido)benzoic acid methyl ester Prepared by general method E but using 5-[2-(5-fluoro-2-methoxyphenyl)cyclopent-1-enyl]-3-aminobenzoic acid methyl instead of 5-2[2-(2-benzyloxy-5-chlorophenyl)-cyclopent-1-enyl]-2-aminobenzoic acid methyl ester.

LC/MS [MH+]=398, RT=3.41 min.

5-[2-(5-fluoro-2-hydroxyphenyl)cyclopent-1-enyl]-3-(propionamido)benzoic acid Prepared by general procedure 4 but using 5-[2-(5-fluoro-2-methoxyphenyl)cyclopent-1-enyl]-3-(propionamido)benzoic acid methyl ester instead of 3-[2-(5-bromo-2-methoxyphenyl)cyclopent-1-enyl]benzoic acid ethyl ester.
LC/MS [MH+]=370, RT=3.12 min.

5-{2-[5-fluoro-2(4-fluorobenzyloxy)phenyl]cyclopent-1-enyl}-3-(propionamido)benzoic acid 4-fluorobenzyl ester Prepared by general procedure 5 but using 5-[2-(5-fluoro-2-hydroxyphenyl)cyclopent-1-enyl]-3-(propionamido)benzoic acid instead of 6-[2-(5-chloro-2-hydroxyphenyl)cyclopent-1-enyl]pyridine-2 carboxylic acid, 4-fluorobenzyl bromide instead of 4-chlorobenzyl bromide and acetone instead of 2-butanone.
LC/MS [MH+]=586, RT=3.95 min.

4-Methyl-2-(2-bromocyclopent-1-enyl)anisole

Prepared using general procedure C(i) but using 2-methoxy-5-methylphenylboronic acid instead of 2-benzyloxy-5-chlorophenylboronic acid.
$^1$H NMR (CDCl$_3$) δ: 2.03–2.09 (2H, m), 2.30 (3H, s) 2.67–2.72 (2H, m), 2.77–2.82 (2H, m), 3.79 (3H, s), 6.80 (1H, d, J=8 Hz), 7.07 (1H, d, J=8 Hz), 7.26 (1H, s).

5-[2-(5-methyl-2-methoxyphenyl)cyclopent-1-enyl]-3-aminobenzoic acid methyl ester Prepared using general procedure D but using 4-methyl-2-(2-bromocyclopent-1-enyl)anisole instead of 1-bromo-2-(2-benzyloxy-5-chlorophenyl)cyclopentene.
LC/MS [MH+]=338, RT=3.38 min.

5-[2-5-methyl-2-methoxyphenyl)cyclopent-1-enyl]-3-(propionamido)benzoic acid methyl ester Prepared by general method E but using 5-[2-(2-methoxyphenyl-5-methyl)cyclopent-1-enyl]-3-aminobenzoic acid methyl ester instead of 5-[2-(2-benzyloxy-5-chlorophenyl)-cyclopent-1-enyl]-2-aminobenzoic acid methyl ester
LC/MS [MH+]=394, RT=3.47 min.

5-[2-(5-methyl-2-hydroxyphenyl)cyclopent-1-enyl]-3-(propionamido)benzoic acid Was prepared by general procedure 4 but using 5-[2-(2-methoxy-5-methylphenyl)cyclopent-1-enyl]-3-(propionamido)benzoic acid methyl ester instead of 3-[2-(5-bromo-2-methoxyphenyl)cyclopent-1-enyl]benzoic acid ethyl ester.
LC/MS [MH+]=366, RT=3.27 min.

5-{2-[5-methyl-2-(4-fluorobenzyloxy)phenyl]cyclopent-1-enyl}-3-(propionamido)benzoic acid 4-fluorobenzyl ester Prepared by general procedure 5 but using 5-[2-(2-hydroxy-5-methylphenyl)cyclopent-1-enyl]-3-(propionamido)benzoic acid instead of 6-[2-(5-chloro-2-hydroxyphenyl)cyclopent-1-enyl]pyridine-2-carboxylic acid, 4-fluorobenzyl bromide instead of 4-chlorobenzyl bromide and acetone instead of 2-butanone.
LC/MS [MH+]=582, RT=4.30 min.

5-{2-[5-methyl-2-(2,4-difluorobenzyloxy)phenyl]cyclopent-1-enyl}-3-(propionamido)benzoic acid 2,4-difluorobenzyl ester Prepared by general procedure 5 but using 5-[2-(2-hydroxy-5-methylphenyl)cyclopent-1-enyl]-3-(propionamido)benzoic acid instead of 6-[2-(5-chloro-2-hydroxyphenyl)cyclopent-1-enyl]pyridine-2-carboxylic acid, 2,4-difluorobenzyl bromide instead of 4-chlorobenzyl bromide and acetone instead of 2-butanone.
LC/MS [MH+]=618, RT=4.36 min.

2-(2-Bromocyclopent-1-enyl)isonicotinic acid ethyl ester

Prepared according to general procedure B(ii) to give the product as a yellow oil 410 mg 28%
LC/MS: Rt=3.34 [M+H] 296,298 (1 Br).

2-{2-[5-Chloro-2-(2,4-difluorobenzyloxy)phenyl]cyclopent-1-enyl}isonicotinic acid ethyl ester Prepared according to general procedure B(iii) to give the product as a yellow oil 76 mg 31%.
LC/MS: Rt=3.92 [M+H] 470 (1 Cl)

2-{2-[5-Chloro-2-(4-fluorobenzyloxy)phenyl]cyclopent-1-enyl}isonicotinic acid ethyl ester Prepared according to general procedure B(iii) to give the product as a yellow oil 53 mg 22%
LC/MS: Rt=3.90 [M+H] 452 (1 Cl)

2-{2-[5-Chloro-2-benzyloxyphenyl]cyclopent-1-enyl}isonicotinic acid ethyl ester Prepared according to general procedure B(iii) to give the product as a yellow oil 67 mg 41%
LC/MS: Rt=3.88 [M+H] 434 (1 Cl)

2-{2-[5-Bromo-2-(benzyloxy)phenyl]cyclopent-1-enyl}isonicotinic acid ethyl ester Prepared according to general procedure B(iii) to give the product as a yellow gum 45 mg 27%
LC/MS: Rt=3.92 [M+H] 496,498 (1 Br).

5-[2-(2-Benzyloxy-5-chlorophenyl)-cyclopent-1-enyl]-3-aminobenzoic acid methyl ester Prepared according to general procedure B(iii) to give the product as a yellow oil 200 mg 56%
LC/MS: Rt=4.00 [M+H] 434 (1 Cl)

5-[2-(2-Benzyloxy-5-chlorophenyl)-cyclopent-1-enyl]-3-propionylaminobenzoic acid methyl ester Prepared by general procedure E but using 5-[2-(2-benzyloxy-5-chlorophenyl)-cyclopent-1-enyl]-3-aminobenzoic acid methyl ester instead of 5-[2-(2-benzyloxy-5-chlorophenyl)-cyclopent-1-enyl]-2-aminobenzoic acid methyl ester.
LC/MS: Rt=4.04 [M+H] 490 (1 Cl).

5-[2-(2-Benzyloxy-5-chlorophenyl)-cyclopent-1-enyl]-3-isobutyrylaminobenzoic acid methyl ester Prepared by general procedure E but using 5-[2-(2-benzyloxy-5-chlorophenyl)-cyclopent-1-enyl]-3-aminobenzoic acid methyl ester instead of 5-[2-(2-benzyloxy-5-chlorophenyl)-cyclopent-1-enyl]-2-aminobenzoic acid methyl ester and 2-methylpropionyl chloride instead of propionyl chloride.

LC/MS: Rt=4.13 [M+H] 504 (1 Cl)

2-[5-trifluoromethyl-2-benzyloxyphenyl]-1-bromocyclopent-1-ene

Prepared by general procedure C(i) using 2-benzyloxy-5-trifluoromethylphenylboronic acid instead of 2-benzyloxy-5-chlorophenylboronic acid.

$^1$H NMR (CDCl$_3$) δ: 2.01–2.08 (2H, m), 2.70–2.74 (2H, m), 2.77–2.82 (2H, m), 5.14 (2H, s), 6.97 (1H, d, J=8.6 Hz), 7.31–7.39 (5H, m), 7.49 (1H, dd, J=8.64, Hz), 7.54 (1H, s).

5-{2-[5-trifluoromethyl-2-benzyloxyphenyl]cyclopent-1-enyl}-3-aminobenzoic acid ethyl ester Prepared by general procedure B(iii)
$^1$H NMR (CDCl$_3$) δ: 1.25 (3H, t, J=7.1 Hz), 2.04–2.08 (2H, m), 2.84–2.92 (2H, m), 3.53 (2H, bs), 4.21 (2H, q, J=7.1 Hz), 5.02 (2H, s), 6.54 (1H, s), 6.93 (1H, d, J=8.6 Hz), 7.12–7.29 (8H, m), 7.32 (1H, d, J=8.5 Hz).
LC/MS [MH+]=482 Rt=4.12.

5-{2-[5-trifluoromethyl-2-(4-fluorobenzyloxy)phenyl]cyclopent-1-enyl}-3-aminobenzoic acid ethyl ester Prepared by general procedure B(iii)
$^1$H NMR (CDCl$_3$) δ: 1.25 (3H, t, J=7.1 Hz), 2.04–2.08 (2H, m), 2.82–2.91 (4H, m), 3.55 (2H, bs), 4.22 (2H, q, J=7.2 Hz), 4.94 (2H, s), 6.53 (1H, s), 6.91 (1H, d, J=8.6 Hz), 6.98 (2H, t, J=8.7 Hz), 7.12–7.16 (4H, m), 7.36 (1H, s), 7.44 (1H, dd, J=8.6 Hz).
LC/MS [MH+]=500 Rt=3.9.

5-{2-[5-trifluoromethyl-2-(2,4-difluorobenzyloxy)phenyl]cyclopent-1-enyl}-3-aminobenzoic acid ethyl ester Prepared by general procedure B(iii)
$^1$H NMR (CDCl$_3$) δ: 1.26 (3H, t, J=7.1 Hz), 1.99–2.08 (2H, m), 2.81 (2H, t, J=7.5 Hz), 2.90 (2H, t, J=7.5 Hz), 3.59 (2H, br s), 4.22 (2H, q, J=7.1 Hz), 5.0 (2H, s), 6.53 (1H, s), 6.79 (2H, t, J=8.4 Hz), 6.95 (1H, d, J=8.6 Hz), 7.06–7.14 (3H, m), 7.36 (1H, s,), 7.46 (1H, d, J=8.0 Hz).
LC/MS [MH+]=518 Rt=3.9.

5-{2-[5-chloro-2-(4-fluorobenzyloxy)phenyl]cyclopent-1-enyl}-3-aminobenzoic acid methyl ester/ethyl ester Prepared by general procedure B(iii)
LC/MS [MH+]=452, 454 Rt=4.06 LC/MS [MH+]=466 Rt=4.15

5-{2-[5-chloro-2-(2,4-difluorobenzyloxy)phenyl]cyclopent-1-enyl}-3-aminobenzoic acid methyl ester/ethyl ester Prepared by general procedure B(iii)
LC/MS [MH+]=470, 472 Rt=4.01 LC/MS [MH+]=484, 486 Rt=4.10

5-{2-[5-chloro-2-(benzyloxy)phenyl]cyclopent-1-enyl}-3-aminobenzoic acid ethyl ester Prepared by general procedure C(iii)
$^1$H NMR (CDCl$_3$) δ: 1.27 (3H, t, J=7.1 Hz), 2.02–2.06 (2H, m), 2.81–290 (4H, m), 3.54 (2H, brs), 4.24 (2H, q, J=7.1 Hz), 4.95 (2H, s), 6.55 (1H, s), 6.80 (1H, d, J=8.7 Hz), 7.02–7.28 (9H, m).
LC/MS [MH+]=448 Rt=3.8.

5-{2-[5-trifluoromethyl-2-(4-fluorobenzyloxy)phenyl]cyclopent-1-enyl}-3-methanesulphonylaminobenzoic acid ethyl ester Prepared according to general procedure G
$^1$H NMR (CDCl$_3$) δ: 1.33 (3H, t, J=7.1 Hz), 2.06–2.10 (2H, m) 2.62 (3H, s), 2.85 (2H, t, J=7.4 Hz), 2.92 (2H, bs), 4.32 (2H, q, J=7.1 Hz), 5.04 (2H, s), 6.53 (1H, s), 7.04–7.26 (6H, m), 7.47 (1H, d, J=8.6 Hz), 7.52 (1H, s), 7.64 (1H, s), 7.64 (1H, s).
LC/MS [MH−]=577 Rt=4.14.

5-{2-[5-trifluoromethyl-2-(2,4-difluorobenzyloxy)phenyl]cyclopent-1-enyl}-3-methanesulphonylaminobenzoic acid ethyl ester Prepared according to general procedure G
$^1$H NMR (CDCl$_3$) δ: 1.33 (3H, t, J=7.1 Hz), 2.04–2.09 (2H, m), 2.65 (3H, s), 2.83 (2H, t, J=7.3 Hz), 2.92 (2H, t, J=7.3 Hz), 4.32 (2H, q, J=7.1 Hz), 5.09 (2H, s), 6.73–7.63 (9H, m).
LC/MS [MH−]=594 Rt=4.16.

5-{2-[5-chloro-2-(4-fluorobenzyloxy)phenyl]cyclopent-1-enyl}-3-methanesulphonylaminobenzoic acid ethyl ester/methyl ester Prepared according to general procedure G.
Product (as a mixture of methyl ester 50.7% and ethyl ester 49.3%) as a yellow oil (91%).
LC/MS [MH−]=528, 530/542, 544 Rt=3.97/4.06.

5-{2-[5-trifluoromethyl-2-(benzyloxy)phenyl]cyclopent-1-enyl}-3-acetylaminobenzoic acid ethyl ester Prepared by general procedure E.
$^1$H NMR (CDCl$_3$) δ: 1.23 (3H, q, J=7.2 Hz), 2.02–2.13 (5H, m), 2.86–2.95 (4H, m), 4.22 (2H, q, J=7.1 Hz), 5.03 (2H, s), 6.95 (1H, d, J=8.6 Hz), 7.09 (1H, bs), 7.20–7.30 (5H, m), 7.43 (1H, d, J=8.6 Hz), 7.47 (1H, s), 7.56 (1H, s), 7.8 (1H, s).
LC/MS [MH−]=522 Rt=4.06.

5-{2-[5-trifluoromethyl-2-(4-fluorobenzyloxy)phenyl]cyclopent-1-enyl}-3-acetylaminobenzoic acid ethyl ester Prepared by general procedure E.
$^1$H NMR (CDCl$_3$) δ: 1.26 (3H, t, J=7.1 Hz), 2.04–2.10 (2H, m), 2.12 (3H, s), 2.86 (2H, t, J=7.5 Hz), 2.96 (2H, t, J=7.4 Hz), 4.22 (2H, q, J=7.0 Hz), 4.96 (2H, s), 6.93–7.03 (3H, m), 7.14–7.17 (2H, t, J=8.2), 7.33 (1H, s), 7.46 (2H, bs), 7.57 (1H, s), 7.76 (1H, s).
LC/MS [MH−]=540 Rt=4.10.

5-{2-[5-trifluoromethyl-2-(2,4-difluorobenzyloxy) phenyl]cyclopent-1-enyl}-3-acetylaminobenzoic acid ethyl ester Prepared according to general procedure E.
$^1$H NMR (CDCl$_3$) δ: 1.26 (3H, t, J=7.1 Hz), 2.02–2.10 (2H, m), 2.12 (3H, s), 2.85 (2H, t, J=7.4 Hz), 2.92 (2H, q, J=7.1Hz), 5.02 (2H, s), 6.76–6.81 (2H, m), 6.99 (1H, d, J=8.7 Hz), 7.08–7.49 (4H, m), 7.60 (1H, s), 7.74 (1H, s).
LC/MS [MH−]=558, 559 Rt=3.8.

5-{2-[5-chloro-2-(benzyloxy)phenyl]cyclopent-1-enyl}-3-acetylaminobenzoic acid ethyl ester Prepared according to general procedure E.
$^1$H NMR (CDCl$_3$) δ: 1.27 (3H, t, J=7.1 Hz), 2.01–2.09 (2H, m), 2.12 (3H, s), 2.84 (2H, t, J=7.5 Hz), 2.91 (2H, t, J=7.4 Hz), 4.24 (2H, q, J=7.1 Hz), 4.96 (2H, s), 6.82 (1H, d, J=8.8 Hz), 7.01 (1H, s), 7.11–7.31 (6H, m), 7.51 (2H, d, J=14), 7.86 (1H, s).
LC/MS [MH−]=488, 490 Rt=4.01.

5-{2-[5-chloro-2-(2,4-difluorobenzyloxy)phenyl] cyclopent-1-enyl}-3-acetylaminobenzoic acid ethyl ester/methyl ester Prepared according to general procedure E.
Product as a mixture of methyl ester and ethyl ester.
LC/MS [MH+]=510, 512 Rt=3.77 LC/MS [MH+]=526 Rt=3.86

5-{2-[5-chloro-2-(4-fluorobenzyloxy)phenyl]cyclopent-1-enyl}-3-acetylaminobenzoic acid ethyl ester/methyl ester Prepared according to general procedure E.
Product as a mixture of methyl ester and ethyl ester.
LC/MS [MH+]=494, 496 Rt=4.0 LC/MS [MH+]=508, 510 Rt=4.09.

5-{2-[5-trifluoromethyl-2-(4-fluorobenzyloxy)phenyl]cyclopent-1-enyl}-3-morpholin-4-ylbenzoic acid ethyl ester Prepared according to general procedure H.
$^1$H NMR (CDCl$_3$) δ: 1.31 (3H, t, J=7.1 Hz), 2.06–2.10 (2H, m), 2.80 (4H, t J=4.8 Hz), 2.83 (2H, t, J=7.3 Hz), 2.92 (2H, t, J=7.5 Hz), 3.70 (4H, t, J=4.8 Hz), 4.29 (2H, q, J=7.1 Hz), 5.29 (2H, s), 6.70 (1H, s), 6.90–7.44 (9H, m).
LC/MS [MH+]=570, 571 Rt=4.38.

5-{2-[5-chloro-2-(-4-fluorobenzyloxy)phenyl]cyclopent-1-enyl}-3-morpholin-4-ylbenzoic acid ethyl ester/methyl ester Prepared according to general procedure H using as solvent N-methyl-2-pyrrolidone (3 mL) instead of 2-butanone and heating at 90° C. Product obtained as a mixture of methyl ester and ethyl ester.
LC/MS [MH+]=522, 524 Rt=3.98 LC/MS [MH+]=536, 538 Rt=4.07.

5-{2-[5-trifluoromethyl-2-benzyloxyphenyl]cyclopent-1-enyl}-3-diethylaminobenzoic acid ethyl ester 5-{2-[5-trifluoromethyl-2-benzyloxyphenyl]cyclopent-1-enyl}-3-aminobenzoic acid ethyl ester (90 mg, 0.18 mmol), potassium carbonate (51 mg, 0.37 mmol), ethyliodide (0.037 mL, 0.47 mmol), in 3 mL of DMF were stirred at 40° C. for 16 hrs, then another 0.037 mL of ethyl iodide were added and the reaction mixture was stirred for another 4 hrs. The mixture was then poured into water and extracted with ethyl acetate (3×10 mL). The combined organic layers were dried (MgSO$_4$), and concentrated. Purification was carried out on a SPE using a gradient of iso-hexane/ethyl acetate.
LC/MS [MH+]=538, 539 Rt=4.55.

5-{2-[5-trifluoromethyl-2-benzyloxyphenyl]cyclopent-1-enyl}-3-methylaminobenzoic acid ethyl ester 5-{2-[5-trifluoromethyl-2-benzyloxyphenyl]cyclopent-1-enyl}-3-aminobenzoic acid ethyl ester (210 mg, 0.43 mmol), sodium hydride (17 mg, 0.43 mmol), iodomethane (0.027 mL, 0.43 mmol), in 3 mL of DMF were stirred at room temperature for 24 hrs, then another 0.027 mL of iodomethane were added and the reaction mixture was stirred for another 48 hrs. The mixture was then poured into water and extracted with ethyl acetate (3×10 mL). The combined organic layers were dried (MgSO$_4$), and concentrated. Purification was carried out on SPE using iso-hexane containing a gradient of ethylacetate (20–30%) to give the required product as a yellow oil. (85 mg, 39%).
LC/MS [MH+]=496 Rt=4.31.

5-{2-[5-trifluoromethyl-2-(4-fluorobenzyloxy)phenyl]cyclopent-1-enyl}-3-methylaminobenzoic acid ethyl ester Prepared according to the procedure for 5-{2-[5-trifluoromethyl-2-benzyloxyphenyl]cyclopent-1-enyl}-3-methylaminobenzoic acid ethyl ester, using 2.5 equivalents of NaH and MeI instead of 1 equivalent.
LC/MS [MH+]=514, 515 Rt=4.35

5-{2-5-chloro-2-(4-fluorobenzyloxy)phenyl]cyclopent-1-enyl}-3-methylaminobenzoic acid ethyl ester/methyl ester Prepared according to the procedure for 5-{2-[5-trifluoromethyl-2-benzyloxyphenyl]cyclopent-1-enyl}-3-methylaminobenzoic acid ethyl ester, using 2.5 equivalents of NaH and MeI instead of 1 equivalent.
LC/MS [MH+]=466, 468 Rt=4.17 LC/MS [MH+]=480, 482 Rt=4.34

5-{2-[5-trifluoromethyl-2-(4-fluorobenzyloxy)phenyl]cyclopent-1-enyl}-3-(4-chlorobutanoylamino) benzoic acid ethyl ester Prepared according to general procedure J.
LC/MS [MH−]=602 Rt=4.0

5-{2-[5-chloro-2-(4-fluorobenzyloxy)phenyl]cyclopent-1-enyl}-3-(4-chloro-butanoylamino)benzoic acid ethyl ester/methyl ester Prepared according to general procedure J.
The product was a mixture of ethyl and methyl ester.
LC/MS [MH+]=556 Rt=3.94 LC/MS [MH+]=570 Rt=4.02.

5-{2-[5-trifluoromethyl-2-(benzyloxy)phenyl]cyclopent-1-enyl}-3-(5-chloro-pentanoylamino)benzoic acid ethyl ester Prepared according to general procedure J using 5-chlorovaleryl chloride instead of 4-chlorobutyryl chloride.

$^1$H NMR (CDCl$_3$) δ: 1.26 (3H, t, J=7.1 Hz), 1.84 (4H, bs), 2.04–2.09 (2H, m), 2.34 (2H, bs), 2.86–2.96 (4H, m), 3.56 (2H, bs), 4.23 (2H, q, J=7.1 Hz), 5.04 (2H, s), 6.95 (1H, d, J=8.6 Hz), 7.02 (1H, s), 7.20–7.33 (5H, m), 7.44 (1H, d, J=8.6 Hz), 7.48 (1H, s), 7.58 (1H, s), 7.80 (1H, s).

5-{2-[5-trifluoromethyl-2-(4-fluorobenzyloxy)phenyl]cyclopent-1-enyl}-3-(5-chloro-pentanoylamino)benzoic acid ethyl ester Prepared according to general procedure J using 5-chlorovaleryl chloride instead of 4-chlorobutyryl chloride.
LC/MS [MH−]=616 Rt=4.04

5-{2-[5-chloro-2-(4-fluorobenzyloxy)phenyl]cyclopent-1-enyl}-3-(5-chloro-pentanoylamino)benzoic acid ethyl ester/methyl ester Prepared according to general procedure J using 5-chlorovaleryl chloride instead of 4-chlorobutyryl chloride.
LC/MS [MH+]=570 Rt=3.98 LC/MS [MH+]=584 Rt=4.05.

5-{2-[5-trifluoromethyl-2-(4-fluorobenzyloxy)phenyl]cyclopent-1-enyl}-3-(2-oxo-pyrrolidin-1-yl)benzoic acid ethyl ester Prepared according to general procedure K.
LC/MS [MH−]=566, 567 Rt=3.93

5-{2-[5-chloro-2-(4-fluorobenzyloxy)phenyl]cyclopent-1-enyl}-3-(2-oxo-pyrrolidin-1-yl)benzoic acid ethyl ester/methyl ester Prepared according to general procedure K.
The product was a mixture of ethyl and methyl ester.
LC/MS [MH+]=506, 508 Rt=3.84 LC/MS [MH+]=520, 522 Rt=3.93.

5-{2-[5-trifluoromethyl-2-(benzyloxy)phenyl]cyclopent-1-enyl}-3-(2-oxo-piperidin-1-yl)benzoic acid ethyl ester Prepared according to general procedure K.
$^1$H NMR (CDCl$_3$) δ: 1.26 (3H, t, J=7.1 Hz), 1.76–1.81 (4H, m), 2.04–2.10 (2H, m), 2.47 (2H, t, J=6.6 Hz), 2.88 (2H, t, J=7.5 Hz), 2.95 (2H, t, J=7.5 Hz), 3.17 (2H, t, J=5.9 Hz), 4.28 (2H, q, J=7.1 Hz), 5.06 (2H, s), 6.95 (1H, d, J=8.6 Hz), 7.00 (1H, s), 7.20–7.31 (6H, m), 7.44 (1H, d, J=8.6 Hz), 7.71 (2H, d, J=8.8 Hz).

5-{2-[5-chloro-2-(4-fluorobenzyloxy)phenyl]cyclopent-1-enyl}-3-(2-oxo-piperidin-1-yl)benzoic acid ethyl ester/methyl ester Prepared according to general procedure K.
The product was a mixture of ethyl and methyl ester.
LC/MS [MH+]=520, 522 Rt=3.67 LC/MS [MH+]=534, 536 Rt=3.78.

5-{2-[5-trifluoromethyl-2-(4-fluorobenzyloxy)phenyl]cyclopent-1-enyl}-3-(2-oxo-piperidin-1-yl)benzoic acid ethyl ester Prepared according to general procedure K.
LC/MS [MH+]=582, 583 Rt=3.88

6-{2-[5-chloro-2-(benzyloxy)phenyl]cyclopent-1-enyl}pyrazine-2-carboxylic acid ethyl ester Prepared using general procedure C(iii).
LC/MS [MH+]=435, 437 Rt=4.00

6-{2-[5-chloro-2-acetoxy)phenyl]cyclopent-1-enyl}-pyrazine-2-carboxylic acid ethyl ester Prepared using general procedure F(i).
LC/MS [MH+]=387, 389 Rt=3.33

6-{2-[5-chloro-2-(hydroxy)phenyl]cyclopent-1-enyl}pyrazine-2-carboxylic acid ethyl ester Prepared using general procedure F(ii).
LC/MS [MH+]=345, 347 Rt=3.51

6-{2-[5-chloro-2-(2,4-difluorobenzyloxy)phenyl]cyclopent-1-enyl}-pyrazine-2-carboxylic acid ethyl ester Prepared using general procedure F(iii).
LC/MS [MH+]=471, 473 Rt=4.02

5-{2-[5-trifluoromethyl-2-(2,4-difluorobenzyloxy)phenyl]cyclopent-1-enyl}-3-morpholin-4-ylbenzoic acid ethyl ester Prepared according to general procedure H using N-methyl-2-pyrrolidone (3 mL) as solvent instead of 2-butanone and heating at 90° C.
LC/MS [MH+]=588, 589 Rt=4.29

5-{2-[5-chloro-2-(2,4-difluorobenzyloxy)phenyl]cyclopent-1-enyl}-3-morpholinyl-4-yl-benzoic acid ethyl ester/methyl ester Prepared according to general procedure H using N-methyl-2-pyrrolidone (3 mL) as solvent instead of 2-butanone and heating at 90° C.
Product as a mixture of methyl ester and ethyl ester.
LC/MS [MH+]=540, 542 Rt=4.21 LC/MS [MH+]=554, 556 Rt=4.31

5-{2-[5-chloro-2-(benzyloxy)phenyl]cyclopent-1-enyl}-3-morpholin-4-yl-benzoic acid ethyl ester Prepared according to general procedure H using N-methyl-2-pyrrolidone (3 mL) as solvent instead of 2-butanone and heating at 90° C.
LC/MS [MH+]=518, 520 Rt=4.28

5-{2-[5-trifluoromethyl-2-benzyloxyphenyl]cyclopent-1-enyl}-3-diethylaminobenzoic acid ethyl ester 5-{2-[5-trifluoromethyl-2-benzyloxyphenyl]cyclopent-1-enyl}-3-aminobenzoic acid ethyl ester (90 mg, 0.18 mmol), potassium carbonate (51 mg, 0.37 mmol), ethyliodide (0.037 mL, 0.47 mmol), in 3 mL of DMF were stirred at 40° C. for 16 hrs, another 0.037 mL of ethyl iodide were added and the reaction mixture was stirred for another 4 hrs. The mixture was then poured into water and extracted with ethyl acetate (3×10 mL). The combined organic layers were dried (MgSO$_4$), and concentrated. Purification was carried out on SPE using a gradient of iso-hexane/ethyl acetate.

LC/MS [MH+]=538, 539 Rt=4.55.

5-{2-[5-chloro-2-(2,4-difluorobenzyloxy)phenyl]cyclopent-1-enyl}-3-methanesulphonylaminobenzoic acid ethyl ester/methyl ester Prepared according to general procedure G.

Product was a mixture of methyl ester 46% and ethyl ester 54%.

LC/MS [MH−]=546, 548/560, 562 Rt=3.79/3.87

5-{2-[5-chloro-2-(benzyloxy)phenyl]cyclopent-1-enyl}-3-methanesulphonylaminobenzoic acid ethyl ester Prepared according to general procedure G.

LC/MS [MH−]=524, 526 Rt=3.85.

6-{2-[5-Methyl-2-acetoxy)phenyl]cyclopent-1-enyl}pyrazine-2-carboxylic acid ethyl ester Prepared by general procedure F(i) but using 6-{2-[5-methyl-2-(benzyloxy)phenyl]cyclopent-1-enyl}pyrazine-2-carboxylic acid ethyl ester instead of 6-{2-[5-methyl-2-(benzyloxy)phenyl]cyclopent-1-enyl}pyridine-2-carboxylic acid ethyl ester.

LC/MS: Rt 3.3, [MH+] 367.4.

6-{2-[5-Methyl-2-(hydroxy)phenyl]cyclopent-1-enyl}pyrazine-2-carboxylic acid ethyl ester Prepared by general procedure F(ii) but using but using 6-{2-[5-methyl-2-(acetoxy)phenyl]cyclopent-1-enyl}pyrazine-2-carboxylic acid ethyl ester instead of 6-[2-(5-methyl-2-acetoxyphenyl)cyclopent-1-enyl]pyridine-2-carboxylic acid ethyl ester.

LC/MS: Rt 3.3, [MH+] 325.4.

6-{2-[5-Methyl-2-(4-fluorobenzyloxy)phenyl]cyclopent-1-enyl}pyrazine-2-carboxylic acid ethyl ester Prepared by general procedure F(iii) but using 6-{2-[5-methyl-2-(hydroxy)phenyl]cyclopent-1-enyl}pyrazine-2-carboxylic acid ethyl ester instead of 6-{2-[5-methyl-2-(hydroxy)phenyl]cyclopent-1-enyl}pyridine-2-carboxylic acid ethyl ester.

LC/MS: Rt 3.77, [MH+] 433.4

6-{2-[5-Methyl-2-(2,4-difluorobenzyloxy)phenyl]cyclopent-1-enyl}pyrazine-2-carboxylic acid ethyl ester Prepared by general procedure F(iii) but using 6-{2-[5-methyl-2-(hydroxy)phenyl]cyclopent-1-enyl}pyrazine-2-carboxylic acid ethyl ester instead of 6-{2-[5-methyl-2-(hydroxy)phenyl]cyclopent-1-enyl}pyridine-2-carboxylic acid ethyl ester and 2,4-difluorobenzyl bromide instead of 4-fluorobenzyl bromide.

LC/MS: Rt 3.8, [MH+] 451.3

2{2-[5-Trifluoromethyl-2-(2,4-difluorobenzyloxy)phenyl]cyclopent-1-enyl}-pyridine-4-carboxylic acid ethyl ester Prepared by general procedure B(iii) but using [5-trifluoromethyl-2-(2,4-diflurobenzyloxy)phenyl]boronic acid instead of (5-chloro-2-benzyloxyphenyl)-boronic acid and 2-(bromocyclopent-1-enyl)pyridine-4-carboxylic acid ethyl ester instead of 3-(2-bromo-cyclopent-1-enyl)-6-methyl benzoic acid ethyl ester LC/MS: Rt 4.20, [MH+] 504.1.

2-{2-[5-bromo-2-(2,4-difluorobenzyloxy)phenyl]cyclopent-1-enyl}pyridine-4-carboxylic acid ethyl ester Prepared by general procedure B(iii) but using [5-bromo-2-(2,4-difluorobenzyloxy)phenyl]boronic acid instead of (5-chloro-2-benzyloxyphenyl)boronic acid and 2-(bromocyclopent-1-enyl)-pyridine carboxylic acid ethyl ester instead of 3-(2-bromocyclopent-1-enyl)-methylbenzoic acid ethyl ester.

$^1$H NMR (CDCl$_3$) δ: 1.28 (3H, t, J=7.16 Hz), 2.04–2.11 (2H, m), 2.89 (2H, t, J=8 Hz), 3.06 (2H, t, J=7 Hz), 4.26 (2H, q, J=7.12 Hz), 4.93 (2H, s), 6.75–6.79 (2H, m), 6.83 (1H, d, J=8.8 Hz), 7.10–7.17 (1H, m), 7.25 (1H, s), 7.34 (1H, d, J=8.72 Hz), 7.47 (1H, s), 7.53 (1H, d, J=5.04 Hz), 8.60 (1H, d, J=5.04 Hz).

2-{2-[5-bromo-2-(benzyloxy)phenyl]cyclopent-1-enyl}-pyridine-4-carboxylic acid ethyl ester Prepared by general procedure B(iii) but using [5-bromo-2-(benzyloxy)phenyl]boronic acid instead of (5-chloro-2-benzyloxyphenyl)boronic acid and 2-(bromocyclopent-1-enyl)pyridine carboxylic-4-acid ethyl ester instead of 3-(2-bromocyclopent-1-enyl)-6-methylbenzoic acid ethyl ester.

$^1$H NMR (CDCl$_3$) δ: 1.20–1.27 (3H, m), 2.04–2.17 (2H, m), 2.90 (2H, t, J=7.4 Hz), 3.09 (2H, t, J=7.5 Hz), 4.23 (2H, q, J=7.1 Hz), 4.95 (2H, s), 6.81 (1H, d, J=8.8 Hz), 7.16–7.32 (7H, m), 7.51 (1H, s), 7.54 (1H, d, J=5.0 Hz), 8.62 (1H, d, J=5.0 Hz).

3-Amino-6-(2-bromocyclopent-1-enyl)-pyrazine-2-carboxylic acid ethyl ester

Prepared by general procedure B(ii) but using 3-amino-6-bromopyrazine-2-carboxylic acid ethyl ester instead of 5-iodo-2-methylbenzoic acid ethyl ester.

$^1$H NMR (CDCl$_3$) δ: 1.44 (3H, t, J=7.1 Hz), 2.01–2.09 (2H, m), 2.88 (4H, t J=7.52 Hz), 4.43 (2H, q, J=7.1 Hz), 5.99–6.94 (2H, br s), 8.80 (1H, s).

3-bromo-5-methylbenzoic acid ethyl ester

Sulphuric acid (10 drops) was added to 3-bromo-5-methylbenzoic acid (1.18 g, 5.49 mmol) in ethanol (20 ml) and refluxed at 90° C. for 20 hours. After cooling, the mixture was diluted with diethyl ether/water and the organic phase washed with sodium hydrogen bicarbonate (saturated solution), dried (magnesium sulphate) and evaporated to dryness to give the title compound as a pale yellow oil (1.249 g, 94%).

$^1$H NMR (CDCl$_3$) δ: 1.39 (3H, t, J=7.1 Hz), 2.39 (3H, s), 4.37 (2H, q, J=7.1 Hz), 7.51 (1H, s), 7.78 (1H, s), 7.97 (1H, s).

3-(2-bromocyclopent-1-enyl)-5-methylbenzoic acid ethyl ester

Prepared by general procedure B(ii) but using 3-bromo-5-methylbenzoic acid ethyl ester instead of 5-iodo-2-methylbenzoic acid ethyl ester.

LC/MS: Rt 4.00, [MH+] 311.

3-{2-[5-Trifluoromethyl-2-(benzyloxy)phenyl]cyclopent-1-enyl}-5-methylbenzoic acid ethyl ester Prepared by general procedure B(iii) but using [5-trifluoromethyl-2-(benzyloxy)phenyl]boronic acid instead of (5-chloro-2-benzyloxyphenyl)boronic acid and 3-(2-bromocyclopent-1-enyl)-5-methylbenzoic acid ethyl ester instead of 3-(2-bromocyclopent-1-enyl)-6-methylbenzoic acid ethyl ester.

$^1$H NMR (CDCl$_3$) δ: 1.25 (3H, t, J=7.1 Hz), 2.03–2.10 (2H, m), 2.18 (3H, s), 2.86–2.95 (4H, m), 4.23 (2H, q, J=7.1 Hz), 4.99 (2H, s), 6.92 (1H, d, 8.6 Hz), 7.05 (1H, s), 7.16–7.30 (5H, m), 7.34 (1H, s), 7.43 (1H, d, J=8.6 Hz), 7.61 (2H, d, J=9.9 Hz).

3-{2-[5-Chloro-2-(benzyloxy)phenyl]cyclopent-1-enyl}-5-methylbenzoic acid ethyl ester Prepared by general procedure B(iii) but using 3-(2-bromocyclopent-1-enyl)-5-methylbenzoic acid ethyl ester instead of 3-(2-bromocyclopent-1-enyl)-6-methylbenzoic acid ethyl ester.

LC/MS: Rt [MH+] 447.2

6-{2-[5-Fluoro-2-(methoxy)phenyl]cyclopent-1-enyl}pyridine-2-carboxylic acid ethyl ester Prepared by general procedure B(iii) but using 5-fluoro-2-methoxyphenylboronic acid instead of (5-chloro-2-benzyloxyphenyl)boronic acid and 6-(2-bromocyclopent-1-enyl)-pyridine-2-carboxylic acid ethyl ester instead of 3-(2-bromocyclopent-1-enyl)-6-methylbenzoic acid ethyl ester.

LC/MS: Rt 3.4, [MH+] 342.4.

6-{2-[5-Fluoro-2-hydroxy)phenyl]cyclopent-1-enyl}pyridine-2-carboxylic acid

A mixture of 6-{2-[5-fluoro-2-(methoxy)phenyl]cyclopent-1-enyl}-pyridine-2-carboxylic acid ethyl ester (336 mg, 0.99 mmol) and sodium methanethiolate (347 mg, 4.95 mmol) in dimethyl formamide (5 ml) was heated under nitrogen at 120° C. for 2.5 hours. After cooling the mixture was diluted with ether/water and the aqueous separated, acidified with acetic acid and extracted with ether. The organic phase was dried (magnesium sulphate) and evaporated to yield the title compound as a yellow gum (366 mg).

LC/MS: Rt 2.53, [MH+] 300.3.

6-{2-[5-Fluoro-2-(benzyloxy)phenyl]cyclopent-1-enyl}-pyridine-2-carboxylic acid benzyl ester Prepared by general procedure 5 but using 6-{2-[5-fluoro-2-(hydroxy)phenyl]cyclopent-1-enyl}pyridine-2-carboxylic acid instead of 6-{2-[5-chloro-2-(hydroxy)phenyl]cyclopent-1-enyl}pyridine-2-carboxylic acid, benzyl bromide instead of 4-chlorobenzyl bromide and with acetone as solvent instead of 2-butanone.

LC/MS: Rt 3.96, [MH+] 480.3.

6-{2-[5-Fluoro-2-(4-fluorobenzyloxy)phenyl]cyclopent-1-enyl}pyridine-2-carboxylic acid 4-fluorobenzyl ester Prepared by general procedure 5 but using 6-{2-[5-fluoro-2-(hydroxy)phenyl]cyclopent-1-enyl}pyridine-2-carboxylic acid instead of 6-{2-[5-chloro-2-(hydroxy)phenyl]cyclopent-1-enyl}pyridine-2-carboxylic acid, 4-fluorobenzyl bromide instead of 4-chlorobenzyl bromide and with acetone as solvent instead of 2-butanone.

LC/MS: Rt 3.96, [MH+] 516.3.

6-{2-[5-Fluoro-2-(2,4-difluorobenzyloxy)phenyl]cyclopent-1-enyl}pyridine-2-carboxylic acid 2,4-difluorobenzyl ester Prepared by general procedure 5 but using 6-{2-[5-fluoro-2-(hydroxy)phenyl]cyclopent-1-enyl}pyridine-2-carboxylic acid instead of 6-{2-[5-chloro-2-(hydroxy)phenyl]cyclopent-1-enyl}pyridine-2-carboxylic acid, 2,4-difluorobenzyl bromide instead of 4-chlorobenzyl bromide and with acetone as solvent instead of 2-butanone.

LC/MS: Rt 3.99, [MH+] 552.3.

6-Chloropyridazine-4-carboxylic acid ethyl ester

Ethyl 2-nitro-4-furoate (990 mg, 5.35 mmol) was dissolved in ethanol (25 ml) and hydrazine hydrate (0.5 g) was added and the mixture refluxed for 20 minutes then cooled and evaporated to dryness. The residue was dissolved in ether/water and the organic phase dried (magnesium sulphate) evaporated and chromatographed on silica gel eluting with ethyl acetate/iso-hexane (2:3) to give a gum (426 mg) which was dissolved in phosphoryl chloride (4 ml) and heated at 90° C. for 30 minutes. The resulting mixture was evaporated to dryness and dissolved in ether/water and the organic phase dried (magnesium sulphate) evaporated and chromatographed twice on silica gel eluting first with ethyl acetate/iso-hexane (3:17) then with methanol/dichloromethane (3:197) to give a solid which was triturated with iso-hexane and filtered off to yield the title compound as an off-white solid. (31 mg, 2.4%).

LC/MS: Rt 2.00, [MH+] 187.2, 189.2.

6-{2-[5-Chloro-2-(benzyloxy)phenyl]cyclopent-1-enyl}pyridazine-4-carboxylic acid ethyl ester Was prepared by general procedure C(iii) but using 6-chloropyridazine-4-carboxylic acid ethyl ester instead of 2-chloropyrimidine-4-carboxylic acid methyl ester.

LC/MS: Rt 3.69, [MH+] 435.3.

6-{2-[5-Chloro-2-(acetoxy)phenyl]cyclopent-1-enyl}pyridazine-4-carboxylic acid ethyl ester Prepared by general method F(i) using 6-{2-[5-Chloro-2-(benzyloxy)phenyl]cyclopent-1-enyl}pyridazine-4-carboxylic acid ethyl ester instead of 6-{2-[5-methyl-2-(benzyloxy)phenyl]cyclopent-1-enyl}pyridine-2-carboxylic acid ethyl ester.

LC/MS: Rt 3.25, [MH+] 387.3, 389.3.

6-{2-[5-Chloro-2-(hydroxy)phenyl]cyclopent-1-enyl}-pyridazine-4-carboxylic acid ethyl ester Prepared by general procedure F(ii) but using 6-{2-[5-chloro-2-(acetoxy)phenyl]cyclopent-1-enyl}pyridazine-4- carboxylic acid ethyl ester instead of 6-[2-(5-methyl-2-acetoxyphenyl)cyclopent-1-enyl]pyridine-2-carboxylic acid ethyl ester.

LC/MS: Rt 3.26, [MH+] 345.3, 347.3.

6-{2-[5-Chloro-2-(4-fluorobenzyloxy)phenyl]cyclopent-1-enyl}-pyridazine-4-carboxylic acid ethyl ester Prepared by general procedure F(iii) but using 6-{2-[5-chloro-2-(hydroxy)phenyl]cyclopent-1-enyl}pyridazine-4-carboxylic acid ethyl ester instead of 6-{2-[5-methyl-2-(hydroxy)phenyl]cyclopent-1-enyl}pyridine-2-carboxylic acid ethyl ester.

LC/MS: Rt 3.69, [MH+] 453.3.

6-{2-[5-Chloro-2-(2,4-difluorobenzyloxy)phenyl]cyclopent-1-enyl}-pyridazine-4-carboxylic acid ethyl ester Prepared by general procedure F(iii) but using 6-{2-[5-chloro-2-(hydroxy)phenyl]cyclopent-1-enyl}-pyridazine-4-carboxylic acid ethyl ester instead of 6-{2-[5-methyl-2-(hydroxy)phenyl]cyclopent-1-enyl}pyridine-2-carboxylic acid ethyl ester and 2,4-difluorobenzyl bromide instead of 4-fluorobenzyl bromide.

LC/MS: Rt 3.71, [MH+] 471.3, 473.3.

5-{2-[-5-chloro-2-(2,4-difluorobenzyloxy)phenyl)cyclopent-1-enyl]-2-methylbenzoic acid t-butyl ester The title compound was prepared using general procedure B(iii) using 3-(2-bromocyclopent-1-enyl)-6-methyl benzoic acid t-butyl ester to give the product as a yellow oil 40 mg 22%.

$^1$HNMR (CDCl$_3$): ) δ: 1.49 (9H, s), 2.02–2.05 (2H, m), 2.47 (3H, s), 2.80 (2H, t, J=6 Hz), 2.91 (2H, t, J=6 Hz), 4.91 (2H, s), 6.50–7.16 (8H, m), 7.57 (1H, s).

3-(2-bromocyclopent-1-enyl)-6-methylbenzoic acid t-butyl ester

The title compound was prepared according to general procedure B(ii) using 5-iodo-2-methylbenzoic acid t-butyl ester to give the product as a yellow oil 120 mg 38%.

$^1$HNMR (CDCl$_3$): δ: 1.55 (9H, s), 2.02–2.06 (2H, m), 2.56 (3H, s), 2.74–2.76 (2H, m), 2.83–2.87 (2H, m), 7.20 (1H, d, J=8 Hz), 7.61 (1H, d, J=8 Hz), 8.07 (1H, s).

5-iodo-2-methylbenzoic acid t-butyl ester

A mixture of 5-iodo-2-methylbenzoic acid (760 mg, 2.9 mmol), 1-(3-dimethylaminopropyl)-3-ethylcarbodiimide hydrochloride (670 mg, 3.5 mmol), 4-dimethylaminopyridine (425 mg, 3.5 mmol), and t-butanol (1.07 g, 14.5 mmol) in dichloromethane (10 ml) was stirred at room temperature overnight. The reaction mixture was diluted with ethyl acetate (25 ml) and washed with 5% NaHCO$_3$, 1M HCl, water and, brine. The organic phase was dried and evaporated to give a pale yellow solid 600 mg 65%.

$^1$H NMR (CDCl$_3$): δ: 1.58 (9H, s), 2.49 (3H, s), 6.95 (1H, d, J=8 Hz), 7.64 (1H, d, J=8 Hz), 8.10 (1H, s).

5-{2-[5-chloro-2-(4-fluorobenzyloxy)phenyl)cyclopent-1-enyl}-2-methylbenzoic acid t-butyl ester The title compound was prepared using general procedure B(iii) using 3-(2-bromocyclopent-1-enyl)-6-methyl benzoic acid t-butyl ester to give the product as a yellow oil 60 mg 21%.

$^1$HNMR (CDCl$_3$): δ: 1.49 (9H, s), 2.00–2.05 (2H, m), 2.48 (3H, s), 2.81 (2H, t, J=6 Hz), 2.89 (2H, t, J=6 Hz), 4.86 (2H, s), 6.79 (1H, d, J=8 Hz), 6.94–7.13 (8H, m), 7.59 (1H, s).

5-[2-(5-chloro-2-(4-fluorobenzyloxy)phenyl)cyclopent-1-enyl]-2-fluorobenzoic acid ethyl ester.

Prepared according to general procedure C(iii) using ethyl 5-bromo-2-fluorobenzoate and 2-(2-(4-fluorobenzyloxy)-5-chlorophenyl)cyclopentene-1-boronic acid to give the product as a colourless solid 43 mg 23%.

LC/MS: Rt=4.10 [M+H] 469 (1 Cl).

5-[2-(2-benzyloxy)-5-chlorophenyl)cyclopent-1-enyl]-2-fluorobenzoic acid ethyl ester Prepared according to general procedure C(iii) using ethyl 5-bromo-2-fluorobenzoate and 2-(2-benzyloxy-5-chlorophenyl)cyclopentene-1-boronic acid to give the product as a colourless oil 61 mg 37%.

LC/MS: Rt=4.13 [M+H] 451 (1 Cl).

4-(2-Bromocyclopent-1-enyl)benzoic acid ethyl ester

Prepared by general procedure 1(a(ii)).

$^1$H NMR (400 MHz, CDCl$_3$) δ: 1.36–1.44 (3H, t, J=7 Hz), 2.02–2.11 (2H, m), 2.75–2.82 (2H, m), 2.84–2.91 (2H, m), 4.35–4.42 (2H, q, J=7 Hz), 7.64–7.69 (2H, m), 8.00–806 (2H, m).

LC/MS [MH+] 297 Rt=3.68 min.

5-{2-[5-Trifluoromethyl-2-(benzyloxy)phenyl]cyclopent-1-enyl}-nicotinic acid ethyl ester Prepared according to general procedure 8.
Product 22 mg, 30%.

$^1$H NMR (400 MHz, CDCl$_3$) δ: 1.33 (3H, t, J=7 Hz), 2.07–2.16 (2H, m), 2.87–2.99 (4H, m), 4.27–4.35 (2H, q, J=7.5 Hz), 5.00 (2H, s), 6.97 (1H, d, J=9 Hz), 7.17 (2H, dd, J=6 Hz), 7.26–7.34 (4H, m), 7.47 (1H, dd, J=8 Hz), 7.94 (1H, t, J=4Hz), 8.42 (1H, d, J=2 Hz), 8.93 (1H, d, J=2 Hz).

4-{2-[2-(Benzyloxy)phenyl]cyclopent-1-enyl}-benzoic acid ethyl ester

Prepared by general procedure B(iii).

$^1$H NMR (400 MHz, CDCl$_3$) δ: 1.32–1.38 (3H, t, J=7 Hz), 2.02–2.12 (2H, m), 2.86–2.96 (4H, m), 4.28–4.36 (2H, q, J=7 Hz), 5.00 (2H, s), 6.82–6.87 (1H, m), 6.90 (1H, d, J=8 Hz), 6.97–7.02 (1H, m), 7.14–7.17 (2H, m), 7.17–7.35 (6H, m), 7.76–7.81 (2H, m).

4-[2-(2-Benzyloxy-5-chlorophenyl)cyclopent-1-enyl]benzoic acid ethyl ester

Prepared by general procedure B(iii).

$^1$H NMR (400 MHz, CDCl$_3$) δ: 1.37 (3H, t, J=7 Hz) 2.01–2.12 (2H, m), 2.82–2.96 (4H, m), 4.33 (2H, q, J=7 Hz), 4.94 (2H, s), 6.82 (1H, d, J=9 Hz), 7.00 (1H, d, J=3 Hz), 7.10–7.22 (5H, m), 7.24–7.34 (3H, m), 7.82 (2H, d, J=9 Hz).

3-{2-[5-Chloro-2-(4-fluorobenzyloxy)phenyl]cyclopent-1-enyl}-5-methylbenzoic acid ethyl ester Prepared by general procedure B(iii) but using 3-(2-bromocyclopent-1-enyl)-5-methylbenzoic acid ethyl ester instead of 3-(2-bromo-cyclopent-1-enyl)-6-methyl benzoic acid ethyl ester and using [5-chloro-2-(4-fluorobenzyloxy)phenyl]boronic acid instead of (5-chloro-2-benzyloxyphenyl)boronic acid.

¹NMR (CDCl₃) δ: 1.30 (3H, t, J=7.1 Hz), 2.06 (2H, m), 2.21 (3H, s), 2.81–2.93 (4H, m), 4.27 (2H, q, J=7.1 Hz), 4.86 (2H, s), 6.79 (1H, d, J=8.8 Hz), 6.94–7.26 (7H, m), 7.60 (2H, m).

3-{2-[5-Chloro-2-(2,4-difluorobenzyloxy)phenyl]cyclopent-1-enyl}-5-methylbenzoic acid ethyl ester Prepared by general procedure B(iii) but using 3-(2-bromocyclopent-1-enyl)-5-methylbenzoic acid ethyl ester instead of 3-(2-bromo-cyclopent-1-enyl)-6-methyl benzoic acid ethyl ester and using [5-chloro-2-(2,4-di-fluorobenzyloxy)phenyl]boronic acid instead of (5-chloro-2-benzyloxyphenyl)boronic acid.

¹H NMR (CDCl₃) δ: 1.31 (3H, t, J=7.2 Hz), 2.01–2.09 (2H, m), 2.21 (3H, s), 2.80–2.93 (4H, m), 4.27 (2H, q, J=7.1 Hz), 4.91 (2H, s), 6.74–6.84 (3H, m), 7.04–7.17 (4H, m), 7.59 (2H, m).

3-{2-[5-Trifluoromethyl-2-(4-fluorobenzyloxy)phenyl]cyclopent-1-enyl}-5-methylbenzoic acid ethyl ester Prepared by general procedure B(iii) but using 3-(2-bromocyclopent-1-enyl)-5-methylbenzoic acid ethyl ester instead of 3-(2-bromo-cyclopent-1-enyl)-6-methyl benzoic acid ethyl ester and using [5-trifluoromethyl-2-(4-fluorobenzyloxy)phenyl]boronic acid instead of (5-chloro-2-benzyloxyphenyl)boronic acid.

¹H NMR (CDCl₃) δ: 1.27 (3H, t, J=7.1 Hz), 2.03–2.11 (2H, m), 2.19 (3H, s), 2.84–2.95 (4H, m), 4.25 (2H, q, J=7.1 Hz), 4.94 (2H, s), 6.91–7.02 (3H, m), 7.11–7.14 (2H, m), 7.26 (1H, s), 7.35 (1H, s), 7.45 (1H, d, J=8.6 Hz), 7.55 (1H, s), 7.61 (1H, s).

3-{2-[5-Trifluoromethyl-2-(2,4-difluorobenzyloxy)phenyl]cyclopent-1-enyl}-5-methylbenzoic acid ethyl ester Prepared by general procedure B(iii) but using 3-(2-bromocyclopent-1-enyl)-5-methylbenzoic acid ethyl ester instead of 3-(2-bromo-cyclopent-1-enyl)-6-methyl benzoic acid ethyl ester and using [5-trifluoromethyl-2-(2,4-di-fluorobenzyloxy)phenyl]boronic acid instead of (5-chloro-2-benzyloxyphenyl)boronic acid.

¹H NMR (CDCl₃) δ: 1.28 (3H, t, J=7.1 Hz), 2.03–2.11 (2H, m), 2.19 (3H, s), 2.83–2.95 (4H, m), 4.25 (2H, q, J=7.1 Hz), 5.00 (2H, s), 6.76–6.81 (2H, m), 6.95–7.01 (3H, m), 7.35 (1H, s), 7.46–7.49 (1H, m), 7.54 (1H, s), 7.60 (1H, s).

3-bromo-5-fluorobenzoic acid ethyl ester

Sulphuric acid (5 drops) was added to 3-bromo-5-fluorobenzoic acid (1.194 g, 5.45 mmol) in ethanol (10 ml) and refluxed with stirring at 90° C. for 17 hours. Reaction mixture partitioned between diethyl ether and water, washed with sodium hydrogen carbonate, dried (MgSO₄) and evaporated to dryness.

¹H NMR (CDCl₃) δ: 1.40 (3H, t, J=7.2 Hz), 4.39 (2H, q, J=7.1 Hz), 7.42–7.45 (1H, m), 7.66–7.69 (1H, m), 7.98 (1H, s).

3-(2-bromocyclopent-1-enyl)-5-fluorobenzoic acid ethyl ester

Prepared by general procedure B(ii) but using 3-bromo-5-fluorobenzoic acid ethyl ester instead of 5-iodo-2-methylbenzoic acid ethyl ester LC/MS: Rt 4.01, [MS+] 313.0

3-{2-[5-Chloro-2-(benzyloxy)phenyl]cyclopent-1-enyl}-5-fluorobenzoic acid ethyl ester Prepared by general procedure B(iii) but using 3-(2-bromocyclopent-1-enyl)-5-fluorobenzoic acid ethyl ester instead of 3-(2-bromo-cyclopent-1-enyl)-6-methyl benzoic acid ethyl ester.

¹H NMR (CDCl₃) δ: 1.31 (3H, t, J=7.2 Hz), 2.03–2.10 (2H, m), 2.83–2.93 (4H, m), 4.28 (2H, q, J=7.1 Hz), 4.95 (2H, s), 6.83–6.85 (1H, m), 6.92–6.94 (1H, m), 7.02 (1H, s), 7.13–7.19 (3H, m), 7.26–7.32 (3H, m), 7.45–7.47 (1H, m), 7.60 (1H, s).

3-{2-[5-Chloro-2-(4-fluorobenzyloxy)phenyl]cyclopent-1-enyl}-5-fluorobenzoic acid ethyl ester Prepared by general procedure B(iii) but using 3-(2-bromocyclopent-1-enyl)-5-fluorobenzoic acid ethyl ester instead of 3-(2-bromo-cyclopent-1-enyl)-6-methylbenzoic acid ethyl ester and using [5-chloro-2-(4-fluorobenzyloxy)phenyl]boronic acid instead of (5-chloro-2-benzyloxyphenyl)boronic acid.

¹H NMR (CDCl₃) δ: 1.32 (3H, t, J=7.1 Hz), 2.02–2.10 (2H, m), 2.82–2.92 (4H, m), 4.29 (2H, q, J=7.1 Hz), 4.88 (2H, s), 6.82 (1H, m), 6.91 (1H, m), 6.95–7.18 (6H, m), 7.45–7.48 (1H, m), 7.58 (1H, s).

3-{2-[5-chloro-2-(2,4-difluorobenzyloxy)phenyl]cyclopent-1-enyl}-5-fluorobenzoic acid ethyl ester Prepared by general procedure B(iii) but using 3-(2-bromocyclopent-1-enyl)-5-fluorobenzoic acid ethyl ester instead of 3-(2-bromo-cyclopent-1-enyl)-6-methylbenzoic acid ethyl ester and using [5-chloro-2-(2,4-di-fluorobenzyloxy)phenyl]boronic acid instead of (5-chloro-2-benzyloxyphenyl)boronic acid.

¹H NMR (CDCl₃) δ: 1.32 (3H, t, J=7.1 Hz), 2.02–2.10 (2H, m), 2.80–2.92 (4H, m), 4.29 (2H, q, J=7.1 Hz), 4.93 (2H, s), 6.78–6.91 (4H, m), 7.05 (1H, s), 7.10–7.17 (1H, m), 7.18–7.21 (1H, m), 7.44–7.47 (1H, m), 7.56 (1H, s).

3-{2-[5-Trifluoromethyl-2-(4-fluorobenzyloxy)phenyl]cyclopent-1-enyl}-5-fluorobenzoic acid ethyl ester Prepared by general procedure B(iii) but using 3-(2-bromocyclopent-1-enyl)-5-fluorobenzoic acid ethyl ester instead of 3-(2-bromo-cyclopent-1-enyl)-6-methyl benzoic acid ethyl ester and using [5-trifluoromethyl-2-(4-fluorobenzyloxy)phenyl]boronic acid instead of (5-chloro-2-benzyloxyphenyl)boronic acid.

¹H NMR (CDCl₃) δ: 1.28 (3H, t, J=7.1 Hz), 2.04–2.12 (2H, m), 2.85–2.93 (4H, m), 4.27 (2H, t, J=7.1 Hz), 4.95 (2H, s), 6.88–7.01 (4H, m), 7.12–7.15 (2H, m), 7.35 (1H, s), 7.45–7.54 (2H, m), 7.54 (1H, s).

3-{2-[5-Trifluoromethyl-2-(2,4-difluorobenzyloxy)phenyl]cyclopent-1-enyl}-5-fluorobenzoic acid ethyl ester Prepared by general procedure B(iii) but using 3-(2-bromocyclopent-1-enyl)-5-fluorobenzoic acid ethyl ester instead of 3-(2-bromo-cyclopent-1-enyl)-6-methyl benzoic acid ethyl ester and using [5-trifluoromethyl-2-(2,4-di-fluorobenzyloxy)phenyl]boronic acid instead of 5-chloro-2-benzyloxyphenyl)boronic acid.

¹H NMR (CDCl₃) δ: 1.27 (3H, t, J=7.1 Hz), 2.04–2.12 (2H, m), 2.83–2.93 (4H, m), 4.27 (2H, q, J=7.1 Hz), 5.01 (2H, s), 6.78–6.89 (3H, m), 6.99–7.01 (1H, m), 7.10–7.15 (1H, m), 7.34 (1H, s), 7.44–7.52 (3H, m).

2-{2-[5-Bromo-2-(4-fluorobenzyloxy)phenyl]-cyclopent-1-enyl}-isonicotinic acid ethyl ester Prepared according to standard procedure B(iii) to give the product as a yellow gum 45 mg 27%
LC/MS: Rt=3.92 [M+H] 496, 498 (1 Br)

6-{2-[5-chloro-2-(benzyloxy)phenyl]cyclopent-1-enyl}pyridine-2-carboxylic acid ethyl ester Prepared using general procedure F(iii).
LC/MS[MH+]=434,436 Rt=4.12

6-{2-[5-chloro-2-(4-bromobenzyloxy)phenyl]cyclopent-1-enyl}pyridine-2-carboxylic acid ethyl ester Prepared using general procedure F(iii).
LC/MS[MH+]=514,516 Rt=4.29.

6-{2-[5-chloro-2-(2-chloro-4-fluorobenzyloxy)phenyl]cyclopent-1-enyl}pyridine-2-carboxylic acid ethyl ester Prepared using general procedure F(iii).
LC/MS[MH+]=486,489 Rt=4.30.

6-{2-[5-chloro-2-(2,4,6-trifluorobenzyloxy)phenyl]cyclopent-1-enyl}-pyridine-2-carboxylic acid ethyl ester Prepared using general procedure F(iii).
LC/MS[MH+]=488,490 Rt=4.12.

6-{2-[5-chloro-2-(2,6-difluorobenzyloxy)phenyl]cyclopent-1-enyl}pyridine-2-carboxylic acid ethyl ester Prepared using general procedure F(iii).
LC/MS[MH+]=470,472 Rt=4.09.

6-{2-[5-chloro-2-(4-trifluoromethyl-2-fluorobenzyloxy)phenyl]cyclopent-1-enyl}pyridine-2-carboxylic acid ethyl ester Prepared using general procedure F(iii).
LC/MS[MH+]=520,522 Rt=4.30.

6-{2-[5-chloro-2-(3,4-difluorobenzyloxy)phenyl]cyclopent-1-enyl}pyridine-2-carboxylic acid ethyl ester Prepared using general procedure F(iii).
LC/MS[MH+]=470,472 Rt=4.16.

6-{2-[5-chloro-2-(2,3-difluorobenzyloxy)phenyl]cyclopent-1-enyl}pyridine-2-carboxylic acid ethyl ester Prepared using general procedure F(iii).
LC/MS[MH+]=470,472 Rt=4.14.

6-{2-[5-chloro-2-(4-methylbenzyloxy)phenyl]cyclopent-1-enyl}pyridine-2-carboxylic acid ethyl ester Prepared using general procedure F(iii).
LC/MS[MH+]=448,450 Rt=4.22.

6-{2-[5-chloro-2-(4-trifluoromethylbenzyloxy)phenyl]cyclopent-1-enyl}pyridine-2-carboxylic acid ethyl ester Prepared using general procedure F(iii).
LC/MS[MH+]=502,504 Rt=4.26.

2-{2-[5-Trifluoromethyl-2-(benzyloxy)phenyl]cyclopent-1-enyl}pyrimidine-4-carboxylic acid ethyl ester Prepared by general procedure C(iii) but using 2-[2-(benzyloxy)-5-trifluoromethylphenyl]cyclopentene-1-boronic acid instead of 2-(2-benzyloxy-5-chlorophenyl)cyclopentene-1-boronic acid.
LC/MS: Rt 3.78, [MH+] 469.3.

3-{2-[5-Methyl-2-(benzyloxy)phenyl]cyclopent-1-enyl}-6-acetamidobenzoic acid ethyl ester Prepared by general procedure E but using 3-{2-[5-methyl-2-(benzyloxy)phenyl]cyclopent-1-enyl}-6-aminobenzoic acid ethyl ester and acetyl chloride.
LC/MS: Rt 4.01, [MH+] 470.4.

3-{2-[5-Trifluoromethyl-2-(benzyloxy)phenyl]cyclopent-1-enyl}-6-fluorobenzoic acid ethyl ester Prepared by general procedure C(iii) but using 2-(2-benzyloxy-5-trifluoromethylphenyl)cyclopentene-1-boronic acid instead of 2-(2-benzyloxy-5-chlorophenyl)cyclopentene-1-boronic acid and 3-bromo-6-fluorobenzoic acid ethyl ester instead of 2-chloropyrimidine-4-carboxylic acid methyl ester.

¹H NMR (CDCl₃) δ: 1.28 (3H, t), 2.05–2.12 (2H, m), 2.86–2.94 (4H, m), 4.28 (2H, q) 5.02 (2H, s), 6.85 (1H, dd, J=9 Hz, 3 Hz), 6.96 (1H, d, J=9 Hz), 7.19–7.32 (6H, m), 7.33 (1H, s), 7.45 (1H, d, J=9 Hz), 7.66 (1H, d, J=9 Hz).

3-{2-[5-Trifluoromethyl-2-(benzyloxy)phenyl]cyclopent-1-enyl}-6-methylbenzoic acid ethyl ester Prepared by general procedure B(iii) but using 2-[5-trifluoromethyl-2-(benzyloxy)phenyl]boronic acid instead of (5-chloro-2-benzyloxyphenyl)boronic acid.

$^1$H NMR (d$_6$DMSO) δ: 1.12 (3H, t), 2.00–2.03 (2H, m), 2.43 (3H, s). 2.83–2.88 (4H, m), 4.10 (2H, q) 5.14 (2H, s), 7.16–7.34 (9H, m), 7.52 (1H, s), 7.62 (1H, d, J=9 Hz).

5-{2-[5-chloro-2-(2,4-difluorobenzyloxy)phenyl]cyclopent-1-enyl}-3-(5-chloropentanoylamino)benzoic acid ethyl ester/methyl ester Prepared according to general procedure J using 5-chlorovaleryl chloride instead of 4-chlorobutyryl chloride.
LC/MS[MH−]=586,588 Rt=3.98 LC/MS[MH−]=602,604 Rt=4.05

5-{2-[5-chloro-2-(benzyloxy)phenyl]cyclopent-1-enyl}-3-(5-chloropentanoylamino)benzoic acid ethyl ester Prepared according to general procedure J using 5-chlorovaleryl chloride instead of 4-chlorobutyryl chloride.
LC/MS[MH−]=564 Rt=4.02.

5-{2-[5-trifluoromethyl-2-(2,4-difluorobenzyloxy)phenyl]cyclopent-1-enyl}-3-(5-chloropentanoylamino)benzoic acid ethyl ester Prepared according to general procedure J using 5-chlorovaleryl chloride instead of 4-chlorobutyryl chloride.
LC/MS[MH−]=634 Rt=3.94

5-{2-[5-trifluoromethyl-2-(2,4-fluorobenzyloxy)phenyl]cyclopent-1-enyl}-3-(4-chlorobutanoylamino)benzoic acid ethyl ester Prepared according to general procedure J.
LC/MS[MH−]=620 Rt=4.00.

5-{2-[5-chloro-2-(2,4-fluorobenzyloxy)phenyl]cyclopent-1-enyl}-3-(4-chlorobutanoylamino)benzoic acid ethyl ester/methyl ester Prepared according to general procedure J.
LC/MS[MH+]=574 (2Cl) Rt=3.92 LC/MS[MH+]=588 (2Cl) Rt=3.99.

5-{2-[5-chloro-2-(benzyloxy)phenyl]cyclopent-1-enyl}-3-(4-chlorobutanoylamino)benzoic acid ethyl ester Prepared according to general procedure J.
LC/MS[MH+]=552 (2Cl) Rt=3.97.

5-{2-[5-chloro-2-(2,4-fluorobenzyloxy)phenyl]cyclopent-1-enyl}-3-(2-oxopyrrolidin-1-yl)benzoic acid ethyl ester/methyl ester Prepared according to general procedure K.
The product was a mixture of ethyl and methyl ester.
LC/MS[MH+]=538,540 Rt=3.81 LC/MS[MH+]=552,554 Rt=3.89.

5-{2-[5-chloro-2-(benzyloxy)phenyl]cyclopent-1-enyl}-3-(2-oxopyrrolidin-1-yl)benzoic acid ethyl ester Prepared according to general procedure K.
LC/MS[MH+]=516,518 Rt=3.92.

5-{2-[5-trifluoromethyl-2-(2,4-difluorobenzyloxy)phenyl]cyclopent-1-enyl}-3-(2-oxopyrrolidin-1-yl)benzoic acid ethyl ester Prepared according to general procedure K.
LC/MS[MH−]=586 Rt=3.94.

5-{2-[5-chloro-2-(2,4-fluorobenzyloxy)phenyl]cyclopent-1-enyl}-3-(2-oxopiperidin-1-yl)benzoic acid ethyl ester/methyl ester Prepared according to general procedure K.
The product was a mixture of ethyl and methyl ester.
LC/MS[MH+]=552,554 Rt=4.0 LC/MS[MH+]=566,568 Rt=4.09.

5-{2-[5-chloro-2-(benzyloxy)phenyl]cyclopent-1-enyl}-3-(2-oxopiperidin-1-yl)benzoic acid ethyl ester Prepared according to general procedure K.
LC/MS[MH+]=530,532 Rt=3.86.

5-{2-[5-trifluoromethyl-2-(2,4-difluorobenzyloxy)phenyl]cyclopent-1-enyl}-3-(2-oxopiperidin-1-yl)benzoic acid ethyl ester Prepared according to general procedure K.
LC/MS[MH+]=600,601 Rt=4.11

Example 44

2-{2-[5-Chloro-2-(benzyloxy)phenyl]cyclopent-1-enyl}pyrimidine-4-carboxylic acid

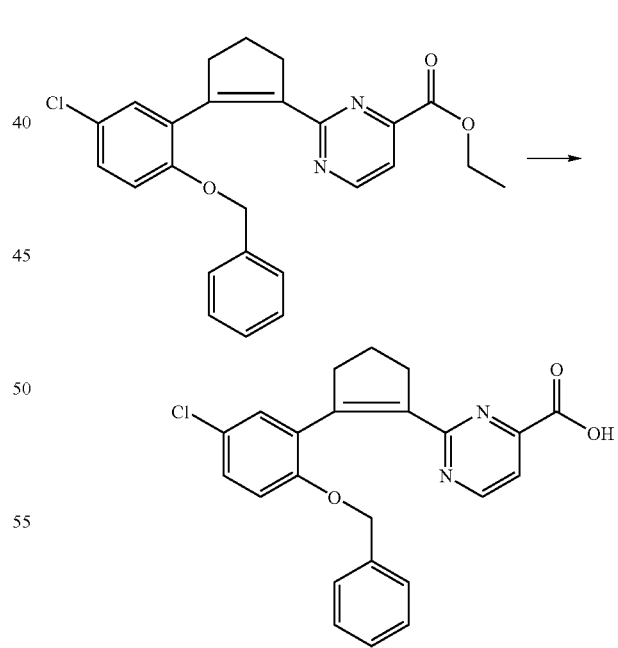

Prepared by the standard hydrolysis procedure.
$^1$H NMR (CDCl$_3$)δ: 2.12–2.18 (2H, m), 2.96 (2H, t, J=8 Hz), 3.11 (2H, t, J=8 Hz), 4.94 (2H, s), 6.94 (1H, d, J=9 Hz), 7.10–7.14 (3H, m), 7.23–7.27 (4H, m), 7.69 (1H, d, J=5 Hz), 8.90 (1H, d, J=5 Hz).
LC/MS Rt 3.74, [MH+] 407.3, 409.4.

Example 45

6-{2-[5-Methyl-2-(benzyloxy)phenyl]cyclopent-1-enyl}pyridine-2-carboxylic acid

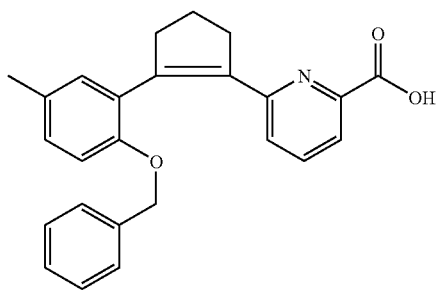

Prepared by the Standard Hydrolysis Procedure.
$^1$H NMR (CDCl$_3$)δ: 2.10–2.15 (2H, m), 2.26 (3H, s), 2.92–2.96 (2H, m), 3.00–3.04 (2H, m), 4.92 (2H, s), 6.88 (1H, d, J=8 Hz), 6.94 (1H, d, J=2 Hz), 7.06–7.15 (2H, m), 7.22–730 (5H, m), 7.67, (1H, t, J=8 Hz), 7.86 (1H, d, J=8 Hz).
LC/MS: Rt 3.3 [MH+] 386.4.

Example 46

6-{2-[5-Methyl-2-(4-fluorobenzyloxy)phenyl]cyclopent-1-enyl}pyridine-2-carboxylic acid

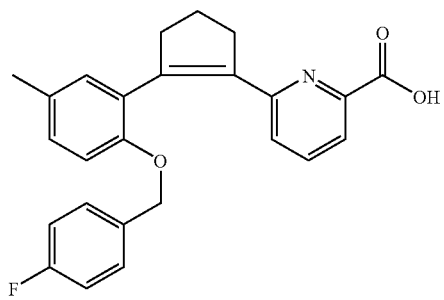

Prepared by the standard hydrolysis procedure.
$^1$H NMR (CDCl$_3$)δ: 2.07–2.15 (2H, m), 2.26 (3H, s), 2.90–2.93 (2H, m), 2.99–3.03 (2H, m), 4.87 (2H, s), 6.87–6.95 (4H, m), 7.07–7.12 (3H, m), 7.29 (1H, d, J=8 Hz), 7.69 (1H, t, J=8 Hz), 7.87 (1H, d, J=8 Hz).
LC/MS: Rt 3.4 [MH+] 404.3.

Example 47

6-{2-[5-Methyl-2-(2,4-difluorobenzyloxy)phenyl]cyclopent-1-enyl}pyridine-2-carboxylic acid

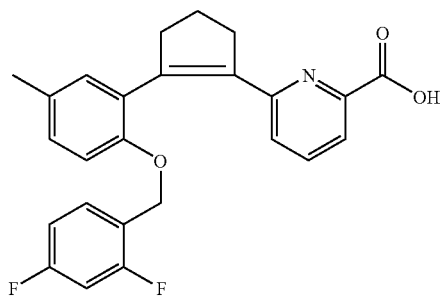

Prepared by the standard hydrolysis procedure.
$^1$H NMR (CDCl$_3$)δ: 2.07–2.14 (2H, m), 2.26 (3H, s), 2.88–2.92 (2H, m), 2.98–3.03 (2H, m), 4.92 (2H, s), 6.70–6.74 (2H, m), 6.91–6.94 (2H, m), 7.09–7.14 (2H, m), 7.28 (1H, d, J=8 Hz), 7.68 (1H, t, J=8 Hz), 7.87 (1H, d, J=8 Hz).
LC/MS: Rt 3.4 [MH+] 422.3.

Example 48

2-{2-[5-Trifluoromethyl-2-(4-fluorobenzyloxy)phenyl]cyclopent-1-enyl}pyridine-4-carboxylic acid

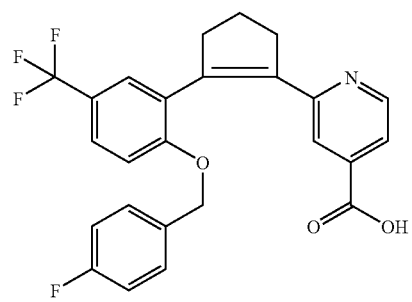

Prepared by the standard hydrolysis procedure.
$^1$H NMR (DMSO-d$_6$) δ: 1.99–2.03 (2H, m), 2.87–2.90 (2H, m), 2.98–3.02 (2H, m), 5.08 (2H, s), 7.10–7.22 (4H, m), 7.26 (1H, d, J=9 Hz), 7.37–7.39 (2H, m), 7.52 (1H, dd, J=5 Hz, 1 Hz), 7.62–7.64 (1H, dd, J=9 Hz, 1 Hz), 8.59 (1H, d, J=5 Hz), 13.3 (1H, br s).
LC/MS: Rt 3.92 [MH+] 458.0.

Example 49

2-{2-[5-Trifluoromethyl-2-(benzyloxy)phenyl]cyclopent-1-enyl}-pyridine-4-carboxylic acid

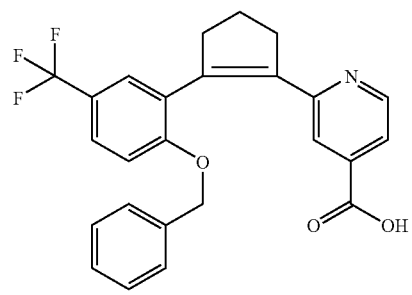

Prepared by the standard hydrolysis procedure.
$^1$H NMR (DMSO-d$_6$) δ: 1.98–2.05 (2H, m), 2.88–2.92 (2H, m), 2.99–3.02 (2H, m), 5.11 (2H, s), 7.16–7.17 (2H, m), 7.26–7.30 (4H, m), 7.38–7.40 (2H, m), 7.53 (1H, dd, J=5 Hz, 1 Hz), 7.62–7.64 (1H, dd, J=9 Hz, 1 Hz), 8.60 (1H, d, J=5 Hz) 13.3 (1H, br s).
LC/MS: Rt 3.90 [MH+] 440.0.

Example 50

4-{2-[5-Trifluoromethyl-2-(4-fluorobenzyloxy)phenyl]cyclopent-1-enyl}pyridine-2-carboxylic acid

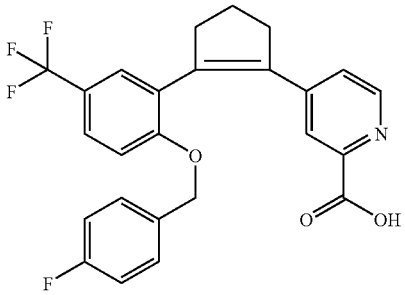

Prepared by the standard hydrolysis procedure.

$^1$H NMR (DMSO-d$_6$) δ: 2.01–2.05 (2H, m), 2.86–2.92 (4H, m), 5.09 (2H, s), 7.11–7.40 (7H, m), 7.63–7.68 (2H, m), 8.46 (1H, d, J=5 Hz), 13.1 (1H, br s).

LC/MS: Rt 3.55 [MH+] 458.0.

Example 51

4-{2-[5-Trifluoromethyl-2-(benzyloxy)phenyl]cyclopent-1-enyl}pyridine-2-carboxylic acid

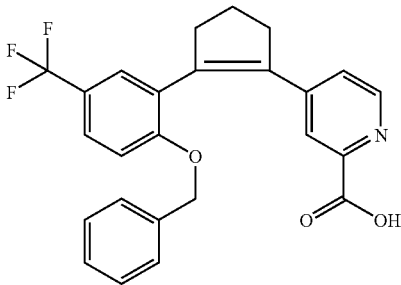

Prepared by the standard hydrolysis procedure.

$^1$H NMR (DMSO-d$_6$) δ: 2.00–2.07 (2H, m), 2.86–2.92 (4H, m), 5.13 (2H, s), 7.15–7.19 (3H, m), 7.30–7.38 (5H, m), 7.63–7.67 (2H, m), 8.46 (1H, d, J=5 Hz), 13.2 (1H, br s).

LC/MS: Rt 3.52 [MH+] 440.0.

Example 52

6-{2-[5-Trifluoromethyl-2-(benzyloxy)phenyl]cyclopent-1-enyl}-3-aminopyrazine-2-carboxylic acid

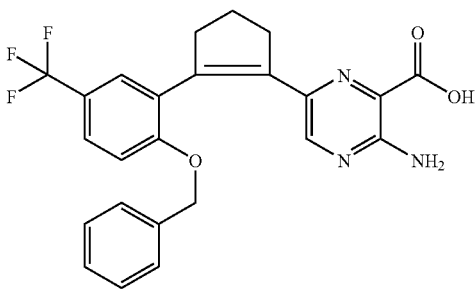

Prepared by the standard hydrolysis procedure.

$^1$H NMR (DMSO-d$_6$) δ: 1.95–2.02 (2H, m), 2.85–2.88 (2H, m), 2.93–2.97 (2H, m), 5.13 (2H, s), 7.18–7.20 (2H, m), 7.25–7.32 (6H, m), 7.42 (1H, d, J=2 Hz), 7.62 (1H, dd, J=8 Hz, 2 Hz), 7.69 (1H, s), 12.7 (1H, br s).

LC/MS: Rt 3.94 [MH+] 456.1.

Example 53

2-{2-[5-Trifluoromethyl-2-(4-fluorobenzyloxy)phenyl]cyclopent-1-enyl}pyrimidine-4-carboxylic acid

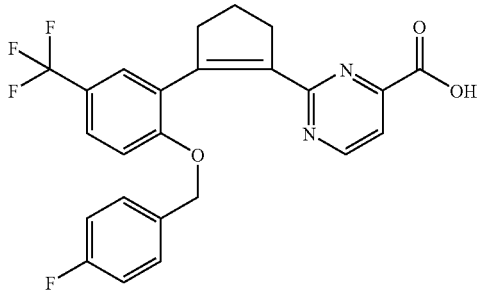

Prepared by the standard hydrolysis procedure.

$^1$H NMR (DMSO-d$_6$) δ: 2.00–2.09 (2H, m), 2.90–2.94 (2H, m), 3.02–3.06 (2H, m), 4.99 (2H, s), 7.07–7.19 (5H, m), 7.46 (1H, d, J=2 Hz), 7.57–7.61 (2H, m), 8.74 (1H, d, J=5 Hz), 13.4 (1H, br s).

LC/MS: Rt 3.7 [MH+] 459.3.

Example 54

2-{2-[5-Chloro-2-(4-fluorobenzyloxy)phenyl]cyclopent-1-enyl}pyrimidine-4-carboxylic acid

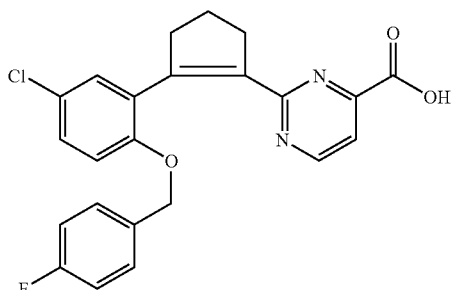

Prepared by the standard hydrolysis procedure.

$^1$H NMR (CDCl$_3$) δ: 2.11–2.17 (2H, m), 2.92–2.96 (2H, m), 3.10–3.14 (2H, m), 4.90 (2H, s), 6.91–6.95 (3H, m), 7.08–7.14 (3H, m), 7.27 (1H, m), 7.71 (1H, d, J=5 Hz), 8.91 (1H, d, J=5 Hz).

LC/MS: Rt 3.8 [MH+] 425.3, 427.3.

Example 55

6-{2-[5-Methyl-2-(benzyloxy)phenyl]cyclopent-1-enyl}pyrazine-2-carboxylic acid

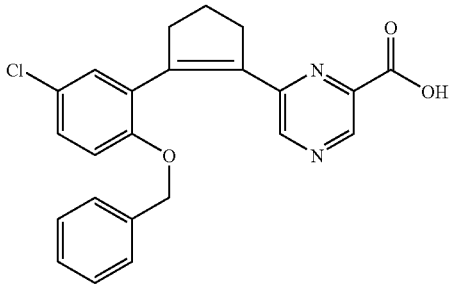

Prepared by the standard hydrolysis procedure.
$^1$H NMR (CDCl$_3$) δ 2.13–2.18 (2H, m), 2.27 (3H, s), 2.96–3.00 (2H, m), 3.02–3.06 (2H, m), 4.89 (2H, s), 6.90 (1H, d, J=9 Hz), 6.96 (1H, d, J=2 Hz), 7.10–7.12 (3H, m), 7.23–7.26 (3H, m), 8.54 (1H, s), 8.99 (1H, s).
LC/MS: Rt 3.7 [MH+] 387.4.

Example 56

3-{2[5-Methyl-2-(benzyloxy)phenyl]cyclopent-1-enyl}-6-aminobenzoic acid

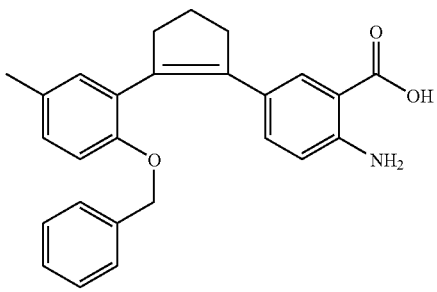

Prepared by the standard hydrolysis procedure.
$^1$H NMR (CDCl$_3$)δ: 1.99–2.06 (2H, m), 2.20 (3H, s), 2.83–2.90 (4H, m), 4.98 (2H, s), 6.37 (1H, d, J=9 Hz), 6.81 (1H, d, J=8 Hz), 6.89 (1H, s), 6.97 (1H, d, J=7 Hz), 7.03 (1H, dd, J=9 Hz, 2 Hz), 7.25–7.32 (5H, m), 7.79 (1H, d, J=2 Hz).
LC/MS: Rt 3.8 [MH+] 400.4.

Example 57

6-{2-[5-Trifluoromethyl-2-(benzyloxy)phenyl]cyclopent-1-enyl}pyridine-2-carboxylic acid

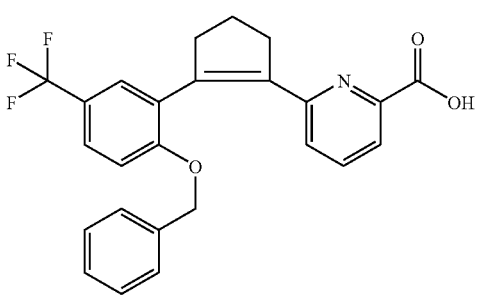

Prepared by the standard hydrolysis procedure.
$^1$H NMR (DMSO-d$_6$) δ: 2.00–2.04 (2H, m), 2.88–2.91 (2H, m), 3.00–3.04 (2H, m), 5.12 (2H, s), 7.04 (1H, d, J=7 Hz), 7.17–7.19 (2H, m), 7.26–7.32 (4H, m), 7.36 (1H, d, J=2 Hz), 7.61 (1H, dd, J=9 Hz, 2 Hz), 7.67 (1H, t, J=8 Hz), 7.78 (1H, d, J=7 Hz), 12.8 (1H, br s).
LC/MS: Rt 3.87 [MH+] 440.0.

Example 58

6-{2-[5-Trifluoromethyl-2-(4-fluorobenzyloxy)phenyl]cyclopent-1-enyl}pyridine-2-carboxylic acid

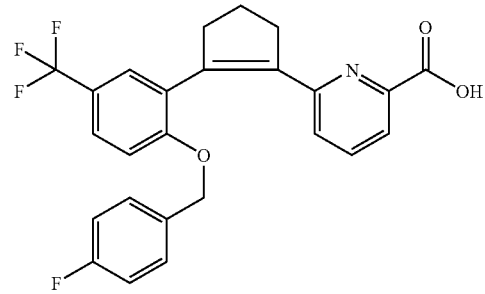

Prepared by the standard hydrolysis procedure.
$^1$H NMR (DMSO-d$_6$) δ: 1.99–2.03 (2H, m), 2.86–2.90 (2H, m), 3.00–3.04 (2H, m), 5.09 (2H, s), 7.04 (1H, d, J=7 Hz), 7.17–7.19 (2H, t, J=9 Hz), 7.22–7.29 (3H, m), 7.38 (1H, d, J=2 Hz), 7.62 (1H, dd, J=9 Hz, 2 Hz), 7.67 (1H, t, J=8 Hz), 7.78 (1H, d, J=7 Hz), 13.3 (1H, br s).
LC/MS: Rt 3.88 [MH+] 458.1.

Example 59

6-{2-[5-Trifluoromethyl-2-(2,4-difluorobenzyloxy)phenyl]cyclopent-1-enyl}pyridine-2-carboxylic acid

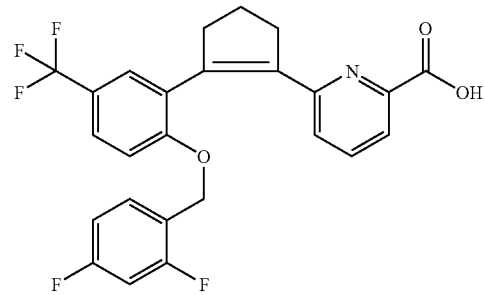

Prepared by the standard hydrolysis procedure.
$^1$H NMR (DMSO-d$_6$) δ: 1.95–2.02 (2H, m), 2.82–2.86 (2H, m), 2.97–3.01 (2H, m), 5.12 (2H, s), 6.99–7.02 (2H, m), 7.23–7.37 (4H, m), 7.66 (2H, t, J=8 Hz), 7.75 (1H, d, J=8 Hz), 12.9 (1H, br s).
LC/MS: Rt 3.91 [MH+] 476.1.

Example 60

3-{2-[5-Trifluoromethyl-2-(benzyloxy)phenyl]cyclopent-1-enyl}-6-aminobenzoic acid

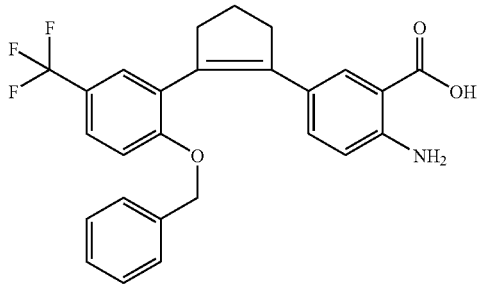

Prepared by the standard hydrolysis procedure.

$^1$H NMR (DMSO-$d_6$) δ: 1.94–1.97 (2H, m), 2.75–2.83 (4H, m), 5.16 (2H, s), 6.49 (1H, d, J=9 Hz), 6.86 (1H, dd, J=9 Hz, 2 Hz), 7.22–7.34 (7H, m), 7.55–7.58 (2H, m).
LC/MS: Rt 3.8 [MH+] 454.4.

Example 61

3-{2-[5-Trifluoromethyl-2-(4-fluorobenzyloxy)phenyl]cyclopent-1-enyl}-6-aminobenzoic acid

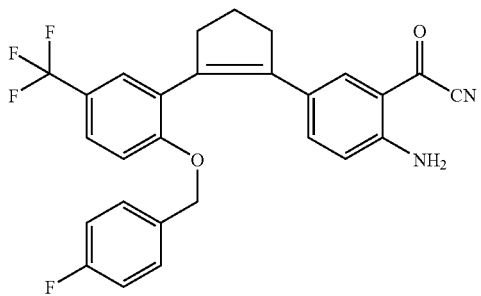

Prepared by the standard hydrolysis procedure.

$^1$H NMR (DMSO-$d_6$) δ: 1.93–1.97 (2H, m), 2.75–2.81 (4H, m), 5.13 (2H, s), 6.49 (1H, d, J=9 Hz), 6.86 (1H, dd, J=9 Hz, 2 Hz), 7.14 (2H, t, J=9 Hz), 7.22–7.31 (4H, m), 7.53 (1H, d, J=2 Hz), 7.57 (1H, dd, J=9 Hz, 2 Hz).
LC/MS: Rt 3.8 [MH+] 472.4.

Example 62

3-{2-[5-Trifluoromethyl-2-(2,4-difluorobenzyloxy)phenyl]cyclopent-1-enyl}-6-aminobenzoic acid

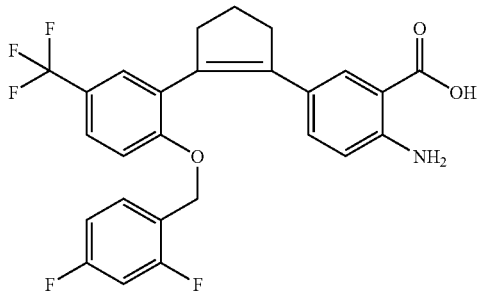

Prepared by the standard hydrolysis procedure.

$^1$H NMR (DMSO-$d_6$) δ: 1.88–1.96 (2H, m), 2.71–2.79 (4H, m), 5.17 (2H, s), 6.47 (1H, d, J=9 Hz), 6.82 (1H, dd, J=9 Hz, 2 Hz), 7.05 (2H, dt, J=9 Hz, 2 Hz), 7.25–7.32 (3H, m), 7.49 (1H, d, J=2 Hz), 7.60 (1H, dd, J=9 Hz, 2 Hz).
LC/MS: Rt 3.8 [MH+] 490.4.

Example 63

3-{2-[5-Trifluoromethyl-2-(benzyloxy)phenyl]cyclopent-1-enyl}-6-acetamidobenzoic acid

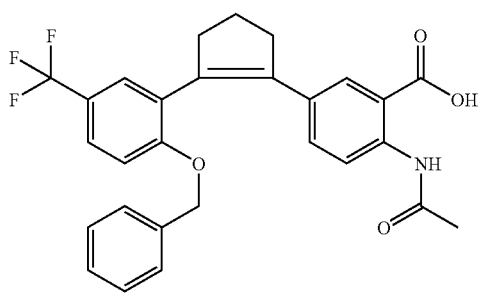

Prepared by the standard hydrolysis procedure.

$^1$H NMR (DMSO-$d_6$) δ: 1.97–2.04 (2H, m), 2.10 (3H, s), 2.81–2.89 (4H, m), 5.15 (2H, s), 7.21–7.33 (8H, m), 7.60 (1H, dd, J=9 Hz, 2 Hz), 7.72 (1H, d, J=2 Hz), 8.25 (1H, d, J=9 Hz), 10.95 (1H, s), 13.4 (1H, br s).
LC/MS: Rt 3.9 [MH+] 496.4.

Example 64

3-{2-[5-Trifluoromethyl-2-(4-fluorobenzyloxy)phenyl]cyclopent-1-enyl}-6-acetamidobenzoic acid

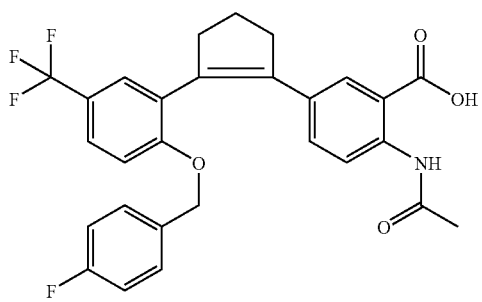

Prepared by the standard hydrolysis procedure.

$^1$H NMR (DMSO-$d_6$) δ: 1.96–2.03 (2H, m), 2.10 (3H, s), 2.79–2.88 (4H, m), 5.11 (2H, s), 7.11–7.27 (6H, m), 7.34 (1H, d, J=2 Hz), 7.60 (1H, dd, J=9 Hz, 2 Hz), 7.69 (1H, d, J=2 Hz), 8.23 (1H, d, J=9 Hz), 10.95 (1H, s), 13.4 (1H, br s).
LC/MS: Rt 3.9 [MH+] 514.3.

Example 65

3-{2-[5-Trifluoromethyl-2-(2,4-difluorobenzyloxy)phenyl]cyclopent-1-enyl}-6-acetamidobenzoic acid

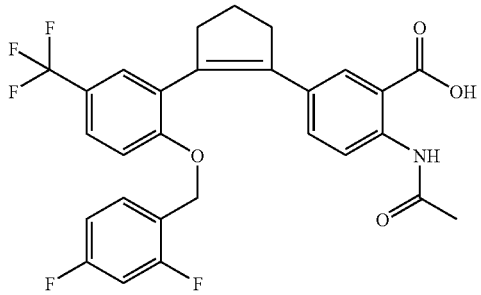

Prepared by the standard hydrolysis procedure.

$^1$H NMR (DMSO-d$_6$) δ: 1.93–2.01 (2H, m), 2.10 (3H, s), 2.75–2.86 (4H, m), 5.14 (2H, s), 7.03 (1H, dt, J=8 Hz, 2 Hz), 7.16–7.36 (5H, m), 7.63 (1H, dd, J=9 Hz, 2 Hz), 7.65 (1H, d, J=2 Hz), 8.21 (1H, d, J=9 Hz), 10.95 (1H, s), 13.4 (1H, brs).

LC/MS: Rt 3.9 [MH+] 532.0.

Example 66

3-{2-[5-Trifluoromethyl-2-(benzyloxy)phenyl]cyclopent-1-enyl}-5-propionamidobenzoic acid

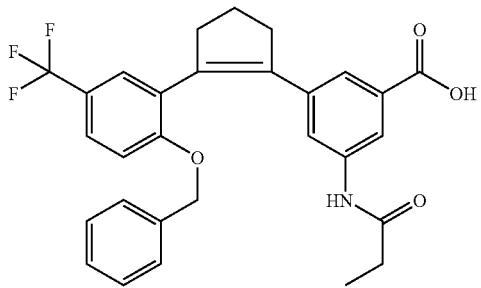

Prepared by the standard hydrolysis procedure.

$^1$H NMR (CDCl$_3$) δ: 1.21 (3H, t, J=8 Hz), 2.05–2.12 (2H, m), 2.31–2.36 (2H, m), 2.87–2.94 (4H, m), 5.05 (2H, s), 6.95 (1H, s), 6.97 (1H, s), 7.23–7.34 (6H, m), 7.44 (1H, d, J=8 Hz), 7.53 (1H, s), 7.57 (1H, s), 7.90 (1H, s).

LC/MS: Rt 3.7 [MH−] 508.1.

Example 67

3-{2-[5-Trifluoromethyl-2-(4-fluorobenzyloxy)phenyl]cyclopent-1-enyl}-5-propionamidobenzoic acid

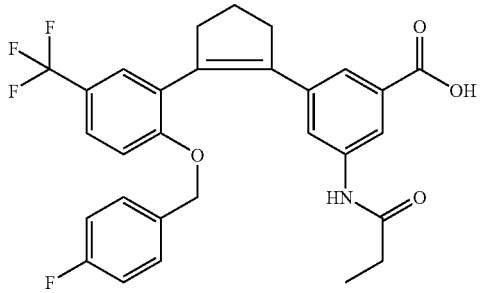

Prepared by the standard hydrolysis procedure.

$^1$H NMR (CDCl$_3$) δ: 1.22 (3H, t, J=8 Hz), 2.04–2.11 (2H, m), 2.32–2.37 (2H, m), 2.85–2.95 (4H, m), 4.98 (2H, s), 6.93–7.02 (4H, m), 7.19 (2H, t, J=8 Hz), 7.32 (1H, s), 7.45 (1H, d, J=8 Hz), 7.50 (1H, s), 7.62 (1H, s), 7.85 (1H, s).

LC/MS: Rt 3.7 [MH−] 526.2.

Example 68

3-{2-[5-Trifluoromethyl-2-(2,4-difluorobenzyloxy)phenyl]cyclopent-1-enyl}-5-propionamidobenzoic acid

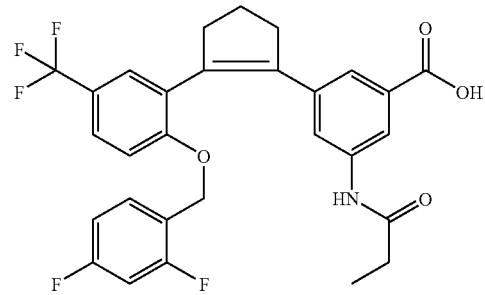

Prepared by the standard hydrolysis procedure.

$^1$H NMR (CDCl$_3$) δ: 1.22 (3H, t, J=8 Hz), 2.03–2.10 (2H, m), 2.32–2.37 (2H, m), 2.83–2.87 (2H, m), 2.91–2.95 (2H, m), 5.04 (2H, s), 6.77–6.84 (2H, m), 6.99 (1H, d, J=9 Hz), 7.04 (1H, s), 7.19 (1H, q, J=8 Hz), 7.32 (1H, s), 7.46–7.49 (2H, m), 7.65 (1H, s), 7.83 (1H, s).

LC/MS: Rt 3.7 [MH−] 544.1.

Example 69

3-{2-[5-Bromo-2-(benzyloxy)phenyl]cyclopent-1-enyl})-5-propionamidobenzoic acid

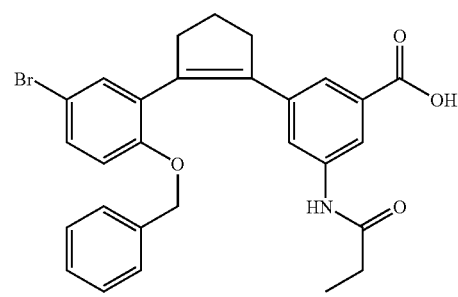

Prepared by the standard hydrolysis procedure.

$^1$H NMR (CDCl$_3$) δ: 1.23 (3H, t, J=8 Hz), 2.03–2.10 (2H, m), 2.32–2.38 (2H, m), 2.83–2.87 (2H, m), 2.91–2.95 (2H, m), 4.96 (2H, s), 6.77 (1H, d, J=9 Hz), 6.98 (1H, s), 7.15 (1H, s), 7.21–7.30 (6H, m), 7.50 (1H, s), 7.56 (1H, s), 7.97 (1H, s).

LC/MS: Rt 3.94 [MH−] 518.0, 520.0.

Example 70

3-{2-[5-Bromo-2-(4-fluorobenzyloxy)phenyl]cyclopent-1-enyl}-5-propionamidobenzoic acid

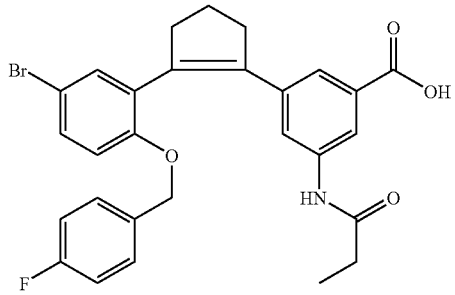

Prepared by the standard hydrolysis procedure.

¹H NMR (CDCl₃)δ: 1.23 (3H, t, J=8 Hz), 2.01–2.09 (2H, m), 2.32–2.39 (2H, m), 2.81–2.84 (2H, m), 2.89–2.95 (2H, m), 4.90 (2H, s), 6.76 (1H, d, J=9 Hz), 6.98 (3H, m), 7.12–7.29 (4H, m), 7.54 (1H, s), 7.55 (1H, s), 7.92 (1H, s).

LC/MS: Rt 3.91 [MH−] 536.0, 538.0.

Example 71

3-{2-[5-Bromo-2-(2,4-difluorobenzyloxy)phenyl]cyclopent-1-enyl}-5-propionamidobenzoic acid

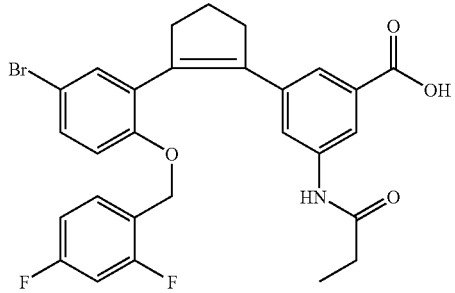

Prepared by the standard hydrolysis procedure.

¹H NMR (CDCl₃)δ: 1.21 (3H, t, J=8 Hz), 2.01–2.09 (2H, m), 2.32–2.39 (2H, m), 2.80–2.84 (2H, m), 2.89–2.93 (2H, m), 4.96 (2H, s), 6.75–6.83 (3H, m), 7.03 (1H, s), 7.13–7.25 (2H, m), 7.27–7.32 (1H, m), 7.53 (1H, s), 7.59 (1H, s), 7.90 (1H, s).

LC/MS: Rt 3.98 [MH−] 554.0, 556.0.

Example 72

5-{2-[Trifluoromethyl-2-(benzyloxy)phenyl]cyclopent-1-enyl}nicotinic acid N-oxide

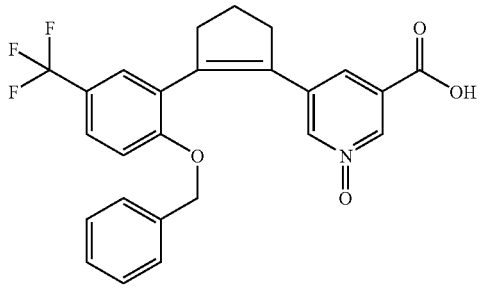

3-Chloroperbenzoic acid (25 mg, 0.11 mmol) was added to a solution of 5-{2-[trifluoromethyl-2-(benzyloxy)phenyl]cyclopent-1-enyl}nicotinic acid (44 mg, 0.1 mmol) in dioxan (2 ml) and left overnight at room temperature. The resulting mixture was evaporated to dryness and purified by preparative mass directed chromatography to give the title compound as an off-white solid (8 mg, 18%).

¹H NMR (DMSO-d₆) δ: 1.97–2.06 (2H, m), 2.84–2.90 (4H, m), 5.16 (2H, s), 7.23–7.35 (7H, m), 7.46 (1H, s), 7.67 (1H, dd J=9 Hz, 2 Hz), 8.01 (1H, s), 8.25 (1H, s), 13.7 (1H, br s).

LC/MS: Rt 3.82 [MH+] 456.1.

Example 73

5-{2-[5-fluoro-2-(4-fluorobenzyloxy)phenyl]cyclopent-1-enyl}-3-(propionamido)benzoic acid

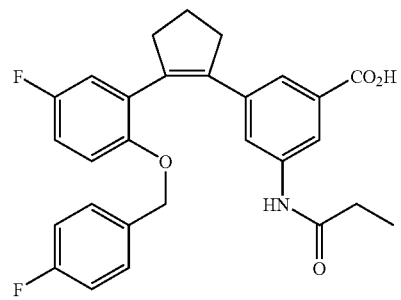

The title compound was prepared from 5-{2-[5-fluoro-2-(4-fluorobenzyloxy) phenyl]cyclopent-1-enyl}-3-(propionamido)benzoic acid 4-fluorobenzyl ester following the standard hydrolysis procedure.

¹H NMR (CDCl₃) δ: 1.21–1.28 (3H, m), 2.03–2.06 (2H, m), 2.36–2.45 (2H, m), 2.84–2.89 (4H, m), 4.87 (2H, s) 6.74–6.85 (3H, m), 6.96–7.07 (3H, m), 7.17–7.34 (2H, m), 7.56 (2H, m), 7.89 (1H, s).

LC/MS [MH+]=478, RT=3.80 min.

Example 74

5-{2-[5-methyl-2-(4-fluorobenzyloxy)phenyl]cyclopent-1-enyl}-3-(propionamido)benzoic acid

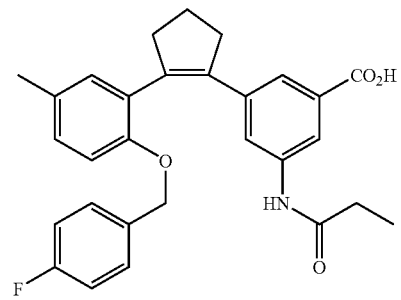

The title compound was prepared from 5-{2-[5-methyl-2-(4-fluorobenzyloxy)phenyl]cyclopent-1-enyl}-3-(propionamido)benzoic acid 4-fluorobenzyl ester following the standard hydrolysis procedure.

¹H NMR (CDCl₃) δ: 1.19–1.27 (3H, m) 2.03–2.07 (2H, m), 2.20 (3H, s), 2.34–2.36 (2H, m), 2.84–2.91 (4H, m), 4.90 (2H, s) 6.78–7.22 (8H, m), 7.47 (1H, s), 7.58 (1H, s), 7.98 (1H, s).

LC/MS [MH+]=474, RT=3.64 min.

Example 75

5-{2-[5-methyl-2-(2,4-difluorobenzyloxy)phenyl]cyclopent-1-enyl}-3-(propionamido)benzoic acid

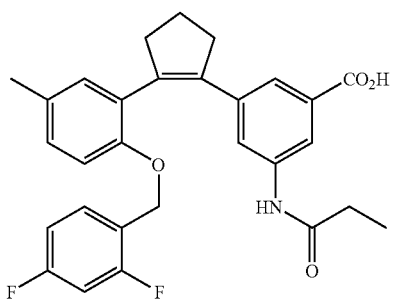

The title compound was prepared from 5-{2-[5-methyl-2-(2,4-difluorobenzyloxy)phenyl]cyclopent-1-enyl}-3-(propionamido)benzoic acid 2,4-difluorobenzyl ester following the standard hydrolysis procedure.

¹H NMR (d₆DMSO) δ: 1.04–1.10 (3H, m) 1.94–1.98 (2H, m), 2.14 (3H, s), 2.25–2.30 (2H, m), 2.73–2.83 (4H, m), 4.97 (2H, s) 6.83 (1H, s), 6.95–7.03 (3H, m), 7.22–7.26 (2H, m), 7.31 (1H, s), 7.61 (1H, s), 7.97 (1H, s), 9.87 (1H, bs).

LC/MS [MH+]=492, RT=3.58 min.

Example 76

5-[2-(2-benzyloxy-5-chlorophenyl)cyclopent-1-enyl]-2-methylbenzoic acid

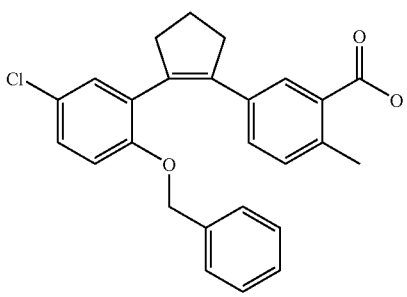

Prepared according to the standard hydrolysis procedure using 5-[2-(2-benzyloxy-5-chlorophenyl)cyclopent-1-enyl]-2-methylbenzoic acid ethyl ester to give the product as a colourless solid 46 mg 43%

¹HNMR (CDCl₃) δ: 2.02–2.09 (2H, m), 2.57 (3H, s), 2.85 (2H, t, J=6 Hz), 2.92 (2H, t, J=6 Hz), 4.88 (2H, s), 6.81 (1H, d, J=12 Hz), 6.98–7.30 (9H, m), 7.88 (1H, s).

LC/MS: Rt=4.03 min [M−H]417 (1 Cl)

Example 77

5-[2-(2-Benzyloxy-5-chlorophenyl)-cyclopent-1-enyl]-2-propionylaminobenzoic acid

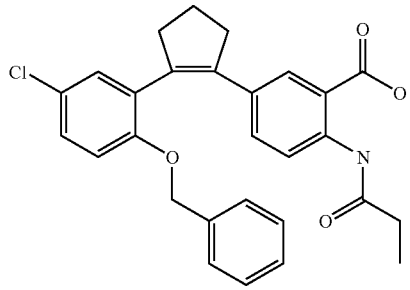

Prepared according to the standard hydrolysis procedure using 5-[2-(2-benzyloxy-5-chlorophenyl)-cyclopent-1-enyl]-2-propionylaminobenzoic acid methyl ester to give the product as a yellow oil 35 mg 73%.

¹H NMR (CDCl₃) δ: 1.25 (3H, t, J=12 Hz), 2.02–2.08 (2H, m), 2.45 (2H, q, J=12 Hz), 2.82–2.90 (4H, m), 4.96 (2H, s), 6.82 (1H, d, J=12 Hz), 7.02 (1H, s), 7.12 (1H, d, J=12 Hz), 7.14–7.36 (6H, m), 7.87 (1H, s), 8.50 (1H, d, J=12 Hz).

LC/MS: Rt=4.10 [M+H] 476 (1 Cl).

Example 78

2-{2-[5-Chloro-2-(2,4-difluorobenzyloxy)phenyl]cyclopent-1-enyl}isonicotinic acid

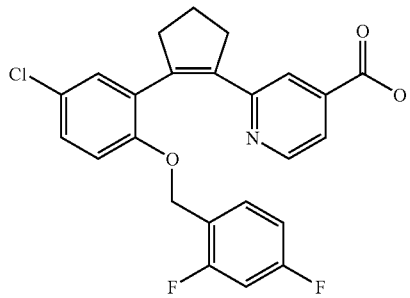

Prepared according to the standard hydrolysis procedure using 2-{2-[5-chloro-2-(2,4-difluorobenzyloxy)phenyl]cyclopent-1-enyl}isonicotinic acid ethyl ester to give the product as a colourless solid 38 mg 54%.

¹HMR (DMSO-d₆) δ: 2.05–2.09 (2H, m), 2.87 (2H, t, J=6 Hz), 3.04 (2H, t, J=6 Hz), 4.92 (2H, s), 6.75–6.86 (3H, m), 7.06–7.18 (3H, m), 7.50–7.54 (2H, m), 8.55 (1H, d, J=6 Hz).

LC/MS: Rt=3.67 [M+H] 442 (1 Cl).

Example 79

2-{2-[5-Chloro-2-(4-fluorobenzyloxy)phenyl]cyclopent-1-enyl}isonicotinic acid

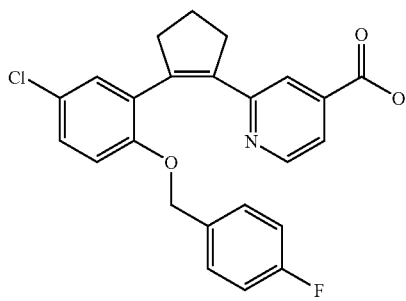

Prepared according to the standard hydrolysis procedure to give the product as a colourless solid 36 mg 71%.

¹HNMR (CDCl₃) δ: 2.05–2.07 (2H, m), 2.86 (2H, m), 3.03 (2H, m), 4.87 (2H, s), 6.81–7.13 (6H, m), 7.40–7.52 (3H, m), 8.56 (1H, br s).

LC/MS: Rt=3.92 [M+H] 424 (1 Cl).

Example 80

2-{2-[5-Chloro-2-benzyloxyphenyl]cyclopent-1-enyl}isonicotinic acid

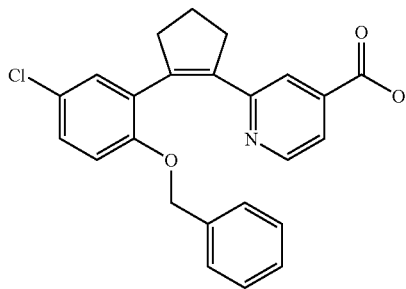

Prepared according to the standard hydrolysis procedure to give the product as a colourless solid 20 mg 32%.

¹HNMR (CDCl₃) δ: 2.07–2.12 (2H, m), 2.92 (2H, t, J=6 Hz), 3.07 (2H, t, J=6 Hz), 4.94 (2H, s), 6.84 (1H, d, J=12 Hz), 7.07 (1H, s), 7.15–7.30 (6H, m), 7.55–7.58 (2H, m), 8.65 (1H, d, J=12 Hz).

LC/MS: Rt=3.61 [M+H] 406 (1 Cl).

Example 81

2-{2-[5-Bromo-2-(4-fluorobenzyloxy)phenyl]cyclopent-1-enyl}isonicotinic acid

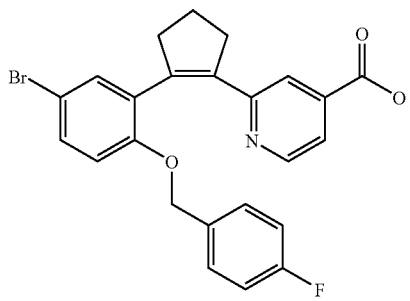

Prepared according to the standard hydrolysis procedure to give the product as a colourless solid 10 mg 25%.

¹H NMR (CDCl₃) δ: 2.05–2.10 (2H, m), 2.88 (2H, t, J=6 Hz), 3.04 (2H, t, J=6 Hz), 4.85 (2H, t), 6.75 (1H, d, J=12 Hz), 6.95 (2H, m), 7.11 (2H, m), 7.26–7.28 (3H, m), 7.53–7.55 (2H, m), 8.56 (1H, d, J=6 Hz).

LC/MS: Rt=3.70 [M+H] 468,470 (1 Br).

Example 82

5-[2-(2-Benzyloxy-5-chlorophenyl)cyclopent-1-enyl]3-propionylaminobenzoic acid

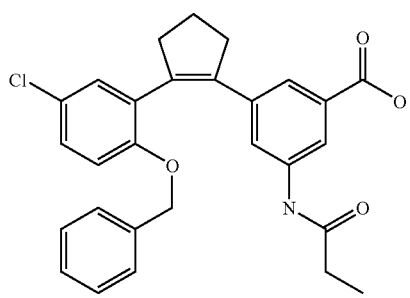

Prepared according to the standard hydrolysis procedure to give the product as a colourless solid 53 mg 53%.

¹H NMR (CDCl₃): δ: 1.19 (3H, t, J=12 Hz), 2.04–2.08 (2H, m), 2.34 (2H, q, J=12 Hz), 2.83–2.93 (4H, m), 4.96 (2H, s), 6.82 (1H, d, J=12 Hz), 6.96–7.00 (2H, m), 7.12–7.32 (5H, m), 7.49 (1H, s), 7.55 (1H, s), 7.96 (1H, s).

LC/MS: Rt=3.89 [M+H] 476 (1 Cl).

Example 83

5-[2-(2-Benzyloxy-5-chlorophenyl)cyclopent-1-enyl]-3-isobutyrylaminobenzoic acid

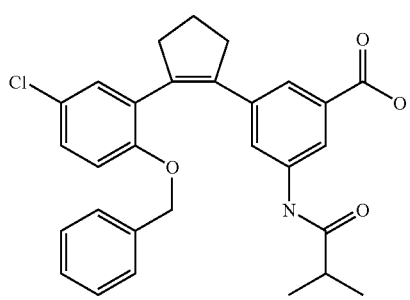

Prepared according to the standard hydrolysis procedure to give the product as a colourless solid 58 mg 66%.

¹H NMR (CDCl₃) δ: 1.17 (6H, d, J=12 Hz), 2.02–2.05 (2H, m), 2.55 (1H, m), 2.83–2.90 (4H, m), 4.98 (2H, s), 6.82 (1H, d, J=12 Hz), 6.96 (1H, s), 7.08 (1H, d, J=12 Hz), 7.22–7.33 (4H, m), 7.45 (1H, s), 7.80 (1H, s), 7.94 (1H, s), 9.09 (1H, s).

LC/MS: Rt=3.99 [M+H] 490 (1 Cl).

Example 84

5-{2-[5-trifluoromethyl-2-(benzyloxy)phenyl]cyclopent-1-enyl}-3-(2-oxo-pyrrolidin-1-yl)benzoic acid

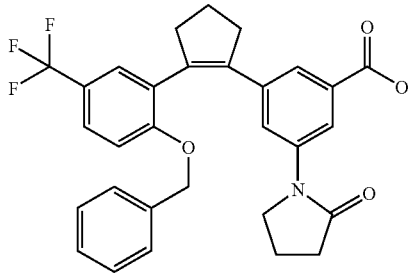

Prepared according to the standard hydrolysis procedure.
¹H NMR (CDCl₃): δ: 2.01–2.13 (4H, m), 2.54 (2H, t, J=7.9 Hz), 2.89 (2H, t, J=7.6 Hz), 2.97 (2H, t, J=7.5 Hz), 3.42 (2H, t, J=7.0 Hz), 5.06 (2H, s), 6.97 (1H, d, J=8.6 Hz), 7.20–7.33 (6H, m), 7.44 (1H, d, J=8.6 Hz), 7.48 (1H, s), 7.65 (1H, s), 8.12 (1H, s).
LC/MS [MH−]=520,521 Rt=3.82.

Example 85

5-{2-[5-trifluoromethyl-2-(4-fluorobenzyloxy)phenyl]cyclopent-1-enyl}-3-(2-oxo-pyrrolidin-1-yl)benzoic acid

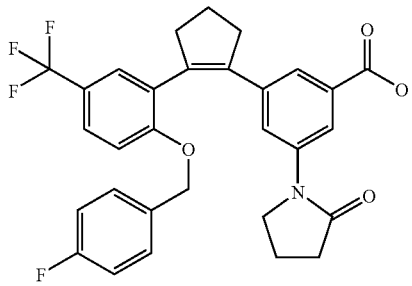

Prepared according to the standard hydrolysis procedure.
¹H NMR (CDCl₃) δ: 2.02–2.12 (4H, m), 2.55 (2H, t, J=8.0 Hz), 2.87 (2H, t, J=7.4 Hz), 2.95 (2H, t, J=7.3 Hz), 3.50 (2H, t, J=7.0 Hz), 4.99 (2H, s), 6.94–7.01 (3H, m), 7.15–7.19 (2H, m), 7.34 (1H, s), 7.45 (1H, d, J=8.6 Hz), 7.56 (1H, s), 7.61 (1H, s), 8.05 (1H, s).
LC/MS[MH−]=538,539 Rt=3.91.

Example 86

5-{2-[5-chloro-2-(4-fluorobenzyloxy)phenyl]cyclopent-1-enyl}-3-(2-oxo-pyrrolidin-1-yl)benzoic acid

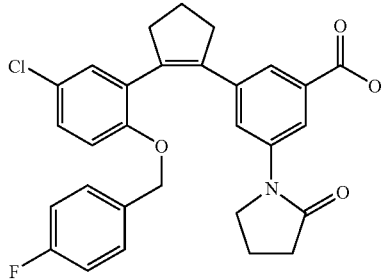

Prepared according to the standard hydrolysis procedure.
¹H NMR (CDCl₃) δ: 2.04–2.09 (4H, m), 2.56 (2H, t, J=8.1 Hz), 2.84 (2H, t, J=7.3 Hz), 2.94 (2H, t, J=7.0 Hz), 3.53 (2H, t, J=7.0 Hz), 4.92 (2H, s), 6.82 (1H, d, J=8.7 Hz), 6.98 (2H, t, J=8.6 Hz), 7.04 (1H, s), 7.13–7.19 (3H, m), 7.57 (1H, s), 7.63 (1H, s), 8.07 (1H, s).
LC/MS[MH−]=504,506 Rt=3.91.

Example 87

5-{2-[5-trifluoromethyl-2-(4-fluorobenzyloxy)phenyl]cyclopent-1enyl}-3-(2-oxo-piperidin-1-yl)benzoic acid

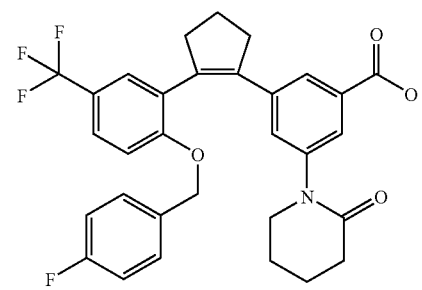

Prepared according to the standard hydrolysis procedure.
¹H NMR (CDCl₃) δ: 1.80 (4H, bs), 2.06–2.10 (2H, m), 2.49 (2H, t, J=6.3 Hz), 2.84–2.93 (4H, m), 3.21 (2H, bs), 4.97 (2H, s), 6.93–7.06 (4H, m), 7.15–7.19 (2H, m), 7.33 (1H, s), 7.44 (1H, d, J=8.4 Hz), 7.71 (2H, s).
LC/MS[MH−]=552,553 Rt=3.87

Example 88

5-{2-[5-trifluoromethyl-2-(benzyloxy)phenyl]cyclopent-1-enyl}-3-(2-oxo-piperidin-1-yl)benzoic acid

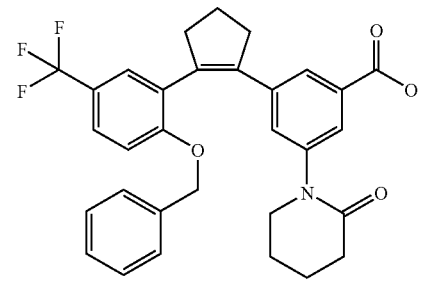

Prepared according to the standard hydrolysis procedure.
¹H NMR (CDCl₃) δ: 1.76–1.83 (4H, m), 2.06–2.13 (2H, m), 2.49 (2H, t, J=6.6 Hz), 2.89 (2H, t, J=7.6 Hz), 2.94 (2H, t, J=7.4 Hz), 3.15 (2H, t, J=6.0 Hz), 5.05 (2H, s), 6.96 (1H, d, J=8.6 Hz), 7.04 (1H, s), 7.20–7.31 (6H, m), 7.72 (1H, d, J=8.6 Hz), 7.74 (2H, d, J=10 Hz).
LC/MS[MH−]=534,535 Rt=3.78.

Example 89

5-{2-[5-chloro-2-(4-fluorobenzyloxy)phenyl]cyclopent-1-enyl}-3-(2-oxo-piperidin-1-yl)benzoic acid

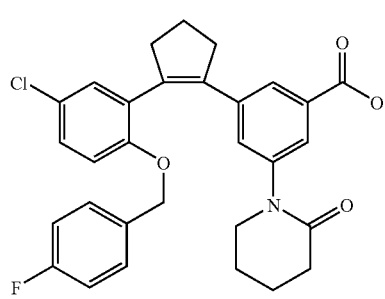

Prepared according to the standard hydrolysis procedure.

$^1$H NMR (CDCl$_3$) δ: 1.84 (2H, bs), 2.03–2.07 (2H, m), 2.51 (2H, t, J=6.2 H), 2.84 (2H, t, J=7.3 Hz), 2.92 (2H, t, J=7.3 Hz), 3.27 (2H, t, J=5.9 Hz), 4.89 (2H, s), 6.80 (1H, d, J=8.8 Hz), 6.97 (2H, t, J=8.7 Hz), 7.04–7.17 (5H, m), 7.72 (2H, s).

LC/MS[MH−]=518,520 Rt=3.87.

Example 90

6-{2-[5-trifluoromethyl-2-(benzyloxy)phenyl]cyclopent-1-enyl}pyrazine-2-carboxylic acid

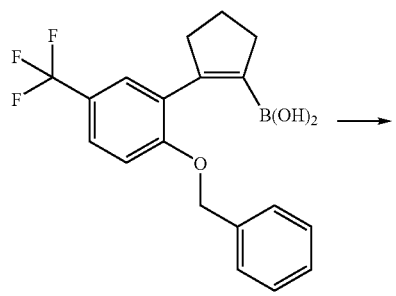

Prepared using general procedure C(iii).

$^1$H NMR (CDCl$_3$) δ: 2.10–2.14 (2H, m), 2.98 (2H, t, J=7.5 Hz), 3.12 (2H, t, J=7.4 Hz), 5.02 (2H, s), 7.1545 (2H, d, J=7.6 Hz), 7.23–7.27 (4H, m), 7.42 (1H, s), 7.58 (1H, d, J=5.2 Hz), 8.17 (1H, s), 8.83 (1H, s).

Example 91

6-{2-[5-chloro-2-(benzyloxy)phenyl]cyclopent-1-enyl}pyrazine-2-carboxylic acid

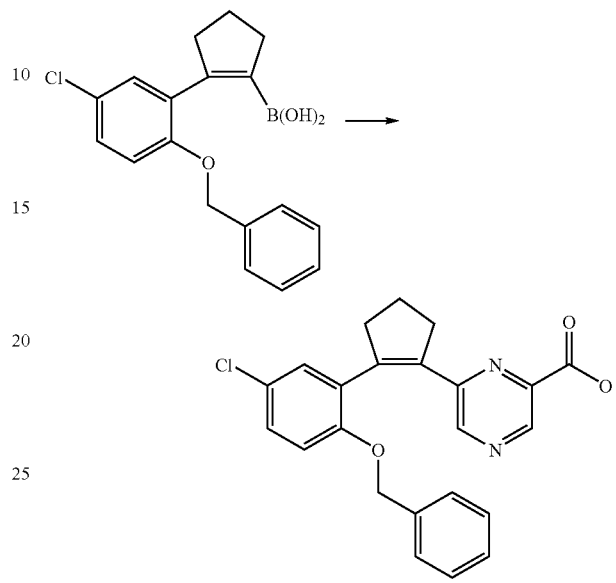

Prepared using general procedure C(iii).

$^1$H NMR (CDCl$_3$) δ: 2.13–2.17 (2H, m), 2.95 (2H, t, J=7.5 Hz), 3.05 (2H, t, J=7.5 Hz), 4.87 (2H, s), 6.92 (1H, d, J=8.8 Hz), 7.06–7.35 (7H, m), 8.53 (1H, s), 9.02 (1H, s).

LC/MS[MH+]=407,409 Rt=4.16.

Example 92

6-{2-[5-chloro-2-(4-fluorobenzyloxy)phenyl]cyclopent-1-enyl}pyrazine-2-carboxylic acid

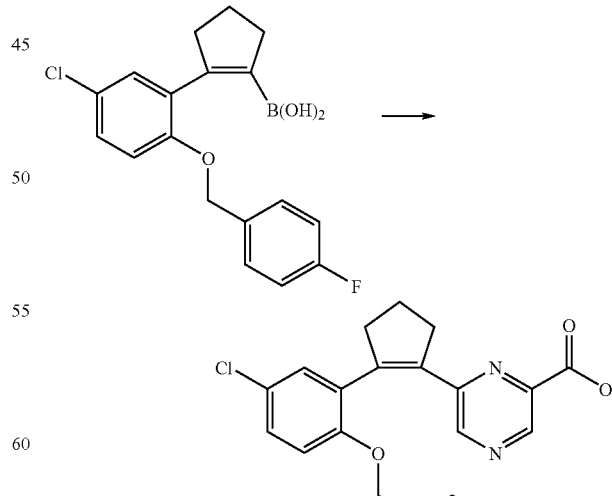

Prepared using general procedure C(iii).
$^1$H NMR (CDCl$_3$) δ: 2.11–2.18 (2H, m), 2.92 (2H, t, J=7.1 Hz), 3.05 (2H, t, J=7.1 Hz), 4.85 (2H, s), 6.89–7.33 (7H, m), 8.54 (1H, s), 9.05 (1H, s).
LC/MS[MH+]=425,427 Rt=3.76.

Example 93

5-{2-[5-trifluoromethyl-2-(benzyloxy)phenyl]cyclopent-1-enyl}-3-aminobenzoic acid

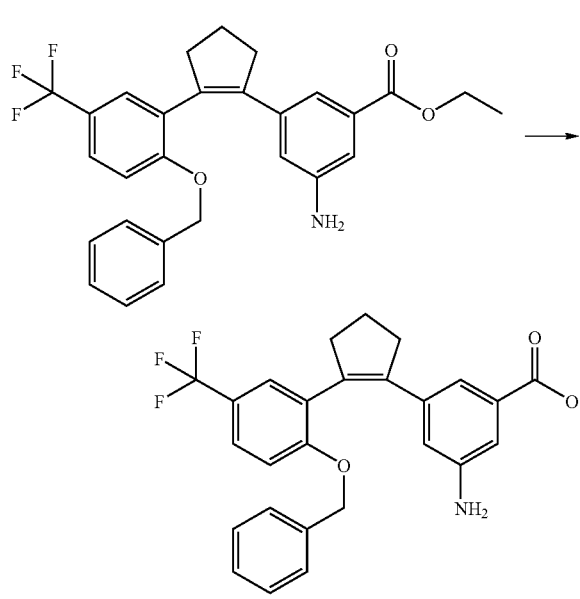

Prepared according to the standard hydrolysis procedure.
$^1$H NMR (CDCl$_3$) δ: 2.02–2.08 (2H, m), 2.85–292 (4H, m), 5.03 (2H, s), 6.55 (1H, s), 6.93 (1H, d, J=8.6 Hz), 7.15 (1H, s), 7.16–7.42 (8H, m).
LC/MS[MH−]=452 Rt=3.6

Example 94

5-{2-[5-trifluoromethyl-2-(4-fluorobenzyloxy)phenyl]cyclopent-1-enyl}-3-aminobenzoic acid

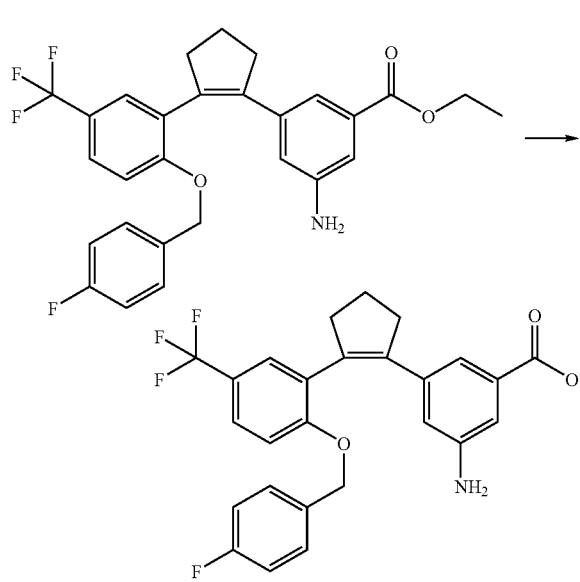

Prepared according to the standard hydrolysis procedure.
$^1$H NMR (CDCl$_3$) δ: 2.02–2.09 (2H, m), 2.82–291 (4H, m), 4.96 (2H, s), 6.55 (1H, s), 6.91 (1H, d, J=8.6 Hz), 6.99 (2H, t, J=8.6 Hz), 7.15–7.33 (5H, m), 7.43 (1H, d, J=8.6 Hz).
LC/MS[MH−]=470 Rt=3.6.

Example 95

5-{2-[5-chloro-2-(benzyloxy)phenyl]cyclopent-1-enyl}-3-aminobenzoic acid

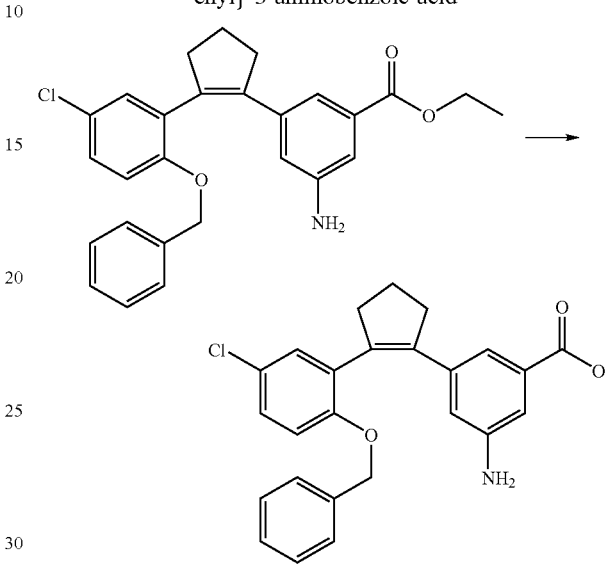

Prepared according to the standard hydrolysis procedure.
$^1$H NMR (CDCl$_3$) δ: 2.01–2.08 (2H, m), 2.83 (2H, t, J=7.4 Hz), 2.89 (2H, t, J=7.4 Hz), 4.96 (2H, s), 6.57 (1H, s), 6.81 (1H, d, J=8.7 Hz), 7.01–7.31 (9H, m).
LC/MS[MH−]=418,420 Rt=3.6.

Example 96

5-{2-[5-chloro-2-(4-fluorobenzyloxy)phenyl]cyclopent-1-enyl}-3-aminobenzoic acid

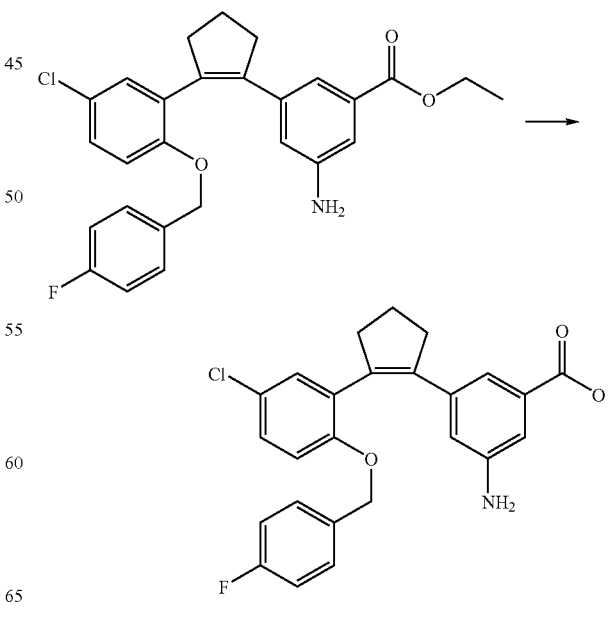

Prepared according to the standard hydrolysis procedure.
¹H NMR (CDCl₃) δ: 1.99–2.06 (2H, m), 2.79–2.87 (4H, m), 4.88 (2H, s), 6.57 (1H, s), 6.78 (1H, d, J=8.7 Hz), 6.96–7.17 (8H, m).
LC/MS[MH–]=436,438 Rt=3.6.

Example 97

5-{2-[5-chloro-2-(2,4-difluorobenzyloxy)phenyl]cyclopent-1-enyl}-3-aminobenzoic acid

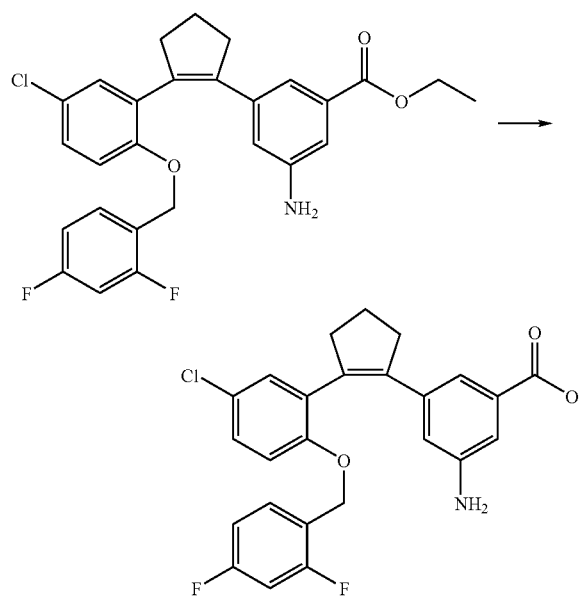

Prepared according to the standard hydrolysis procedure.
¹H NMR (CDCl₃) δ: 1.99–2.05 (2H, m), 2.80 (2H, t, J=7.3 Hz), 2.88 (2H, t, J=7.3 Hz), 4.94 (2H, s), 6.56 (1H, s), 6.75–6.83 (3H, m), 7.04 (1H, s), 7.12–7.17 (4H, m).
LC/MS[MH–]=454,456 Rt=3.6.

Example 98

5-{2-[5-chloro-2-(4-fluorobenzyloxy)phenyl]cyclopent-1-enyl}-3-methanesulphonylaminobenzoic acid

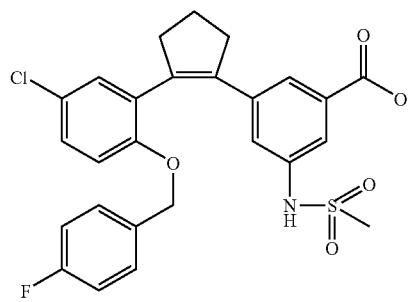

Prepared according to the standard hydrolysis procedure.
¹H NMR (CDCl₃) δ: 2.03–2.10 (2H, m), 2.72 (3H, s), 2.83 (2H, t, J=7.3 Hz), 2.92 (2H, t, J=7.3 Hz), 4.97 (2H, s), 6.70 (1H, s), 6.86 (1H,s).(1H, d, J=8.8 Hz), 6.96–7.03 (3H, m), 7.13–7.25 (3H, m), 7.6 (1H, s), 7.72 (1H, s).
LC/MS[MH–]=514,516 Rt=3.84.

Example 99

5-{2-[5-trifluoromethyl-2-(benzyloxy)phenyl]cyclopent-1-enyl}-3-methanesulphonylaminobenzoic acid

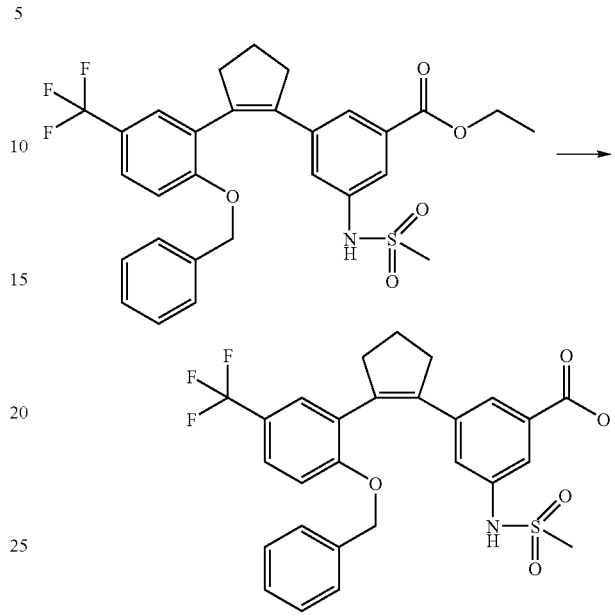

Prepared according to the standard hydrolysis procedure.
¹HNMR (CDCl₃) δ: 2.08–2.12 (2H, m), 2.61 (3H, s), 2.88 (2H, t, J=7.6 Hz), 2.94 (2H, t, J=7.6 Hz), 5.11 (2H, s), 6.49 (1H, bs), 7.01 (1H, d), 7.13 (1H, s) 7.23–7.34 (6H, m), 7.45 (1H, d, J=8.7 Hz), 7.58 (1H, s), 7.72 (1H, s).
LC/MS[MH–]=530 Rt=3.84.

Example 100

5-{2-[5-trifluoromethyl-2-(4-fluorobenzyloxy)phenyl]cyclopent-1-enyl}-3-methanesulphonylaminobenzoic acid

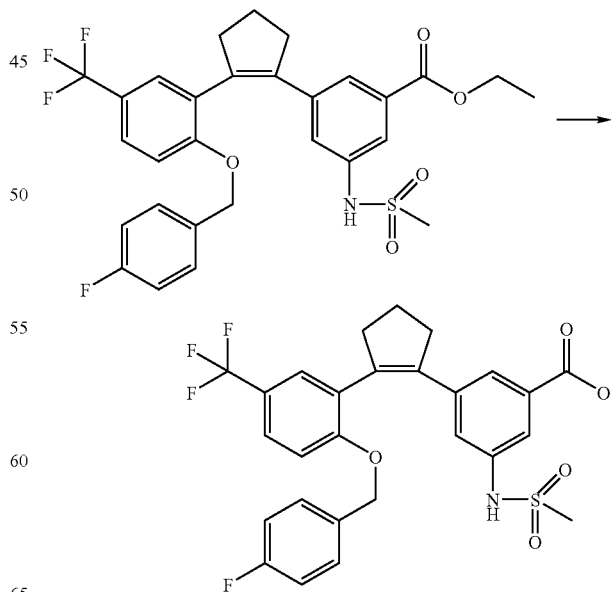

Prepared according to the standard hydrolysis procedure.
¹H NMR (CDCl₃) δ: 2.06–2.10 (2H, m), 2.64 (3H, s), 2.84–2.95 (4H, m), 5.05 (2H, s), 6.72 (1H, br s), 6.98–7.04 (3H, m), 7.12–7.26 (3H, m), 7.46 (1H, d, J=8.6 Hz), 7.58 (1H, s), 7.70 (1H, s).
LC/MS[MH−]=548 Rt=3.93.

Example 101

5-{2-[5-trifluoromethyl-2-(2,4-difluorobenzyloxy)phenyl]cyclopent-1-enyl}-3-methanesulphonylamino Benzoic acid

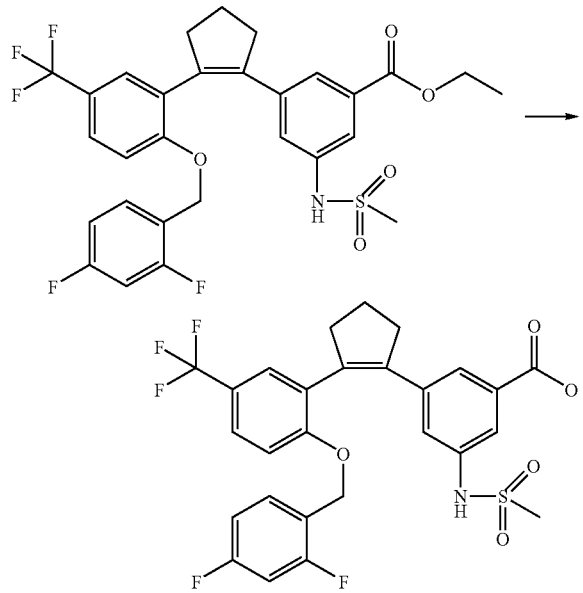

Prepared according to the standard hydrolysis procedure.
¹H NMR (CDCl₃) δ: 2.06–2.10 (2H, bm), 2.64 (3H, s), 2.83 (2H, bs), 2.91 (2H, bs), 5.09 (2H, s), 6.79–6.86 (3H, m), 7.04 (1H, d, J=8.6 Hz), 7.17 (1H, s), 7.23–7.26 (1H, m), 7.48 (1H, d, J=8.4 Hz), 7.56 (1H, s), 7.68 (1H, s).
LC/MS[MH−]=566 Rt=3.7.

Example 102

5-{2-[5-trifluoromethyl-2-(4-fluorobenzyloxy)phenyl]cyclopent-1-enyl}-3-acetamidobenzoic acid

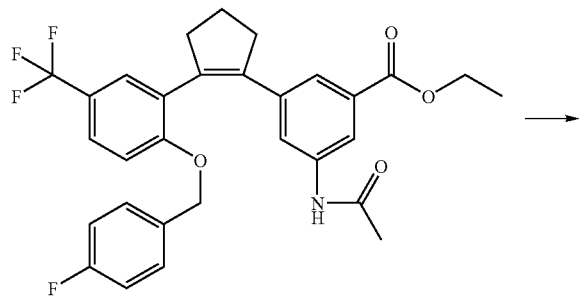

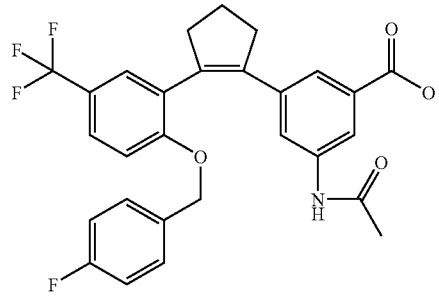

Prepared according to the standard hydrolysis procedure.
¹H NMR (CDCl₃) δ: 2.04–2.11 (5H, m), 2.85–2.91 (4H, m), 4.97 (2H, s), 6.92–7.56 (9H, m), 7.80 (1H, s).
LC/MS[MH−]=512,513 Rt=3.6.

Example 103

5-{2-[5-trifluoromethyl-2-(2,4-difluorobenzyloxy)phenyl]cyclopent-1-enyl}-3-acetamidobenzoic acid

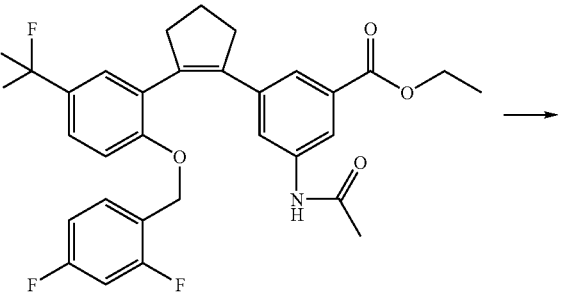

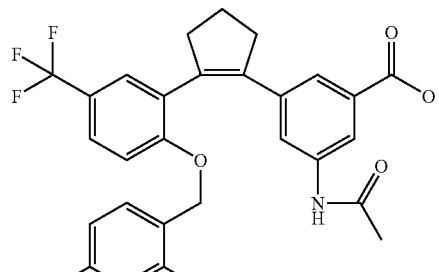

Prepared according to the standard hydrolysis procedure.
¹H NMR (CDCl₃) δ: 2.02–2.1 (2H, bm), 2.13 (3H, s), 2.84 (2H, t, J=7.1), 2.91 (2H, t, J=7.1 Hz), 5.03 (2H, s), 6.76–6.83 (2H, m), 6.97 (1H, d, J=8.6 Hz), 7.16–7.2 (1H, m), 7.31 (1H, s), 7.46 (1H, d, J=7.3 Hz), 7.51 (1H, s), 7.59 (1H, s), 7.85 (1H, s).
LC/MS[MH−]=530,531 Rt=3.6.

Example 104

5-{2-[5-trifluoromethyl-2-(benzyloxy)phenyl]cyclopent-1-enyl}-3-acetamidobenzoic acid

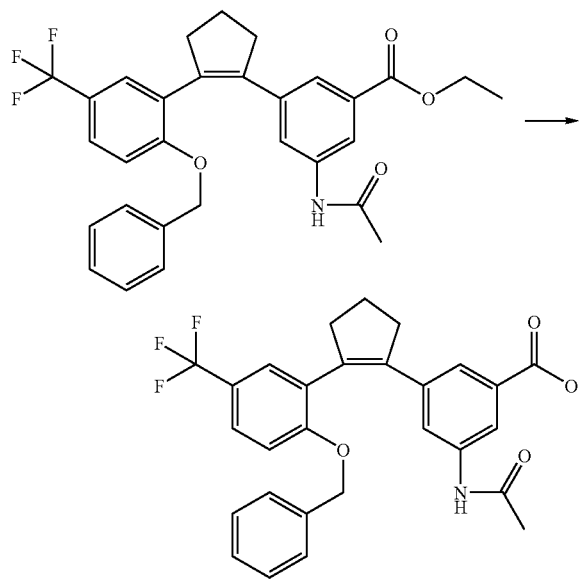

Prepared according to the standard hydrolysis procedure.
¹H NMR (CDCl₃) δ: 2.04 (3H, s), 2.07–2.11 (2H, bm), 2.88–2.92 (4H, m), 5.03 (2H, s), 6.95 (1H, d), 7.11 (1H, bs), 7.21–7.31 (5H, m), 7.43 (1H, d), 7.54 (2H, s), 7.85 (1H, s).
LC/MS[MH−]=494 Rt=3.78.

Example 105

5-{2-[5-chloro-2-(2,4-difluorobenzyloxy)phenyl]cyclopent-1-enyl}-3-acetamidobenzoic acid

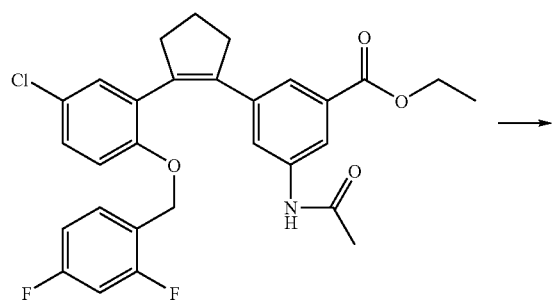

Prepared according to the standard hydrolysis procedure.
¹H NMR (CDCl₃) δ: 2.01–2.09 (2H, m), 2.13 (3H, s), 2.82 (2H, t, J=7.1 Hz), 2.91 (2H, t, J=7.1 Hz), 4.95 (2H, s), 6.76–7.18 (6H, m), 7.54 (2H, s), 7.86 (1H, s).
LC/MS[MH−]=496,498 Rt=3.63.

Example 106

5-{2-[5-chloro-2-(4-fluorobenzyloxy)phenyl]cyclopent-1-enyl}-3-acetamidobenzoic acid

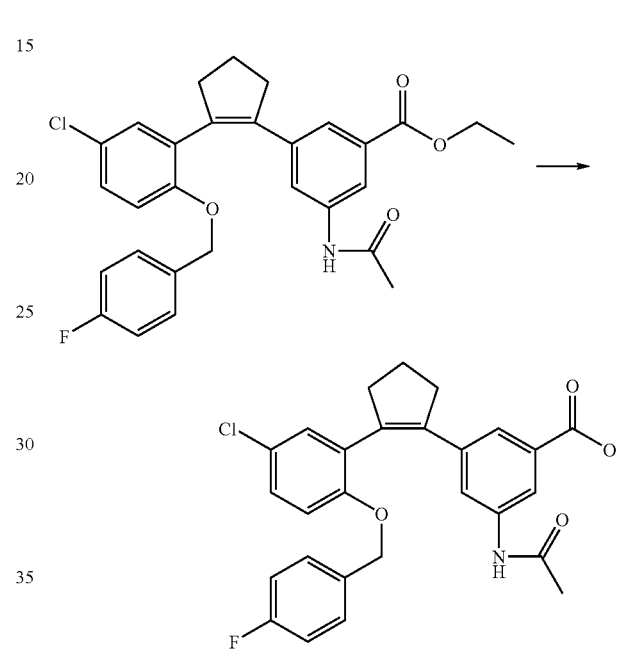

Prepared according to the standard hydrolysis procedure.
¹H NMR (CDCl₃) δ: 2.03–2.07 (2H, m), 2.13 (3H, s), 2.83 (2H, t, J=7.1 Hz), 2.90 (2H, t, J=7.1 Hz), 4.89 (2H, s), 6.80 (1H, d, J=8.8 Hz), 6.96–7.18 (6H, m), 7.53 (2H, d, J=13 Hz), 7.87 (1H, s).
LC/MS[MH−]=478,480 Rt=3.78.

Example 107

5-{2-[5-chloro-2-(benzyloxy)phenyl]cyclopenten-1-enyl}-3-acetamidobenzoic acid

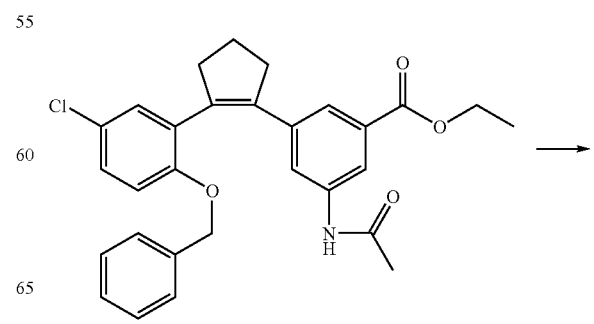

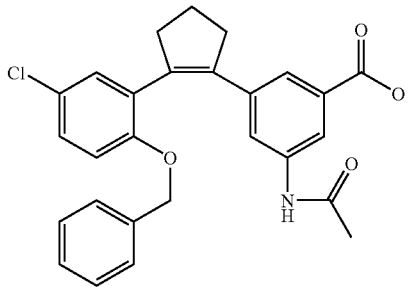

Prepared according to the standard hydrolysis procedure.
$^1$H NMR (CDCl$_3$) δ: 2.03–2.10 (2H, m), 2.13 (3H, s), 2.85 (2H, t, J=7.2 Hz), 2.89 (2H, t, J=7.2 Hz), 4.96 (2H,s), 6.82 (1H, d, J=8.8 Hz), 7.00 (2H, s), 7.13 (1H, d, J=8.8 Hz), 7.21–7.32 (5H, m), 7.45 (1H, s), 7.58 (1H, s), 7.93 (1H, s).
LC/MS[MH−]=460,462 Rt=3.59.

Example 108

5-{2-[5-trifluoromethyl-2-(benzyloxy)phenyl]cyclopent-1-enyl}-3-(morpholin-4-yl)benzoic acid

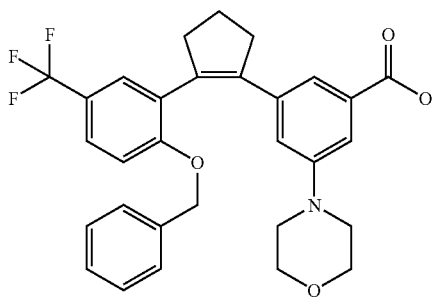

Prepared according to the standard hydrolysis procedure.
$^1$H NMR (CDCl$_3$) δ: 2.08–2.11 (2H, m), 2.77 (4H, t, J=4.8 Hz), 2.88 (2H, t, J=7.1), 2.96 (2H, t, J=7.1 Hz), 3.68 (4H, t, J=4.7 Hz), 5.04 (2H, s), 6.75 (1H, s), 6.93 (1H, d, J=8.6 Hz), 7.19–7.46 (9H, m).
LC/MS [MH−]=522,523 Rt=4.08.

Example 109

5-{2-[5-trifluoromethyl-2-(4-fluorobenzyloxy)phenyl]cyclopent-1-enyl}-3-(morpholin-4-yl)benzoic acid

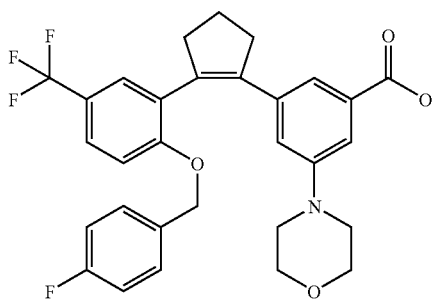

Prepared according to the standard hydrolysis procedure.
$^1$H NMR (CDCl$_3$) δ: 2.06–2.11 (2H, m), 2.78 (4H, t, J=4.8 Hz), 2.85 (2H, t, J=7.1 Hz), 2.94 (2H, t, J=7.1 Hz), 3.69 (4H, t, J=4.7 Hz), 4.97 (2H, s), 6.73 (1H, s), 6.91 (1H, d J=8.6 Hz), 6.97 (2H, t, J=8.6 Hz), 7.11–7.14 (2H, m), 7.38 (2H, d, J=7.3 Hz), 7.43 (2H, bs).
LC/MS[MH−]=540,541 Rt=4.11.

Example 110

5-{2-[5-chloro-2-(-4-fluorobenzyloxy)phenyl]cyclopenten-1-enyl}-3-(morpholinyl)benzoic acid

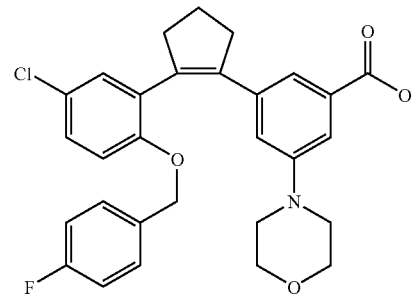

Prepared according to the standard hydrolysis procedure.
$^1$H NMR (CDCl$_3$) δ: 2.03–2.11 (2H, m), 2.82–2.86 (6H, m), 2.93 (2H, t, J=7.1 Hz), 3.73 (4H, t, J=4.7 Hz), 4.90 (2H, s), 6.80 (1H, s), 6.96 (2H, t, J=6.7 Hz), 7.0–7.18 (5H, m), 7.40 (1H, s), 7.45 (1H, s).
LC/MS[MH−]=506,508 Rt=3.82.

Example 111

5-{2-[5-chloro-2-(4-fluorobenzyloxy)phenyl]cyclopent-1-enyl}-3-methylaminobenzoic acid

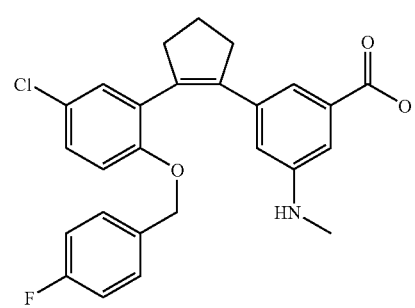

Prepared according to the standard hydrolysis procedure.
$^1$H NMR (CDCl$_3$) δ: 2.01–2.08 (2H, m), 2.61 (3H, s), 2.82 (2H, t, J=7.4 Hz), 2.91 (2H, t, J=7.4 Hz), 4.89 (2H, s), 6.50 (1H, s), 6.79 (1H, d, J=8.7 Hz), 6.98 (2H, t, J=8.7 Hz), 7.06–7.17 (6H, m).
LC/MS[MH−]=450,452 Rt=3.80.

Example 112

5-{2-[5-trifluoromethyl-2-(4-fluorobenzyloxy)phenyl]cyclopent-1-enyl}-3-methylaminobenzoic acid

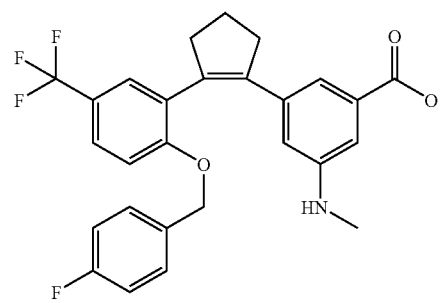

Prepared according to general procedure for ester deprotection.

$^1$H NMR (CDCl$_3$) δ: 2.05–2.10 (2H, m), 2.56 (3H, s), 2.85 (2H, t, J=7.4 Hz), 2.93 (2H, t, J=7.4 Hz), 4.96 (2H, s), 6.45 (1H, s), 6.91 (1H, d, J=8.6 Hz), 6.98 (2H, t, J=8.7 Hz), 7.09 (1H, s), 7.13–7.16 (2H, m), 7.24 (1H, s), 7.37 (1H, s), 7.43 (1H, d, J=8.6 Hz).

LC/MS[MH−]=484,485 Rt=3.81

Example 113

5-{2-[5-trifluoromethyl-2-(benzyloxy)phenyl]cyclopent-1-enyl}-3-methylaminobenzoic acid

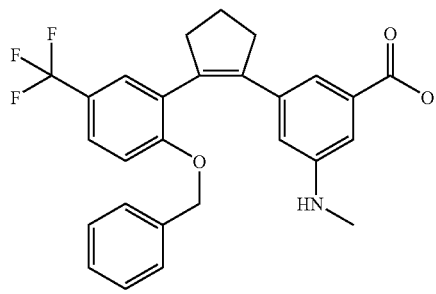

Prepared according to the standard hydrolysis procedure.

$^1$H NMR (CDCl$_3$) δ: 2.04–2.09 (2H, m), 2.55 (3H, s), 2.87 (2H, t, J=7.3 Hz), 2.91 (2H, t, J=7.2 Hz), 5.03 (2H, s), 6.46 (1H, s), 6.93 (1H, d, J=8.7 Hz), 7.08 (1H, s), 7.19–7.35 (7H, m), 7.42 (1H, d, J=8.6 Hz).

Example 114

2{2-[5-Trifluoromethyl-2-(2,4-diflurobenzyloxy)phenyl]cyclopent-1-enyl}pyridine-4-carboxylic acid

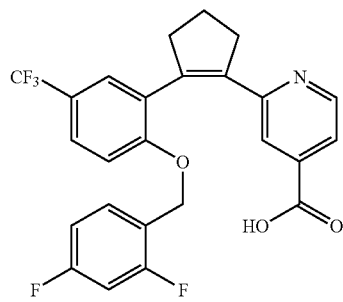

Prepared by the standard hydrolysis procedure.

$^1$H NMR (CDCl$_3$) δ: 2.07–2.14 (2H, m), 2.93 (2H, t, J=8 Hz), 3.08 (2H, t, J=7.5 Hz), 5.01 (2H, s), 6.76–6.82 (2H, m), 7.00 (1H, d, J=8.6 Hz), 7.13–7.19 (1H, m), 7.38 (1H, s), 7.48 (2H, s), 7.57 (1H, d, J=6.5 Hz), 8.62 (1H, d, J=4.7 Hz).

LC/MS: Rt 3.93, [MH−] 474.0, [MH+] 476.0

Example 115

2{2-[5-bromo-2-(2,4-diflurobenzyloxy)phenyl]cyclopent-1-enyl}pyridine-4-carboxylic acid

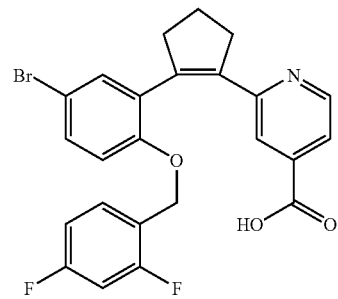

Prepared by the standard hydrolysis procedure.

$^1$H NMR (CDCl$_3$) δ: 2.05–2.12 (2H, m), 2.89 (2H, t, J=8 Hz), 3.06 (2H, t, J=7 Hz), 4.93 (2H, s), 6.83–6.77 (3H, m), 7.12–7.18 (1H, m), 7.24 (1H, s), 7.33 (1H, d, J=8.8 Hz), 7.52 (1H, s), 7.57 (1H, d, J=5 Hz), 8.63 (1H, d, J=5 Hz).

LC/MS: Rt 3.99, [MH+] 487.9, [MH−] 485.9.

Example 116

2{2-[5-bromo-2-(benzyloxy)phenyl]cyclopent-1-enyl}pyridine-4-carboxylic acid

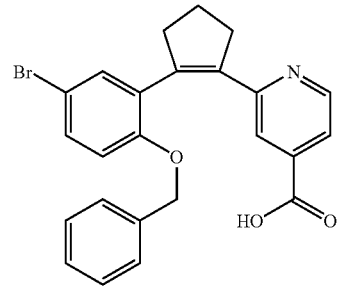

Prepared by the standard hydrolysis procedure.

$^1$H NMR (CDCl$_3$) δ: 2.05–2.13 (2H, m), 2.92 (2H, t, J=7.2 Hz), 3.07 (2H, t, J=7.4 Hz), 4.95 (2H, s), 6.80 (1H, d, J=8.8 Hz), 7.17–7.32 (7H, m), 7.54 (1H, s), 7.58 (1H, d, J=5.1 Hz) 8.66 (1H, d, J=5 Hz).

LC/MS: Rt 3.95, [MH+] 451.9, [MH−] 449.9.

Example 117

2-{2-[5-Trifluoromethyl-2-(2,4-difluorobenzyloxy)phenyl]cyclopent-1-enyl}pyrazine-5-amino-6-carboxylic acid

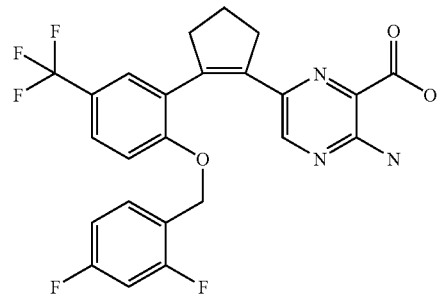

Prepared by general procedure B(iii) but using 2-[5-trifluoromethyl-2-(2,4-diflurobenzyloxy)phenyl]boronic acid instead of (5-chloro-2-benzyloxyphenyl)-boronic acid and 3-amino-6-(2-bromocyclopent-1-enyl)pyrazine-2-carboxylic acid ethyl ester instead of 3-(2-bromocyclopent-1-enyl)-6-methylbenzoic acid ethyl ester.

$^{1}$H NMR (CDCl$_3$) δ: 2.08–2.15 (2H, m), 2.88 (2H, t, J=7.5 Hz), 2.97 (2H, t, J=7.6 Hz), 5.02 (2H, s), 6.78–6.82 (2H, m), 7.08–7.18 (2H, m), 7.41 (1H, s), 7.57 (1H, d, J=8.6 Hz), 8.03 (1H, s), 9.80–10.09 (1H, br s).

LC/MS: Rt 3.73, [MH+] 492.0, [MH−] 490.0.

Example 118

2-{2-[5-Chloro-2-(benzyloxy)phenyl]cyclopent-1-enyl}-5-aminopyrazine-6-carboxylic acid

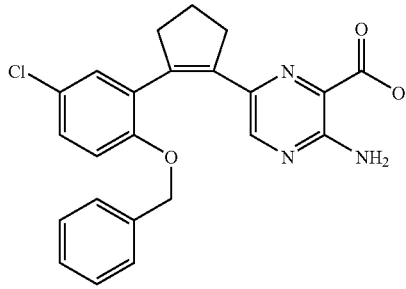

Prepared by general procedure B(iii) but using 3-amino-6-(2-bromocyclopent-1-enyl)-pyrazine-2-carboxylic acid ethyl ester instead of 3-(2-bromocyclopent-1-enyl)-6-methylbenzoic acid ethyl ester.

$^{1}$H NMR (CDCl$_3$) δ: 2.08–2.14 (2H, m), 2.89 (2H, t, J=7.4 Hz), 2.96 (2H, t, J=7.5 Hz), 4.93 (2H, s), 6.91 (1H, d, J=8.8 Hz), 7.13–7.15 (3H, m), 7.22 (1H, d, J=8.7 Hz), 7.28–7.30 (3H, m), 8.05 (1H, s), 9.85–10.20 (1H, br s).

LC/MS: Rt 3.72, [MH+] 422.0, [MH−] 420.0.

Example 119

3-{2-[5-Trifluoromethyl-2-(benzyloxy)phenyl]cyclopent-1-enyl}-5-methylbenzoic acid

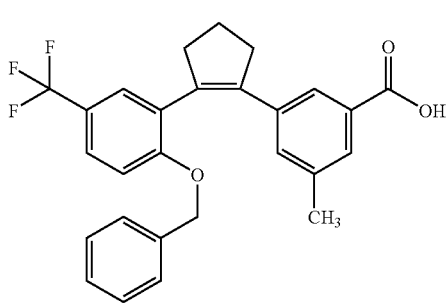

Prepared by the standard hydrolysis procedure.

$^{1}$H NMR (CDCl$_3$) δ: 2.05–2.12 (2H, m), 2.18 (3H, s), 2.87–2.96 (4H, m), 5.03 (2H, s) 6.94 (1H, d, J=8.6 Hz), 7.06 (1H, s), 7.20–7.33 (6H, m), 7.44 (1H, d, J=8.6 Hz), 7.65 (2H, s).

LC/MS: Rt 3.99, [MH−] 451.3.

Example 120

3-{2-[5-Chloro-2-(benzyloxy)phenyl]cyclopent-1-enyl}-5-methylbenzoic acid

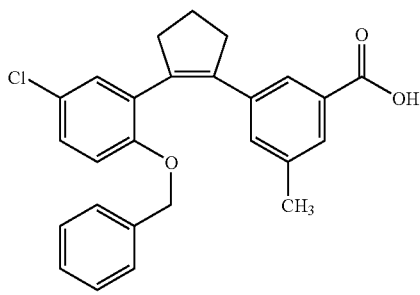

Prepared by the standard hydrolysis procedure.

$^{1}$H NMR (CDCl$_3$) δ: 2.03–2.11 (2H, m), 2.21 (3H, s), 2.84–2.94 (4H, m), 4.95 (2H, m) 6.81 (1H, d, J=8.8 Hz), 7.02 (1H, s), 7.09 (1H, s), 7.13 (1H, d, J=8.7 Hz), 7.19–7.33 (5H, m), 7.66–7.68 (2H, m).

LC/MS: Rt 4.23, [MS−] 417.1.

Example 121

6-{2-[5-chloro-2-(2,4-difluorobenzyloxy)phenyl]cyclopent-1-enyl}pyrazine-2-carboxylic acid

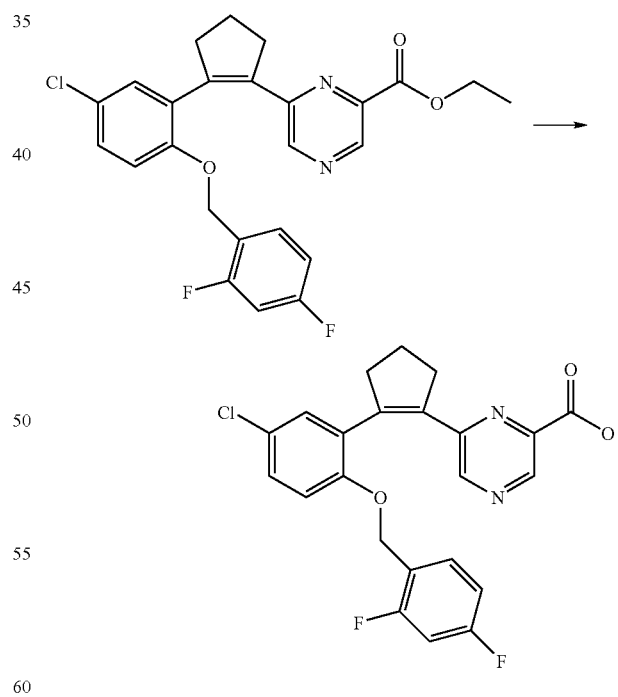

Prepared using the standard hydrolysis procedure.

$^{1}$HNMR (CDCl$_3$): 2.10–2.17 (2H, m), 2.91 (2H, t, J=7.1), 3.05 (2H, t, J=7.1), 4.90 (2H, s), 6.72–6.80 (2H, m), 6.95 (1H, d, J=8.8), 7.06–7.12 (2H, m), 7.26–7.29 (1H, m), 8.52 (1H, s), 9.06 (1H, s).

LC/MS [MH+]=443, 445 Rt=3.80.

Example 122

5-{2-[5-trifluoromethyl-2-(2,4-difluorobenzyloxy)phenyl]cyclopent-1-enyl}-3-(morpholin-4-yl)benzoic acid

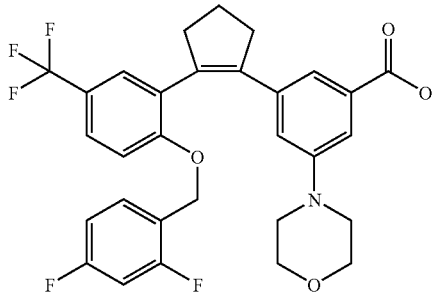

Prepared using the standard hydrolysis procedure.
¹HNMR (CDCl3): 2.04–2.10 (2H, m), 2.79 (4H, t, J=4.8), 2.84 (2H, t, J=7.1), 2.94 (2H, t, J=7.1), 3.70 (4H, t, J=4.7), 5.02 (2H, s), 6.72 (1H, s), 6.76–6.81 (2H, m), 6.96 (1H, d, J=8.6), 7.07–7.10 (1H, m), 7.39 (3H, d, J=10.6), 7.46 (1H, d, J=8.6).
LC/MS [MH−]=558, 559 Rt=4.05.

Example 123

5-{2-[5-chloro-2-(benzyloxy)phenyl]cyclopenten-1-enyl}-3-morpholin-4-ylbenzoic acid

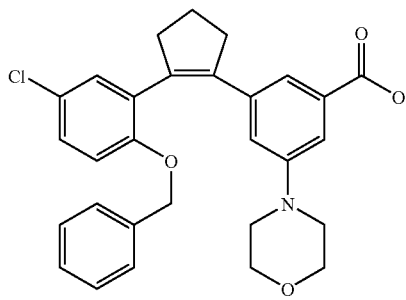

Prepared using the standard hydrolysis procedure.
¹H NMR (CDCl₃): 2.06–2.09 (2H, m), 2.82–2.87 (6H, m), 2.94 (2H, t, J=7.1), 3.72 (4H, t, J=4.7), 4.97 (2H, s), 6.80–6.82 (2H, m), 7.04 (1H, s), 7.10 (1H, dd, J=2.6, J=8.7), 7.19–7.31 (5H, m), 7.41 (1H, s), 7.48 (1H, s).
LC/MS [MH−]=488, 490 Rt=3.80.

Example 124

5-{2-[5-chloro-2-(2,4-difluorobenzyloxy)phenyl]cyclopenten-1-enyl}-3-(morpholin-4-yl)benzoic acid

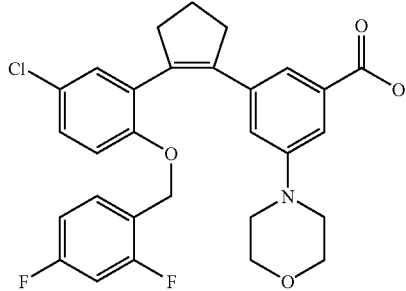

Prepared using the standard hydrolysis procedure.
¹H NMR (CDCl₃) δ: 2.04–2.08 (2H, m), 2.80–2.86 (6H, m), 2.92 (2H, t, J=7.1 Hz), 3.73 (4H t, J=4.7 Hz), 4.95 (2H, s), 6.76–6.85 (4H, m), 7.06–7.16 (3H, m), 7.38 (1H, s), 7.41 (1H, s).
LC/MS [MH−]=524, 526 Rt=4.06.

Example 125

5-{2-[5-chloro-2-(2,4-difluorobenzyloxy)phenyl]cyclopent-1-enyl}-3-methanesulphonylaminobenzoic acid

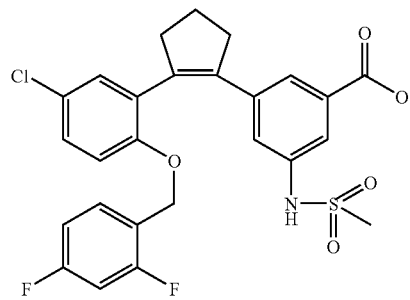

Prepared using the standard hydrolysis procedure.
¹H NMR (CDCl₃) δ: 2.03–2.10 (2H, m), 2.73 (3H, s), 2.81 (2H, t, J=7 Hz), 2.91 (2H, t, J=7 Hz), 5.02 (2H, s), 6.70 (1H, bs), 6.78–6.96 (4H, m), 7.16–7.26 (3H, m), 7.6 (1H, s), 7.70 (1H, s).
LC/MS [MH−]=532, 534 Rt=3.68.

Example 126

5-{2-[5-chloro-2-(benzyloxy)phenyl]cyclopent-1-enyl}-3-methanesulphonylamino Benzoic acid

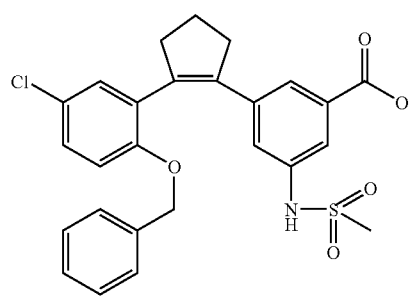

Prepared using the standard hydrolysis procedure.
¹H NMR (CDCl₃): δ: 2.06–2.10 (2H, m), 2.67 (3H, s), 2.86 (2H, t, J=7 Hz), 2.92 (2H, t, J=7 Hz), 5.03 (2H, s), 6.50 (1H, bs), 6.87 (1H, d, J=9 Hz), 6.94 (1H, s), 7.13–7.15 (2H, m), 7.26–7.34 (5H, m), 7.61 (1H, s), 7.74 (1H, s).
LC/MS [MH−]=496, 498 Rt=3.64.

Example 127

5-{2-[5-trifluoromethyl-2-(benzyloxy)phenyl]cyclopent-1-enyl}-3-diethylaminobenzoic acid

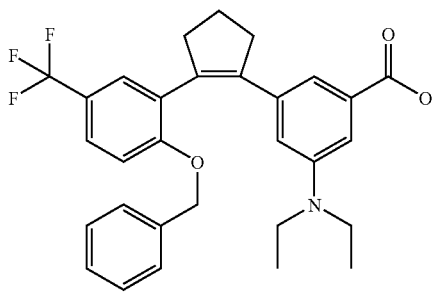

Prepared using the standard hydrolysis procedure.
¹HNMR (CDCl₃): 0.86 (6H, t, J=7 Hz), 2.04–2.09 (2H, m), 2.86 (2H, t, J=7 Hz), 2.96 (2H, t J=7 Hz), 3.04 (4H, q, J=7 Hz), 5.03 (2H, s), 6.53 (1H, s), 6.93 (1H, d, J=8 Hz), 7.17–7.42 (9H, m).
LC/MS [MH−]=508, 509 Rt=4.29.

Example 128

6-{2-[5-Methyl-2-(4-fluorobenzyloxy)phenyl]cyclopent-1-enyl}pyrazine-2-carboxylic acid

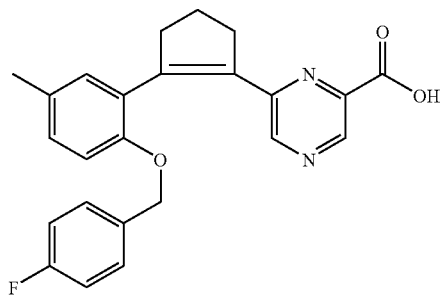

Prepared by the standard hydrolysis procedure using 6-{2-[5-methyl-2-(4-fluorobenzyloxy)phenyl]cyclopent-1-enyl}-pyrazine-2-carboxylic acid ethyl ester.
¹H NMR (CDCl₃) δ: 2.12–2.16 (2H, m), 2.27 (3H, s), 2.93–2.97 (2H, m). 3.02–3.06 (2H, m), 4.86 (2H, s), 6.88 (1H, d, J=8 Hz), 6.92–6.97 (3H, m), 7.08–7.12 (3H, m), 8.55 (1H, s), 9.02 (1H, s).
LC/MS: Rt 4.04, [MH+] 405.2.

Example 129

6-{2-[5-Methyl-2-(2,4-difluorobenzyloxy)phenyl]cyclopent-1-enyl}pyrazine-2-carboxylic acid

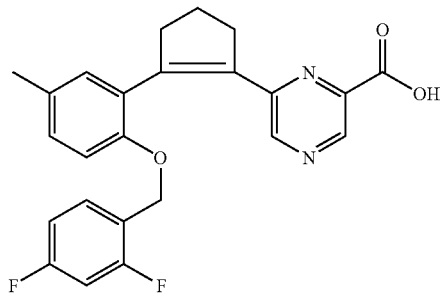

Prepared by the standard hydrolysis procedure using 6-{2-[5-methyl-2-(2,4-difluorobenzyloxy)phenyl]cyclopent-1-enyl}pyrazine-2-carboxylic acid ethyl ester.
¹H NMR (CDCl₃) δ: 2.10–2.17 (2H, m), 2.27 (3H, s), 2.91–2.95 (2H, m). 3.01–3.05 (2H, m), 4.91 (2H, s), 6.71–6.78 (2H, m), 6.92–6.94 (2H, m), 7.09–7.14 (2H, m), 8.54 (1H, s), 9.04 (1H, s).
LC/MS: Rt 3.77, [MH+] 423.4.

Example 130

6-{2-[5-Fluoro-2-(benzyloxy)phenyl]cyclopent-1-enyl}pyridine-2-carboxylic acid

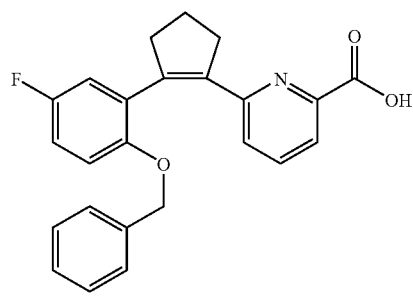

Prepared by the standard hydrolysis procedure using 6-{2-[5-fluoro-2-(benzyloxy)phenyl]cyclopent-1-enyl}pyridine-2-carboxylic acid benzyl ester.
¹H NMR (CDCl₃) δ: 2.09–2.17 (2H, m), 2.90–2.94 (2H, m). 3.01–3.05 (2H, m), 4.91 (2H, s), 6.83 (1H, dd, J=9 Hz, 3 Hz), 6.92–6.97 (2H, m), 7.12–7.14 (2H, m), 7.25–7.29 (4H, m), 7.69 (1H, t, J=8 Hz), 7.89 (1H, d, J=8 Hz).
LC/MS: Rt 3.33, [MH+] 390.4.

Example 131

6-{2-[5-Fluoro-2-(4-fluorobenzyloxy)phenyl]cyclopent-1-enyl}pyridine-2-carboxylic acid

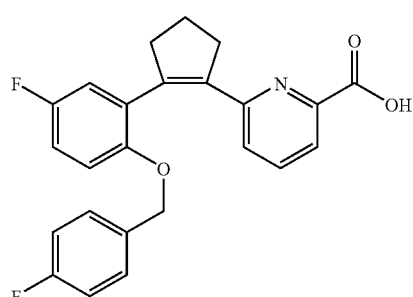

Was prepared by the standard hydrolysis procedure using 6-{2-[5-fluoro-2-(4-fluorobenzyloxy)phenyl]cyclopent-1-enyl}pyridine-2-carboxylic acid 4-fluorobenzyl ester.

¹H NMR (CDCl₃) δ: 2.08–2.16 (2H, m), 2.88–2.92 (2H, m). 3.00–3.04 (2H, m), 4.86 (2H, s), 6.82 (1H, dd, J=9 Hz, 3 Hz), 6.84–6.98 (4H, m), 7.08–7.12 (2H, m), 7.28 (1H, d, J=8 Hz), 7.71 (1H, t, J=8 Hz), 7.90 (1H, d, J=8 Hz).

LC/MS: Rt 3.36, [MH+] 408.4.

Example 132

6-{2-[5-Fluoro-2-(2,4-difluorobenzyloxy)phenyl]cyclopent-1-enyl}-pyridine-2-carboxylic acid

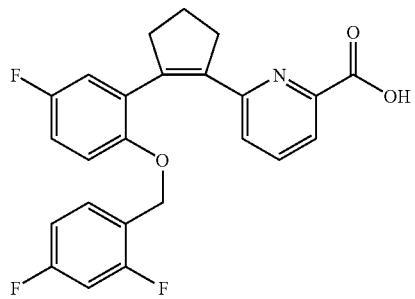

Prepared by the standard hydrolysis procedure using 6-{2-[5-fluoro-2-(2,4-difluorobenzyloxy)phenyl]cyclopent-1-enyl}pyridine-2-carboxylic acid 2,4-difluorobenzyl ester.

¹H NMR (CDCl₃) δ: 2.08–2.15 (2H, m), 2.87–2.91 (2H, m). 3.00–3.03 (2H, m), 4.91 (2H, s), 6.72–6.77 (2H, m), 6.83 (1H, dd, J=9 Hz, 3 Hz), 6.95–7.00 (2H, m), 7.10 (1H, q, J=8 Hz), 7.28 (1H, d, J=8 Hz), 7.71 (1H, t, J=8 Hz), 7.91 (1H, d, J=8 Hz).

LC/MS: Rt 3.41, [MH+] 426.3.

Example 133

6-{2-[5-Chloro-2-(benzyloxy)phenyl]cyclopent-1-enyl}-pyridazine-4-carboxylic acid

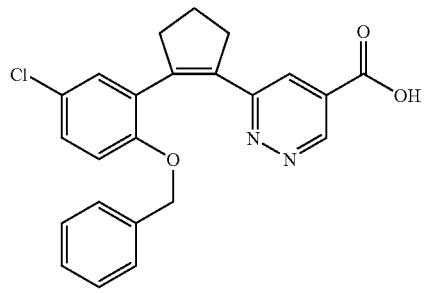

Prepared by the standard hydrolysis procedure using 6-{2-[5-chloro-2-(benzyloxy)phenyl]cyclopent-1-enyl}pyridazine-4-carboxylic acid ethyl ester.

¹H NMR (DMSO-d₆) δ: 2.03–2.10 (2H, m), 2.89–2.93 (2H, m), 3.09–3.13 (2H, m), 4.96 (2H, s), 7.07–7.09 (2H, m), 7.14 (1H, d, J=9 Hz), 7.23–7.26 (4H, m), 7.35 (1H, dd, J=9 Hz, 2 Hz), 7.47 (1H, s), 9.27 (1H, s), 13.9 (1H, br s).

LC/MS: Rt 3.79, [MH+] 407.3, 409.3.

Example 134

6-{2-[5-Chloro-2-(4-fluorobenzyloxy)phenyl]cyclopent-1-enyl}pyridazine-4-carboxylic acid

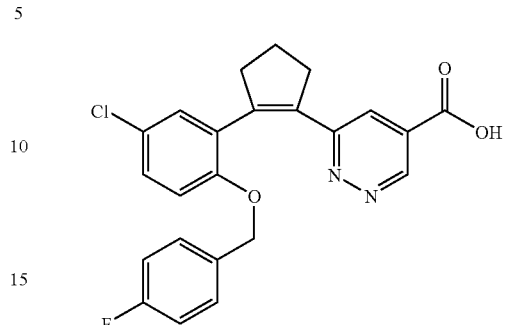

Prepared by the standard hydrolysis procedure using 6-{2-[5-chloro-2-(4-fluorobenzyloxy)phenyl]cyclopent-1-enyl}pyridazine-4-carboxylic acid ethyl ester.

¹H NMR (DMSO-d₈) δ: 2.03–2.09 (2H, m), 2.89–2.92 (2H, m). 3.08–3.12 (2H, m), 4.93 (2H, s), 7.06–7.15 (5H, m), 7.24 (1H, d, J=3 Hz), 7.36 (1H, dd, J=9 Hz, 3 Hz), 7.43 (1H, d, J=2 Hz), 9.26 (1H, s), 13.8 (1H, br s).

LC/MS: Rt 3.82, [MH+] 425.3, 427.3.

Example 135

6-{2-[5-Chloro-2-(2,4-difluorobenzyloxy)phenyl]cyclopent-1-enyl}pyridazine-4-carboxylic acid

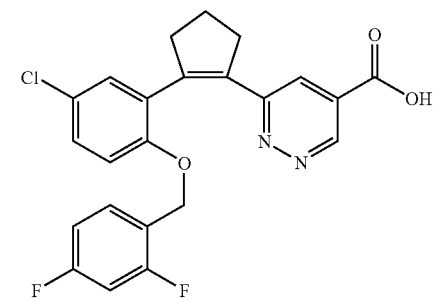

Prepared by the standard hydrolysis procedure using 6-{2-[5-chloro-2-(2,4-difluorobenzyloxy)phenyl]cyclopent-1-enyl}pyridazine-4-carboxylic acid ethyl ester.

¹H NMR (DMSO-d₆) δ: 1.99–2.06 (2H, m), 2.85–2.88 (2H, m). 3.05–3.09 (2H, m), 4.95 (2H, s), 6.98 (1H, dt, J=8 Hz, 2 Hz), 7.15 (1H, dt, J=8 Hz, 2 Hz), 7.21–7.24 (3H, m), 7.37–7.40 (2H, m), 9.24 (1H, d, J=2 Hz), 13.8 (1H, br s).

LC/MS: Rt 3.85, [MH+] 443.3, 445.3.

Example 136

5-{2-[5-chloro-2-(2,4-difluorobenzyloxy)phenyl]cyclopent-1-enyl}-2-methylbenzoic acid

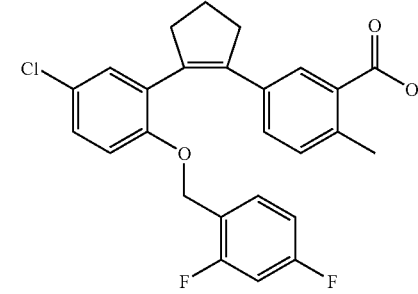

Trifluoroacetic acid (1 ml) was added to a solution of 5-{2-[5-chloro-2-(2,4-difluorobenzyloxy)phenyl]cyclopent-1-enyl}-2-methylbenzoic acid (40 mg 0.08 mmol) in dichloromethane (5 ml). The reaction mixture was stirred at room temperature for three hours. The solvent was evaporated, and the residue chromatographed (RP silica C18, acetonitrile/water 30:70–100:0) to give the title compound as a colourless solid 24 mg 67%.

¹HMR (CDCl₃): 2.00–2.09 (2H, m), 2.56 (3H, s), 2.82 (2H, t, J=6 Hz), 2.91 (2H, t, J=6 Hz), 4.93 (2H, s), 6.75–7.17 (7H, m), 7.25 (1H, s), 7.83 (1H, s).

LC/MS: Rt=4.25 [M–H] 453 (1 Cl).

Example 137

5-[2-(2-(4-fluorobenzyloxy)-5-chlorophenyl)cyclopent-1-enyl]-2-methylbenzoic acid

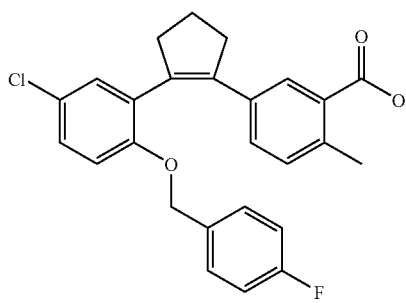

Trifluoroacetic acid (1 ml) was added to a solution of 5-[2-(2-(4-fluorobenzyloxy)-5-chlorophenyl)cyclopent-1-enyl]-2-methylbenzoic acid t-butyl ester (60 mg 0.12 mmol) in dichloromethane (5 ml). The reaction mixture was stirred at room temperature for three hours. The solvent was evaporated, and the residue chromatographed (RP silica C18, acetonitrile/water 30:70–100:0) to give the title compound as a colourless solid 17 mg 33%.

¹H NMR (CDCl₃): 2.01 (2H, m), 2.56 (3H, s), 2.83 (2H, t, J=6 Hz), 2.91 (2H, J=6 Hz), 4.89 (2H, s), 6.80 (1H, d, J=8 Hz), 6.95–7.15 (8H, m), 7.84 (1H, s).

LC/MS: Rt=4.22 [M–H] 435 (1 Cl).

Example 138

5-[2-(2-(4-fluorobenzyloxy)-5-chlorophenyl)cyclopent-1-enyl]-2-fluorobenzoic acid

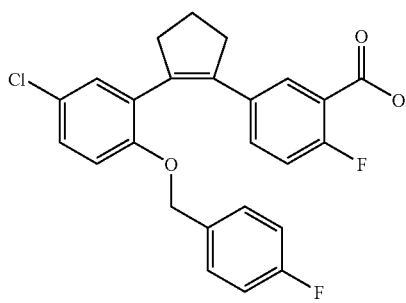

Prepared according to the standard hydrolysis procedure using 5-[2-(2-(4-fluorobenzyloxy)-5-chlorophenyl)cyclopent-1-enyl]-2-fluorobenzoic acid ethyl ester.

¹HMR (CDCl₃): 2.01–2.09 (2H, m), 2.83 (2H, t, J=6 Hz), 2.89 (2H, t, J=6 Hz), 4.88 (2H, s), 6.80–7.19 (9H, m), 7.75 (1H, d, J=8 Hz).

Example 139

5-[2-(2-benzyloxy)-5-chlorophenyl)cyclopent-1-enyl]-2-fluorobenzoic acid

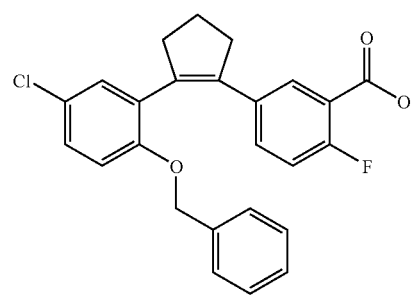

Prepared according to the standard hydrolysis procedure using 5-[2-(2-benzyloxy-5-chlorophenyl)cyclopent-1-enyl]-2-fluorobenzoic acid ethyl ester.

¹H NMR (CDCl₃): δ: 2.01–2.08 (2H, m), 2.78–2.91 (4H, m), 4.95 (2H, s), 6.82–7.33 (10H, m), 7.78 (1H, d, J=8 Hz).

Example 140

5-{2-[5-Trifluoromethyl-2-(benzyloxy)phenyl]cyclopent-1-enyl}nicotinic acid

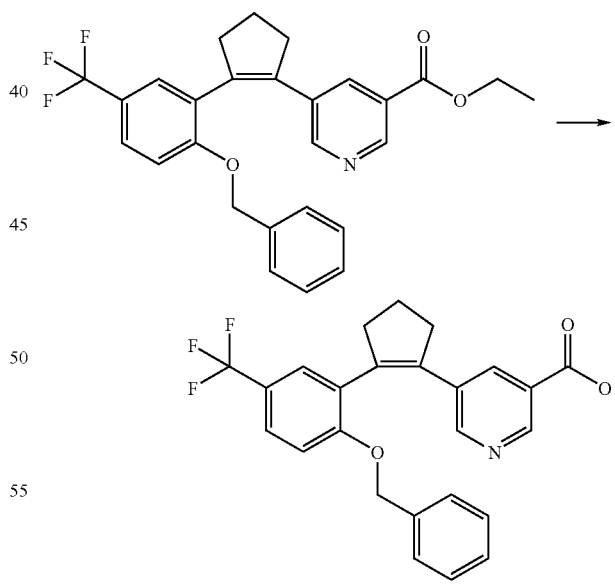

Prepared by the standard hydrolysis procedure.
Product (18 mg, 90%)
LC/MS [MH+] 440 Rt=3.92 min.
¹H NMR (400 MHz, CDCl₃) δ: 2.32–2.14 (2H, m), 2.85–2.96 (4H, m) 4.98 (2H, s), 6.93–6.98 (1H, d, J=8 Hz), 7.14–7.20 (2H, m), 7.24–7.33 (4H, m), 7.42–7.47 (1H, d, J=8 Hz), 8.30 (1H, s), 8.39 (1H, s), 8.96 (1H, s).

Example 141

4-{2-[2-(Benzyloxy)phenyl]cyclopent-1-enyl}benzoic acid

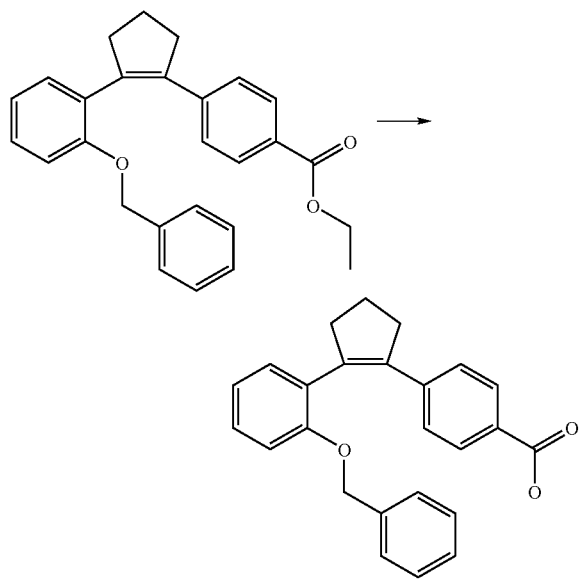

Prepared by the standard hydrolysis procedure.
LC/MS [MH+] 371 Rt 3.72 min.
$^1$H NMR (400 MHz, CDCl$_3$) δ: 2.03–2.13 (2H, m), 2.87–2.97 (4H, m), 4.99 (2H, s), 6.86 (1H, t, J=8 Hz), 6.93 (1H, d, J=8 Hz), 7.10 (1H, d, J=7 Hz), 7.14–7.35 (8H, m), 7.84 (2H, d, J=8 Hz).

Example 142

4-{2-[5-Chloro-2-(benzyloxy)phenyl]cyclopent-1-enyl}benzoic acid

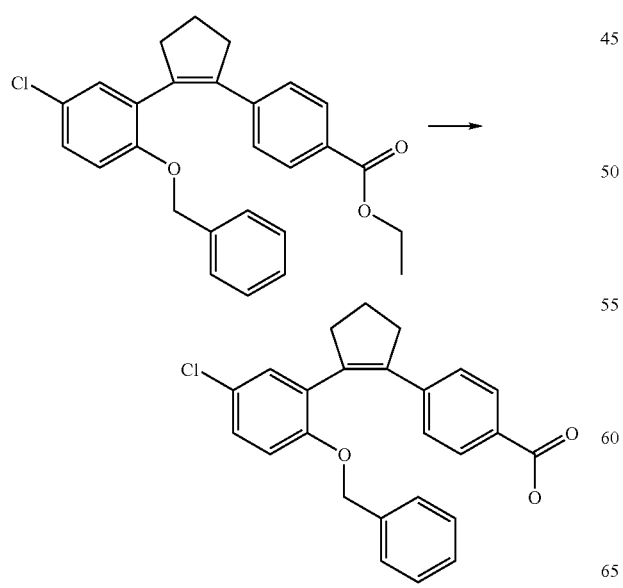

Was prepared by the standard hydrolysis procedure.
$^1$H NMR (400 MHz, CDCl$_3$) δ: 2.02–2.12 (2H, m), 2.83–2.96 (4H, m), 4.93 (2H, s), 6.82 (1H, d, J=9 Hz), 7.02 (1H, d, J=3 Hz), 7.12–7.20 (5H, m), 7.24–7.33 (3H, m), 7.86 (2H, d, J=8 Hz).
LC/MS [MH−] 403 Rt=4.01 min.

Example 143

3-{2-[5-Chloro-3-(4-fluorobenzyloxy)phenyl]cyclopent-1-enyl}-5-methylbenzoic acid

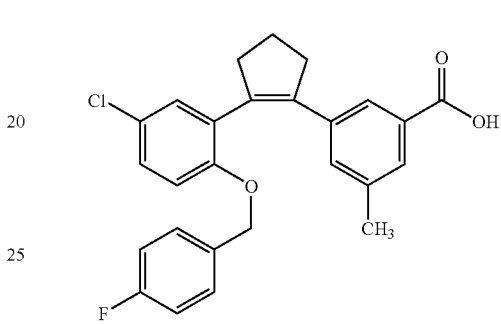

Prepared by the standard hydrolysis procedure.
$^1$H NMR (CDCl$_3$) δ: 2.04–2.10 (2H, m), 2.22 (3H, s), 2.82–2.93 (4H, m), 4.88 (2H, s), 6.80 (1H, d, J=8.8), 6.96–7.16 (7H, m), 7.66 (2H, m).
LC/MS: Rt 4.03, [MH−] 436.5.

Example 144

3-{2-[5-Chloro-2-(2,4-difluorobenzyloxy)phenyl]cyclopent-1-enyl}-5-methylbenzoic acid

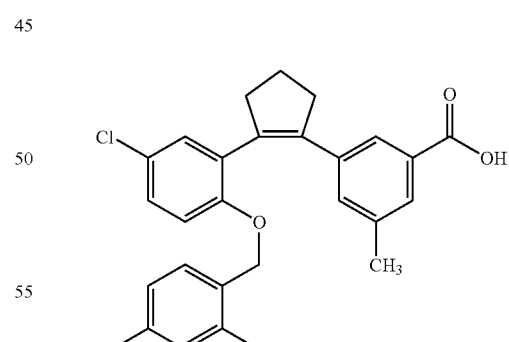

Prepared by the standard hydrolysis procedure.
$^1$H NMR (CDCl$_3$) δ: 2.02–2.10 (2H, m), 2.21 (3H, s), 2.81–2.93 (4H, m), 4.93 (2H, s), 6.77–6.85 (3H, m), 7.03–7.18 (4H, m), 7.64 (2H, m).
LC/MS: Rt 4.05, [MH−] 453.3.

Example 145

3-{2-[5-Trifluoromethyl-2-(4-fluorobenzyloxy)phenyl]cyclopent-1-enyl}-5-methylbenzoic acid

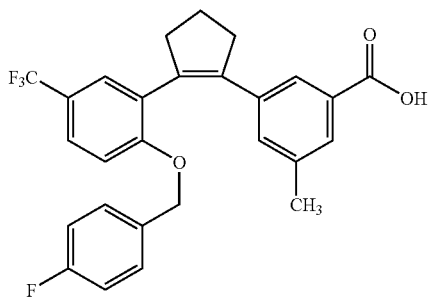

Prepared by the standard hydrolysis procedure.
$^1$H NMR (CDCl$_3$) δ: 2.05–2.11 (2H, m), 2.19 (3H, s), 2.85–2.95 (4H, m), 4.97 (2H, s), 6.92–7.05 (4H, m), 7.14–7.18 (2H, m), 7.32 (1H, s), 7.45 (1H, m), 7.64 (2H, m).
LC/MS: Rt 4.00, [MH−] 469.3.

Example 146

3-{2-[5-Trifluoromethyl-2-(2,4-difluorobenzyloxy)phenyl]cyclopent-1-enyl}-5-methylbenzoic acid

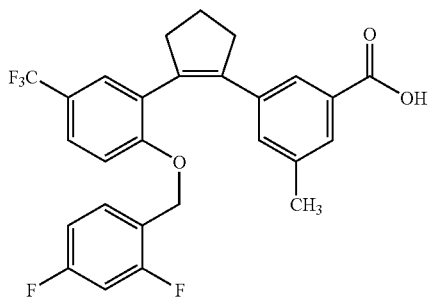

Prepared by the standard hydrolysis procedure.
$^1$H NMR (CDCl$_3$) δ: 2.04–2.12 (2H, m), 2.28–2.95 (4H, m), 5.02 (2H, s), 6.78–6.83 (2H, m), 6.96–6.98 (1H, m), 7.04 (1H, s), 7.10–7.18 (1H, m), 7.32 (1H, s), 7.46–7.49 (1H, m), 7.61 (1H, s), 7.65 (1H, s).
LC/MS: Rt 4.02, [MH−] 487.3.

Example 147

3-{2-[5-Chloro-2-(benzyloxy)phenyl]cyclopent-1-enyl}-5-fluorobenzoic acid

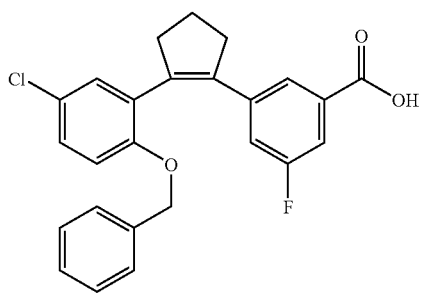

Prepared by the standard hydrolysis procedure.
$^1$H NMR (CDCl$_3$) δ: 2.05–2.12 (2H, m), 2.84–2.94 (4H, m), 4.96 (2H, s), 6.84–6.86 (1H, m), 6.95–6.98 (1H, m), 7.02 (1H, s), 7.15–7.20 (3H, m), 7.21–7.34 (3H, m), 7.50–7.52 (1H, m), 7.66 (1H, s).
LC/MS: Rt 4.05 [MH−] 421.3

Example 148

3-{2-[5-Chloro-2-(4-fluorobenzyloxy)phenyl]cyclopent-1-enyl}-5-fluorobenzoic acid

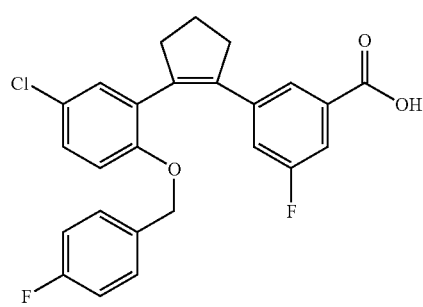

Prepared by the standard hydrolysis procedure.
$^1$H NMR (CDCl$_3$) δ: 2.03–2.11 (2H, m), 2.83–2.93 (4H, m), 4.89 (2H, s), 6.82–6.84 (1H, m), 6.95–7.08 (4H, m), 7.14–7.20 (3H, m), 7.50–7.52 (1H, m), 7.64 (1H, s).
LC/MS: Rt 4.03 [MH−] 439.2.

Example 149

3-{2-[5-Chloro-2-(2,4-difluorobenzyloxy)phenyl]cyclopent-1-enyl}-5-fluorobenzoic acid

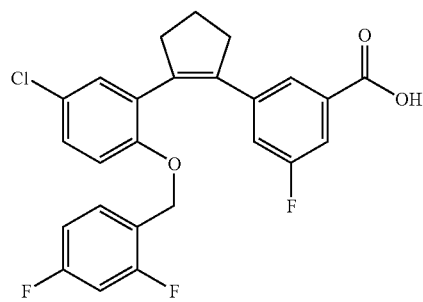

Prepared by the standard hydrolysis procedure.
$^1$H NMR (CDCl$_3$) δ: 2.03–2.11 (2H, m), 2.81–2.93 (4H, m), 4.94 (2H, s), 6.78–6.95 (4H, m), 7.04 (1H, s), 7.12–7.20 (2H, m), 7.50–7.52 (1H, m), 7.62 (1H, s).
LC/MS:
[MH−] 457.2.

Example 150

3-{2-[5-Trifluoromethyl-2-(4-fluorobenzyloxy)phenyl]cyclopent-1-enyl}-5-fluorobenzoic acid

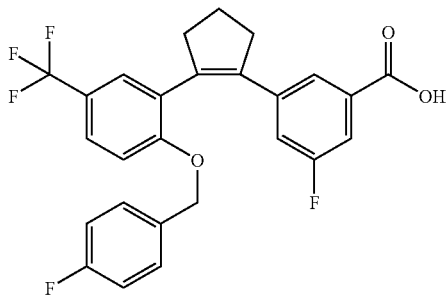

Prepared by the standard hydrolysis procedure.

¹H NMR (CDCl₃) δ: 2.05–2.13 (2H, m), 2.86–2.94 (4H, m), 4.97 (2H, s), 6.91–7.03 (4H, m), 7.15–7.19 (2H, m), 7.33 (1H, s), 7.48–7.52 (2H, m), 7.60 (1H, s).
LC/MS: Rt 3.98 [MH−] 473.3.

Example 152

2-{2-[2-(4-fluorobenzyloxy)phenyl]-cyclopent-1-enyl}-isonicotinic acid

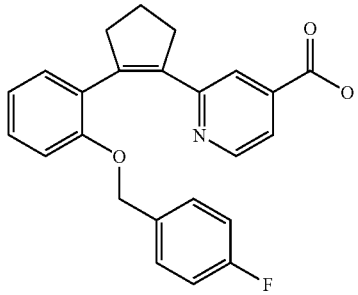

isolated from the reaction mixture by filtration during preparation of Example 81.
Yield 10 mg 25%.

¹H NMR (CDCl₃): 2.06–2.10 (2H, m), 2.93 (2H, br t), 3.05 (2H, br t), 4.93 (2H, s), 6.88–7.23 (8H, m), 7.52–7.55 (2H, m), 8.66 (1H, d, J=6 Hz).

Example 153

6-{2-[5-chloro-2-(benzyloxy)phenyl]cyclopent-1-enyl}pyridine-2-carboxylic acid

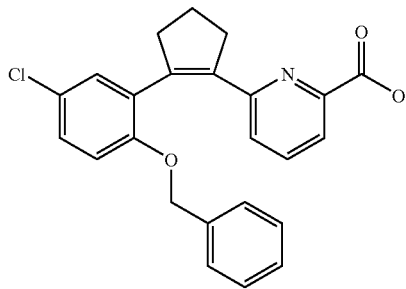

Prepared using the standard hydrolysis procedure.

¹H NMR (CDCl₃): 2.10–2.14 (2H, m), 2.91 (2H, t, J=7.4 Hz), 3.04 (2H, t, J=7.4 Hz), 4.92 (2H, s), 6.90 (1H, d, J=8.8 Hz), 7.09–7.12 (3H, m), 7.21–7.29 (5H, m), 7.68 (1H, t, J=7.8 Hz), 7.91 (1H, d, J=7.6 Hz).
LC/MS [MH+]=406, 408 Rt=3.83

Example 154

6-{2-[5-chloro-2-(4-bromobenzyloxy)phenyl]cyclopent-1-enyl}pyridine-2-carboxylic acid Sodium Salt

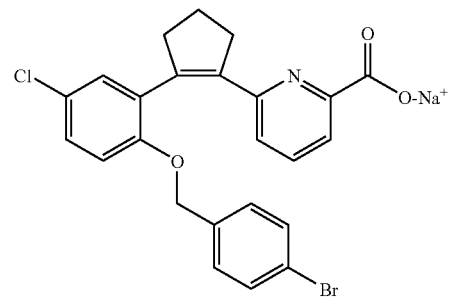

Prepared using the standard hydrolysis procedure, but after dilution with water the solid was filtered, washed with water and dried in vacuo.

¹H NMR (DMSO-d₆): 1.92–1.98 (2H, m), 2.77–2.83 (2H, m), 2.82–2.89 (2H, m), 5.03 (2H, s), 6.63 (1H, d), 7.0 (1H, s), 7.06 (1H, d), 7.14 (2H, d, J=8.3 Hz), 7.23 (1H, d), 7.34 (1H, t), 7.50–7.54 (3H, m).
LC/MS [MH+]=486, 488 Rt=4.08.

Example 155

6-{2-[5-chloro-2-(2-chloro-fluorobenzyloxy)phenyl]cyclopent-1-enyl}pyridine-2-carboxylic acid

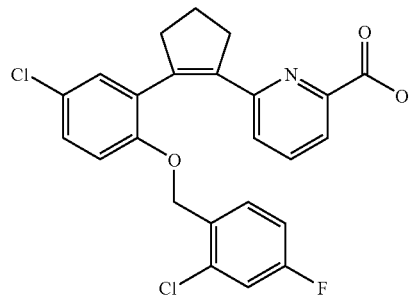

Prepared using the standard hydrolysis procedure.

¹H NMR (CDCl₃): 2.10–2.17 (2H, m), 2.90 (2H, t, J=7.4 Hz), 3.03 (2H, t, J=7.4 Hz), 4.95 (2H, s), 6.86 (1H, t, J=8.4), 6.92 (1H, d, J=8.8 Hz), 7.06 (1H, d, J=8.4 Hz), 7.11–7.13 (2H, m), 7.24–7.30 (2H, m), 7.71 (1H, t, J=7.8 Hz), 7.90 (1H, d, J=7.6 Hz).
LC/MS [MH+]=458, 461 (2 Cl) Rt=4.06.

Example 156

6-{2-[5-chloro-2-(2,4,6-trifluorobenzyloxy)phenyl]cyclopent-1-enyl}pyridine-2-carboxylic acid

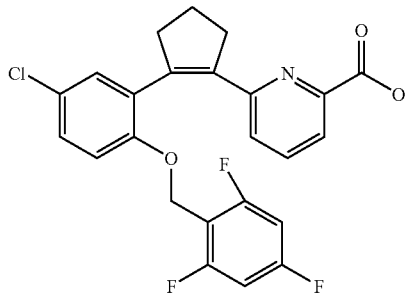

Prepared using the standard hydrolysis procedure.
$^1$H NMR (CDCl$_3$): 2.02–2.09 (2H, m), 2.82 (2H, t, J=7.4 Hz), 2.96 (2H, t, J=7.4 Hz), 4.94 (2H, s), 6.86 (2H, t, J=8.4 Hz), 7.02–7.07 (2H, m), 7.22–7.28 (2H, m), 7.71 (1H, t, J=7.8 Hz), 7.90 (1H, d, J=7.6 Hz).
LC/MS [MH+]=460, 462 Rt=3.84.

Example 157

6-{2-[5-chloro-2-(2,6-difluorobenzyloxy)phenyl]cyclopent-1-enyl}pyridine-2-carboxylic acid

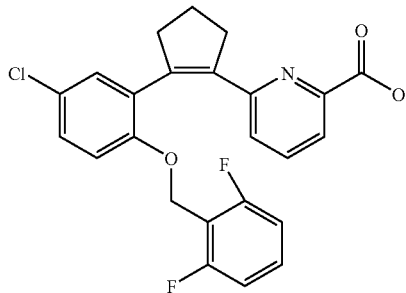

Prepared using the standard hydrolysis procedure.
$^1$H NMR (CDCl$_3$): 2.02–2.09 (2H, m), 2.82 (2H, t, J=7.4 Hz), 2.95 (2H, t, J=7.4 Hz), 4.98 (2H, s), 6.77 (2H, t, J=7.9 Hz), 7.04–7.07 (2H, m), 7.20–7.28(3H, m), 7.66 (1H, J=7.8 Hz), 7.87 (1H, d, J=7.5 Hz).
LC/MS [MH+]=442, 444 Rt=3.79.

Example 158

6-{2-[5-chloro-2-(2-fluoro-4-trifluoromethylbenzyloxy)phenyl]cyclopent-1-enyl}pyridine-2-carboxylic acid

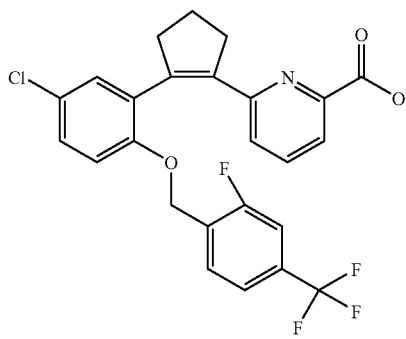

Prepared using the standard hydrolysis procedure.
$^1$H NMR (CDCl$_3$): 2.10–2.17 (2H, m), 2.90 (2H, t, J=7.4 Hz), 3.04 (2H, t, J=7.4 Hz), 5.02 (2H, s), 6.94 (1H, d, J=8.8 Hz), 7.12 (1H, s), 7.26–7.32(5H, m), 7.71 (1H, t, J=7.8 Hz), 7.92 (1H, d, J=7.6 Hz).
LC/MS [MH+]=492, 494 Rt=4.07.

Example 159

6-{2-[5-chloro-2-(3,4-difluorobenzyloxy)phenyl]cyclopent-1-enyl}pyridine-2-carboxylic acid

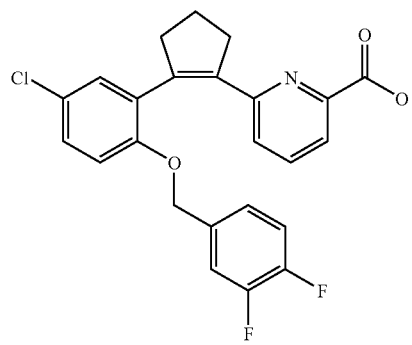

Prepared using the standard hydrolysis procedure.
$^1$H NMR (CDCl$_3$): 2.09–2.16 (2H, m), 2.89 (2H, t, J=7.4 Hz), 3.04 (2H, t, J=7.4 Hz), 4.85 (2H, s), 6.85–6.91(3H, m), 7.01–7.11 (2H, m), 7.22–7.30 (2H, m), 7.71 (1H, br t, J=7.1 Hz), 7.90 (1H, d, J=7.5 Hz).
LC/MS [MH+]=442, 444 Rt=3.90

Example 160

6-{2-[5-chloro-2-(2,3-difluorobenzyloxy)phenyl]cyclopent-1-enyl}pyridine-2-carboxylic acid Sodium Salt

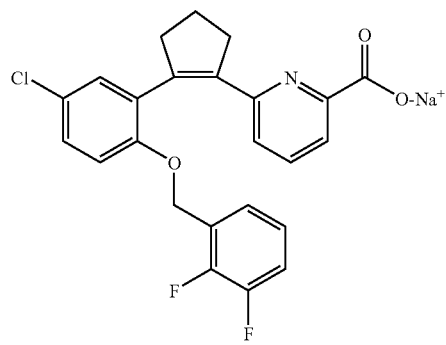

Prepared using the standard hydrolysis procedure, but after dilution with water the solid was filtered, washed with water and dried in vacuo.
$^1$H NMR (DMSO-d$_6$): 1.90–1.97 (2H, m), 2.75–2.79 (2H, m), 2.92–2.95 (2H, m), 5.19 (2H, s), 6.60 (1H, d, J=7.8 Hz), 6.95 (1H, s), 7.07–7.58 (7H, m).
LC/MS [MH+]=442, 444 Rt=3.88.

Example 161

6-{2-[5-chloro-2-(4-methylbenzyloxy)phenyl]cyclopent-1-enyl}pyridine-2-carboxylic acid Sodium Salt

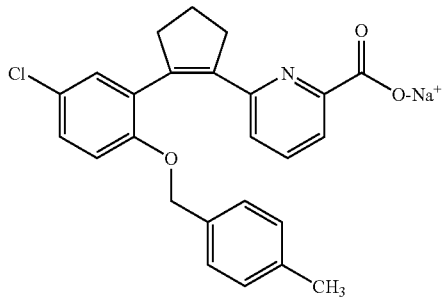

Prepared using the standard hydrolysis procedure, but after dilution with water the solid was filtered, washed and dried in vacuo.

$^1$H NMR (DMSO-d$_6$): 1.92–1.98 (2H, m), 2.27 (3H, s), 2.79–2.97 (4H, m), 5.04 (2H, s), 6.61 (1H, d), 6.93 (1H, s), 7.08–7.14(5H, m), 7.25 (1H, d), 7.35 (1H, t), 7.53 (1H, d).
LC/MS[MH−]=418, 420 Rt=3.96.

Example 162

6-{2-[5-chloro-2-(4-trifluoromethylbenzyloxy)phenyl]cyclopent-1-enyl}pyridine-2-carboxylic acid

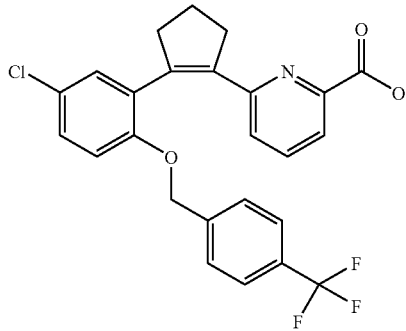

Prepared using the standard hydrolysis procedure.
$^1$H NMR (CDCl$_3$): 2.04–2.17 (2H, m), 2.89 (2H, br s), 3.04 (2H, t, J=7.4 Hz), 4.97 (2H, s) 6.87 (1H,d, J=8.7 Hz), 7.09 (1H, s), 7.22–7.27(4H, m), 7.52 (2H, d, J=8.1 Hz), 7.68 (1H, s), 7.88 (1H, br s).
LC/MS[MH+]=474, 476 Rt=4.04.

Example 163

3-{2[5-Trifluoromethyl-2-(2,4-difluorobenzyloxy)phenyl]cyclopent-1-enyl}-5-aminobenzoic acid

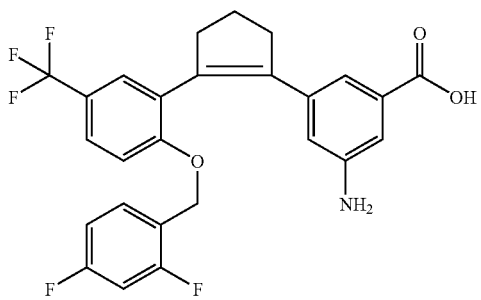

Prepared by the standard hydrolysis procedure using 3-{2[5-trifluoromethyl-2-(2,4-difluorobenzyloxy)phenyl]cyclopent-1-enyl}-5-aminobenzoic methyl ester.

$^1$H NMR (CDCl$_3$) δ: 2.02–2.10 (2H, m), 2.82–2.86 (2H, m), 2.88–2.92 (2H, m), 5.02 (2H, s), 6.54 (1H, d, J=2 Hz), 6.78–6.83 (2H, m), 6.96 (1H, d, 9 Hz), 7.14–7.18 (2H, m), 7.23 (1H, s), 7.34 (1H, d, J=2 Hz), 7.46 (1H, dd, J=9 Hz, 2 Hz).
LC/MS: Rt 3.84, [MH+] 490.

Example 164

2-{2-[5-Trifluoromethyl-2-(benzyloxy)phenyl]cyclopent-1-enyl}pyrimidine-4-carboxylic acid

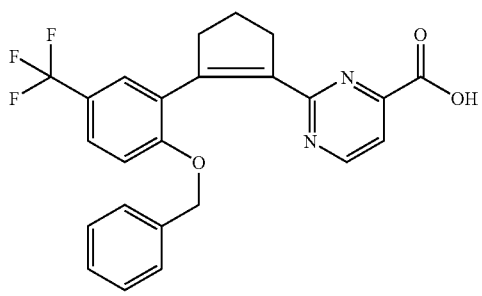

Prepared by the standard hydrolysis procedure using 2-{2-[5-trifluoromethyl-2-(benzyloxy)phenyl]cyclopent-1-enyl}pyrimidine-4-carboxylic acid ethyl ester $^1$H NMR (DMSO-d$_6$) δ: 1.98–2.06 (2H, m), 2.91–2.95 (2H, m), 3.02–3.06 (2H, m), 5.02 (2H, s), 7.09–7.11 (2H, m), 7.18 (1H, d, J=9 Hz), 7.26–7.30 (3H, m), 7.45 (1H, d, J=2 Hz), 7.56–7.62(2 H, m), 8.74 (1H, d, J=5 Hz), 13.4 (1H, br s).
LC/MS: Rt 3.73, [MH+] 441.4.

Example 165

5-{2-[5-Methyl-2-(benzyloxy)phenyl]cyclopent-1-enyl}-2-acetamidobenzoic acid

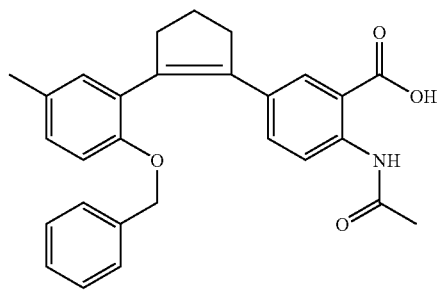

Prepared by the standard hydrolysis procedure using 5-{2-[5-methyl-2-(benzyloxy)phenyl]cyclopent-1-enyl}-2-acetamidobenzoic acid ethyl ester $^1$H NMR (CDCl$_3$) δ: 2.02–2.09 (2H, m), 2.20 (3H, s), 2.21 (3H, s) 2.85–2.93 (4H, m), 4.96 (2H, s), 6.81 (1H, d, J=8 Hz), 6.86 (1H, d, J=2 Hz), 6.99 (1H, dd, J=8 Hz, 2 Hz), 7.22–7.32 (6H, m), 7.92 (1H, d, J=2 Hz), 8.42 (1H, d, J=9 Hz), 10.8 (1H, s).
LC/MS: Rt 3.91, [MH+] 442.4.

Example 166

3-{2-[5-Trifluoromethyl-2-(benzyloxy)phenyl]cyclopent-1-enyl}-6-fluorobenzoic acid

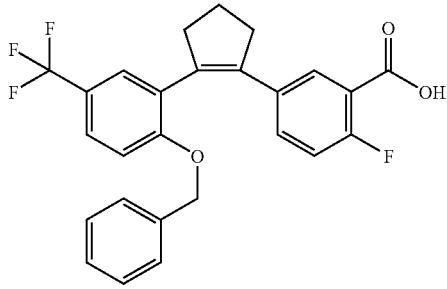

Prepared by the standard hydrolysis procedure.

$^1$H NMR (CDCl$_3$) δ: 2.06–2.13 (2H, m), 2.87–2.94 (4H, m), 5.03 (2H, s), 6.88 (1H, d, J=9 Hz, 3 Hz), 6.98 (1H, d, J=9 Hz), 7.18–7.33 (7H, m), 7.46 (1H, d, J=9 Hz), 7.76 (1H, d, J=9 Hz).

LC/MS: Rt 3.88 [MH−] 455.

Example 167

5-{2-[5-Trifluoromethyl-2-(benzyloxy)phenyl]cyclopent-1-enyl}-2-methylbenzoic acid

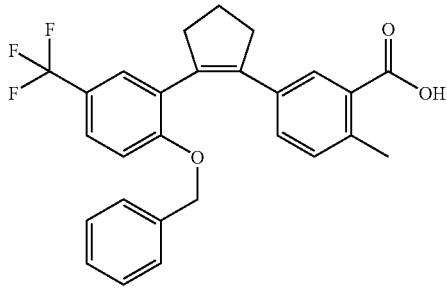

Prepared by the standard hydrolysis procedure.

$^1$H NMR (CDCl$_3$) δ: 2.05–2.12 (2H, m), 2.56 (3H, s), 2.86–2.96 (4H, m), 5.03 (2H, s), 6.95 (1H, d, J=9 Hz,), 6.98 (1H, d, J=8 Hz), 7.07 (1H, d, J=2 Hz), 7.19 (2H, d, J=2 Hz), 7.26–7.33 (4H, m), 7.43 (1H, d, J=2 Hz), 7.85 (1H, s).

LC/MS: Rt 3.97 [MH−] 451.

Example 168

5-{2-[5-chloro-2-(2,4-fluorobenzyloxy)phenyl]cyclopent-1-enyl}-3-(2-oxopyrrolidin-1-yl)benzoic acid

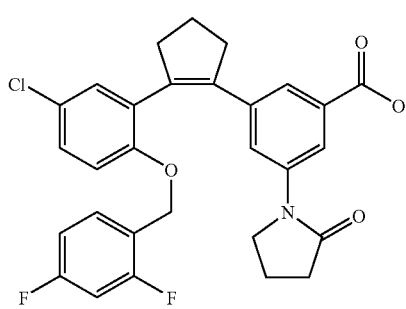

Prepared according to general ester deprotection.

$^1$H NMR (CDCl$_3$) δ: 2.02–2.12 (4H, m), 2.56 (2H, t, J=8.1 Hz), 2.82 (2H, t, J=7.3Hz), 2.94 (2H, t, J=7.0 Hz), 3.55 (2H, t, J=7.0 Hz), 4.97 (2H, s), 6.75–6.81 (2H, m), 6.80 (1H, d, J=8.1 Hz), 7.04 (1H, s), 7.14–7.18 (2H, m), 7.57 (1H, s), 7.62 (1H, s), 8.05 (1H, s).

LC/MS[MH+]=524, 526 Rt=3.94.

Example 169

5-{2-[5-chloro-2-(benzyloxy)phenyl]cyclopent-1-enyl}-3-(2-oxopyrrolidin-1-yl)benzoic acid

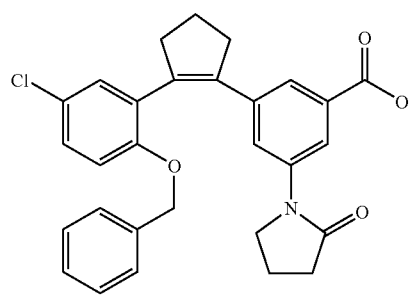

Prepared according to general ester deprotection.

$^1$H NMR (CDCl$_3$) δ: 2.0–2.09 (4H, m), 2.54 (2H, t, J=8.1 Hz), 2.86(2 H, t, J=7.3 Hz), 2.95 (2H, t, J=7.0 Hz), 3.45 (2H, t, J=7.0 Hz), 4.99 (2H, s), 6.84 (1H, d, J=8.8 Hz), 7.02 (1H, s), 7.13 (1H, d, J=8.7 Hz), 7.20–7.31 (5H, m), 7.49 (1H, s), 7.66 (1H, s), 8.15 (1H, s).

LC/MS[MH−]=486, 488 Rt=3.91.

Example 170

5-{2-[5-trifluoromethyl-2-(2,4-difluorobenzyloxy)phenyl]cyclopent-1-enyl}-3-(2-oxopyrrolidin-1-yl)benzoic acid

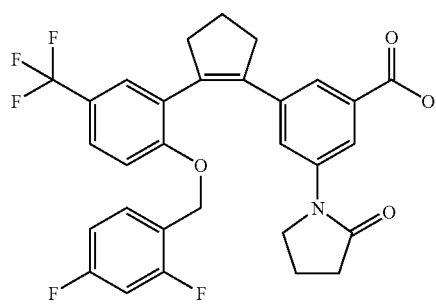

$^1$H NMR (CDCl$_3$) δ: 2.04–2.10 (4H, m), 2.54 (2H, t, J=8.1 Hz), 2.85 (2H, t, J=7.3 Hz), 2.95 (2H, t, J=7.0 Hz), 3.51 (2H, t, J=7.0 Hz), 5.05 (2H, s), 6.77–6.82 (2H, m), 7.01 (1H, t, J=8.7 Hz), 7.14–7.16 (1H, m), 7.34 (1H, s), 7.48 (1H, d, J=8.9 Hz), 7.57 (2H, d, J=10 Hz), 8.03 (1H, s).

LC/MS[MH−]=556 Rt=3.94.

Example 171

5-{2-[5-chloro-2-(2,4-fluorobenzyloxy)phenyl]cyclopent-1-enyl}-3-(2-oxopiperidin-1-yl)benzoic acid

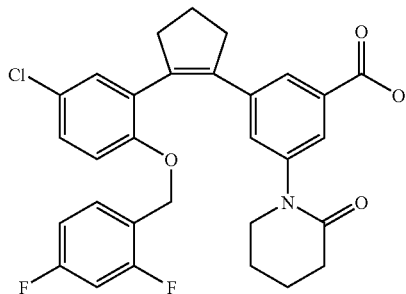

Prepared according to general procedure for ester deprotection.

$^1$H NMR (CDCl$_3$) δ: 1.84(4H, bs), 2.04–2.10 (2H, m), 2.50 (2H, t, J=6.3 Hz), 2.82 (2H, t, J=7.5 Hz), 2.91 (2H, t, J=7.3 Hz), 3.29 (2H, bs), 4.95 (2H, s), 6.74–6.76 (3H, m), 7.04 (2H, bs), 7.12–7.17 (2H, m), 7.71 (2H, s).

LC/MS[MH−]=536, 538 Rt=3.91.

Example 172

5-{2-[5-chloro-2-(benzyloxy)phenyl]cyclopent-1-enyl}-3-(2-oxopiperidin-1-yl)benzoic acid

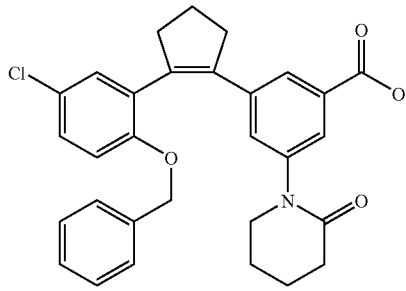

Prepared according to general procedure for ester deprotection.

$^1$H NMR (CDCl$_3$) δ: 1.79–1.84(4H, m), 2.04–2.10 (2H, m), 2.50 (2H, t, J=6.3 Hz), 2.86 (2H, t, J=7.5 Hz), 2.93 (2H, t, J=7.3 Hz), 3.22 (2H, t, J=6.0 Hz), 4.97 (2H, s), 6.82 (1H, d, J=8.8 Hz), 7.03 (2H, d, J=11 Hz), 7.11 (2H, d, J=8.7 Hz), 7.19–7.31 (5H, m), 7.74 (1H, d, J=6 Hz).

LC/MS[MH+]=502, 504 Rt=3.87.

Example 173

5-{2-[5-trifluoromethyl-2-(2,4-difluorobenzyloxy)phenyl]cyclopent-1-enyl}-3-(2-oxopiperidin-1-yl)benzoic acid

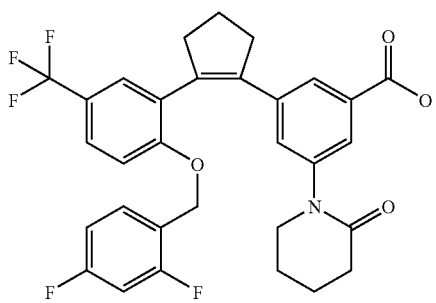

Prepared according to general procedure for ester deprotection.

$^1$H NMR (CDCl$_3$) δ: 1.80–1.84 (4H, m), 2.03–2.09 (2H, m), 2.48 (2H, t, J=6.3 Hz), 2.85 (2H, t, J=7.5 Hz), 2.93 (2H, t, J=7.3 Hz), 3.23 (2H, t, J=6.0 Hz), 5.04 (2H, s), 6.77–6.83 (2H, m), 6.98–7.02 (2H, m), 7.15–7.16 (1H, m), 7.33 (1H, s), 7.47 (1H, d, J=8.4 Hz), 7.71 (2H, s).

LC/MS[MH−]=570, 571 Rt=3.91.

It is to be understood that the present invention covers all combinations of particular and preferred subgroups described herein above.

Assays for Determining Biological Activity

The compounds of formula (I) can be tested using the following assays to demonstrate their prostanoid antagonist or agonist activity in vitro and in vivo and their selectivity. The prostaglandin receptors investigated are DP, EP$_1$, EP$_2$, EP$_3$, EP$_4$, FP, IP and TP.

The ability of compounds to antagonise EP$_1$ & EP$_3$ receptors may be demonstrated using a functional calcium mobilisation assay. Briefly, the antagonist properties of compounds are assessed by their ability to inhibit the mobilisation of intracellular calcium ([Ca$^{2+}$]$_i$) in response to activation of EP$_1$ or EP$_3$ receptors by the natural agonist hormone prostaglandin E$_2$ (PGE$_2$). Increasing concentrations of antagonist reduce the amount of calcium that a given concentration of PGE$_2$ can mobilise. The net effect is to displace the PGE$_2$ concentration-effect curve to higher concentrations of PGE$_2$. The amount of calcium produced is assessed using a calcium-sensitive fluorescent dye such as Fluo-3, AM and a suitable instrument such as a Fluorimetric Imaging Plate Reader (FLIPR). Increasing amounts of [Ca$^{2+}$]$_i$ produced by receptor activation increase the amount of fluorescence produced by the dye and give rise to an increasing signal. The signal may be detected using the FLIPR instrument and the data generated may be analysed with suitable curve-fitting software.

The human EP$_1$ or EP$_3$ calcium mobilisation assay (hereafter referred to as 'the calcium assay') utilises Chinese hamster ovary-K1 (CHO-K1) cells into which a stable vector containing either EP$_1$ or EP$_3$ cDNA has previously been transfected. Cells are cultured in suitable flasks containing culture medium such as DMEM:F-12 supplemented with 10% v/v foetal calf serum, 2 mM L-glutamine, 0.25 mg/ml geneticin and 10 □g/ml puromycin.

For assay, cells are harvested using a proprietary reagent that dislodges cells such as Versene. Cells are re-suspended in a suitable quantity of fresh culture media for introduction into a 384-well plate. Following incubation for 24 hours at 37° C. the culture media is replaced with a medium containing fluo-3 and the detergent pluronic acid, and a further incubation takes place. Concentrations of compounds are then added to the plate in order to construct concentration-effect curves. This may be performed on the FLIPR in order to assess the agonist properties of the compounds. Concentrations of PGE$_2$ are then added to the plate in order to assess the antagonist properties of the compounds.

The data so generated may be analysed by means of a computerised curve-fitting routine. The concentration of compound that elicits a half-maximal inhibition of the calcium mobilisation induced by PGE$_2$ (pIC$_{50}$) may then be estimated.

By application of this technique, compounds of the examples had an antagonist pIC$_{50}$ value of between 7.0 and 9.5 at EP$_1$ receptors and pIC50 value of <6.0 at EP$_3$ receptors. Preferred compounds have an antagonist pIC$_{50}$ value of greater than 8.0 at EP$_1$ receptors.

No toxicological effects are indicated/expected when a compound (of the invention) is administered in the above mentioned dosage range.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

The invention claimed is:

1. A compound of formula (II):

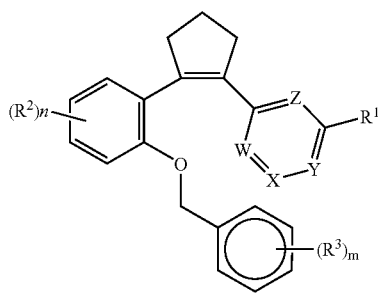

wherein:
$R^1$ is $CO_2H$;
$R^2$ is halo, optionally substituted $C_{1-6}$alkyl, CN, $SC_{1-6}$alkyl, or $SO_2C_{1-6}$alkyl;
each $R^3$ is independently halo, optionally substituted $OC_{1-6}$alkyl, or optionally substituted $C_{1-6}$alkyl;
$R^5$ is hydrogen or an optionally substituted alkyl;
$R^6$ is hydrogen or an optionally substituted alkyl, optionally substituted $SO_2$aryl, optionally substituted $SO_2$heterocyclyl group, CN, optionally substituted $CH_2$aryl or $COR^7$;
$R^7$ is hydrogen, optionally substituted heteroaryl or optionally substituted aryl;
$R^{10}$ and $R^{11}$ together with the nitrogen atom to which they are attached form a morpholine ring, a 5- or 6-membered lactam ring or a 5- or 6-membered cyclic sulphonamide
m is an integer from 0 to 3;
n is an integer from 0 to 2;
W, X, Y and Z are each $CR^{12}$ or N wherein at least two of W, X, Y or Z is $CR^{12}$; and when each of W, X, Y, and Z is $CR^{12}$ then each $R^{12}$ is independently selected from hydrogen, halogen, $NR^5R^6$, $NHCOC_{1-6}$alkyl, $NHSO_2C_{1-6}$alkyl, $C_{1-6}$alkyl and $NR^{10}R^{11}$, and when at least one of W, X, Y and Z is N then each $R^{12}$ is selected from hydrogen and $NH_2$;
or a pharmaceutically acceptable salt, ester, salt of such ester, or solvate thereof.

2. A compound selected from:
3-{2-[5-chloro-2-(benzyloxy)-phenyl]-cyclopent-1-enyl}-benzoic acid;
3-{2-[2-(benzyloxy)-phenyl]-cyclopent-1-enyl]-benzoic acid;
3-{2-[5-bromo-2-(benzyloxy)-phenyl]-cyclopent-1-enyl}-benzoic acid;
3-{2-[5-bromo-2-(4-Chlorobenzyloxy)-phenyl]-cyclopent-1-enyl}-benzoic acid;
3-{2-[5-bromo-2-(4-fluorobenzyloxy)-phenyl]-cyclopent-1-enyl}-benzoic acid;
3-{2-[5-bromo-2-(3,4-dichlorobenzyloxy)-penyl]-cyclopent-1-enyl}-benzoic acid;
3-{2-[5-bromo-2-(2,4-difluorobenzyloxy)-phenyl]-cyclopent-1-enyl}-benzoic acid;
3-{2-[5-bromo-2-(4-chloro-2-fluorobenzyloxy)-phenyl]-cyclopent-1-enyl}-benzoic acid;
3-{2-[5-bromo-2-(4-methoxybenzyloxy)-phenyl]-cyclopent-1-enyl}-benzoic acid;
5-{2-[5-chloro-2-(4-chlorobenzyloxy)-phenyl]-cyclopent-1-enyl}-nicotinic acid;
5-{2-[5-chloro-2-(benzyloxy)-phenyl]-cyclopent-1-enyl}-nicotinic acid;
5-{2-[5-chloro-2-(4-fluorobenzyloxy)-phenyl]-cyclopent-1-enyl}-nicotinic acid;
5-{2-[5-chloro-2-(3,4-dichlorobenzyloxy)-phenyl]-cyclopent-1-enyl}-nicotinic acid;
5-{2-[5-chloro-2-(2,4-difluorobenzyloxy)-phenyl]-cyclopent-1-enyl}-nicotinic acid;
5-{2-[5-chloro-2-(4-chloro-2-fluorobenzyloxy)-phenyl]-cyclopent-1-enyl}-nicotinic acid;
5-{2-[5-chloro-2-(4-methoxybenzyloxy)-phenyl]-cyclopent-1-enyl}-nicotinic acid;
5-{2-[5-bromo-2-(benzyloxy)-phenyl]-cyclopent-1-enyl}-nicotinic acid;
5-{2-[5-bromo-2-(4-chlorobenzyloxy)-phenyl]-cyclopent-1-enyl}-nicotinic acid;
5-{2-[5-bromo-2-(4-fluorobenzyloxy)-phenyl]-cyclopent-1-enyl}-nicotinic acid;
5-{2-[5-bromo-2-(2,4-difluorobenzyloxy)-phenyl]-cyclopent-1-enyl}-nicotinic acid;
5-{2-[5-bromo-2-(4-chloro-2-fluorobenzyloxy)-phenyl]-cyclopent-1-enyl}-nicotinic acid;
5-{2-[5-bromo-2-(4-methoxybenzyloxy)-phenyl]-cyclopent-1-enyl}-nicotinic acid;
5-{2-[5-bromo-2-(cyclohexylmethoxy)-phenyl]-cyclopent-1-enyl}-nicotinic acid;
5-{2-[5-trifluoromethyl-2-(4-chlorobenzyloxy)-phenyl]-cyclopent-1-enyl}-nicotinic acid;
5-{2-[5-trifluoromethyl-2-(4-fluorobenzyloxy)-phenyl]-cyclopent-1-enyl}-nicotinic acid;
5-{2-[5-trifluoromethyl-2-(2,4-difluorobenzyloxy)-phenyl]-cyclopent-1-enyl}-nicotinic acid;
5-{2-[5-trifluoromethyl-2-(4-chloro-2-fluorobenzyloxy)-phenyl]-cyclopent-1-enyl}-nicotinic acid;
5-{2-[5-trifluoromethyl-2-(cyclohexylmethoxy)-phenyl]-cyclopent-1-enyl]-nicotinic acid;
6-{2-[5-chloro-2-(2,4-difluorobenzyloxy)-phenyl]-cyclopent-1-enyl}-pyridine-2-carboxylic acid;
6-{2-[5-chloro-2-(4-chloro-2-fluorobenzyloxy)-phenyl]-cyclopent-1-enyl}-pyridine-2-carboxylic acid;
6-{2-[5-chloro-2-(4-chlorobenzyloxy)-phenyl]-cyclopent-1-enyl}-pyridine 2-carboxylic acid;
6-{2-[5-chloro-2-(4-fluorobenzyloxy)-phenyl]-cyclopent-1-enyl}-pyridine2-carboxylic acid;
3-{2-[5-methylsulfinyl-2-(benzyloxy)-phenyl]-cyclopent-1-enyl}-benzoic acid;
3-{2-[5-methylsulfonyl-2-(benzyloxy)-phenyl]-cyclopent-1-enyl}-benzoic acid;
3-{2-[5-methylsulfinyl-2-(4-fluoro-benzyloxy)-phenyl]-cyclopent-1-enyl}-benzoic acid;
3-{2-[5-methanesulfonyl-2-(4-fluoro-benzyloxy)-phenyl]-cyclopent-1-enyl}-benzoic acid;
3-{2-[5-methylsulfinyl-2-(2,4-difluoro-benzyloxy)-phenyl]-cyclopent-1-enyl}-benzoic acid;
3-{2-[5-methanesulfonyl-2-(2,4-difluoro-benzyloxy)-phenyl]-cyclopent-1-enyl}-benzoic acid;

3-{2-[2-(2,4-difluoro-benzyloxy)-phenyl]-cyclopent-1-enyl}-benzoic acid;
3-{2-[2-(4-chloro-2-fluoro-benzyloxy)-phenyl]-cyclopent-1-enyl}-benzoic acid;
3-{2-[2-(4-methoxy-benzyloxy)-phenyl]-cyclopent-1-enyl}-benzoic acid;
3-{2-[5-cyano-2-(benzyloxy)-phenyl]-cyclopent-1-enyl}-benzoic acid;
3-{2-[5-cyano-2-(2,4-difluoro-benzyloxy)-phenyl]-cyclopent-1-enyl}-benzoic acid;
2-{2-[5-chloro-2-(benzyloxy)phenyl]cyclopent-1-enyl}pyrimidine-4-carboxylic acid;
6-{2-[5-methyl[-2-(benzyloxy)phenyl]cyclopent-1-enyl}pyridine-2-carboxylic acid;
6-{2-[5-methyl-2-(4-fluorobenzyloxy)phenyl]cyclopent-1-enyl}pyridine-2-carboxylic acid;
6-{2-[5-methyl-2-(2,4-difluorobenzyloxy)phenyl]cyclopent-1-enyl}pyridine-2-carboxylic acid;
2-{2-[5-trifluoromethyl-2-(4fluorobenzyloxy)phenyl]cyclopent-1-enyl}pyridine-4-carboxylic acid;
2-{2-[5-trifluoromethyl-2-(benzyloxy)phenyl]cyclopent-1-enyl}pyridine-4-carboxylic acid;
4-{2-[5-trifluoromethyl-2-(4-fluorobenzyloxy)phenyl]cyclopent-1-enyl}pyridine-2-carboxylic acid;
4-{2-[5-trifluoromethyl-2-(benzyloxy)phenyl]cyclopent-1-enyl}pyridine-2-carboxylic acid;
6-{2-[5-trifluoromethyl-2-(benzyloxy)phenyl]cyclopent-1-enyl}-3-aminopyrazine-2-carboxylic acid;
2-{2-[5-trifluoromethyl-2-(4-fluorobenzyloxy)phenyl]cyclopent-1-enyl}pyrimidine-4-carboxylic acid;
2-{2-[5-chloro-2-(4-fluorobenzyloxy)phenyl]cyclopent-1-enyl}pyrimidine-4-carboxylic acid;
6-{2-[5-methyl-2-(benzyloxy)phenyl]cyclopent-1-enyl}pyrazine-2-carboxylic acid;
3-{2[5-methyl-2-(benzyloxy)phenyl]cyclopent-1-enyl}-6-aminobenzoic acid;
6-{2-[5-trifluoromethyl-2-(benzyloxy)phenyl]cyclopent-1-enyl}pyridine-2-carboxylic acid;
6-{2-[5-trifluoromethyl-2-(4-fluorobenzyloxy)phenyl]cyclopent-1-enyl}pyridine-2-carboxylic acid;
6-{2-[5-trifluoromethyl-2-(2,4-difluorobenzyloxy)phenyl]cyclopent-1-enyl}pyridine-2-carboxylic acid;
3-{2-[5-trifluoromethyl-2-(benzyloxy)phenyl]cyclopent-1-enyl}-6-aminobenzoic acid;
3-{2-[5-trifluoromethyl-2-(4-fluorobenzyloxy)phenyl]cyclopent-1-enyl}-6-aminobenzoic acid;
3-{2-[5-trifluoromethyl-2-(2,4-difluorobenzyloxy)phenyl]cyclopent-1-enyl}-6-aminobenzoic acid;
3-{2-[5-trifluoromethyl-2-(benzyloxy)phenyl]cyclopent-1-enyl}-6-acetamidobenzoic acid;
3-{2-[5-trifluoromethyl-2-(4-fluorobenzyloxy)phenyl]cyclopent-1-enyl}-6-acetamidobenzoic acid;
3-{2-[5-trifluoromethyl-2-(2,4-difluorobenzyloxy)phenyl]cyclopent-1-enyl}-6-acetamidobenzoic acid;
3-{2-[5-trifluoromethyl-2-(benzyloxy)phenyl]cyclopent-1-enyl}-5-propionylaminobenzoic acid;
3-{2-[5-trifluoromethyl-2-(4-fluorobenzyloxy)phenyl]cyclopent-1-enyl}-5-propionylaminobenzoic acid;
3-{2-[5-trifluoromethyl2-(2,4-difluorobenzyloxy)phenyl]cyclopent-1-enyl}-5-propionylaminobenzoic acid;
3-{2-[5-bromo-2-(benzyloxy)phenyl]cyclopent-1-enyl}-5-propionylaminobenzoic acid;
3-{2-[5-bromo-2-(4-fluorobenzyloxy)phenyl]cyclopent-1-enyl}-5-propionylaminobenzoic acid;
3-{2-[5-bromo-2-(2,4difluorobenzyloxy)phenyl]cyclopent-1-enyl}-5-propionylaminobenzoic acid;
5-{2-[trifluoromethyl-2-(benzyloxy)phenyl]cyclopent-1-enyl}nicotinic acid N-oxide;
5-{2-[5-fluoro-2-(4-fluorobenzyloxy)phenyl]cyclopent-1-enyl}-3-(propionamide)benzoic acid;
5-{2-[5-methyl-2-(4-fluorobenzyloxy)phenyl]cyclopent-1-enyl}-3-(propionamide)benzoic acid;
5-{2-[5-methyl-2-(2,4-difluorobenzyloxy)phenyl]cyclopent-1-enyl}-3-(propionamide)benzoic acid;
5-[2-(2-benzyloxy-5-chlorophenyl)cyclopent-1-enyl]-2-methylbenzoic acid;
5-[2-(2-Benzyloxy-5-chlorophenyl)-cyclopent-1-enyl]-2-propionylaminobenzoic acid;
2-{2-[5-chloro-2-(2,4-difluorobenzyloxy)phenyl]cyclopent-1-enyl}isonicotinic acid;
2-{2-[5-chloro-2-(4-fluorobenzyloxy)phenyl]cyclopent-1-enyl}isonicotinic acid;
2-{2-[5-chloro-2-benzyloxyphenyl]cyclopent-1-enyl}isonicotinic acid;
2-{2-[5-bromo-2-(4-fluorobenzyloxy)phenyl]cyclopent-1-enyl}isonicotinic acid;
5-[2-(2-benzyloxy-5-chlorophenyl)cyclopent-1-enyl]-3-propionylaminobenzoic acid;
5-[2-(2-benzyloxy-5-chlorophenyl )cyclopent-1-enyl]-3-isobutyrylaminobenzoic acid;
5-{2-[5-trifluoromethyl-2-(benzyloxy)phenyl]cyclopent-1-enyl}-3-(2-oxo-pyrrolidin-1-yl)benzoic acid;
5-{2-[5-trifluoromethyl-2-(4-fluorobenzyloxy)phenyl]cyclopent-1-enyl}-3-(2-oxo-pyrrolidin-1-yl)benzoic acid;
5-{2-[5-chloro-2-(4-fluorobenzyloxy)phenyl]cyclopent-1-enyl}-3-(2-oxo-pyrrolidin-1-yl)benzoic acid;
5-{2-[5-trifluoromethyl-2-(4-fluorobenzyloxy)phenyl]cyclopent-1-enyl}-3-(2-oxo-piperidin-1-yl)benzoic acid;
5-{2-[5-trifluoromethyl-2-(benzyloxy)phenyl]cyclopent-1 -enyl}-3-(2-oxo-piperidin-1-yl)benzoic acid;
5-{2-[5-chloro-2-(4-fluorobenzyloxy)phenyl]cyclopent-1-enyl}-3-(2-oxo-piperidin-1-yl)benzoic acid;
6-{2-[5-trifluoromethyl-2-(benzyloxy)phenyl]cyclopent-1-enyl}pyrazine-2-carboxylic acid;
6-{2-[5-chloro-2-(benzyloxy)phenyl]cyclopent-1-enyl}pyrazine-2-carboxylic acid;
6-{2-[5-chloro-2-(4-fluorobenzyloxy)phenyl]cyclopent-1-enyl}pyrazine-2-carboxylic acid;
5-{2-[5-trifluoromethyl-2-(benzyloxy)phenyl]cyclopent-1-enyl}-3-aminobenzoic acid;
5-{2-[5-trifluoromethyl-2-(4-fluorobenzyloxy)phenyl]cyclopent-1-enyl}-3-aminobenzoic acid;
5-{2-[5-chloro-2-(benzyloxy)phenyl]cyclopent-1-enyl}-3-aminobenzoic acid;
5-{2-(5-chloro-2-(4-fluorobenzyloxy)phenyl]cyclopent-1-enyl}-3-aminobenzoic acid;
5-{2-[5-chloro-2-(2,4-difluorobenzyloxy)phenyl]cyclopent-1-enyl}-3-aminobenzoic acid;
5-{2-[5-chloro-2-(4-fluorobenzyloxy)phenyl]cyclopent-1-enyl}-3-methanesulphonylaminobenzoic acid;
5-{2-[5-trifluoromethyl-2-(benzyloxy)phenyl]cyclopent-1-enyl}-3-methanesulphonylaminobenzoic acid;
5-{2-[5-trifluoromethyl-2-(4fluorobenzyloxy)phenyl]cyclopent-1-enyl}-3-methanesulphonylaminobenzoic acid;
5-{2-[5-trifluoromethyl-2-(2,4-difluorobenzyloxy)phenyl]cyclopent-1-enyl}-3-methanesulphonylamino benzoic acid;
5-{2-[5-trifluoromethyl-2-(4-fluorobenzyloxy)phenyl]cyclopent-1-enyl}-3-acetamidobenzoic acid 5-{2-[5-trifluoromethyl-2-(2,4-difluorobenzyloxy)phenyl]cyclopent-1-enyl}-3-acetamidobenzoic acid;
5-{2-[5-trifluoromethyl-2-(benzyloxy)phenyl]cyclopent-1-enyl}-3-acetamidobenzoic acid;
5-{2-[5-chloro-2-(2,4-difluorobenzyloxy)phenyl]cyclopent-1-enyl}-3-acetamidobenzoic acid;
5-{2-[5-chloro-2-(4-fluorobenzyloxy)phenyl]cyclopent-1-enyl}-3-acetamidobenzoic acid;
5-{2-[5-chloro-2-(benzyloxy)phenyl]cyclopenten-1-enyl}-3-acetamidobenzoic acid;
5-{2-[5-trifluoromethyl-2-(benzyloxy)phenyl]cyclopent-1-enyl}-3-(morpholin-4-yl)benzoic acid;
5-{2-[5-trifluoromethyl-2-(4-fluorobenzyloxy)phenyl]cyclopent-1-enyl}-3-(morpholin-4-yl)benzoic acid;
5-{2-[5-chloro-2-(-4-fluorobenzyloxy)phenyl]cyclopenten-1-enyl}-3-(morpholin-4-yl)benzoic acid;
5-{2-[5-chloro-2-(4-fluorobenzyloxy)phenyl]cyclopent-1-enyl}-3-methylaminobenzoic acid;
5-{2-[5-trifluoromethyl-2-(4-fluorobenzyloxy)phenyl]cyclopent-1-enyl}-3-methylaminobenzoic acid;
5-{2-[5-trifluoromethyl-2-(benzyloxy)phenyl]cyclopent-1-enyl}-3-methylaminobenzoic acid;
2-{2-[5-trifluoromethyl-2-(2,4-difluorobenzyloxy)phenyl]cyclopent-1-enyl}pyridine-4-carboxylic acid;
2{2-[5-bromo-2-(2,4-difluorobenzyloxy)phenyl]cyclopent-1-enyl}pyridine-4-carboxylic acid;
2{2-[5-bromo-2-(benzyloxy)phenyl]cyclopent-1-enyl}pyridine-4-carboxylic acid;
2-{2-[5-trifluoromethyl-2-(2,4-difluorobenzyloxy)phenyl]cyclopent-1-enyl}pyrazine-5-amino-6-carboxylic acid;
2-{2-[5-chloro-2-(benzyloxy)phenyl]cyclopent-1-enyl}-5-aminopyrazine-6-carboxylic acid;
3-{2-[5-trifluoromethyl-2-(benzyloxy)phenyl]cyclopent-1-enyl}-5-methylbenzoic acid;
3-{2-[5-chloro-2-(benzyloxy)phenyl]cyclopent-1-enyl}-5-methylbenzoic acid;
6-{2-[5-chloro-2-(2,4-difluorobenzyloxy)phenyl]cyclopent-1-enyl}pyrazine-2-carboxylic acid;
5-{2-[5-trifluoromethyl-2-(2,4-difluorobenzyloxy)phenyl]cyclopent-1-enyl}-3-(morpholin-4-yl)benzoic acid;
5-{2-[5-chloro-2-(benzyloxy)phenyl]cyclopenten-1-enyl}-3-morpholin-4-ylbenzoic acid;
5-{2-[5-chloro-2-(2,4-difluorobenzyloxy)phenyl]cyclopenten-1-enyl}-3-(morpholin-4-yl)benzoic acid;
5-{2-[5-chloro-2-(2,4-difluorobenzyloxy)phenyl]cyclopent-1-enyl}-3-methanesulphonylaminobenzoic acid;
5-{2-[5-chloro-2-(benzyloxy)phenyl]cyclopent-1-enyl}-3-methanesulphonylamino benzoic acid;
5-{2-[5-trifluoromethyl-2-(benzyloxy)phenyl]cyclopent-1-enyl}-3-diethylaminobenzoic acid;
6-{2-[5-methyl-2-(4-fluorobenzyloxy)phenyl]cyclopent-1-enyl}pyrazine-2-carboxylic acid;
6-{2-[5-methyl-2-(2,4-difluorobenzyloxy)phenyl]cyclopent-1-enyl}pyrazine-2-carboxylic acid;
6-{2-[5-fluoro-2-(benzyloxy)phenyl]cyclopent-1-enyl}pyridine-2-carboxylic acid;
6-{2-[5-fluoro-2-(4-fluorobenzyloxy)phenyl]cyclopent-1-enyl}pyridine-2-carboxylic acid;
6-{2-[5-fluoro-2-(2,4-difluorobenzyloxy)phenyl]cyclopent-1-enyl}pyridine-2-carboxylic acid;
6-{2-[5-chloro-2-(benzyloxy)phenyl]cyclopent-1-enyl}pyridazine-4-carboxylic acid;
6-{2-[5-chloro-2-(4-fluorobenzyloxy)phenyl]cyclopent-1-enyl}pyridazine-4-carboxylic acid;
6-{2-[5-chloro-2-(2,4-difluorobenzyloxy)phenyl]cyclopent-1-enyl}pyridazine-4-carboxylic acid;
5-{2-[5-chloro-2-(2,4-difluorobenzyloxy)phenyl]cyclopent-1-enyl}-2-methylbenzoic acid;
5-[2-(2-(4-fluorobenzyloxy)-5-chlorophenyl)cyclopent-1-enyl]]-2-methylbenzoic acid;
5-[2-(2-(4-fluorobenzyloxy)-5-chlorophenyl)cyclopent-1-enyl]]-2-fluorobenzoic acid;
5-[2-(2-benzyloxy)-5-chlorophenyl)cyclopent-1-enyl]-2-fluorobenzoic acid;
5-{2-[5-trifluoromethyl-2-(benzyloxy)phenyl]cyclopent-1-enyl}nicotinic acid;
4-{2-[2-(benzyloxy)phenyl]cyclopent-1-enyl}benzoic acid;
4-{2-[5-chloro-2-(benzyloxy)phenyl]cyclopent-1-enyl}benzoic acid;
3-{2-[5-chloro-2-(4-fluorobenzyloxy)phenyl]cyclopent-1-enyl}-5-methylbenzoic acid;
3-{2-[5-chloro-2-(2,4-difluorobenzyloxy)phenyl]cyclopent-1-enyl}-5-methylbenzoic acid;
3-{2-[5-trifluoromethyl-2-(4-fluorobenzyloxy)phenyl]cyclopent-1-enyl}-5-methylbenzoic acid;
3-{2-[5-trifluoromethyl-2-(2,4-difluorobenzyloxy)phenyl]cyclopent-1-enyl}-5-methylbenzoic acid;
3-{2-[5-chloro-2-(benzyloxy)phenyl]cyclopent-1-enyl}-5-fluorobenzoic acid;
3-{2-[5-chloro-2-(4-fluorobenzyloxy)phenyl]cyclopent-1-enyl}-5-fluorobenzoic acid;
3-{2-[5-chloro-2-(2,4-difluorobenzyloxy)phenyl]cyclopent-1-enyl}-5-fluorobenzoic acid;
3-{2-[5-trifluoromethyl-2-(4-fluorobenzyloxy)phenyl]cyclopent-1-enyl}-5-fluorobenzoic acid;
3-{2-[5-trifluoromethyl-2-(2,4-difluorobenzyloxy)phenyl]cyclopent-1-enyl}-5-fluorobenzoic acid;
2-{2-[5-bromo-2-(4-fluorobenzyloxy)phenyl]cyclopent-1-enyl}-isonicotinic acid;
2-{2-[2-(4-fluorobenzyloxy)phenyl]-cyclopent-1-enyl}isonicotinic acid;
6-{2-[5-chloro-2-(benzyloxy)phenyl]cyclopent-1-enyl}pyridine-2-carboxylic acid;
6-{2-[5-chloro-2-(4-bromobenzyloxy)phenyl]cyclopent-1-enyl}pyridine-2-carboxylic acid;
6-{2-[5-chloro-2-(2-chloro-4-fluorobenzyloxy)phenyl]cyclopent-1-enyl}pyridine-2-carboxylic acid;
6-{2-[5-chloro-2-(2,4,6-trifluorobenzyloxy)phenyl]cyclopent-1-enyl}pyridine-2-carboxylic acid;
6-{2-[5-chloro-2-(2,6-difluorobenzyloxy)phenyl]cyclopent-1-enyl}pyridine-2-carboxylic acid;
6-{2-[5-chloro-2-(2-fluoro-4-trifluoromethylbenzyloxy)phenyl]cyclopent-1-enyl}pyridine-2-carboxylic acid;
6-{2-[5-chloro-2-(3,4-difluorobenzyloxy)phenyl]cyclopent-1-enyl}pyridine-2-carboxylic acid;
6-{2-[5-chloro-2-(2,3-difluorobenzyloxy)phenyl]cyclopent-1-enyl}pyridine-2-carboxylic acid;
6-{2-[5-chloro-2-(4-methylbenzyloxy)phenyl]cyclopent-1-enyl}pyridine-2-carboxylic acid;
6-{2-[5-chloro-2-(4-trifluoromethylbenzyloxy)phenyl]cyclopent-1-enyl}pyridine-2-carboxylic acid;
3-{2[5-trifluoromethyl-2-(2,4difluorobenzyloxy)phenyl]cyclopent-1-enyl}-5-aminobenzoic acid;
2-{2-[5-trifluoromethyl-2-(benzyloxy)phenyl]cyclopent-1-enyl}pyrimidine-4-carboxylic acid;
5-{2-[5-methyl-2-(benzyloxy)phenyl]cyclopent-1-enyl}-2-acetamidobenzoic acid;
3-{2-[5-trifluoromethyl-2-(benzyloxy)phenyl]cyclopent-1-enyl}-6-fluorobenzoic acid;

5-{2-[5-trifluoromethyl-2-(benzyloxy)phenyl]cyclopent-1-enyl}-2-methylbenzoic acid;

5-{2-[5-chloro-2-(2,4-fluorobenzyloxy)phenyl]cyclopent-1-enyl}-3-(2-oxopyrrolidin-1-yl)benzoic acid;

5-{2-[5-chloro-2-(benzyloxy)phenyl]cyclopent1-enyl}-3-(2-oxopyrrolidin-1-yl)benzoic acid;

5-{2-[5-trifluoromethyl-2-(2,4-difluorobenzyloxy)phenyl]cyclopent-1-enyl}-3-(2-oxopyrrolidin-1-yl)benzoic acid;

5-{2-[5-chloro-2-(2,4-fluorobenzyloxy)phenyl]cyclopent-1-enyl}-3-(2-oxopiperidin-1-yl)benzoic acid;

5-{2-[5-chloro-2-(benzyloxy)phenyl]cyclopent-1-enyl}-3-(2-oxopiperidin-1-yl)benzoic acid; and 5-{2-[5-trifluoromethyl-2-(2,4-difluorobenzyloxy)phenyl]cyclopent-1-enyl}-3-(2-oxopiperidin-1-yl)benzoic acid and pharmaceutically acceptable salt, ester, salt of such ester, or solvate thereof.

3. A pharmaceutical composition comprising a compound according to claim 1 together with a pharmaceutical carrier and/or excipient.

4. A method of treating a human or animal subject suffering from inflammatory pain, neuropathic pain or visceral pain which method comprises administering to said subject an effective amount of a compound according to claim 1.

5. The compound according to claim 1, wherein
$R^2$ is halo, $C_{1-4}$alkyl, $CF_3$, CN, $SC_{1-6}$alkyl, or $SO_2C_{1-6}$alkyl;
W, X, Y and Z are each $CR^{12}$ or N wherein at least two of W, X, Y or Z is $CR^{12}$; and when each of W, X, Y and Z is $CR^{12}$ then each $R^{12}$ is independently selected from hydrogen, halogen, $NR^5R^6$, $C_{1-6}$alkyl, $NHSO_2C_{1-6}$alkyl, $C_{1-6}$alkyl and $NR^{10}R^{11}$, and when at least one of W, X, Y and Z is N then each $R^{12}$ is selected from hydrogen and $NH_2$;
or a pharmaceutically acceptable salt, ester, salt of such ester, or solvate thereof.

6. 6-{2-[5-Chloro-2-(2,4-difluorobenzyloxy)-phenyl]cyclopent-1-enyl}-pyridine-2-carboxylic acid or a pharmaceutically acceptable salt, ester, salt of such ester, or solvate thereof.

7. A pharmaceutical composition comprising the compound according to claim 6 together with a pharmaceutical carrier and/or excipient.

8. A method of treating a human or animal subject suffering from inflammatory pain, neuropathic pain or visceral pain which method comprises administering to said subject an effective amount of a compound according to claim 6.

9. 6-{2-[5-Chloro-2-(2,4-difluorobenzyloxy)-phenyl]cyclopent-1-enyl}-pyridine-2-carboxylic acid.

10. The compound according to claim 1, wherein m is an integer from 0 to 2; and
W, X, Y and Z represents CH or N wherein at least one of W, X, Y or Z is CH;
or pharmaceutically acceptable salt, ester, salt of such ester, or solvate thereof.

11. The compound according to claim 1, wherein
$R^2$ is halogen, optionally substituted $C_{1-6}$alkyl, CN, or $SO_2C_{1-6}$alkyl.

12. The compound according to claim 1, wherein
$R^3$ represents halo, optionally substituted $C_{1-4}$alkyl, or optionally substituted $OC_{1-4}$alkyl.

* * * * *